US011396502B2

(12) United States Patent
Shepard et al.

(10) Patent No.: US 11,396,502 B2
(45) Date of Patent: Jul. 26, 2022

(54) SUBSTITUTED HETEROCYCLIC DERIVATIVES AS PI3K INHIBITORS

(71) Applicant: Incyte Corporation, Wilmington, DE (US)

(72) Inventors: Stacey Shepard, Wilmington, DE (US); Andrew P. Combs, Kennett Square, PA (US)

(73) Assignee: Incyte Corporation, Wilmington, DE (US)

( * ) Notice: Subject to any disclaimer, the term of this patent is extended or adjusted under 35 U.S.C. 154(b) by 164 days.

(21) Appl. No.: 16/681,267

(22) Filed: Nov. 12, 2019

(65) Prior Publication Data

US 2020/0148667 A1  May 14, 2020

Related U.S. Application Data

(60) Provisional application No. 62/760,479, filed on Nov. 13, 2018.

(51) Int. Cl.
*C07D 401/14* (2006.01)
*C07D 413/14* (2006.01)
*C07D 403/14* (2006.01)
*C07D 405/14* (2006.01)
*C07D 491/107* (2006.01)

(52) U.S. Cl.
CPC ......... *C07D 401/14* (2013.01); *C07D 403/14* (2013.01); *C07D 405/14* (2013.01); *C07D 491/107* (2013.01)

(58) Field of Classification Search
CPC ............................. C07D 401/14; C07D 413/14
See application file for complete search history.

(56) References Cited

U.S. PATENT DOCUMENTS

| 5,521,184 | A | 5/1996 | Zimmerman |
| 8,377,940 | B2 | 2/2013 | Clayton et al. |
| 8,748,426 | B2 | 6/2014 | Jadhav et al. |
| 11,078,204 | B2 | 8/2021 | Shepard et al. |
| 11,161,838 | B2 | 11/2021 | Shepard et al. |
| 2007/0105864 | A1 | 5/2007 | Guzi et al. |
| 2007/0225286 | A1 | 10/2007 | Ren et al. |
| 2011/0245247 | A1 | 10/2011 | Braje et al. |
| 2013/0203995 | A1 | 8/2013 | Boyd et al. |
| 2017/0145002 | A1 | 5/2017 | Duggan |
| 2018/0086737 | A1 | 3/2018 | Argiriadi et al. |
| 2020/0148671 | A1 | 5/2020 | Shepard et al. |
| 2020/0148689 | A1 | 5/2020 | Shepard et al. |
| 2021/0395258 | A1 | 12/2021 | Shepard et al. |

FOREIGN PATENT DOCUMENTS

| CN | 107417738 | 12/2017 |
| WO | WO 00/09495 | 2/2000 |
| WO | WO 00/053595 | 9/2000 |
| WO | WO 01/014402 | 3/2001 |
| WO | WO 01/064655 | 9/2001 |
| WO | WO 2002/000196 | 1/2002 |
| WO | WO 03/037347 | 5/2003 |
| WO | WO 03/024967 | 9/2003 |
| WO | WO 03/099771 | 12/2003 |
| WO | WO 04/005281 | 1/2004 |
| WO | WO 04/046120 | 8/2004 |
| WO | WO 04/080980 | 9/2004 |
| WO | WO 04/056786 | 10/2004 |
| WO | WO 05/028444 | 3/2005 |
| WO | WO 2005/047280 | 5/2005 |
| WO | WO 2006/020879 | 2/2006 |
| WO | WO 2006/038041 | 4/2006 |
| WO | WO 2006/056399 | 6/2006 |
| WO | WO 2007/016674 | 2/2007 |
| WO | WO 2007/021308 | 2/2007 |
| WO | WO 2007/021309 | 2/2007 |
| WO | WO 2007/095024 | 8/2007 |
| WO | WO 2008/047831 | 4/2008 |
| WO | WO 2008/130853 | 10/2008 |
| WO | WO 2008/150232 | 12/2008 |
| WO | WO 2008/150233 | 12/2008 |
| WO | WO 2009/100130 | 8/2009 |
| WO | WO 2009/148403 | 12/2009 |
| WO | WO 2010/019899 | 2/2010 |

(Continued)

OTHER PUBLICATIONS

International Preliminary Report on Patentability in International Application No. PCT/US2019/060923, dated May 27, 2021, 8 pages.
International Preliminary Report on Patentability in International Application No. PCTUS/2019/060955, dated May 27, 2021, 8 pages.
International Preliminary Report on Patentability in International Application No. PCT/US2019/060852, dated May 27, 2021, 8 pages.
Sigmaaldrich.com, "L-α-Phosphatidyl-D-myo-inositol 4,5-diphosphate, dioctanoyl," CAS 204858-53-7, retrieved from URL <https://www.sigmaaldrich.com/US/en/product/sigma/p3584?context=product>.

(Continued)

*Primary Examiner* — Brian E McDowell
(74) *Attorney, Agent, or Firm* — Fish & Richardson P.C.

(57) ABSTRACT

This application relates to compounds of Formula (I):

or pharmaceutically acceptable salts thereof, which are inhibitors of PI3K-γ which are useful for the treatment of disorders such as autoimmune diseases, cancer, cardiovascular diseases, and neurodegenerative diseases.

34 Claims, No Drawings

(56) References Cited

FOREIGN PATENT DOCUMENTS

| | | |
|---|---|---|
| WO | WO 2010/136723 | 12/2010 |
| WO | WO 2010/148074 | 12/2010 |
| WO | WO 2011/008487 | 1/2011 |
| WO | WO 2011/006794 | 5/2011 |
| WO | WO 2011/075630 | 6/2011 |
| WO | WO 2011/075643 | 6/2011 |
| WO | WO 2011/080718 | 7/2011 |
| WO | WO 2011/084098 | 7/2011 |
| WO | WO 2011/087776 | 7/2011 |
| WO | WO 2011/130342 | 10/2011 |
| WO | WO 2011/143365 | 11/2011 |
| WO | WO 2013/000994 | 1/2013 |
| WO | WO 2013/033569 | 3/2013 |
| WO | WO 2013/151975 | 10/2013 |
| WO | WO 2014/028968 | 2/2014 |
| WO | WO 2014/075387 | 5/2014 |
| WO | WO 2014/154760 | 10/2014 |
| WO | WO 2016/012930 | 1/2016 |
| WO | WO 2016/130501 | 8/2016 |
| WO | WO 2016/176457 | 11/2016 |
| WO | WO 2017/055305 | 4/2017 |
| WO | WO 2017/153527 | 9/2017 |
| WO | WO 2017/223414 | 12/2017 |
| WO | WO 2018/055040 | 3/2018 |

OTHER PUBLICATIONS

International Search Report and Written Opinion in International Application No. PCT/US2019/060955, dated May 7, 2020, 17 pages.
Pemberton et al., "Discovery of Highly Isoform Selective Orally Bioavailable Phosphoinositide 3-Kinase (PI3K)-γ Inhibitors," J. Med. Chem., 2018, 61(12):5435-5441.
International Search Report and Written Opinion in International Application No. PCT/US2019/060852, dated May 6, 2020, 15 pages.
Leahy et al., "Discovery of a novel series of potent and orally bioavailable phosphoinositide 3-kinase γ inhibitors," J. Med. Chem., Jun. 14, 2012, 55(11):5467-5482.
Spicer et al., "Benzenesulphonamide inhibitors of the cytolytic protein perforin," Bioorg Med Chem Lett., Feb. 15, 2017, 27(4):1050-1054.
Atzrodt et al., "The Renaissance of HID Exchange," Angew. Chem. Int. Ed., 2007, 46:7744-7765.
Barber et al., "PI3Kgamma inhibition blocks glomerulonephritis and extends lifespan in a mouse model of systemic lupus," Nat. Medicine, 2005, 9:933-935.
Berod et al., "PI3Kγ deficiency delays the onset of experimental autoimmune encephalomyelitis and ameliorates its clinical outcome," Euro. J Immunol. 2011, 41:833-844.
Blom et al., "Optimizing Preparative LC-MS Configurations and Methods for Parallel Synthesis Purification," J Cambi. Chem., 2003, 5:670-683.
Blom et al., "Preparative LC-MS Purification: Improved Compound Specific Method Optimization," J Cambi. Chem., 2004, 6:874-883.
Blom et al., "Two-Pump at Column Dilution Configuration for Preparative LC-MS," J Comb Chem., 2002, 4(4):295-301.
Brock, et al., "Roles of G beta gamma in membrane recruitment and activation of p110 gamma/p101 phosphoinositide 3-kinase gamma," J Cell Biol., 2003, 160(1):89-99.
Camps et al., "Blockade of PI3Kγ suppresses joint inflammation and damage in mouse models of rheumatoid arthritis," Nat. Medicine, Sep. 2005, 11(9):936-943.
Cantley, "The phosphoinositide 3-kinase pathway," Science, 2002, 296(5573):1655-7.
Carter et al., "Prioritization of driver mutations in pancreatic cancer using cancer-specific high-throughput annotation of somatic mutations (CHASM)," Cancer Biol. Ther., 2010, 10:582-587.
Comerford et al., "PI3Kγ drives priming and survival of autoreactive CD4(+) T cells during experimental autoimmune encephalomyelitis," PLOS one, 2012, 7(9):e45095.
Doukas et al., "Aerosolized phosphoinositide 3-kinase gamma/delta inhibitor TG100-115 [3-[2,4-diamino-6-(3-hydroxyphenyl)pteridin-7-yl]phenol] as a therapeutic candidate for asthma and chronic obstructive pulmonary disease," J Pharmacol. Exp. Ther., 2009, 328:758-765.
Doukas et al., "Phosphoinositide 3-kinase gamma/delta inhibition limits infarct size after myocardial ischemia/reperfusioninjury," Proc. Natl. Acad. Sci. USA, 2006, 103:19866-19871.
El Khoury et al., "Ccr2 deficiency impairs microglial accumulation and accelerates progression of Alzheimer-like disease," Nat. Med., 2007, 13:432-438.
Falasca and Maffucci, "Targeting p110gamma in gastrointestinal cancers: attack on multiple fronts," Frontiers in Physiology, 2014, 5:1-10.
Giri et al., "Mechanism of amyloid peptide induced CCR5 expression in monocytes and its inhibition by siRNA for Egr-1," Am. J. Physiol. Cell Physiol., 2005, 289:C264-C276.
Gonzalez-Garcia et al., "Phosphatidylinositol 3-Kinase γ Inhibition Ameliorates Inflammation and Tumor Growth in a Model of Colitis-Associated Cancer," Gastroenterology, 2010, 138:1373-1384.
Hanahan and Weinberg, "Hallmarks of Cancer: The Next Generation," Cell, 2011, 144:646-674.
Hayer et al., "PI3Kgamma regulates cartilage damage in chronic inflammatory arthritis," FASB J, 2009, 23(12):4288-4298.
International Search Report and Written Opinion in International Application No. PCT/US2019/060923, dated Mar. 9, 2020, 15 pages.
Jimenez et al., "The p85 regulatory subunit controls sequential activation of phosphoinositide 3-kinase by Tyr kinases and Ras," J Biol Chem., 2002, 277(44):41556-62.
Kaneda et al., "Abstract 3650: PI3-kinase gamma controls the macrophage M1-M2 switch, thereby promoting tumor immunosuppression and progression," Cancer Res., Oct. 1, 2014, 74:(Suppl 19:Abstact 3650).
Kerekes et al., "Aurora kinase inhibitors based on the imidazo[1,2-a]pyrazine core: fluorine and deuterium incorporation improve oral absorption and exposure," J. Med. Chem., 2011, 54:201-210.
Kolb et al., "Catalytic Asymmetric Dihydroxylation," Chem. Rev., 1994, 94(8):2483-2547.
Laffargue et al., "Phosphoinositide 3-kinase gamma is an essential amplifier of mast cell function," Immunity, 2002, 16:441-451.
Li et al., "PI3Kγ inhibition alleviates symptoms and increases axon number in experimental autoimmune encephalomyelitis mice," Nemoscience, 2013, 253:89-99.
Lupia et al., "Ablation of phosphoinositide 3-kinase-gamma reduces the severity of acute pancreatitis," Am. J. Pathology, 2004, 165:2003-2011.
Martin et al., "PI3Kγ mediates Kaposi's sarcoma-associated herpesvirus vGPCR-induced sarcomagenesis," Cancer Cell, 2011, 19:805-813.
Mejdrova et al., "Highly Selective Phosphatidylinositol 4-Kinase IIIβ Inhibitors and Structural Insight into Their Mode of Action," J. Med. Chem., 2015, 58:3767-3793.
Moreno-Dorado et al., "Enantioselective synthesis of arylmethoxyacetic acid derivatives," Tetrahedron: Asymmetiy, 2003, 14:503-510.
Passos et al., "Involvement of phosphoinositide 3-kinase gamma in the neuro-inflammatory response and cognitive impairments induced by beta-amyloid 1-40 peptide in mice," Brain Behav. Immun. 2010, 24:493-501.
Pinho et al., "Phosphoinositide-3 kinases critically regulate the recruitment and survival of eosinophils in vivo: importance for the resolution of allergic inflammation," Leukocyte Biology, 2005, 77:800-810.
Prete et al., "Defective dendritic cell migration and activation of adaptive immunity in PI3Kgamma-deficient mice," The EMBO Journal, 2004, 23:3505-3515.
Randis et al., "Role of PI3Kdelta and PI3Kgamma in inflammatory arthritis and tissue localization of neutrophils," Eur. J. Immunol., 2008, 38:1215-1224.
Rodrigues et al., "Absence of PI3Kgamma leads to increased leukocyte apoptosis and diminished severity of experimental autoimmune encephalomyelitis," J. Neuroimmunol., 2010, 222:90-94.

(56) References Cited

OTHER PUBLICATIONS

Ruckle et al., "PI3Kgamma inhibition: towards an 'aspirin of the 21st century'?" Nat. Rev. Drug Discovery, 2006, 5:903-918.

Schmid et al., "Receptor tyrosine kinases and TLR/IL1Rs unexpectedly activate myeloid cell PI3kγ, a single convergent point promoting tumor inflammation and progression," Cancer Cell, 2011, 19:715-727.

Schmidt et al., "Abstract 411: PI3 Kinase gamma control of Arginase-1 expression promotes tumor immunosuppression," Cancer Res., 2012, 72(Suppl 1):Abstract411.

Sharpless, "The Osmium-Catalyzed Asymmetric Dihydroxylation: A New Ligand Class and a Process Improvement," J Org. Chem., 1992, 57(10):2768-2771.

Subramaniam et al., "Targeting Nonclassical Oncogenes for Therapy in T-ALL," Cancer Cell, 2012, 21:459-472.

Thomas et al., "Airway inflammation: chemokine-induced neutrophilia and the class I phosphoinositide 3-kinases," Eur. J Immunol, 2005, 35:1283-1291.

Vanhaesebroeck et al., "Signalling by PI3k isoforms: insights from gene-targeted mice," Trends Biochem. Sci., 2005, 30(4):194-204.

Vecchione et al., "Protection from angiotensin II-mediated vasculotoxic and hypertensive response in mice lacking PI3Kγ," J. Exp. Med., 2005, 201:1217-1228.

Xu et al., "Design, synthesis and biological evaluation of deuterated nintedanib for improving pharmacokinetic properties," Label Compd. Radiopharm, 2015, 58:308-312.

SUBSTITUTED HETEROCYCLIC DERIVATIVES AS PI3K INHIBITORS

TECHNICAL FIELD

The present disclosure provides compounds that modulate the activity of phosphoinositide 3-kinases-gamma (PI3Kγ) and are useful in the treatment of diseases related to the activity of PI3Kγ including, for example, autoimmune diseases, cancer, cardiovascular diseases, and neurodegenerative diseases.

BACKGROUND

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4):194-204).

Expression of PI3Kγ is mainly restricted to hematopoietic system, although it can be also detected at lower level in endothelium, heart and brain. PI3Kγ knock-out or kinase dead knock in mice are normal and fertile and do not present any overt adverse phenotypes. Analysis at the cellular level indicates that PI3Kγ is required for GPCR ligand-induced PtdINs (3,4,5)P3 production, chemotaxis and respiratory burst in neutrophils. PI3Kγ-null macrophages and dendritic cell exhibit reduced migration towards various chemoattractants. T-cells deficient in PI3Kγ show impaired cytokine production in response to anti-CD3 or Con A stimulation. PI3Kγ working downstream of adenosine A3A receptor is critical for sustained degranulation of mast cells induced by FCεRI cross-linking with IgE. PI3Kγ is also essential for survival of eosinophils (Ruckle et al., Nat. Rev. Drug Discovery, 2006, 5, 903-918)

Given its unique expression pattern and cellular functions, the potential role of PI3Kγ in various autoimmune and inflammatory disease models has been investigated with genetic and pharmacological tools. In asthma and allergy models, PI3Kγ$^{-/-}$ mice or mice treated with PI3Kγ inhibitor showed a defective capacity to mount contact hypersensitivity and delayed-type hypersensitivity reactions. In these models, PI3Kγ was shown to be important for recruitment of neutrophils and eosinopohils to airways and degranulation of mast cells (see e.g. Laffargue et al., Immunity, 2002, 16, 441-451; Prete et al., The EMBO Journal, 2004, 23, 3505-3515; Pinho et al., L. Leukocyte Biology, 2005, 77, 800-810; Thomas et al., Eur. J. Immunol. 2005, 35, 1283-1291; Doukas et al., J. Pharmacol. Exp Ther. 2009, 328, 758-765).

In two different acute pancreatitis models, genetic ablation of PI3Kγ significantly reduced the extent of acinar cell injury/necrosis and neutrophil infiltration without any impact on secretive function of isolated pancreatic acini (Lupia et al., Am. J. Pathology, 2004, 165, 2003-2011). PI3Kγ$^{-/-}$ mice were largely protected in four different models of rheumatoid arthritis (CIA, α-CII-IA, K/BxN serum transfer and TNF transgenic) and PI3Kγ inhibition suppressed the progression of joint inflammation and damage in the CIA and α-CII-IA models (see e.g., Camps et al., Nat. Medicine, 2005, 11, 939-943; Randis et al., Eur. J. Immunol, 2008, 38, 1215-1224; Hayer et al., FASB J, 2009, 4288-4298). In the MRL-lpr mouse model of human systemic lupus erythematous, inhibition of PI3Kγ reduced glomerulonephritis and prolonged life span (Barber et al., Nat. Medicine, 2005, 9, 933-935).

There is evidence suggesting that chronic inflammation due to infiltration by myeloid-derived cells is a key component in the progression of neurodegeneration diseases, such as Alzheimer's disease (AD) (Giri et al., Am. J. Physiol. Cell Physiol., 2005, 289, C264-C276; El Khoury et al., Nat. Med., 2007, 13, 432-438). In line with this suggestion, PI3Kγ inhibition was shown to attenuate Aβ(1-40)-induced accumulation of activated astrocytes and microglia in the hippocampus and prevent the peptide-induced cognitive deficits and synaptic dysfunction in a mouse model of AD (Passos et al., Brain Behav. Immun. 2010, 24, 493-501). PI3Kγ deficiency or inhibition also was shown to delay onset and alleviate symptoms in experimental autoimmune encephalomyelitis in mice, a mouse model of human multiple sclerosis, which is another form of neurodegeneration disease (see e.g., Rodrigues et al., J. Neuroimmunol. 2010, 222, 90-94; Berod et al., Euro. J. Immunol. 2011, 41, 833-844; Comerford et al., PLOS one, 2012, 7, e45095; Li et al., Neuroscience, 2013, 253, 89-99).

Chronic inflammation has been formally recognized as one of the hallmarks for many different types of cancers. Accordingly, selective anti-inflammatory drugs represent a novel class of anti-cancer therapies (Hanahan and Weinberg, Cell, 2011, 144, 646-674). Since PI3Kγ is reported to mediate various inflammatory processes, its role as an immune oncology target has also been investigated. A recent study reported that PI3Kγ deficiency suppressed tumor growth in the syngeneic models of lung cancer, pancreatic cancer and melanoma (LLC, PAN02 and B16). PI3Kγ deficiency or inhibition also inhibited tumor growth in a spontaneous breast cancer model (Schmid et al., Cancer Cell, 2011, 19, 715-727). A further study reported that PI3Kγ deficiency could ameliorate inflammation and tumor growth in mice having colitis-associated colon cancer, (Gonzalez-Garcia et al., Gastroenterology, 2010, 138, 1373-1384). Detailed mechanistic analysis indicates that tumor infiltration by CD11b$^+$ myeloid cells can cause protumorigenic inflammation at tumor sites and PI3Kγ in the myeloid cells is critical in mediating signaling of various chemoattractants in bring the cells to the tumor (Schmid et al., Cancer Cell, 2011, 19, 715-727). Other studies suggest that PI3Kγ is also required for differentiation of naïve myeloid cells into M2 macrophges at tumor sites. M2 macrophages promote tumor growth and progression by secreting immunosuppressive factors such arginase 1, which depletes the tumor microenvironment of arginine, thereby promoting T-cell death and NK cell inhibition (Schmidt et al., *Cancer Res.* 2012, 72 (*Suppl* 1: *Abstract,* 411; Kaneda et al., *Cancer Res.,* 74 (*Suppl* 19: *Abstact* 3650)).

In addition to its potential role in promoting protumorigenic microenvironment, PI3Kγ may play a direct role in cancer cells. PI3Kγ is reported to be required for signaling from the Kaposi's sarcoma-associated herpevirus encoded vGPCR oncogene and tumor growth in a mouse model of sarcoma (Martin et al., *Cancer Cell,* 2011, 19, 805-813). PI3Kγ was also suggested to be required for growth of T-ALL (Subramanjam et al., *Cancer Cell,* 2012, 21, 459-472), PDAC and HCC cells (Falasca and Maffucci, *Frontiers in Physiology,* 2014, 5, 1-10). Moreover, in a survey of driver mutations in pancreatic cancer, PI3Kγ gene was found to contain second highest scoring predicted driven mutation (R839C) among the set of genes not previously identified as a driver in pancreatic cancer (Carter et al., *Cancer Biol. Ther.* 2010, 10, 582-587).

Finally, PI3Kγ deficiency also has been reported to offer protection to experimental animals in different cardiovascular disease models. For examples, lack of PI3Kγ would reduce angiotension-evoked smooth muscle contraction and, therefore, protect mice from angiotension-induced hypertension (Vecchione et al., *J. Exp. Med.* 2005, 201, 1217-1228). In rigorous animal myocardial infarction models, PI3Kγ inhibition provided potent cardioprotection, reducing infarct development and preserving myocardial function (Doukas et al., *Proc. Natl. Acad. Sci. USA,* 2006, 103, 19866-19871).

For these reasons, there is a need to develop new PI3Kγ inhibitors that can be used for the treatment of diseases such as cancer, autoimmune disorders, and inflammatory and cardiac diseases. This application is directed to this need and others.

SUMMARY

The present disclosure relates to, inter alia, compounds of Formula (I):

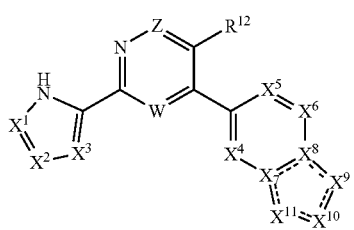

or a pharmaceutically acceptable salt thereof, wherein constituent members are defined herein.

The present disclosure further provides pharmaceutical compositions comprising a compound of Formula (I), or a pharmaceutically acceptable salt thereof, and a pharmaceutically acceptable carrier.

The present disclosure further provides methods of inhibiting an activity of PI3Kγ kinase comprising contacting the kinase with a compound of Formula (I), or a pharmaceutically acceptable salt thereof.

The present disclosure further provides methods of treating a disease or a disorder associated with abnormal PI3Kγ kinase expression or activity in a patient by administering to said patient a therapeutically effective amount of a compound of Formula (I), or a pharmaceutically acceptable salt thereof.

The present disclosure further provides a compound of Formula (I), or a pharmaceutically acceptable salt thereof, for use in any of the methods described herein.

The present disclosure further provides use of a compound of Formula (I), or a pharmaceutically acceptable salt thereof, for the preparation of a medicament for use in any of the methods described herein.

DETAILED DESCRIPTION

Compounds

The present application provides, inter alia, compounds of Formula (I):

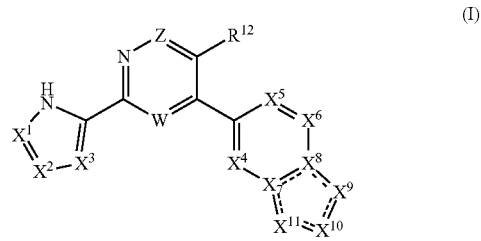

or a pharmaceutically acceptable salt thereof, wherein:
each bond symbol represented by ===== is independently a single or double bond;
W is $CW^1$ or N;
Z is $CZ^1$ or N;
$X^1$ is $CR^1$ or N;
$X^2$ is $CR^2$ or N;
$X^3$ is $CR^3$ or N;
wherein $X^1$, $X^2$, and $X^3$ are not each simultaneously N;
$W^1$, $Z^1$, and $R^{12}$ are each independently selected from H, D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-6}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOH)R^{b1}$, $C(=NCN)R^{b1}$, $C(=NR^{e1})NR^{c1}R^{d1}$, $NR^{c1}C(=NR^{e1})NR^{c1}R^{d1}$, $NR^{c1}C(=NOH)NR^{c1}R^{d1}$, $NR^{c1}C(=NCN)NR^{c1}R^{d1}$, $NR^{c1}C(=NR^{e1})R^{b1}$, $NR^{c1}S(O)NR^{c1}R^{d1}$, $NR^{c1}S(O)R^{b1}$, $NR^{c1}S(O)_2R^{b1}$, $NR^{c1}S(O)(=NR^{e1})R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $S(O)(=NR^{e1})R^{b1}$, $OS(O)(=NR^{e1})R^{b1}$, $OS(O)_2R^{b1}$, $SF_5$, $P(O)R^{f1}R^{g1}$, $OP(O)$ $(OR^{h1})(OR^{i1})$, $P(O)(OR^{h1})(OR^{i1})$, and $BR^{j1}R^{k1}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^{1A}$ substituents;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{b1}$, $R^{c1}$ and $R^{d1}$ are each optionally substituted with 1, 2, 3, 4, 5, 6, 7, or 8 independently selected $R^{1A}$ substituents;

or, any $R^{c1}$ and $R^{d1}$, attached to the same N atom, together with the N atom to which they are attached, form a 5-10 membered heteroaryl group or a 4-10 membered heterocloalkyl group, wherein the 5-10 membered heteroaryl group or 4-10 membered heterocycloalkyl group is optionally substituted with 1, 2, 3, 4, 5, 6, 7, or 8 independently selected $R^{1A}$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f1}$ and $R^{g1}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h1}$ and $R^{i1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j1}$ and $R^{k1}$ is independently selected from OH, $C_{1-6}$ alkoxy, and $C_{1-6}$ haloalkoxy;

or any $R^{j1}$ and $R^{k1}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered heterocycloalkyl;

each $R^{1A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NOH)R^{b11}$, $C(=NCN)R^{b11}$, $C(=NR^{e11})NR^{c11}R^{d11}$, $NR^{c11}(=NR^{e11})NR^{c11}R^{d11}$, $NR^{c11}(=NOH)NR^{c11}R^{d11}$, $NR^{c11}C(=NCN)NR^{c11}R^{d11}$, $NR^{c11}(=NR^{e11})R^{b11}$, $NR^{c11}S(O)NR^{c11}R^{d11}$, $NR^{c11}S(O)R^{b11}$, $NR^{c11}S(O)_2R^{b11}$, $NR^{c11}S(O)(=NR^{e11})R^{b11}$, $NR^{c11}S(O)_2NR^{c11}R^{d11}$, $S(O)R^{b11}$, $S(O)NR^{c11}R^{d11}$, $S(O)_2R^{b11}S(O)_2NR^{c11}R^{d11}$, $S(O)(=NR^{e11})R^{b11}$, $OS(O)(=NR^{e11})R^{b11}$, $OS(O)_2R^{b11}$, $SF_5$, $P(O)R^{f11}R^{g11}$, $OP(O)(OR^{h11})(OR^{i11})$, $P(O)(OR^{h11})(OR^{i11})$, and $BR^{j11}R^{k11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1A}$ are each optionally substituted with 1, 2, 3, 4, 5, 6, 7, or 8 independently selected $R^M$ substituents;

each $R^{a11}$, $R^{b11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{b11}$, $R^{c11}$ and $R^{d11}$ are each optionally substituted with 1, 2, 3, 4, 5, 6, 7, or 8 independently selected $R^M$ substituents;

or, any $R^{c11}$ and $R^{d11}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f11}$ and $R^{g11}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-; each $R^{h11}$ and $R^{i11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j11}$ and $R^{k11}$ is independently selected from OH, $C_{1-6}$ alkoxy, and $C_{1-6}$ haloalkoxy; or any $R^{j11}$ and $R^{k11}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered heterocycloalkyl;

each $R^M$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-6}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$alkyl-, (4-10 membered heterocycloalkyl)-$C_{1-6}$ alkyl-, CN, NO$_2$, OR$^{a2}$, SR$^{a2}$, NHOR$^{a2}$, C(O)R$^{b2}$, C(O)NR$^{c2}$R$^{d2}$, C(O)NR$^{c2}$(OR$^{a2}$), C(O)OR$^{a2}$, OC(O)R$^{b2}$, OC(O)NR$^{c2}$R$^{d2}$, NR$^{c2}$R$^{d2}$, NR$^{c2}$NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NOH)R$^{b2}$, C(=NCN)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$C(=NOH)NR$^{c2}$R$^{d2}$, NR$^{c2}$C(=NCN)NR$^{c2}$R$^{d2}$, NR$^{c2}$C(=NR$^{e2}$)R$^{b2}$, NR$^{c2}$S(O)NR$^{c2}$R$^{d2}$, NR$^{c2}$S(O)R$^{b2}$, NR$^{c2}$S(O)$_2$R$^{b2}$, NR$^{c2}$S(O)(=NR$^{e2}$)R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, S(O)$_2$NR$^{c2}$R$^{d2}$, S(O)(=NR$^{e2}$)R$^{b2}$, OS(O)(=NR$^{e2}$)R$^{b2}$, OS(O)$_2$R$^{b2}$, SF$_5$, P(O)R$^{f2}$R$^{g2}$, OP(O)(OR$^{h2}$)(OR$^{i2}$), P(O)(OR$^{h2}$)(OR$^{i2}$), and BR$^{j2}$R$^{k2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, 6, 7, or 8 independently selected $R^{2A}$ substituents;

each R$^{a2}$, R$^{b2}$, R$^{c2}$, and R$^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^{a2}$, R$^{b2}$, R$^{c2}$ and R$^{d2}$ are each optionally substituted with 1, 2, 3, 4, 5, 6, 7, or 8 independently selected $R^{2A}$ substituents;

or, any R$^{c2}$ and R$^{d2}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{2A}$ substituents;

each R$^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each R$^{f2}$ and R$^{g2}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each R$^{h2}$ and R$^{i2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each R$^{j2}$ and R$^{k2}$ is independently selected from OH, $C_{1-6}$ alkoxy, and $C_{1-6}$ haloalkoxy;

or any R$^{j2}$ and R$^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{2A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a21}$, SR$^{a21}$, NHOR$^{a21}$, C(O)R$^{b21}$, C(O)NR$^{c21}$R$^{d21}$, C(O)NR$^{c21}$(OR$^{a21}$), C(O)OR$^{a21}$, OC(O)R$^{b21}$, OC(O)NR$^{c21}$R$^{d21}$, NR$^{c21}$R$^{d21}$, NR$^{c21}$NR$^{c21}$R$^{d21}$, NR$^{c21}$C(O)R$^{b21}$, NR$^{c21}$C(O)OR$^{a21}$, NR$^{c21}$C(O)NR$^{c21}$R$^{d21}$, C(=NR$^{e21}$)R$^{b21}$, C(=NOH)R$^{b21}$, C(=NCN)R$^{b21}$, C(=NR$^{e21}$)NR$^{c21}$R$^{d21}$, NR$^{c21}$C(=NR$^{e21}$)NR$^{c21}$R$^{d21}$, NR$^{c21}$C(=NOH)NR$^{c21}$R$^{d21}$, NR$^{c21}$C(=NCN)NR$^{c21}$R$^{d21}$, NR$^{c21}$C(=NR$^{e21}$)R$^{b21}$, NR$^{c21}$S(O)NR$^{c21}$R$^{d21}$, NR$^{c21}$S(O)R$^{b21}$, NR$^{c21}$S(O)$_2$R$^{b21}$, NR$^{c21}$S(O)(=NR$^{e21}$)R$^{b21}$, NR$^{c21}$S(O)$_2$NR$^{c21}$R$^{d21}$, S(O)R$^{b21}$, S(O)NR$^{c21}$R$^{d21}$, S(O)$_2$R$^{b21}$, S(O)$_2$NR$^{c21}$R$^{d21}$, S(O)(=NR$^{e21}$)R$^{b21}$, OS(O)(=NR$^{e21}$)R$^{b21}$, OS(O)$_2$R$^{b21}$, SF$_5$, P(O)R$^{f21}$R$^{g21}$, OP(O)(OR$^{h21}$)(OR$^{i21}$), P(O)(OR$^{h21}$)(OR$^{i21}$), and BR$^{j21}$R$^{k21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, 4, 5, 6, 7, or 8 independently selected $R^M$ substituents;

each R$^{a21}$, R$^{b21}$, R$^{c21}$, and R$^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^{a21}$, R$^{b21}$, R$^{c21}$ and R$^{d21}$ are each optionally substituted with 1, 2, 3, 4, 5, 6, 7, or 8 independently selected $R^M$ substituents;

or, any R$^{c21}$ and R$^{d21}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each R$^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each R$^{f21}$ and R$^{g21}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each R$^{h21}$ and R$^{g21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j21}$ and $R^{k21}$ is independently selected from OH, $C_{1-6}$ alkoxy, and $C_{1-6}$ haloalkoxy;

or any $R^{j21}$ and $R^{k21}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

or alternatively, $R^1$ and $R^2$, taken together with the carbon atoms to which they are attached form a monocyclic 4-7 membered cycloalkyl ring, a phenyl ring, a monocyclic 4-7 membered heterocycloalkyl ring, or a monocyclic 5-6 membered heteroaryl ring, each of which is optionally substituted by 1, 2, 3, 4, 5, 6, 7 or 8 independently selected $R^{1A}$ groups;

$R^3$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$alkyl-, (4-10 membered heterocycloalkyl)-$C_{1-6}$ alkyl-, CN, $NO_2$, $OR^{a3}$, $SR^{a3}$, $NHOR^{a3}$, $C(O)R^{b3}$, $C(O)NR^{c3}R^{d3}$, $C(O)NR^{c3}(OR^{a3})$, $C(O)OR^{a3}$, $OC(O)R^{b3}$, $OC(O)NR^{c3}R^{d3}$, $NR^{c3}R^{d3}$, $NR^{c3}NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NOH)R^{b3}$, $C(=NCN)R^{b3}$, $C(=NR^{e3})NR^{c3}R^{d3}$, $NR^{c3}C(=NR^{e3})NR^{c3}R^{d3}$, $NR^{c3}C(=NOH)NR^{c3}R^{d3}$, $NR^{c3}C(=NCN)NR^{c3}R^{d3}$, $NR^{c3}C(=NR^{e3})R^{b3}$, $NR^{c3}S(O)NR^{c3}R^{d3}$, $NR^{c3}S(O)R^{b3}$, $NR^{c3}S(O)_2R^{b3}$, $NR^{c3}S(O)(=NR^{e3})R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$, $S(O)(=NR^{e3})R^{b3}$, $OS(O)(=NR^{e3})R^{b3}$, $OS(O)_2R^{b3}$, $SF_5$, $P(O)R^{f3}R^{g3}$, $OP(O)(OR^{h3})(OR^{i3})$, $P(O)(OR^{h3})(OR^{i3})$, and $BR^{j3}R^{k3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, 4, 5, 6, 7, or 8 independently selected $R^M$ substituents;

each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{b3}$, $R^{c3}$ and $R^{d3}$ are each optionally substituted with 1, 2, 3, 4, 5, 6, 7, or 8 independently selected $R^M$ substituents;

or, any $R^{c3}$ and $R^{d3}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f3}$ and $R^{g3}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h3}$ and $R^{i3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j3}$ and $R^{k3}$ is independently selected from OH, $C_{1-6}$ alkoxy, and $C_{1-6}$ haloalkoxy; or any $R^{j3}$ and $R^{k3}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

or alternatively, $R^2$ and $R^3$, taken together with the carbon atoms to which they are attached form a monocyclic 4-7 membered cycloalkyl ring, a phenyl ring, a monocyclic 4-7 membered heterocycloalkyl ring, or a monocyclic 5-6 membered heteroaryl ring, each of which is optionally substituted by 1, 2, 3, 4, 5, 6, 7 or 8 independently selected $R^{2A}$ groups;

$X^4$ is N or $CR^4$;

$X^5$ is N or $CR^5$;

$R^4$ and $R^5$ are each independently selected from H, D, halo, CN, OH, $NH_2$, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, cyano-$C_{1-6}$ alkyl, HO—$C_{1-6}$ alkyl, $C_{1-6}$ alkoxy-$C_{1-6}$ alkyl, $C_{3-6}$ cycloalkyl, $C_{1-6}$ alkylamino, di($C_{1-6}$ alkyl)amino, and $C(O)NR^{a4}R^{b4}$;

each $R^{a4}$ and $R^{b4}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a4}$ and $R^{b4}$ are each optionally substituted with 1, 2, 3 or 4 independently selected $R^M$ substituents;

or, any $R^{a4}$ and $R^{b4}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$X^6$ is N or $CR^6$;

$R^6$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOH)R^{b6}$, $C(=NCN)R^{b6}$, $C(=NR^{e6})NR^{c6}R^{d6}$, $NR^{c6}C(=NR^{e6})NR^{c6}R^{d6}$, $NR^{c6}C(=NOH)NR^{c6}R^{d6}$, $NR^{c6}C(=NCN)NR^{c6}R^{d6}$, $NR^{c6}C(=NR^{e6})R^{b6}$, $NR^{c6}S(O)NR^{c6}R^{d6}$, $NR^{c6}S(O)R^{b6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $S(O)(=NR^{e6})R^{b6}$, $OS(O)(=NR^{e6})R^{b6}$, $OS(O)_2R^{b6}$, $SF_5$, $P(O)R^{f6}R^{g6}$, $OP(O)$ $(OR^{h6})(OR^{i6})$, $P(O)(OR^{h6})(OR^{i6})$, and $BR^{j6}R^{k6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, 4, 5, 6, 7, or 8 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$ and $R^{d6}$ are each optionally substituted with 1, 2, 3, 4, 5, 6, 7, or 8 independently selected $R^{6A}$ substituents;

or, any $R^{c6}$ and $R^{d6}$, attached to the same N atom, together with the N atom to which they are attached, form a 5-10 membered heteroaryl group or a 4-10 membered heterocloalkyl group, wherein the 5-10 membered heteroaryl group or 4-10 membered heterocycloalkyl group is optionally substituted with 1, 2, 3, 4, 5, 6, 7, or 8 independently selected $R^{6A}$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j6}$ and $R^{k6}$ is independently selected from OH, $C_{1-6}$ alkoxy, and $C_{1-6}$ haloalkoxy; or any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{6A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, $OR^{a61}$, $SR^{a61}$, $NHOR^{a61}$, $C(O)R^{b61}$, $C(O)NR^{c61}R^{d61}$, $C(O)NR^{c61}(OR^{a61})$, $C(O)OR^{a61}$, $OC(O)R^{b61}$, $OC(O)NR^{c61}R^{d61}$, $NR^{c61}R^{d61}$, $NR^{c61}NR^{c61}R^{d61}$, $NR^{c61}C(O)R^{b61}$, $NR^{c61}C(O)OR^{a61}$, $NR^{c61}C(O)NR^{c61}R^{d61}$, $C(=NR^{e61})R^{b61}$, $C(=NOH)R^{b61}$, $C(=NCN)R^{b61}$, $C(=NR^{e61})NR^{c61}R^{d61}$, $NR^{c61}C(=NR^{e61})NR^{c61}R^{d61}$, $NR^{c61}C(=NOH)NR^{c61}R^{d61}$, $NR^{c61}C(=NCN)NR^{c61}R^{d61}$, $NR^{c61}C(=NR^{e61})R^{b61}$, $NR^{c61}S(O)NR^{c61}R^{d61}$, $NR^{c61}S(O)R^{b61}$, $NR^{c61}S(O)_2R^{b61}$, $NR^{c61}S(O)(=NR^{e61})R^{b61}$, $NR^{c61}S(O)_2NR^{c61}R^{d61}$, $S(O)R^{b61}$, $S(O)NR^{c61}R^{d61}$, $S(O)_2R^{b61}$, $S(O)_2NR^{c61}R^{d61}$, $S(O)(=NR^{e61})$ $R^{b61}$, $OS(O)(=NR^{e61})R^{b61}$, $OS(O)_2R^{b61}$, $SF_5$, $P(O)R^{f61}R^{g61}$, $OP(O)(OR^{h61})(OR^{i61})$, $P(O)(OR^{h61})(OR^{i61})$, and $BR^{j61}R^{k61}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{6A}$ are each optionally substituted with 1, 2, 3, 4, 5, 6, 7, or 8 independently selected $R^{6B}$ substituents;

each $R^{a61}$, $R^{b61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a61}$, $R^{b61}$, $R^{c61}$ and $R^{d61}$ are each optionally substituted with 1, 2, 3, 4, 5, 6, 7, or 8 independently selected $R^{6B}$ substituents;

or, any $R^{c61}$ and $R^{d61}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{6B}$ substituents; each $R^{e61}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f61}$ and $R^{g61}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h61}$ and $R^{i61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j61}$ and $R^{k61}$ is independently selected from OH, $C_{1-6}$ alkoxy, and $C_{1-6}$ haloalkoxy; or any $R^{j61}$ and $R^{k61}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{6B}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, $OR^{a62}$, $SR^{a62}$, $NHOR^{a62}$, $C(O)R^{b62}$, $C(O)NR^{c62}R^{d62}$, $C(O)NR^{c62}(OR^{a62})$, $C(O)OR^{a62}$, $OC(O)R^{b62}$, $OC(O)NR^{c62}R^{d62}$, $NR^{c62}R^{d62}$, $NR^{c62}NR^{c62}R^{d62}$, $NR^{c62}C(O)R^{b62}$, $NR^{c62}C(O)OR^{a62}$, $NR^{c62}C(O)NR^{c62}R^{d62}$, $C(=NR^{e62})R^{b62}$, $C(=NOH)R^{b62}$, $C(=NCN)R^{b62}$, $C(=NR^{e62})NR^{c62}R^{d62}$, $NR^{c62}C(=NR^{e62})NR^{c62}R^{d62}$, $NR^{c62}C(=NOH)NR^{c62}R^{d62}$, $NR^{c62}C(=NCN)NR^{c62}R^{d62}$, $NR^{c62}C(=NR^{e62})R^{b62}$, $NR^{c62}S(O)NR^{c62}R^{d62}$, $NR^{c62}S(O)R^{b62}$, $NR^{c62}S(O)_2R^{b62}$, $NR^{c62}S(O)$ (=NR$^{e62}$)R$^{b62}$, NR$^{c62}$S(O)$_2$NR$^{c62}$R$^{d62}$, S(O)R$^{b62}$, S(O)NR$^{c62}$R$^{d62}$, S(O)$_2$R$^{b62}$, S(O)$_2$NR$^{c62}$R$^{d62}$, S(O)(=NR$^{e62}$)R$^{b62}$, OS(O)(=NR$^{e62}$)R$^{b62}$, OS(O)$_2$R$^{b62}$, SF$_5$, P(O)R$^{f62}$R$^{g62}$, OP(O)(OR$^{h62}$)(OR$^{i62}$), P(O)(OR$^{h62}$)(OR$^{i62}$), and BR$^{j62}$R$^{k62}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{6B}$ are each optionally substituted with 1, 2, 3, 4, 5, 6, 7, or 8 independently selected R$^{6C}$ substituents;

each R$^{a62}$, R$^{b62}$, R$^{c62}$, and R$^{d62}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a62}$, R$^{b62}$, R$^{c62}$ and R$^{d62}$ are each optionally substituted with 1, 2, 3, 4, 5, 6, 7, or 8 independently selected R$^{6C}$ substituents;

or, any R$^{c62}$ and R$^{d62}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected R$^{6C}$ substituents;

each R$^{e62}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, and C$_{2-6}$ alkynyl;

each R$^{f62}$ and R$^{g62}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered hetereocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered hetereocycloalkyl)-C$_{1-6}$ alkyl-;

each R$^{h62}$ and R$^{i62}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered hetereocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered hetereocycloalkyl)-C$_{1-6}$ alkyl-;

each R$^{j62}$ and R$^{k62}$ is independently selected from OH, C$_{1-6}$ alkoxy, and C$_{1-6}$ haloalkoxy; or any R$^{j62}$ and R$^{k62}$ attached to the same B atom, together with the B atom to which they are attached, form a 5- or 6-membered heterocycloalkyl group optionally substituted with 1, 2, 3, or 4 substituents independently selected from C$_{1-6}$ alkyl, C$_{1-6}$ haloalkyl, C$_{3-10}$ cycloalkyl, and 4-10 membered hetereocycloalkyl;

each R$^{6C}$ is selected from H, D, halo, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, (4-7 membered heterocycloalkyl)-C$_{1-6}$ alkyl-, CN, NO$_2$, OR$^{a63}$, SR$^{a63}$, NHOR$^{a63}$, C(O)R$^{b63}$, C(O)NR$^{c63}$R$^{d63}$, C(O)NR$^{c63}$(OR$^{a63}$), C(O)OR$^{a63}$, OC(O)R$^{b63}$, OC(O)NR$^{c63}$R$^{d63}$, NR$^{c63}$R$^{d63}$, NR$^{c63}$NR$^{c63}$R$^{d63}$, NR$^{c63}$C(O)R$^{b63}$, NR$^{c63}$C(O)OR$^{a63}$, NR$^{c63}$C(O)NR$^{c63}$R$^{d63}$, C(=NR$^{e63}$)R$^{b63}$, C(=NOH)R$^{b63}$, C(=NCN)R$^{b63}$, C(=NR$^{e63}$)NR$^{c63}$R$^{d63}$, NR$^{c63}$C(=NR$^{e63}$) NR$^{c63}$R$^{d63}$, NR$^{c63}$C(=NOH)NR$^{c63}$R$^{d63}$, NR$^{c63}$C(=NCN) NR$^{c63}$R$^{d63}$, NR$^{c63}$C(=NR$^{e63}$)R$^{b63}$, NR$^{c63}$S(O)NR$^{c63}$R$^{d63}$, NR$^{c63}$S(O)R$^{b63}$, NR$^{c63}$S(O)$_2$R$^{b63}$, NR$^{c63}$S(O)(=NR$^{e63}$) R$^{b63}$, NR$^{c63}$S(O)$_2$NR$^{c63}$R$^{d63}$, S(O)R$^{b63}$, S(O)NR$^{c63}$R$^{d63}$, S(O)$_2$R$^{b63}$, S(O)$_2$NR$^{c63}$R$^{d63}$, S(O)(=NR$^{e63}$)R$^{b63}$, OS(O) (=NR$^{e63}$)R$^{b63}$, OS(O)$_2$R$^{b63}$, SF$_5$, P(O)R$^{f63}$R$^{g63}$, OP(O) (OR$^{h63}$)(OR$^{i63}$), P(O)(OR$^{h63}$)(OR$^{i63}$), and BR$^{j63}$R$^{k63}$, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{6C}$ are each optionally substituted with 1, 2, 3, or 4 independently selected R$^M$ substituents;

each R$^{a63}$, R$^{b63}$, R$^{c63}$, and R$^{d63}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$alkyl-, and (4-7 membered heterocycloalkyl)-C$_{1-6}$ alkyl- of R$^{a63}$, R$^{b63}$, R$^{c63}$ and R$^{d63}$ are each optionally substituted with 1, 2, 3, or 4 independently selected R$^M$ substituents;

or, any R$^{c63}$ and R$^{d63}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected R$^M$ substituents;

each R$^{e63}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, and C$_{2-6}$ alkynyl;

each R$^{f63}$ and R$^{g63}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-;

each R$^{h63}$ and R$^{i63}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-;

each R$^{j63}$ and R$^{k63}$ is independently selected from OH, C$_{1-6}$ alkoxy, and C$_{1-6}$ haloalkoxy; or any R$^{j63}$ and R$^{k63}$ attached to the same B atom, together with the B atom to which they are attached, form a 5- or 6-membered heterocycloalkyl group optionally substituted with 1, 2, 3, or 4 substituents independently selected from C$_{1-6}$ alkyl, C$_{1-6}$ haloalkyl, C$_{3-10}$ cycloalkyl, and 4-10 membered hetereocycloalkyl;

X$^7$ is N, C, or CH;

X$^8$ is N, C, or CH;

X$^9$ is N, NR$^{9N}$, O, S, S(O), S(O)$_2$, CR$^9$, or C(R$^9$)$_2$;

X$^{10}$ is N, NR$^{10N}$, O, S, CR$^{10}$, or C(R$^{10}$)$_2$;

X$^{11}$ is N, NR$^{11N}$, O, S, CR$^{11}$, or C(R$^{11}$)$_2$;

wherein no more than three of X$^4$, X$^5$, X$^6$, X$^7$, and X$^8$ are simultaneously N; and at least two of X$^7$, X$^8$, X$^9$, X$^{10}$, and X$^{11}$ are independently selected from C, CH, CR$^9$, C(R$^9$)$_2$, CR$^{10}$, C(R$^{10}$)$_2$, CR$^{11}$, and C(R$^{11}$)$_2$; and no two adjacent members of $X^9$, $X^{10}$, and $X^{11}$ are simultaneously O, S, S(O) or S(O)$_2$;

provided that (a) when $X^7$ is N, then $X^8$ is C or CH; or (b) when $X^8$ is N, then $X^7$ is C or CH;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, C(O)$R^{b9N}$, C(O)N$R^{c9N}R^{d9N}$, C(O)O$R^{a9N}$, C(=N$R^{e9N}$)$R^{b9N}$, C(=N$R^{e9N}$)N$R^{c9N}R^{d9N}$, C(=NCN)N$R^{c9N}R^{d9N}$, C(=NO$R^{a9N}$)N$R^{c9N}$, S(O)$_2R^{b9N}$, S(O)(=N$R^{c9N}$)$R^{a9N}$, and S(O)$_2$N$R^{c9N}R^{d9N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{9N}$ are each optionally substituted with 1, 2, 3, 4, 5, 6, 7, or 8 independently selected $R^{9NA}$ substituents;

each $R^{a9N}$, $R^{b9N}$, $R^{c9N}$, and $R^{d9N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9N}$, $R^{b9N}$, $R^{c9N}$, and $R^{d9N}$ are each optionally substituted with 1, 2, 3, 4, 5, 6, 7, or 8 independently selected $R^{9NA}$ substituents;

or, any $R^{c9N}$ and $R^{d9N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9NA}$ substituents;

each $R^{e9N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{9NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, NO$_2$, O$R^{a9N2}$, S$R^{a9N2}$, NHO$R^{a9N2}$, C(O)$R^{b9N2}$, C(O)N$R^{c9N2}R^{d9N2}$, C(O)N$R^{c9N2}$(O$R^{a9N2}$), C(O)O$R^{a9N2}$, OC(O)$R^{b9N2}$, OC(O)N$R^{c9N2}R^{d9N2}$, N$R^{c9N2}R^{d9N2}$, N$R^{c9N2}$N$R^{c9N2}R^{d9N2}$, N$R^{c9N2}$C(O)$R^{b9N2}$, N$R^{c9N2}$C(O)O$R^{a9N2}$, N$R^{c9N2}$C(O)N$R^{c9N2}R^{d9N2}$, C(=N$R^{e9N2}$)$R^{b9N2}$, C(=NOH)$R^{b9N2}$, C(=NCN)$R^{b9N2}$, C(=N$R^{e9N2}$)N$R^{c9N2}R^{d9N2}$, N$R^{c9N2}$C(=N$R^{e9N2}$)N$R^{c9N2}R^{d9N2}$, N$R^{c9N2}$C(=NOH)N$R^{c9N2}R^{d9N2}$, N$R^{c9N2}$C(=NCN)N$R^{c9N2}R^{d9N2}$, N$R^{c9N2}$C(=N$R^{e9N2}$)$R^{b9N2}$, N$R^{c9N2}$S(O)N$R^{c9N2}R^{d9N2}$, N$R^{c9N2}$S(O)$R^{b9N2}$, N$R^{c9N2}$S(O)$_2R^{b9N2}$, N$R^{c9N2}$S(O)(=N$R^{e9N2}$)$R^{b9N2}$, N$R^{c9N2}$S(O)$_2$N$R^{c9N2}R^{d9N2}$, S(O)$R^{b9N2}$, S(O)N$R^{c9N2}R^{d9N2}$, S(O)$_2R^{b9N2}$, S(O)$_2$N$R^{c9N2}R^{d9N2}$, S(O)(=N$R^{e9N2}$)$R^{b9N2}$, OS(O)$R^{b9N2}$, OS(O)$_2R^{b9N2}$, SF$_5$, P(O)$R^{f9N2}R^{g9N2}$, OP(O)(O$R^{h9N2}$)(O$R^{i9N2}$), P(O)(O$R^{h9N2}$)(O$R^{i9N2}$), and B$R^{j9N2}R^{k9N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9NA}$ are each optionally substituted with 1, 2, 3, or 4 independently selected $R^M$ substituents;

each $R^{a9N2}$, $R^{b9N2}$, $R^{c9N2}$, and $R^{d9N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a9N2}$, $R^{b9N2}$, $R^{c9N2}$ and $R^{d9N2}$ are each optionally substituted with 1, 2, 3, or 4 independently selected $R^M$ substituents;

or, any $R^{c9N2}$ and $R^{d9N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e9N2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f9N2}$ and $R^{g9N2}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h9N2}$ and $R^{i9N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j9N2}$ and $R^{k9N2}$ is independently selected from OH, $C_{1-6}$ alkoxy, and $C_{1-6}$ haloalkoxy; or any $R^{j9N2}$ and $R^{k9N2}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^9$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, O$R^{a91}$, S$R^{a91}$, NHO$R^{a91}$, C(O)$R^{b91}$, C(O)N$R^{c91}R^{d91}$, C(O)N$R^{c91}$(O$R^{a91}$), C(O)O$R^{a91}$, OC(O)$R^{b91}$, OC(O)N$R^{c91}R^{d91}$, N$R^{c91}R^{d91}$, N$R^{c91}$N$R^{c91}R^{d91}$, N$R^{c91}$C(O)$R^{b91}$, N$R^{c91}$C(O)O$R^{a91}$, N$R^{c91}$C(O)N$R^{c91}R^{d91}$, C(=N$R^{e91}$)$R^{b91}$, C(=NOH)$R^{b91}$, C(=NCN)$R^{b91}$, C(=N$R^{e91}$)N$R^{c91}R^{d91}$, N$R^{c91}$C(=N$R^{e91}$)N$R^{c91}R^{d91}$, N$R^{c91}$C(=NOH)N$R^{c91}R^{d91}$, N$R^{c91}$C(=NCN)N$R^{c91}R^{d91}$, N$R^{c91}$C(=N$R^{e91}$)$R^{b91}$, N$R^{c91}$S(O)N$R^{c91}R^{d91}$, N$R^{c91}$S(O)$R^{b91}$, N$R^{c91}$S(O)$_2R^{b91}$, N$R^{c91}$S(O)(=N$R^{e91}$)$R^{b91}$, N$R^{c91}$S(O)$_2$N$R^{c91}R^{d91}$, S(O)$R^{b91}$, S(O)N$R^{c91}R^{d91}$, S(O)$_2R^{b91}$, S(O)$_2$N$R^{c91}R^{d91}$, S(O)(=N$R^{e91}$)$R^{b91}$, OS(O)(=N$R^{e91}$)$R^{b91}$, OS(O)$_2R^{b91}$, SF$_5$, P(O)$R^{f91}R^{g91}$, OP(O)(O$R^{h91}$)(O$R^{i91}$), P(O)(O$R^{h91}$)(O$R^{i91}$), and B$R^{j91}R^{k91}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^9$ are each optionally substituted with 1, 2, 3, 4, 5, 6, 7, or 8 independently selected $R^{9A}$ substituents;

or, alternatively, two $R^9$ groups together form an oxo group;

each $R^{a91}$, $R^{b91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a91}$, $R^{b91}$, $R^{c91}$ and $R^{d91}$ are each optionally substituted with 1, 2, 3, 4, 5, 6, 7, or 8 independently selected $R^{9A}$ substituents;

or, any $R^{c91}$ and $R^{d91}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9A}$ substituents;

each $R^{e91}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f91}$ and $R^{g91}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h91}$ and $R^{i91}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j91}$ and $R^{k91}$ is independently selected from OH, $C_{1-6}$ alkoxy, and $C_{1-6}$ haloalkoxy;

or any $R^{j91}$ and $R^{k91}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{9A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a92}$, $SR^{a92}$, $NHOR^{a92}$, $C(O)R^{b92}$, $C(O)NR^{c92}R^{d92}$, $C(O)NR^{c92}(OR^{a92})$, $C(O)OR^{a92}$, $OC(O)R^{b92}$, $OC(O)NR^{c92}R^{d92}$, $NR^{c92}R^{d92}$, $NR^{c92}NR^{c92}R^{d92}$, $NR^{c92}C(O)R^{b92}$, $NR^{c92}C(O)OR^{a92}$, $NR^{c92}C(O)NR^{c92}R^{d92}$, $C(=NR^{e92})R^{b92}$, $C(=NOH)R^{b92}$, $C(=NCN)R^{b92}$, $C(=NR^{e92})NR^{c92}R^{d92}$, $NR^{c92}C(=NR^{e92})$ $NR^{c92}R^{d92}$, $NR^{c92}C(=NOH)NR^{c92}R^{d92}$, $NR^{c92}C(=NCN)$ $NR^{c92}R^{d92}$, $NR^{c92}C(=NR^{e92})R^{b92}$, $NR^{c92}S(O)NR^{c92}R^{d92}$, $NR^{c92}S(O)R^{b92}$, $NR^{c92}S(O)_2R^{b92}$, $NR^{c92}S(O)(=NR^{e92})$ $R^{b92}$, $NR^{c92}S(O)_2NR^{c92}R^{d92}$, $S(O)R^{b92}$, $S(O)NR^{c92}R^{d92}$, $S(O)_2R^{b92}$, $S(O)_2NR^{c92}R^{d92}$, $S(O)(=NR^{e92})R^{b92}$, $OS(O)$ $(=NR^{e92})R^{b92}$, $OS(O)_2R^{b92}$, $SF_5$, $P(O)R^{f92}R^{g92}$, $OP(O)$ $(OR^{h92})(OR^{i92})$, $P(O)(OR^{h92})(OR^{i92})$, and $BR^{j92}R^{k92}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9A}$ are each optionally substituted with 1, 2, 3, or 4 independently selected $R^M$ substituents;

each $R^{a92}$, $R^{b92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a92}$, $R^{b92}$, $R^{c92}$ and $R^{d92}$ are each optionally substituted with 1, 2, 3, or 4 independently selected $R^M$ substituents;

or, any $R^{c92}$ and $R^{d92}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e92}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f92}$ and $R^{g92}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h92}$ and $R^{i92}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j92}$ and $R^{k92}$ is independently selected from OH, $C_{1-6}$ alkoxy, and $C_{1-6}$ haloalkoxy;

or any $R^{j92}$ and $R^{k92}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b10N}$, $C(O)NR^{c10N}R^{d10N}$, $C(O)OR^{a10N}$, $C(=NR^{e10N})R^{b10N}$, $C(=NR^{e10N})$ $NR^{c10N}R^{d10N}$, $C(=NCN)NR^{c10N}R^{d10N}$, $C(=NOR^{a10N})$ $NR^{c10N}$, $S(O)_2R^{b10N}$, $S(O)(=NR^{c10N})R^{d10N}$, and $S(O)_2$ $NR^{c10N}R^{d10N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, C$_{3-10}$ cycloalkyl-C$_{1-6}$ alkyl-, (5-10 membered heteroaryl)-C$_{1-6}$alkyl- and (4-10 membered heterocycloalkyl)-C$_{1-6}$ alkyl- of R$^{10N}$ are each optionally substituted with 1, 2, 3, 4, 5, 6, 7, or 8 independently selected R$^{10NA}$ substituents;

each R$^{a10N}$, R$^{b10N}$, R$^{c10N}$, and R$^{d10N}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a10N}$, R$^{b10N}$, R$^{c10N}$, and R$^{d10N}$ are each optionally substituted with 1, 2, 3, 4, 5, 6, 7, or 8 independently selected R$^{10NA}$ substituents;

or, any R$^{c10N}$ and R$^{d10N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected R$^{10NA}$ substituents;

each R$^{e10N}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, and C$_{2-6}$ alkynyl;

each R$^{10NA}$ is selected from H, D, halo, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, (4-7 membered heterocycloalkyl)-C$_{1-6}$ alkyl-, CN, NO$_2$, OR$^{a10N2}$, SR$^{a10N2}$, NHOR$^{a10N2}$, C(O)R$^{b10N2}$, C(O)NR$^{c10N2}$R$^{d10N2}$, C(O)NR$^{c10N2}$(OR$^{a10N2}$), C(O)OR$^{a10N2}$, OC(O)R$^{b10N2}$, OC(O)NR$^{c10N2}$R$^{d10N2}$, NR$^{c10N2}$R$^{d10N2}$, NR$^{c10N2}$NR$^{c10N2}$R$^{d10N2}$, NR$^{c10N2}$C(O)R$^{b10N2}$, NR$^{c10N2}$C(O)OR$^{a10N2}$, NR$^{c10N2}$C(O)NR$^{c10N2}$R$^{d10N2}$, C(=NR$^{e10N2}$)R$^{b10N2}$, C(=NOH)R$^{b10N2}$, C(=NCN)R$^{b10N2}$, C(=NR$^{e10N2}$)NR$^{c10N2}$R$^{d10N2}$, NR$^{c10N2}$C(=NR$^{e10N2}$)NR$^{c10N2}$R$^{d10N2}$, NR$^{c10N2}$C(=NOH)NR$^{c10N2}$R$^{d10N2}$, NR$^{c10N2}$C(=NCN)NR$^{c10N2}$R$^{d10N2}$, NR$^{c10N2}$C(=NR$^{e10N2}$)R$^{b10N2}$, NR$^{c10N2}$S(O)NR$^{c10N2}$R$^{d10N2}$, NR$^{c10N2}$S(O)R$^{b10N2}$, NR$^{c10N2}$S(O)$_2$R$^{b10N2}$, NR$^{c10N2}$S(O)(=NR$^{e10N2}$)R$^{b10N2}$, NR$^{c10N2}$S(O)$_2$NR$^{c10N2}$R$^{d10N2}$, S(O)R$^{b10N2}$, S(O)NR$^{c10N2}$R$^{d10N2}$, S(O)$_2$R$^{b10N2}$, S(O)$_2$NR$^{c10N2}$R$^{d10N2}$, S(O)(=NR$^{e10N2}$)R$^{b10N2}$, OS(O)(=NR$^{e10N2}$)R$^{b10N2}$, OS(O)$_2$R$^{b10N2}$, SF$_5$, P(O)R$^{f10N2}$R$^{g10N2}$, OP(O)(OR$^{h10N2}$)(OR$^{i10N2}$), P(O)(OR$^{h10N2}$)(OR$^{i10N2}$), and BR$^{j10N2}$R$^{k10N2}$, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{10NA}$ are each optionally substituted with 1, 2, 3, or 4 independently selected R$^M$ substituents;

each R$^{a10N2}$, R$^{b10N2}$, R$^{c10N2}$, and R$^{d10N2}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{a10N2}$, R$^{b10N2}$, R$^{c10N2}$ and R$^{d10N2}$ are each optionally substituted with 1, 2, 3, or 4 independently selected R$^M$ substituents;

or, any R$^{c10N2}$ and R$^{d10N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected R$^M$ substituents;

each R$^{e10N2}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, and C$_{2-6}$ alkynyl;

each R$^{f10N2}$ and R$^{g10N2}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-;

each R$^{h10N2}$ and R$^{i10N2}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-;

each R$^{j10N2}$ and R$^{k10N2}$ is independently selected from OH, C$_{1-6}$ alkoxy, and C$_{1-6}$ haloalkoxy;

or any R$^{j10N2}$ and R$^{k10N2}$ attached to the same B atom, together with the B atom to which they are attached, form a 5- or 6-membered heterocycloalkyl group optionally substituted with 1, 2, 3, or 4 substituents independently selected from C$_{1-6}$ alkyl, C$_{1-6}$ haloalkyl, C$_{3-10}$ cycloalkyl, and 4-10 membered hetereocycloalkyl;

each R$^{10}$ is independently selected from H, D, halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a101}$, SR$^{a101}$, NHOR$^{a101}$, C(O)R$^{b101}$, C(O)NR$^{c101}$R$^{d011}$, C(O)NR$^{c101}$(OR$^{a101}$), C(O)OR$^{a101}$, OC(O)R$^{b101}$, OC(O)NR$^{c101}$R$^{d101}$, NR$^{c101}$R$^{d101}$, NR$^{c101}$NR$^{c101}$R$^{d101}$, NR$^{c101}$C(O)R$^{b101}$, NR$^{c101}$C(O)OR$^{a101}$, NR$^{c101}$C(O)NR$^{c110}$R$^{d101}$, C(=NR$^{e101}$)R$^{b101}$, C(=NOH)R$^{b101}$, C(=NCN)R$^{b101}$, C(=NR$^{e101}$)NR$^{c101}$R$^{d101}$, NR$^{c101}$C(=NR$^{e101}$)NR$^{c101}$R$^{d101}$, NR$^{c101}$C(=NOH)NR$^{c101}$R$^{d101}$, NR$^{c101}$C(=NCN)NR$^{c101}$R$^{d101}$, NR$^{c101}$C(=NR$^{e101}$)R$^{b101}$, NR$^{c101}$S(O)NR$^{c101}$R$^{d101}$, NR$^{c101}$S(O)R$^{b101}$, NR$^{c101}$S(O)$_2$R$^{b101}$, NR$^{c101}$S(O)(=NR$^{e101}$)R$^{b101}$, NR$^{c101}$S(O)$_2$NR$^{c101}$R$^{d101}$S(O)R$^{b101}$, S(O)NR$^{c101}$R$^{d101}$, S(O)$_2$R$^{b101}$, S(O)$_2$NR$^{c101}$R$^{d101}$, S(O)(=NR$^{e101}$)R$^{b101}$, OS(O)(=NR$^{e101}$)R$^{b101}$, OS(O)$_2$R$^{b101}$, SF$_5$, P(O)R$^{f101}$R$^{g101}$, OP(O)(OR$^{h101}$)(OR$^{i101}$), P(O)(OR$^{h101}$)(OR$^{i101}$) and BR$^{j101}$R$^{k101}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{10}$ are each optionally substituted with 1, 2, 3, 4, 5, 6, 7, or 8 independently selected R$^{10A}$ substituents;

or, alternatively, two R$^{10}$ groups together form an oxo group;

each R$^{a101}$, R$^{b101}$, R$^{c101}$, and R$^{d101}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a101}$, $R^{b101}$, $R^{c101}$ and $R^{d101}$ are each optionally substituted with 1, 2, 3, 4, 5, 6, 7, or 8 independently selected $R^{10A}$ substituents;

or, any $R^{c101}$ and $R^{d101}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{10A}$ substituents;

each $R^{e101}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f101}$ and $R^{g101}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h101}$ and $R^{i101}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j101}$ and $R^{k101}$ is independently selected from OH, $C_{1-6}$ alkoxy, and $C_{1-6}$ haloalkoxy;

or any $R^{j101}$ and $R^{k101}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{10A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a102}$, $SR^{a102}$, $NHOR^{a102}$, $C(O)R^{b102}$, $C(O)NR^{c102}R^{d102}$, $C(O)NR^{c102}(OR^{a102})$, $C(O)OR^{a102}$, $OC(O)R^{b102}$, $OC(O)NR^{c102}R^{d102}$, $NR^{c102}R^{d102}$, $NR^{c102}NR^{c102}R^{d102}$, $NR^{c102}C(O)R^{b102}$, $NR^{c102}C(O)OR^{a102}$, $NR^{c102}C(O)NR^{c102}R^{d102}$, $C(=NR^{e102})R^{b102}$, $C(=NOH)R^{b102}$, $C(=NCN)R^{b102}$, $C(=NR^{e102})NR^{c102}R^{d102}$, $NR^{c102}C(=NR^{e102})NR^{e102}R^{d102}$, $NR^{c102}C(=NOH)NR^{c102}R^{d102}$, $NR^{c102}C(=NCN)NR^{c102}R^{d102}$, $NR^{c102}C(=NR^{e102})R^{b102}$, $NR^{c102}S(O)NR^{c102}R^{d102}$, $NR^{c102}S(O)R^{b102}$, $NR^{c102}S(O)_2R^{b102}$, $NR^{c102}S(O)(=NR^{e102})R^{b102}$, $NR^{c102}S(O)_2NR^{c102}R^{d102}$, $S(O)R^{b102}$, $S(O)NR^{c102}R^{d102}$, $S(O)_2R^{b102}$, $S(O)_2NR^{c102}R^{d102}$, $S(O)(=NR^{e102})R^{b102}$, $OS(O)(=NR^{e102})R^{b102}$, $OS(O)_2R^{b102}$, $SF_5$, $P(O)R^{f102}R^{g102}$, $OP(O)(OR^{h102})(OR^{i102})$, $P(O)(OR^{h102})(OR^{i102})$, and $BR^{j102}R^{k102}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{10A}$ are each optionally substituted with 1, 2, 3, or 4 independently selected $R^M$ substituents;

each $R^{a102}$, $R^{b102}$, $R^{c102}$, and $R^{d102}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a102}$, $R^{b102}$, $R^{c102}$ and $R^{d102}$ are each optionally substituted with 1, 2, 3, or 4 independently selected $R^M$ substituents;

or, any $R^{c102}$ and $R^{d102}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e102}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f102}$ and $R^{g102}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h102}$ and $R^{i102}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j102}$ and $R^{k102}$ is independently selected from OH, $C_{1-6}$ alkoxy, and $C_{1-6}$ haloalkoxy;

or any $R^{j102}$ and $R^{k102}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

$R^{11N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b11N}$, $C(O)NR^{c11N}R^{d11N}$, $C(O)OR^{a11N}$, $C(=NR^{e11N})R^{b11N}$, $C(=NR^{e11N})NR^{c11N}R^{d11N}$, $C(=NCN)NR^{c11N}R^{d11N}$, $C(=NOR^{a11N})NR^{c11N}$, $S(O)_2R^{b11N}$, $S(O)(=NR^{e11N})R^{d11N}$, and $S(O)_2NR^{c11N}R^{d11N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$alkyl- and (4-10 membered heterocycloalkyl)-$C_{1-6}$ alkyl- of $R^{11N}$ are each optionally substituted with 1, 2, 3, 4, 5, 6, 7, or 8 independently selected $R^{11NA}$ substituents;

each $R^{a11N}$, $R^{b11N}$, $R^{c11N}$, and $R^{d11N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11N}$, $R^{b11N}$, $R^{c11N}$, and $R^{d11N}$ are each optionally substituted with 1, 2, 3, 4, 5, 6, 7, or 8 independently selected $R^{11NA}$ substituents;

or, any $R^{c11N}$ and $R^{d11N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{11NA}$ substituents; each $R^{e11N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{11NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, NO$_2$, $OR^{a11N2}$, $SR^{a11N2}$, $NHOR^{a11N2}$, $C(O)R^{b11N2}$, $C(O)NR^{c11N2}R^{d11N2}$, $C(O)NR^{c11N2}(OR^{a11N2})$, $C(O)OR^{a11N2}$, $OC(O)R^{b11N2}$, $OC(O)NR^{c11N2}R^{d11N2}$, $NR^{c11N2}R^{d11N2}$, $NR^{c11N2}NR^{c11N2}R^{d11N2}$, $NR^{c11N2}C(O)R^{b11N2}$, $NR^{c11N2}C(O)OR^{a11N2}$, $NR^{c11N2}C(O)NR^{c11N2}R^{d11N2}$, $C(=NR^{e11N2})R^{b11N2}$, $C(=NOH)R^{b11N2}$, $C(=NCN)R^{b11N2}$, $C(=NR^{e11N2})NR^{c11N2}R^{d11N2}$, $NR^{c11N2}C(=NR^{e11N2})NR^{c11N2}R^{d11N2}$, $NR^{c11N2}C(=NOH)NR^{c11N2}R^{d11N2}$, $NR^{c11N2}C(=NCN)NR^{c11N2}R^{d11N2}$, $NR^{c11N2}C(=NR^{e11N2})R^{b11N2}$, $NR^{c11N2}S(O)NR^{c11N2}R^{d11N2}$, $NR^{c11N2}S(O)R^{b11N2}$, $NR^{c11N2}S(O)_2R^{b11N2}$, $NR^{c11N2}S(O)(=NR^{e11N2})R^{b11N2}$, $NR^{c11N2}S(O)_2NR^{c11N2}R^{d11N2}$, $S(O)R^{b11N2}$, $S(O)NR^{c11N2}R^{d11N2}$, $S(O)_2R^{b11N2}$, $S(O)_2NR^{c11N2}R^{d11N2}$, $S(O)(=NR^{e11N2})R^{b11N2}$, $OS(O)(=NR^{e11N2})R^{b11N2}$, $OS(O)_2R^{b11N2}$, $SF_5$, $P(O)R^{f11N2}R^{g11N2}$, $OP(O)(OR^{h11N2})(OR^{i11N2})$, $P(O)(OR^{h11N2})(OR^{i11N2})$, and $BR^{j11N2}R^{k11N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{11NA}$ are each optionally substituted with 1, 2, 3, or 4 independently selected $R^M$ substituents;

each $R^{a11N2}$, $R^{b11N2}$, $R^{c11N2}$, and $R^{d11N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a11N2}$, $R^{b11N2}$, $R^{c11N2}$ and $R^{d11N2}$ are each optionally substituted with 1, 2, 3, or 4 independently selected $R^M$ substituents;

or, any $R^{c11N2}$ and $R^{d11N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e11N2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f11N2}$ and $R^{g11N2}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h11N2}$ and $R^{i11N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j11N2}$ and $R^{k11N2}$ is independently selected from OH, $C_{1-6}$ alkoxy, and $C_{1-6}$ haloalkoxy;

or any $R^{j11N2}$ and $R^{k11N2}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered heterecocycloalkyl;

each $R^{11}$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, $OR^{a111}$, $SR^{a111}$, $NHOR^{a111}$, $C(O)R^{b111}$, $C(O)NR^{c111}R^{d111}$, $C(O)NR^{c111}(OR^{a111})$, $C(O)OR^{a111}$, $OC(O)R^{b111}$, $OC(O)NR^{c111}R^{d111}$, $NR^{c111}R^{d111}$, $NR^{c111}NR^{c111}R^{d111}$, $NR^{c111}C(O)R^{b111}$, $NR^{c111}C(O)OR^{a111}$, $NR^{c111}C(O)NR^{c111}R^{d111}$, $C(=NR^{e111})R^{b111}$, $C(=NOH)R^{b111}$, $C(=NCN)R^{b111}$, $C(=NR^{e111})NR^{c111}R^{d111}$, $NR^{c111}C(=NR^{e111})NR^{c111}R^{d111}$, $NR^{c111}C(=NOH)NR^{c111}R^{d111}$, $NR^{c111}C(=NCN)NR^{c111}R^{d111}$, $NR^{c111}C(=NR^{e111})R^{b111}$, $NR^{c111}S(O)NR^{c111}R^{d111}$, $NR^{c111}S(O)R^{b111}$, $NR^{c111}S(O)_2R^{b111}$, $NR^{c111}S(O)(=NR^{e111})R^{b111}$, $NR^{c111}S(O)_2NR^{c111}R^{d111}$, $S(O)R^{b111}$, $S(O)NR^{c111}R^{d111}$, $S(O)_2R^{b111}$, $S(O)_2NR^{c111}R^{d111}$, $S(O)(=NR^{e111})R^{b111}$, $OS(O)(=NR^{e111})R^{b111}$, $OS(O)_2R^{b111}$, $SF_5$, $P(O)R^{f111}R^{g111}$, $OP(O)(OR^{h111})(OR^{i111})$, $P(O)(OR^{h111})(OR^{i111})$, and $BR^{j111}R^{k111}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{11}$ are each optionally substituted with 1, 2, 3, 4, 5, 6, 7, or 8 independently selected $R^{11A}$ substituents;

or, alternatively, two $R^{11}$ groups together form an oxo group;

each $R^{a111}$, $R^{b111}$, $R^{c111}$, and $R^{d111}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a111}$, $R^{b111}$, $R^{c111}$ and $R^{d111}$ are each optionally substituted with 1, 2, 3, 4, 5, 6, 7, or 8 independently selected $R^{11A}$ substituents;

or, any $R^{c111}$ and $R^{d111}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{11A}$ substituents;

each $R^{e111}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f111}$ and $R^{g111}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h111}$ and $R^{i111}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j111}$ and $R^{k111}$ is independently selected from OH, $C_{1-6}$ alkoxy, and $C_{1-6}$ haloalkoxy;

or any $R^{j111}$ and $R^{k111}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl; and each $R^{11A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a112}$, $SR^{a112}$, $NHOR^{a112}$, $C(O)R^{b112}$, $C(O)NR^{c221}R^{d112}$, $C(O)NR^{c112}(OR^{a112})$, $C(O)OR^{a112}$, $OC(O)R^{b112}$, $OC(O)NR^{c112}R^{d112}$, $NR^{c112}R^{d112}$, $NR^{c112}NR^{c112}R^{d112}$, $NR^{c1112}C(O)R^{b112}$, $NR^{c112}C(O)OR^{a112}$, $NR^{c112}C(O)NR^{c112}R^{d112}$, $C(=NR^{e112})R^{b112}$, $C(=NOH)R^{b112}$, $C(=NCN)R^{b112}$, $C(=NR^{e112})NR^{c112}R^{d112}$, $NR^{c112}C(=NR^{e112})NR^{c112}R^{d12}$, $NR^{c112}C(=NOH)NR^{c112}R^{d112}$, $NR^{c112}C(=NCN)NR^{c112}R^{d112}NR^{c112}C(=NR^{e112})R^{b112}$, $NR^{c112}S(O)NR^{c112}R^{d112}$, $NR^{c112}S(O)R^{b112}$, $NR^{c112}S(O)_2R^{b112}$, $NR^{c112}S(O)(=NR^{e112})R^{b112}$, $NR^{c112}S(O)_2NR^{c112}R^{d112}$, $S(O)R^{b112}$, $S(O)NR^{c112}R^{d112}$, $S(O)_2R^{b112}$, $S(O)_2NR^{c112}R^{d112}$, $S(O)(=NR^{e112})R^{b112}$, $OS(O)(=NR^{e112})R^{b112}$, $OS(O)_2R^{b112}$, $SF_5$, $P(O)R^{f112}R^{g112}$, $OP(O)(OR^{h112})(OR^{i112})$, $P(O)(OR^{h112})(OR^{i112})$ and $BR^{j112}R^{k112}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{11A}$ are each optionally substituted with 1, 2, 3, or 4 independently selected $R^M$ substituents;

each $R^{a112}$, $R^{b112}$, $R^{c112}$, and $R^{d112}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a112}R^{b112}$, $R^{c112}$ and $R^{d112}$ are each optionally substituted with 1, 2, 3, or 4 independently selected $R^M$ substituents;

or, any $R^{c112}$ and $R^{d112}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e112}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f112}$ and $R^{g112}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h112}$ and $R^{i112}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j112}$ and $R^{k112}$ is independently selected from OH, $C_{1-6}$ alkoxy, and $C_{1-6}$ haloalkoxy;

or any $R^{j112}$ and $R^{k112}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl.

In some embodiments, Formula (I) is as otherwise defined above, wherein:

$R^6$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOH)R^{b6}$, $C(=NCN)R^{b6}$, $C(=NR^{e6})NR^{c6}R^{d6}$, $NR^{c6}C(=NR^{e6})NR^{c6}R^{d6}$, $NR^{c6}C(=NOH)NR^{c6}R^{d6}$, $NR^{c6}C(=NCN)NR^{c6}R^{d6}$, $NR^{c6}C(=NR^{e6})R^{b6}$, $NR^{c6}S(O)NR^{c6}R^{d6}$, $NR^{c6}S(O)R^{b6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $S(O)(=NR^{e6})R^{b6}$, $N=S(O)R^{a6}R^{b6}$, $OS(O)(=NR^{e6})R^{b6}$, $OS(O)_2R^{b6}$, $SF_5$, $P(O)R^{f6}R^{g6}$, $OP(O)(OR^{h6})(OR^{i6})$, $P(O)(OR^{h6})(OR^{i6})$, and $BR^{j6}R^{k6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, 4, 5, 6, 7, or 8 independently selected $R^{6A}$ substituents.

In some embodiments, each bond symbol represented by ═════ is independently a single or double bond;

W is $CW^1$ or N;

Z is $CZ^1$ or N;

$X^1$ is $CR^1$ or N;

$X^2$ is $CR^2$ or N;

$X^3$ is $CR^3$ or N;

wherein $X^1$, $X^2$, and $X^3$ are not each simultaneously N;

$W^1$, $Z^1$, and $R^{12}$ are each independently selected from H, D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-6}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino; $R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOH)R^{b1}$, $C(=NCN)R^{b1}$, $C(=NR^{e1})NR^{c1}R^{d1}$, $NR^{c1}C(=NR^{e1})NR^{c1}R^{d1}$, $NR^{c1}C(=NOH)NR^{c1}R^{d1}$, $NR^{c1}C(=NCN)NR^{c1}R^{d1}$, $NR^{c1}C(=NR^{e1})R^{b1}$, $NR^{c1}S(O)NR^{c1}R^{d1}$, $NR^{c1}S(O)R^{b1}$, $NR^{c1}S(O)_2 R^{b1}$, $NR^{c1}S(O)(=NR^{e1})R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $S(O)(=NR^{e1})R^{b1}$, $OS(O)(=NR^{e1})R^{b1}$, $OS(O)_2R^{b1}$, $SF_5$, $P(O)R^{f1}R^{g1}$, $OP(O)(OR^{h1})(OR^{i1})$, $P(O)(OR^{h1})(OR^{i1})$, and $BR^{j1}R^{k1}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^M$ substituents;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{b1}$, $R^{c1}$ and $R^{d1}$ are each optionally substituted with 1, 2, 3, 4, 5, 6, 7, or 8 independently selected $R^M$ substituents; or, any $R^{c1}$ and $R^{d1}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f1}$ and $R^{g1}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h1}$ and $R^{i1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j1}$ and $R^{k1}$ is independently selected from OH, $C_{1-6}$ alkoxy, and $C_{1-6}$ haloalkoxy;

or any $R^{j1}$ and $R^{k1}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^M$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$alkyl, $C_{3-6}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOH)R^{b2}$, $C(=NCN)R^{b2}$, $C(=NR^{e2})NR^{c2}R^{d2}$, $NR^{c2}C(=NR^{e2})NR^{c2}R^{d2}$, $NR^{c2}C(=NOH)NR^{c2}R^{d2}$, $NR^{c2}C(=NCN)NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $S(O)(=NR^{e2})R^{b2}$, $OS(O)(=NR^{e2})R^{b2}$, $OS(O)_2R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, 6, 7, or 8 independently selected $R^{2A}$ substituents;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{b2}$, $R^{c2}$ and $R^{d2}$ are each optionally substituted with 1, 2, 3, 4, 5, 6, 7, or 8 independently selected $R^{2A}$ substituents;

or, any $R^{c2}$ and $R^{d2}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f2}$ and $R^{g2}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h2}$ and $R^{i2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j2}$ and $R^{k2}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{2A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}NR^{c21}R^{d21}$, $NR^{c21}C(O)R^{b21}$, $NR^{c21}C(O)OR^{a21}$, $NR^{c21}C(O)NR^{c21}R^{d21}$, $C(=NR^{e21})R^{b21}$, $C(=NOH)R^{b21}$, $C(=NCN)R^{b21}$, $C(=NR^{e21})NR^{c21}R^{d21}$, $NR^{c21}C(=NR^{e21})NR^{c21}R^{d21}$, $NR^{c21}C(=NOH)NR^{c21}R^{d21}$, $NR^{c21}C(=NCN)NR^{c21}R^{d21}$, $NR^{c21}C(=NR^{e21})R^{b21}$, $NR^{c21}S(O)NR^{c21}R^{d21}$, $NR^{c21}S(O)R^{b21}$, $NR^{c21}S(O)_2R^{b21}$, $NR^{c21}S(O)(=NR^{e21})R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, $S(O)(=NR^{e21})R^{b21}$, $OS(O)(=NR^{e21})R^{b21}$, $OS(O)_2R^{b21}$, $SF_5$, $P(O)R^{f21}R^{g21}$, $OP(O)(OR^{h21})(OR^{i21})$, $P(O)(OR^{h21})(OR^{i21})$, and $BR^{j21}R^{k21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, 4, 5, 6, 7, or 8 independently selected $R^M$ substituents;

each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$ and $R^{d21}$ are each optionally substituted with 1, 2, 3, 4, 5, 6, 7, or 8 independently selected $R^M$ substituents;

or, any $R^{c21}$ and $R^{d21}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f21}$ and $R^{g21}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h21}$ and $R^{i21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j21}$ and $R^{k21}$ is independently selected from OH, $C_{1-6}$ alkoxy, and $C_{1-6}$ haloalkoxy;

or any $R^{j21}$ and $R^{k21}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

or alternatively, $R^1$ and $R^2$, taken together with the carbon atoms to which they are attached form a monocyclic 4-7 membered cycloalkyl ring, a phenyl ring, a monocyclic 4-7 membered heterocycloalkyl ring, or a monocyclic 5-6 membered heteroaryl ring, each of which is optionally substituted by 1, 2, 3, 4, 5, 6, 7 or 8 independently selected $R^{1A}$ groups;

each $R^{1A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, and $NR^{c11}C(O)NR^{c11}R^{d11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$alkyl-, and (4-10 membered heterocycloalkyl)-$C_{1-6}$ alkyl- of $R^{1A}$ are each optionally substituted with 1, 2, 3, 4, 5, 6, 7, or 8 independently selected $R^M$ substituents;

each $R^{a11}$, $R^{b11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-

$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{b11}$, $R^{c11}$ and $R^{d11}$ are each optionally substituted with 1, 2, 3, 4, 5, 6, 7, or 8 independently selected $R^M$ substituents;

or, any $R^{c11}$ and $R^{d11}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents; $R^3$ is selected H, D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-6}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

or alternatively, $R^2$ and $R^3$, taken together with the carbon atoms to which they are attached form a monocyclic 4-7 membered cycloalkyl ring, a phenyl ring, a monocyclic 4-7 membered heterocycloalkyl ring, or a monocyclic 5-6 membered heteroaryl ring, each of which is optionally substituted by 1, 2, 3, 4, 5, 6, 7 or 8 independently selected $R^{2A}$ groups;

$X^4$ is N or $CR^4$;

$X^5$ is N or $CR^5$;

$R^4$ and $R^5$ are each independently selected from H, D, halo, CN, OH, $NH_2$, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, cyano-$C_{1-6}$ alkyl, HO—$C_{1-6}$ alkyl, $C_{1-6}$ alkoxy-$C_{1-6}$ alkyl, $C_{3-6}$ cycloalkyl, $C_{1-6}$ alkylamino, di($C_{1-6}$ alkyl)amino, and $C(O)NR^{a4}R^{b4}$; each $R^{a4}$ and $R^{b4}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$alkyl-, and (4-7 membered heterocycloalkyl)-$C_{1-6}$ alkyl- of $R^{a4}$ and $R^{b4}$ are each optionally substituted with 1, 2, 3 or 4 independently selected $R^M$ substituents;

or, any $R^{a4}$ and $R^{b4}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$X^6$ is N or $CR^6$;

$R^6$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOH)R^{b6}$, $C(=NCN)R^{b6}$, $C(=NR^{e6})NR^{c6}R^{d6}$, $NR^{c6}C(=NR^{e6})NR^{c6}R^{d6}$, $NR^{c6}C(=NOH)NR^{c6}R^{d6}$, $NR^{c6}C(=NCN)NR^{c6}R^{d6}$, $NR^{c6}C(=NR^{e6})R^{b6}$, $NR^{c6}S(O)NR^{c6}R^{d6}$, $NR^{c6}S(O)R^{b6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $S(O)(=NR^{e6})R^{b6}$, $OS(O)(=NR^{e6})R^{b6}$, $OS(O)_2R^{b6}$, $SF_5$, $P(O)R^{f6}R^{g6}$, $OP(O)(OR^{h6})(OR^{i6})$, $P(O)(OR^{h6})(OR^{i6})$, and $BR^{j6}R^{k6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, 4, 5, 6, 7, or 8 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$ and $R^{d6}$ are each optionally substituted with 1, 2, 3, 4, 5, 6, 7, or 8 independently selected $R^{6A}$ substituents;

or, any $R^{c6}$ and $R^{d6}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{6A}$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered heterocycloalkyl;

each $R^{6A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a61}$, SR$^{a61}$, NHOR$^{a61}$, C(O)R$^{b61}$, C(O)NR$^{c61}$R$^{d61}$, C(O)NR$^{c61}$(OR$^{a61}$), C(O)OR$^{a61}$, OC(O)R$^{b61}$, OC(O)NR$^{c61}$R$^{d61}$, NR$^{c61}$R$^{d61}$, NR$^{c61}$NR$^{c61}$R$^{d61}$, NR$^{c61}$C(O)R$^{b61}$, NR$^{c61}$C(O)OR$^{a61}$, NR$^{c61}$C(O)NR$^{c61}$R$^{d61}$, C(=NR$^{e61}$)R$^{b61}$, C(=NOH)R$^{b61}$, C(=NCN)R$^{b61}$, C(=NR$^{e6}$)NR$^{c61}$R$^{d61}$, NR$^{c61}$C(=NR$^{e61}$)NR$^{c61}$R$^{d61}$, NR$^{c61}$C(=NOH)NR$^{c61}$R$^{d61}$, NR$^{c61}$C(=NCN)NR$^{c61}$R$^{d61}$, NR$^{c61}$C(=NR$^{e61}$)R$^{b61}$, NR$^{c61}$S(O)NR$^{c61}$R$^{d61}$, NR$^{c61}$S(O)R$^{b61}$, NR$^{c61}$S(O)$_2$R$^{b61}$, NR$^{c61}$S(O)(=NR$^{e61}$)R$^{b61}$, NR$^{c61}$S(O)$_2$NR$^{c61}$R$^{d61}$, S(O)R$^{b61}$, S(O)NR$^{c61}$R$^{d61}$, S(O)$_2$R$^{b61}$, S(O)$_2$NR$^{c61}$R$^{d61}$, S(O)(=NR$^{e61}$)R$^{b61}$, OS(O)(=NR$^{e61}$)R$^{b61}$, OS(O)$_2$R$^{b61}$, SF$_5$, P(O)R$^{f61}$R$^{g61}$, OP(O)(OR$^{h61}$)(OR$^{i61}$), P(O)(OR$^{h61}$)(OR$^{i61}$), and BR$^{j61}$R$^{k61}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{6A}$ are each optionally substituted with 1, 2, 3, 4, 5, 6, 7, or 8 independently selected $R^M$ substituents;

each $R^{a61}$, $R^{b61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a61}$, $R^{b61}$, $R^{c61}$ and $R^{d61}$ are each optionally substituted with 1, 2, 3, 4, 5, 6, 7, or 8 independently selected $R^M$ substituents;

or, any $R^{c61}$ and $R^{d61}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^{e61}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f61}$ and $R^{g61}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h61}$ and $R^{i61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j61}$ and $R^{k61}$ is independently selected from OH, $C_{1-6}$ alkoxy, and $C_{1-6}$ haloalkoxy;

or any $R^{j61}$ and $R^{k61}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered heterocycloalkyl;

$X^7$ is N, C, or CH;
$X^8$ is N, C, or CH;
$X^9$ is N, NR$^{9N}$, O, S, S(O), S(O)$_2$, CR$^9$, or C(R$^9$)$_2$;
$X^{10}$ is N, NR$^{10N}$, O, S, CR$^{10}$, or C(R$^{10}$)$_2$;
$X^{11}$ is N, NR$^{11N}$, O, S, CR$^{11}$, or C(R$^{11}$)$_2$;

wherein no more than three of $X^4$, $X^5$, $X^6$, $X^7$, and $X^8$ are simultaneously N; and at least two of $X^7$, $X^8$, $X^9$, $X^{10}$, and $X^{11}$ are independently selected from C, CH, CR$^9$, C(R$^9$)$_2$, CR$^{10}$, C(R$^{10}$)$_2$, CR$^{11}$, and C(R$^{11}$)$_2$; and no two adjacent members of $X^9$, $X^{10}$, and $X^{11}$ are simultaneously O, S, S(O) or S(O)$_2$;

provided that (a) when $X^7$ is N, then $X^8$ is C or CH; or (b) when $X^8$ is N, then $X^7$ is C or CH;

R$^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, C(O)R$^{b9N}$, C(O)NR$^{c9N}$R$^{d9N}$, C(O)OR$^{a9N}$, C(=NR$^{e9N}$)R$^{b9N}$, C(=NR$^{e9N}$)NR$^{c9N}$R$^{d9N}$, C(=NCN)NR$^{c9N}$NR$^{d9N}$, C(=NOR$^{a9N}$)NR$^{c9N}$, S(O)$_2$R$^{b9N}$, S(O)(=NR$^{c9N}$)R$^{d9N}$, and S(O)$_2$NR$^{c9N}$R$^{d9N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of R$^{9N}$ are each optionally substituted with 1, 2, 3, 4, 5, 6, 7, or 8 independently selected $R^M$ substituents;

each R$^{a9N}$, R$^{b9N}$, R$^{c9N}$, and R$^{d9N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^{a9N}$, R$^{b9N}$, R$^{c9N}$, and R$^{d9N}$ are each optionally substituted with 1, 2, 3, 4, 5, 6, 7, or 8 independently selected $R^M$ substituents;

or, any R$^{c9N}$ and R$^{d9N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each R$^{e9N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each R$^9$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a91}$, SR$^{a91}$, NHOR$^{a91}$, C(O)R$^{b91}$, C(O)NR$^{c91}$R$^{d91}$, C(O)NR$^{c91}$(OR$^{a91}$), C(O)OR$^{a91}$, OC(O)R$^{b91}$, OC(O)NR$^{c91}$R$^{d91}$, NR$^{c91}$R$^{d91}$, NR$^{c91}$NR$^{c91}$R$^{d91}$, NR$^{c91}$C(O)R$^{b91}$, NR$^{c91}$C(O)OR$^{a91}$, NR$^{c91}$C(O)NR$^{c91}$R$^{d91}$, C(=NR$^{e91}$)R$^{b91}$, C(=NOH)

$R^{b91}$, C(=NCN)$R^{b91}$, C(=N$R^{e91}$)N$R^{c91}R^{d91}$, N$R^{c91}$C(=N$R^{e91}$)N$R^{c91}R^{d91}$, N$R^{c91}$C(=NOH)N$R^{c91}R^{d91}$, N$R^{c91}$C(=NCN)N$R^{c91}R^{d91}$, N$R^{c91}$C(=N$R^{e91}$)$R^{b91}$, N$R^{c91}$S(O)N$R^{c91}R^{d91}$, N$R^{c91}$S(O)$R^{b91}$, N$R^{c91}$S(O)$_2R^{b91}$, N$R^{c91}$S(O)(=N$R^{e91}$)$R^{b91}$, N$R^{c91}$S(O)$_2$N$R^{c91}R^{d91}$, S(O)$R^{b91}$, S(O)N$R^{c91}R^{d91}$, S(O)$_2R^{b91}$, S(O)$_2$N$R^{c91}R^{d91}$, S(O)(=N$R^{e91}$)$R^{b91}$, OS(O)(=N$R^{e91}$)$R^{b91}$, OS(O)$_2R^{b91}$, SF$_5$, P(O)$R^{f91}R^{g91}$, OP(O)(O$R^{h91}$)(O$R^{i91}$), P(O)(O$R^{h91}$)(O$R^{i91}$), and B$R^{j91}R^{k91}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^9$ are each optionally substituted with 1, 2, 3, 4, 5, 6, 7, or 8 independently selected $R^M$ substituents;

or, alternatively, two $R^9$ groups together form an oxo group;

each $R^{a91}$, $R^{b91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a91}$, $R^{b91}$, $R^{c91}$ and $R^{d91}$ are each optionally substituted with 1, 2, 3, 4, 5, 6, 7, or 8 independently selected $R^M$ substituents;

or, any $R^{c91}$ and $R^{d91}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^{e91}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f91}$ and $R^{g91}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h91}$ and $R^{i91}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j91}$ and $R^{k91}$ is independently selected from OH, $C_{1-6}$ alkoxy, and $C_{1-6}$ haloalkoxy;

or any $R^{j91}$ and $R^{k91}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

$R^{10N}$ is selected from H, $C_{1-6}$ alkyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered hetero-cycloalkyl)-$C_{1-6}$ alkyl-, C(O)$R^{b10N}$, C(O)N$R^{c10N}R^{d10N}$, C(O)O$R^{a10N}$, C(=N$R^{e10N}$)$R^{b10N}$, C(=N$R^{e10N}$)N$R^{c10N}R^{d10N}$, C(=NCN)N$R^{c10N}R^{d10N}$, C(=NO$R^{a10N}$)N$R^{c10N}R^{d10N}$, S(O)$_2R^{b10N}$, S(O)(=N$R^{c10N}$)$R^{d10N}$, and S(O)$_2$N$R^{c10N}R^{d10N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, 4, 5, 6, 7, or 8 independently selected $R^M$ substituents;

each $R^{a10N}$, $R^{b10N}$, $R^{c10N}$, and $R^{d10N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a10N}$, $R^{b10N}$, $R^{c10N}$, and $R^{d10N}$ are each optionally substituted with 1, 2, 3, 4, 5, 6, 7, or 8 independently selected $R^M$ substituents;

or, any $R^{c10N}$ and $R^{d10N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^{e10N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{10}$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, O$R^{a101}$, S$R^{a101}$, NHO$R^{a101}$, C(O)$R^{b101}$, C(O)N$R^{c101}R^{d101}$, C(O)N$R^{c101}$(O$R^{a101}$), C(O)O$R^{a101}$, OC(O)$R^{b101}$, OC(O)N$R^{c101}R^{d101}$, N$R^{c101}R^{d101}$, N$R^{c101}$N$R^{c101}R^{d101}$, N$R^{c101}$C(O)$R^{b101}$, N$R^{c101}$C(O)O$R^{a101}$, N$R^{c101}$C(O)N$R^{c101}R^{d101}$, C(=N$R^{e101}$)$R^{b101}$, C(=NOH)$R^{b101}$, C(=NCN)$R^{b101}$, C(=N$R^{e101}$)N$R^{c101}R^{d101}$, N$R^{c101}$C(=N$R^{e101}$)N$R^{c101}R^{d101}$, N$R^{c101}$C(=NOH)N$R^{c101}R^{d101}$N$R^{c101}$C(=NCN)N$R^{c101}R^{d101}$, N$R^{c101}$C(=N$R^{e101}$)$R^{b101}$, N$R^{c101}$S(O)N$R^{c101}R^{d101}$, N$R^{c101}$S(O)$R^{b101}$, N$R^{c101}$S(O)$_2R^{b101}$, N$R^{c101}$S(O)(=N$R^{e101}$)$R^{b101}$, N$R^{c101}$S(O)$_2$N$R^{c101}R^{d011}$, S(O)$R^{b101}$, S(O)N$R^{c101}R^{d101}$, S(O)$_2R^{b101}$, S(O)$_2$N$R^{c101}R^{d101}$, S(O)(=N$R^{e101}$)$R^{b101}$, OS(O)(=N$R^{e101}$)$R^{b101}$, OS(O)$_2R^{b101}$, SF$_5$, P(O)$R^{f101}R^{g101}$, OP(O)(O$R^{h101}$)(O$R^{i101}$), P(O)(O$R^{h101}$)(O$R^{i101}$), and B$R^{j101}R^{k101}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{10}$ are each optionally substituted with 1, 2, 3, 4, 5, 6, 7, or 8 independently selected $R^M$ substituents;

or, alternatively, two $R^{10}$ groups together form an oxo group;

each $R^{a101}$, $R^{b101}$, $R^{c101}$, and $R^{d101}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a101}$, $R^{b101}$, $R^{c101}$ and $R^{d101}$ are each optionally substituted with 1, 2, 3, 4, 5, 6, 7, or 8 independently selected $R^M$ substituents;

or, any $R^{c101}$ and $R^{d101}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^{e101}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f101}$ and $R^{g101}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h101}$ and $R^{i101}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j101}$ and $R^{k101}$ is independently selected from OH, $C_{1-6}$ alkoxy, and $C_{1-6}$ haloalkoxy;

or any $R^{j101}$ and $R^{k101}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

$R^{11N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b11N}$, $C(O)NR^{c11N}R^{d11N}$, $C(O)OR^{a11N}$, $C(=NR^{e11N})R^{b11N}$, $C(=NR^{e11N})NR^{c11N}R^{d11N}$, $C(=NCN)NR^{c11N}R^{d11N}$, $C(=NOR^{a11N})NR^{c11N}$, $S(O)_2R^{b11N}$, $S(O)(=NR^{e11N})R^{d11N}$, and $S(O)_2NR^{c11N}R^{d11N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^N$ are each optionally substituted with 1, 2, 3, 4, 5, 6, 7, or 8 independently selected $R^M$ substituents;

each $R^{a11N}$, $R^{b11N}$, $R^{c11N}$, and $R^{d11N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11N}$, $R^{b11N}$, $R^{c11N}$, and $R^{d11N}$ are each optionally substituted with 1, 2, 3, 4, 5, 6, 7, or 8 independently selected $R^M$ substituents;

or, any $R^{c11N}$ and $R^{d11N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^{e11N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{11}$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a111}$, $SR^{a111}$, $NHOR^{a111}$, $C(O)R^{b111}$, $C(O)NR^{c111}R^{d111}$, $C(O)NR^{c111}(OR^{a111})$, $C(O)OR^{a111}$, $OC(O)R^{b111}$, $OC(O)NR^{c111}R^{d111}$, $NR^{c111}R^{d111}$, $NR^{c111}NR^{c111}R^{d111}$, $NR^{c111}C(O)R^{b111}$, $NR^{c111}C(O)OR^{a111}$, $NR^{c111}C(O)NR^{c111}R^{d111}$, $C(=NR^{e111})R^{b111}$, $C(=NOH)R^{b111}$, $C(=NCN)R^{b111}$, $C(=NR^{e111})NR^{c111}R^{d111}$, $NR^{c111}C(=NR^{e111})NR^{c111}R^{d111}$, $NR^{c111}C(=NOH)NR^{c111}R^{d111}$, $NR^{c111}C(=NCN)NR^{c111}R^{d111}$, $NR^{c111}C(=NR^{e111})R^{b111}$, $NR^{c111}S(O)R^{b111}$, $NR^{c111}S(O)_2R^{b111}$, $NR^{c111}S(O)(=NR^{e111})R^{b111}$, $NR^{c111}S(O)_2NR^{c111}R^{d111}$, $S(O)R^{b111}$, $S(O)NR^{c111}R^{d111}$, $S(O)_2R^{b111}$, $S(O)_2NR^{c111}R^{d111}$, $S(O)(=NR^{e111})R^{b111}$, $OS(O)(=NR^{e111})R^{b111}$, $OS(O)_2R^{b111}$, $SF_5$, $P(O)R^{f111}R^{g111}$, $OP(O)(OR^{h111})(OR^{i111})$, $P(O)(OR^{h111})(OR^{i111})$, and $BR^{j111}R^{k111}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{11}$ are each optionally substituted with 1, 2, 3, 4, 5, 6, 7, or 8 independently selected $R^M$ substituents;

or, alternatively, two $R^{11}$ groups together form an oxo group;

each $R^{a111}$, $R^{b111}$, $R^{c111}$, and $R^{d111}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a111}$, $R^{b111}$, $R^{c111}$ and $R^{d111}$ are each optionally substituted with 1, 2, 3, 4, 5, 6, 7, or 8 independently selected $R^M$ substituents;

or, any $R^{c111}$ and $R^{d111}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^{e111}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f111}$ and $R^{g111}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h111}$ and $R^{i111}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j111}$ and $R^{k111}$ is independently selected from OH, $C_{1-6}$ alkoxy, and $C_{1-6}$ haloalkoxy;

or any $R^{j111}$ and $R^{k111}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl.

In some embodiments, $X^1$ is N.

In some embodiments, $X^1$ is $CR^1$.

In some embodiments, $R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3 or 4 independently selected $R^{1A}$ substituents; and each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{b1}$, $R^{c1}$ and $R^{d1}$ are each optionally substituted with 1, 2, 3, or 4 independently selected $R^{1A}$ substituents;

or, any $R^{c1}$ and $R^{d1}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, or 4 independently selected $R^{1A}$ substituents.

In some embodiments, $R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, $NR^{c1}C(O)NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, $R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, and $NR^{c1}C(O)NR^{c1}R^{d1}$.

In some embodiments, $R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, and $NO_2$.

In some embodiments, $R^1$ is selected from H and $C_{1-6}$ alkyl.

In some embodiments, $R^1$ is selected from H and methyl.

In some embodiments, $R^1$ is H.

In some embodiments, $R^1$ is $C_{1-3}$ alkyl.

In some embodiments, $R^1$ is methyl.

In some embodiments, $X^2$ is N.

In some embodiments, $X^2$ is $CR^2$.

In some embodiments, $R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $S(O)R^{b2}$, $S(O)NR^{c2}R^{d2}$, $S(O)_2R^{b2}$, and $S(O)_2NR^{c2}R^{d2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents; and each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{b2}$, $R^{c2}$ and $R^{d2}$ are each optionally substituted with 1, 2, 3, or 4 independently selected $R^{2A}$ substituents;

or, any $R^{c2}$ and $R^{d2}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, or 4 independently selected $R^{2A}$ substituents.

In some embodiments, $R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}C(O)R^{b2}$, $NR^{c2}C(O)OR^{a2}$, $NR^{c2}C(O)NR^{c2}R^{d2}$, $S(O)R^{b2}$, $S(O)NR^{c2}R^{d2}$, $S(O)_2R^{b2}$, and $S(O)_2NR^{c2}R^{d2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents; and each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a2}$, $R^{b2}$, $R^{c2}$ and $R^{d2}$ are each optionally substituted with 1 or 2 independently selected $R^{2A}$ substituents.

In some embodiments, $R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}C(O)R^{b2}$, $NR^{c2}C(O)OR^{a2}$, and $NR^{c2}C(O)NR^{c2}R^{d2}$.

In some embodiments, $R^2$ is selected from H, $C_{1-6}$ alkyl, $C(O)R^{b2}$, $C(O)NR^{c2}R^{d2}$, $NR^{c2}C(O)R^{b2}$, $NR^{c2}C(O)OR^{a2}$, and $NR^{c2}C(O)NR^{c2}R^{d2}$.

In some embodiments, $R^2$ is selected from $C_{1-6}$ alkyl and $C(O)NR^{c2}R^{d2}$.

In some embodiments, $R^2$ is selected from H, $C_{1-6}$ alkyl, $C(O)R^{b2}$, and $C(O)NR^{c2}R^{d2}$.

In some embodiments, each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a2}$, $R^{b2}$, $R^{c2}$ and $R^{d2}$ are each optionally substituted with 1 or 2 independently selected $R^{2A}$ substituents.

In some embodiments, each $R^{b2}$, $R^{c2}$ and $R^{d2}$ is independently selected from H, $C_{1-6}$ alkyl, $C_{3-7}$ cycloalkyl and 4-7 membered heterocycloalkyl, wherein the $C_{1-6}$ alkyl, $C_{3-7}$ cycloalkyl and 4-7 membered heterocycloalkyl of $R^{b2}$, $R^{c2}$ and $R^{d2}$ are each optionally substituted with 1 or 2 independently selected $R^{2A}$ substituents.

In some embodiments, $R^{b2}$ is a 4-7 membered heterocycloalkyl group optionally substituted with 1 or 2 independently selected $R^{2A}$ substituents.

In some embodiments, $R^{b2}$ is selected from azetidinyl and 2-oxa-6-azaspiro[3.3]heptanyl, each optionally substituted with 1 or 2 independently selected $R^{2A}$ substituents.

In some embodiments, each $R^{c2}$ and $R^{d2}$ is independently selected from H, $C_{1-6}$ alkyl, $C_{3-7}$ cycloalkyl and 4-7 membered heterocycloalkyl, wherein the $C_{1-6}$ alkyl, $C_{3-7}$ cycloalkyl and 4-7 membered heterocycloalkyl of $R^{c2}$ and $R^{d2}$ are each optionally substituted with 1 or 2 independently selected $R^{2A}$ substituents.

In some embodiments, $R^{c2}$ and $R^{d2}$, attached to the same N atom, together with the N atom to which they are attached, form a 4-7 membered heterocycloalkyl group, wherein the 4-7 membered heterocycloalkyl group is optionally substituted with 1 or 2 independently selected $R^{2A}$ substituents.

In some embodiments, each $R^{c2}$ and $R^{d2}$ is independently selected from H, methyl, ethyl, isopropyl, tetrahydropyranyl, bicyclo[1.1.1]pentanyl, cyclobuytl, bicycle[2.1.1]hexan-1yl, 2-oxa-6-azaspiro[3.3]heptanyl, sec-butyl, azetidinyl, and tetrahydrofuranyl, wherein each methyl, ethyl, isopropyl, tetrahydropyranyl, bicyclo[1.1.1]pentanyl, cyclobuytl, bicycle[2.1.1]hexan-1yl, 2-oxa-6-azaspiro[3.3]heptanyl, sec-butyl, azetidinyl, and tetrahydrofuranyl are optionally substituted with 1 or 2 independently selected $R^{2A}$ substituents;

or $R^{c2}$ and $R^{d2}$, attached to the same N atom, together with the N atom to which they are attached, form an azetidinyl or 2-oxa-6-azaspiro[3.3]heptanyl which are each optionally substituted with 1 or 2 independently selected $R^{2A}$ substituents.

In some embodiments, each $R^{2A}$ is independently selected from halo, $C_{1-6}$ alkyl, $C_{1-6}$ haloalkyl, CN, and OH.

In some embodiments, each $R^{2A}$ is independently selected from F, methyl, $CF_3$, CN, and OH.

In some embodiments, $R^{b2}$ is selected from azetidin-1-yl, 3,3-difluoroazetidin-1-yl, 3-hydroxyazetidin-1-yl and 2-oxa-6-azaspiro[3.3]heptan-6-yl.

In some embodiments, each $R^{c2}$ and $R^{d2}$ is independently selected from H, methyl, ethyl, isopropyl, tetrahydro-2H-pyran-4-yl, bicyclo[1.1.1]pentanyl, cyclobut-1-yl, 3-hydroxycyclobut-1-yl, 1,1,1-trifluoropropan-2-yl, 4-cyanobicyclo[2.1.1]hexan-1-yl, 2-oxaspiro[3.3]heptan-6-yl, sec-butyl, 1-methylazetidin-3-yl, and tetrahydrofuran-3-yl;

or $R^{c2}$ and $R^{d2}$, attached to the same N atom, together with the N atom to which they are attached, form an azetidin-1-yl, 3,3-difluoroazetidin-1-yl, 3-hydroxyazetidin-1-yl or 2-oxa-6-azaspiro[3.3]heptan-6-yl group.

In some embodiments, each $R^{c2}$ and $R^{d2}$ is independently selected from H, $C_{1-6}$ alkyl, and 4-6 membered heterocycloalkyl, wherein the $C_{1-6}$ alkyl and 4-6 membered heterocycloalkyl of $R^{c2}$ and $R^{d2}$ are each optionally substituted with 1 or 2 independently selected $R^{2A}$ substituents.

In some embodiments, each $R^{c2}$ and $R^{d2}$ is independently selected from H, $C_{1-6}$ alkyl, and 4-6 membered heterocycloalkyl. In some embodiments, each $R^{c2}$ and $R^{d2}$ is independently selected from H, methyl, isopropyl, and tetrahydropyranyl.

In some embodiments, $R^2$ is selected from $C_{1-6}$ alkyl and $C(O)NR^{c2}R^{d2}$, wherein $R^{c2}$ and $R^{d2}$ are each independently selected from H, $C_{1-6}$ alkyl, and 4-6 membered heterocycloalkyl.

In some embodiments, $R^2$ is selected from $C_{1-6}$ alkyl and $C(O)NR^{c2}R^{d2}$, wherein each $R^{c2}$ and $R^{d2}$ is independently selected from H, methyl, isopropyl, and tetrahydropyranyl.

In some embodiments, $R^2$ is selected from H, methyl, methylaminocarbonyl, dimethylaminocarbonyl, tetrahydropyranylaminocarbonyl, and isopropylaminocarbonyl.

In some embodiments, $R^2$ is selected from methyl, methylaminocarbonyl, dimethylaminocarbonyl, tetrahydropyranylaminocarbonyl, and isopropylaminocarbonyl.

In some embodiments, $R^2$ is selected from H, methyl, methylaminocarbonyl, dimethylaminocarbonyl, tetrahydropyranylaminocarbonyl, isopropylaminocarbonyl, bicyclo[1.1.1]pentan-1-ylcarbamoyl, 3,3-difluoroazetidine-1-carbonyl, 3-hydroxyazetidine-1-carbonyl, (3-hydroxycyclobutyl)carbamoyl, (1,1,1-trifluoropropan-2-yl)carbamoyl, (4-cyanobicyclo[2.1.1]hexan-1-yl)carbamoyl, (2-oxaspiro[3.3]heptan-6-yl)carbamoyl, azetidine-1-carbonyl, cyclobutylcarbamoyl, sec-butylcarbamoyl, (1-methylazetidin-3-yl)carbamoyl, (tetrahydrofuran-3-yl)carbamoyl, methyl(tetrahydro-2H-pyran-4-yl)carbamoyl, 2-oxa-6-azaspiro[3.3]heptane-6-carbonyl, aminocarbonyl, ethylaminocarbonyl, ethylmethylaminocarbonyl, isopropylmethylaminocarbonyl, and cyclobutylmethylaminocarbonyl In some embodiments, $X^3$ is N.

In some embodiments, $X^3$ is $CR^3$.

In some embodiments, $R^3$ is selected from H, D, halo, CN, OH, $NH_2$, $C_{1-6}$ alkyl, $C_{1-6}$ haloalkyl, $C_{2-6}$ alkenyl, and $C_{2-6}$ alkynyl.

In some embodiments, $R^3$ is selected from H, D, $C_{1-6}$ alkyl, $C_{1-6}$ haloalkyl, $C_{2-6}$ alkenyl, and $C_{2-6}$ alkynyl.

In some embodiments, $R^3$ is selected from H, D, halo, CN, OH, $NH_2$, and $C_{1-6}$ alkyl.

In some embodiments, $R^3$ is H or methyl.

In some embodiments, $X^3$ is CH.

In some embodiments, W is N.

In some embodiments, W is $CW^1$.

In some embodiments, $W^1$ is selected from H, D, $C_{1-3}$ alkyl, $C_{1-3}$ haloalkyl, $C_{2-3}$ alkenyl, and $C_{2-3}$ alkynyl.

In some embodiments, $W^1$ is H or methyl.

In some embodiments, W is CH.

In some embodiments, Z is N.

In some embodiments, Z is $CZ^1$.

In some embodiments, Z is selected from H, D, $C_{1-3}$ alkyl, $C_{1-3}$ haloalkyl, $C_{2-3}$ alkenyl, and $C_{2-3}$ alkynyl.

In some embodiments, $Z^1$ is H or methyl.

In some embodiments, Z is CH.

In some embodiments, $R^{12}$ is selected from H, D, $C_{1-3}$ alkyl, $C_{1-3}$ haloalkyl, $C_{2-3}$ alkenyl, and $C_{2-3}$ alkynyl.

In some embodiments, $R^{12}$ is H or methyl.

In some embodiments, $R^{12}$ is H.

In some embodiments, $X^4$ is N.

In some embodiments, $X^4$ is $CR^4$.

In some embodiments, $X^4$ is $CR^4$, wherein $R^4$ is selected from H, D, halo, CN, OH, $NH_2$, $C_{1-6}$ alkyl, $C_{1-6}$ haloalkyl, $C_{2-6}$ alkenyl, and $C_{2-6}$ alkynyl.

In some embodiments, $X^4$ is $CR^4$, wherein $R^4$ is selected from H, D, $C_{1-6}$ alkyl, $C_{1-6}$ haloalkyl, $C_{2-6}$ alkenyl, and $C_{2-6}$ alkynyl.

In some embodiments, $X^4$ is $CR^4$, wherein $R^4$ is selected from H, D, halo, CN, OH, $NH_2$, and $C_{1-6}$ alkyl.

In some embodiments, $X^4$ is CH.

In some embodiments, $X^5$ is N.

In some embodiments, $X^5$ is $CR^5$, wherein $R^5$ is selected from H, D, halo, CN, OH, $NH_2$, $C_{1-6}$ alkyl, $C_{1-6}$ haloalkyl, $C_{2-6}$ alkenyl, and $C_{2-6}$ alkynyl.

In some embodiments, $X^5$ is $CR^5$, wherein $R^5$ is selected from H, D, $C_{1-6}$ alkyl, $C_{1-6}$ haloalkyl, $C_{2-6}$ alkenyl, and $C_{2-6}$ alkynyl.

In some embodiments, $X^5$ is $CR^5$, wherein $R^5$ is selected from H, D, halo, CN, OH, $NH_2$, and $C_{1-6}$ alkyl.

In some embodiments, $X^5$ is CH.

In some embodiments, $X^6$ is N.

In some embodiments, $X^6$ is $CR^6$.

In some embodiments, $R^6$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)OR^{a6}$, $NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOH)R^{b6}$, $C(=NCN)R^{b6}$, $C(=NR^{e6})NR^{c6}R^{d6}$, $NR^{c6}C(=NR^{e6})NR^{c6}R^{d6}$, $NR^{c6}C(=NOH)NR^{c6}R^{d6}$, $NR^{c6}C(=NCN)NR^{c6}R^{d6}$, $NR^{c6}C(=NR^{e6})R^{b6}$, $NR^{c6}S(O)NR^{c6}R^{d6}$, $NR^{c6}S(O)R^{b6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $S(O)(=NR^{e6})R^{b6}$, $N=S(O)R^{a6}R^{b6}$, $OS(O)(=NR^{e6})R^{b6}$, $OS(O)_2R^{b6}$, and $SF_5$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, 4, 5, 6, 7, or 8 independently selected $R^{6A}$ substituents.

In some embodiments, $R^6$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $NR^{c6}C(O)OR^{a6}$, $NR^{c6}C(O)NR^{c6}R^{d6}$, $S(O)_2R^{b6}$, $S(O)(=NR^{e6})R^{b6}$, and $N=S(O)R^{a6}R^{b6}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^6$ are each optionally substituted with 1, 2, 3, or 4 independently selected $R^{6A}$ substituents;

each $R^{a6}$, $R^{b6}$, $R^{c6}$, $R^{d6}$ and $R^{e6}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{a6}$, $R^{b6}$, $R^{c6}$, $R^{d6}$ and $R^{e6}$ are each optionally substituted with 1, 2, 3, or 4 independently selected $R^{6A}$ substituents; and each $R^{6A}$ is independently selected from H, D, halo, CN, OH, $NH_2$, and $C_{1-6}$ alkyl.

In some embodiments, $R^6$ is selected from H, D, halo, $C_{1-6}$ alkyl, $C_{1-6}$ haloalkyl, $SR^{a6}$, $C(O)NR^{c6}R^{d6}$, $C(O)R^{b6}$, $S(O)_2R^{b6}$, $S(O)(=NR^{e6})R^{b6}$, and $N=S(O)R^{a6}R^{b6}$, wherein the $C_{1-6}$ alkyl is optionally substituted with 1, 2, 3, or 4 independently selected $R^{6A}$ substituents;

each $R^{a6}$, $R^{b6}$, $R^{c6}$, $R^{d6}$ and $R^{e6}$ are independently selected from H and $C_{1-6}$ alkyl; and each $R^{6A}$ is independently selected from H, D, halo, CN, OH, $NH_2$, and $C_{1-6}$ alkyl.

In some embodiments, $R^6$ is selected from H, halo, $C_{1-6}$ alkyl, $S(O)_2R^{b6}$, $S(O)(=NR^{e6})R^{b6}$ and $N=S(O)R^{a6}R^{b6}$, wherein the $C_{1-6}$ alkyl is optionally substituted with 1, 2, 3, or 4 independently selected $R^{6A}$ substituents;

each $R^{a6}$, $R^{b6}$, and $R^{e6}$ are independently selected from H and $C_{1-6}$ alkyl; and each $R^{6A}$ is OH.

In some embodiments, $R^6$ is selected from H, chloro, $S(O)_2CH_3$, 1,2-dihydroxyethyl, $S(O)(=NH)CH_3$, $S(O)(=NCH_3)CH_3$, and $N=S(O)(CH_3)_2$.

In some embodiments, $R^6$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NOH)R^{b6}$, $C(=NCN)R^{b6}$, $NR^{c6}C(=NOH)NR^{c6}R^{d6}$, $NR^{c6}C(=NCN)NR^{c6}R^{d6}$, $NR^{c6}S(O)$ $NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $OS(O)_2R^{b6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$ and $R^{d6}$ are each optionally substituted with 1, 2, 3, or 4 independently selected $R^{6A}$ substituents;

each $R^{6A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a61}$, $SR^{a61}$, $NHOR^{a61}$, $C(O)R^{b61}$, $C(O)NR^{c61}R^{d61}$, $C(O)NR^{c61}(OR^{a61})$, $C(O)OR^{a61}$, $OC(O)R^{b61}$, $OC(O)NR^{c61}R^{d61}$, $NR^{c61}R^{d61}$, $NR^{c61}NR^{c61}R^{d61}$, $NR^{c61}C(O)R^{b61}$, $NR^{c61}C(O)OR^{a61}$, $NR^{c61}C(O)NR^{c61}R^{d61}$, $C(=NOH)R^{b61}$, $C(=NCN)R^{b61}$, $NR^{c61}C(=NOH)NR^{c61}R^{d61}$, $NR^{c61}C(=NCN)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, $S(O)_2NR^{c61}R^{d61}$, and $OS(O)_2R^{b61}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$alkyl-, $C_{3-10}$ cycloalkyl-$C_{1-6}$ alkyl-, (5-10 membered heteroaryl)-$C_{1-6}$alkyl-, and (4-10 membered heterocycloalkyl)-$C_{1-6}$ alkyl- of $R^{6A}$ are each optionally substituted with 1, 2, 3, or 4 independently selected $R^M$ substituents; and wherein each $R^{a61}$, $R^{b61}$, $R^{c61}$, and $R^{d61}$ is independently selected from H and $C_{1-6}$ alkyl.

In some embodiments, $R^6$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $NR^{c6}C(O)OR^{a6}$, $NR^{c6}C(O)NR^{c6}R^{d6}$, and $S(O)_2R^{b6}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^6$ are each optionally substituted with 1, 2, 3, or 4 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{a6}$, $R^{b6}$, $R^{c6}$ and $R^{d6}$ are each optionally substituted with 1, 2, 3, or 4 independently selected $R^{6A}$ substituents; and each $R^{6A}$ is selected from H, D, halo, CN, OH, $NH_2$, and $C_{1-6}$ alkyl.

In some embodiments, $R^6$ is selected from H, D, halo, $C_{1-6}$ alkyl, $C_{1-6}$ haloalkyl, $SR^{a6}$, $C(O)NR^{c6}R^{d6}$, $C(O)R^{b6}$, and $S(O)_2R^{b6}$, wherein the $C_{1-6}$ alkyl is optionally substituted with 1, 2, 3, or 4 independently selected $R^{6A}$ substituents;

each $R^{a6}$, $R^{b6}$, $R^{c6}$ and $R^{d6}$ is independently selected from H and $C_{1-6}$ alkyl; and each $R^{6A}$ is selected from H, D, halo, CN, OH, $NH_2$, and $C_{1-6}$ alkyl.

In some embodiments, $R^6$ is selected from H, D, halo, $C_{1-6}$ alkyl, $C_{1-6}$ haloalkyl, $C_{2-6}$ alkenyl, $C_{2-6}$ alkynyl, $S(O)R^{b6}$, $S(O)NR^{c6}R^{d6}$, $S(O)_2R^{b6}$, and $S(O)_2NR^{c6}R^{d6}$.

In some embodiments, $R^6$ is selected from H, halo, $C_{1-6}$ alkyl, $S(O)R^{b6}$, and $S(O)_2R^{b6}$, and $R^{b6}$ is selected from H, $C_{1-6}$ alkyl, $C_{1-6}$ haloalkyl, $C_{2-6}$ alkenyl, and $C_{2-6}$ alkynyl.

In some embodiments, each $R^{b6}$, $R^{c6}$, and $R^{d6}$ is independently selected from H, $C_{1-6}$ alkyl, $C_{1-6}$ haloalkyl, $C_{2-6}$ alkenyl, and $C_{2-6}$ alkynyl.

In some embodiments, $R^6$ is selected from H, D, halo, $C_{1-6}$ alkyl, $SR^{a6}$, $C(O)R^{b6}$, and $S(O)_2R^{b6}$, wherein the $C_{1-6}$ alkyl is optionally substituted with 1, 2, 3, or 4 independently selected $R^{6A}$ substituents;

each $R^{a6}$ and $R^{b6}$ is independently selected from H and $C_{1-6}$ alkyl; and each $R^{6A}$ is selected from H, D, halo, CN, OH, $NH_2$, and $C_{1-6}$ alkyl.

In some embodiments, $R^6$ is selected from H, halo, and $S(O)_2R^{b6}$, wherein $R^{b6}$ is $C_{1-6}$ alkyl.

In some embodiments, $R^6$ is selected from H, D, halo, methyl, $C(CH_3)_2OH$, $CH(CH_3)OH$, $C(O)CH_3$, $S(O)_2CH_3$, and $SCH_3$.

In some embodiments, $R^6$ is selected from D, halo, methyl, $C(CH_3)_2OH$, $CH(CH_3)OH$, $C(O)CH_3$, $S(O)_2CH_3$, and $SCH_3$.

In some embodiments, $R^6$ is $CH(OH)$—$CH_2OH$.

In some embodiments, $R^6$ is $C(CH_3)(OH)$—$CH_2OH$.

In some embodiments, $R^6$ is $C(OH)(C_1\text{-haloalkyl})$-$CH_2OH$.

In some embodiments, $R^6$ is $C(OH)(S(=O)R^{b6})$—$CH_2OH$.

In some embodiments, $R^6$ is $C(OH)(C_1\text{-haloalkyl})$-$C(O)NH_2$.

In some embodiments, $R^6$ is $C(O)NH_2$.

In some embodiments, $R^6$ is methyl.

In some embodiments, $R^6$ is H.

In some embodiments, $R^6$ is a $C(OH)(R^{6A})_2$, wherein at least one $R^{6A}$ is $C_{1-6}$ haloalkyl. In some embodiments, $R^6$ is a $C(OH)(R^{6A})_2$, wherein at least one $R^{6A}$ is $C_{1-6}$ haloalkyl and each halogen of the haloalkyl group of $R^{6A}$ is F. In some embodiments, $R^6$ is a $C(OH)(R^{6A})_2$, wherein at least one $R^{6A}$ is $C_{1-6}$ haloalkyl and the haloalkyl group of $R^{6A}$ is optionally substituted with 1 or 2 independently selected $Y^2$ substituents.

In some embodiments, each $Y^2$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, at least one $R^{6A}$ is selected from $CF_3$, $CCl_3$, $CF_2H$, $CCl_2H$, $CF_2Y^2$, $CCl_2Y^2$, $CFH_2$, $CClH_2$, $CFHY^2$, $CClHY^2$, $CF(Y^2)_2$ and $CCl(Y^2)_2$.

In some embodiments, at least one $R^{6A}$ is selected from $CF_3$, $CF_2H$, $CF_2Y^2$, $CFH_2$, $CFHY^2$, and $CF(Y^2)_2$.

In some embodiments, at least one $R^{6A}$ is $C_{1-6}$ haloalkyl, wherein each halogen is F.

In some embodiments, at least one $R^{6A}$ is $C_{1-6}$ haloalkyl, wherein each halogen is Cl.

In some embodiments, at least one $R^{6A}$ is selected from $CH_2F$, $CHF_2$, $CF_3$, and $CF_2CF_3$.

In some embodiments, at least one $R^{6A}$ is $CF_3$.
In some embodiments, at least one $R^{6A}$ is $CH_2F$.
In some embodiments, at least one $R^{6A}$ is $CHF_2$.
In some embodiments, at least one $R^{6A}$ is $CF_2CF_3$.

In some embodiments, $R^6$ is selected from H, chloro, and $S(O)_2CH_3$.

In some embodiments, $X^7$ is N.
In some embodiments, $X^7$ is C.
In some embodiments, $X^8$ is N.
In some embodiments, $X^8$ is C.
In some embodiments, both $X^7$ and $X^8$ are C.
In some embodiments, $X^7$ is N and $X^8$ is C.
In some embodiments, $X^7$ is C and $X^8$ is N.
In some embodiments, $X^9$ is $NR^{9N}$.
In some embodiments, $X^9$ is N.
In some embodiments, $X^9$ is O.
In some embodiments, $X^9$ is S.
In some embodiments, $X^9$ is S(O).
In some embodiments, $X^9$ is $S(O)_2$.
In some embodiments, $X^9$ is $CR^9$.
In some embodiments, $X^9$ is $C(R^9)_2$.

In some embodiments, each $R^9$ is independently selected from H, D, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl, of $R^9$ are each optionally substituted with 1, 2, 3, or 4 independently selected $R^{9A}$ substituents; or, alternatively, two $R^9$ groups together form an oxo group.

In some embodiments, each $R^9$ is H.

In some embodiments, $X^9$ is $CR^9$, wherein $R^9$ is selected from H, D, halo, CN, OH, $NH_2$, and $C_{1-6}$ alkyl.

In some embodiments, $X^9$ is CH.
In some embodiments, $X^9$ is C(O).
In some embodiments, $X^{10}$ is $NR^{10N}$.

In some embodiments, $R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, $C(O)R^{b10N}$, $C(O)NR^{c10N}R^{d10N}$, $C(O)OR^{a10N}$, $C(=NCN)NR^{c10N}R^{d10N}$, $C(=NOR^{a10N})NR^{c10N}$, $S(O)_2R^{b10N}$, $S(O)(=NR^{c10N})R^{d10N}$, and $S(O)_2NR^{c10N}R^{d10N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, or 4 independently selected $R^{10NA}$ substituents;

each $R^{a10N}$, $R^{b10N}$, $R^{c10N}$, and $R^{d10N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a10N}$, $R^{b10N}$, $R^{c10N}$, and $R^{d10N}$ are each optionally substituted with 1, 2, 3, or 4 independently selected $R^{10NA}$ substituents;

each $R^{10NA}$ is selected from H, D, halo, CN, OH, $NH_2$, $C_{1-6}$ alkyl, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-.

In some embodiments, $R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, or 4 independently selected $R^{10NA}$ substituents.

In some embodiments, $R^{10N}$ is selected from $C_{1-6}$ alkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the $C_{1-6}$ alkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl- and (4-6 membered heterocycloalkyl)-$C_{1-6}$ alkyl- of $R^{10N}$ are each optionally substituted with 1 or 2 independently selected $R^{10NA}$ substituents.

In some embodiments, $R^{10N}$ is selected from $C_{1-6}$ alkyl, $C_{3-6}$ cycloalkyl, and $C_{3-6}$ cycloalkyl-$C_{1-6}$ alkyl-, wherein the $C_{1-6}$ alkyl, $C_{3-6}$ cycloalkyl, and $C_{3-6}$ cycloalkyl-$C_{1-6}$ alkyl- of $R^{10N}$ are each optionally substituted with 1 or 2 independently selected $R^{10NA}$ substituents.

In some embodiments, $R^{10N}$ is selected from H, $C_{1-6}$ alkyl, $C_{6-10}$ aryl-$C_{1-6}$ alkyl-, and $C_{3-10}$ cycloalkyl-$C_{1-6}$ alkyl-.

In some embodiments, $R^{10N}$ is $C_{3-6}$ cycloalkyl-$C_{1-6}$ alkyl-.
In some embodiments, $R^{10N}$ is cyclopropylethyl.
In some embodiments, $R^{10N}$ is 1-cyclopropylethyl.
In some embodiments, $R^{10N}$ is (S)-1-cyclopropylethyl.
In some embodiments, $X^{10}$ is N.
In some embodiments, $X^{10}$ is O.
In some embodiments, $X^{10}$ is S.
In some embodiments, $X^{10}$ is $CR^{10}$.
In some embodiments, $X^{10}$ is $C(R^{10})_2$.

In some embodiments, $X^{10}$ is $CR^{10}$, wherein $R^{10}$ is selected from H, D, halo, CN, OH, $NH_2$, and $C_{1-6}$ alkyl.

In some embodiments, $X^{10}$ is CH.

In some embodiments, $X^{10}$ is $C(R^{10})$, wherein each $R^{10}$ is independently selected from H, D, halo, CN, OH, $NH_2$, and $C_{1-6}$ alkyl.

In some embodiments, two $R^{10}$ groups together form an oxo group.

In some embodiments, $X^{11}$ is $NR^{11N}$.
In some embodiments, $X^{11}$ is N.
In some embodiments, $X^{11}$ is O.
In some embodiments, $X^{11}$ is S.
In some embodiments, $X^{11}$ is $CR^{11}$.

In some embodiments, $X^{11}$ is $C(R^{11})_2$.

In some embodiments, each $R^{11}$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^{11}$ are each optionally substituted with 1, 2, 3, or 4 independently selected $R^{11A}$ substituents.

In some embodiments, $X^{11}$ is $CR^{11}$, wherein $R^{11}$ is selected from H, D, halo, CN, OH, $NH_2$, and $C_{1-6}$ alkyl.

In some embodiments, $X^{11}$ is CH.

In some embodiments, $X^{11}$ is $C(R^{11})_2$, wherein each $R^{11}$ is independently selected from H, D, halo, CN, OH, $NH_2$, and $C_{1-6}$ alkyl.

In some embodiments, two $R^{11}$ groups together form an oxo group.

In some embodiments, $X^{11}$ is $CH_2$.

In some embodiments, $X^1$ is $CR^1$; $X^2$ is $CR^2$; and $X^3$ is N.

In some embodiments, $X^1$ is N; $X^2$ is $CR^2$; and $X^3$ is N.

In some embodiments, $X^1$ is $CR^1$; $X^2$ is N; and $X^3$ is N.

In some embodiments, W is $CW^1$; and Z is $CZ^1$.

In some embodiments, W is N; and Z is $CZ^1$.

In some embodiments, W is $CW^1$; and Z is N.

In some embodiments, $X^1$ is $CR^1$; $X^2$ is $CR^2$; $X^3$ is N; W is $CW^1$; and Z is $CZ^1$.

In some embodiments:
$X^7$ is N or C;
$X^8$ is N or C;
$X^9$ is N or $C(R^9)_2$;
$X^{10}$ is N or $NR^{10N}$; and
$X^{11}$ is N, $CR^{11}$, or $C(R^{11})_2$.

In some embodiments:
$X^7$ is C;
$X^8$ is C;
$X^9$ is N or $C(R^9)_2$;
$X^{10}$ is N or $NR^{10N}$; and
$X^{11}$ is N, $CR^{11}$, or $C(R^{11})_2$.

In some embodiments:
each bond symbol represented by ====== is independently a single or double bond;
$X^1$ is N or $CR^1$;
$R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, $NR^{c1}C(O)NR^{c1}R^{d1}$, $S(O)R^{b1}$, $S(O)NR^{c1}R^{d1}$, $S(O)_2R^{b1}$, and $S(O)_2NR^{c1}R^{d1}$;

$X^2$ is N or $CR^2$;
$R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{c2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}C(O)R^{b2}$, $NR^{c2}C(O)OR^{a2}$, $NR^{c2}C(O)NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a2}$, $R^{b2}$, $R^{c2}$ and $R^{d2}$ are each optionally substituted with 1 or 2 independently selected $R^{2A}$ substituents;

$X^3$ is N or $CR^3$;
W is N or $CW^1$;
$W^1$ is selected from H, D, $C_{1-3}$ alkyl, $C_{1-3}$ haloalkyl, $C_{2-3}$ alkenyl, and $C_{2-3}$ alkynyl;
Z is N or $CZ^1$;
$Z^1$ is selected from H, D, $C_{1-3}$ alkyl, $C_{1-3}$ haloalkyl, $C_{2-3}$ alkenyl, and $C_{2-3}$ alkynyl;
$R^{12}$ is selected from H, D, $C_{1-3}$ alkyl, $C_{1-3}$ haloalkyl, $C_{2-3}$ alkenyl, and $C_{2-3}$ alkynyl.

$X^4$ is N or $CR^4$;
$X^5$ is N or $CR^5$;
$R^4$ and $R^5$ are each independently selected from H, D, $C_{1-6}$ alkyl, $C_{1-6}$ haloalkyl, $C_{2-6}$ alkenyl, and $C_{2-6}$ alkynyl;
$X^6$ is N or $CR^6$;
$R^6$ is selected from H, D, halo, $C_{1-6}$ alkyl, $C_{1-6}$ haloalkyl, $C_{2-6}$ alkenyl, $C_{2-6}$ alkynyl, $S(O)R^{b6}$, $S(O)NR^{c6}R^{d6}$, $S(O)_2R^{b6}$, and $S(O)_2NR^{c6}R^{d6}$;
each $R^{b6}$, $R^{c6}$, and $R^{d6}$ is independently selected from H, $C_{1-6}$ alkyl, $C_{1-6}$ haloalkyl, $C_{2-6}$ alkenyl, and $C_{2-6}$ alkynyl;
$X^7$ is N or C;
$X^8$ is N or C;
$X^9$ is N or $C(R^9)_2$;
$X^{10}$ is N or $NR^{10N}$;
$X^{11}$ is N or $C(R^{11})_2$;
wherein no more than three of $X^4$, $X^5$, $X^6$, $X^7$, and $X^8$ are simultaneously N; and at least two of $X^7$, $X^8$, $X^9$, and $X^{11}$ are independently selected from C, $C(R^9)_2$, and $C(R^{11})_2$;
provided that (a) when $X^7$ is N, then $X^8$ is C; or (b) when $X^8$ is N, then $X^7$ is C;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^9$ are each optionally substituted with 1, 2, 3, or 4 independently selected $R^{9A}$ substituents; or, alternatively, two $R^9$ groups together form an oxo group;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, or 4 independently selected $R^{10NA}$ substituents; and each $R^{11}$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^{11}$ are each optionally substituted with 1, 2, 3, or 4 independently selected $R^{11A}$ substituents.

In some embodiments:
each bond symbol represented by ====== is independently a single or double bond;
$X^1$ is $CR^1$;
$R^1$ is selected from H and $C_{1-6}$ alkyl;
$X^2$ is $CR^2$;
$R^2$ is selected from H, $C_{1-6}$ alkyl, $C(O)R^{b2}$, $C(O)NR^{c2}R^{d2}$, $NR^{c2}C(O)R^{b2}$, $NR^{c2}C(O)OR^{a2}$, and $NR^{c2}C(O)NR^{c2}R^{d2}$;
each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, and 4-6 membered heterocycloalkyl, wherein the $C_{1-6}$ alkyl, $C_{2-6}$ alkenyl, $C_{2-6}$ alkynyl, and 4-6 membered heterocycloalkyl of $R^{a2}$, $R^{b2}$, $R^{c2}$ and $R^{d2}$ are each optionally substituted with 1 or 2 independently selected $R^{24}$ substituents;

$X^3$ is N;

W is $CW^1$;

$W^1$ is selected from H, D, $C_{1-3}$ alkyl, $C_{1-3}$ haloalkyl, $C_{2-3}$ alkenyl, and $C_{2-3}$ alkynyl;

Z is $CZ^1$;

$Z^1$ is selected from H, D, $C_{1-3}$ alkyl, $C_{1-3}$ haloalkyl, $C_{2-3}$ alkenyl, and $C_{2-3}$ alkynyl;

$R^{12}$ is H or methyl;

$X^4$ is $CR^4$;

$X^5$ is $CR^5$;

$R^4$ and $R^5$ are each independently selected from H, D, $C_{1-6}$ alkyl, $C_{1-6}$ haloalkyl, $C_{2-6}$ alkenyl, and $C_{2-6}$ alkynyl;

$X^6$ is $CR^6$;

$R^6$ is selected from H, halo, $C_{1-6}$ alkyl, $S(O)R^{b6}$, and $S(O)_2R^{b6}$;

$X^7$ is C;

$X^8$ is C;

$X^9$ is $C(R^9)_2$;

$X^{10}$ is $NR^{10N}$;

$X^{11}$ is $C(R^{11})_2$;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^9$ are each optionally substituted with 1, 2, 3, or 4 independently selected $R^{9A}$ substituents; or, alternatively, two $R^9$ groups together form an oxo group;

$R^{10N}$ is selected from $C_{1-6}$ alkyl, $C_{3-6}$ cycloalkyl, and $C_{3-6}$ cycloalkyl-$C_{1-6}$ alkyl-, wherein the $C_{1-6}$ alkyl, $C_{3-6}$ cycloalkyl, and $C_{3-6}$ cycloalkyl-$C_{1-6}$ alkyl- of $R^{10N}$ are each optionally substituted with 1 or 2 independently selected $R^{10NA}$ substituents; and each $R^{11}$ is independently selected from H, D, $C_{1-6}$ alkyl, $C_{1-6}$ haloalkyl, $C_{2-6}$ alkenyl, $C_{2-6}$ alkynyl.

In some embodiments, the compound of Formula (I) is a compound of Formula (Ib):

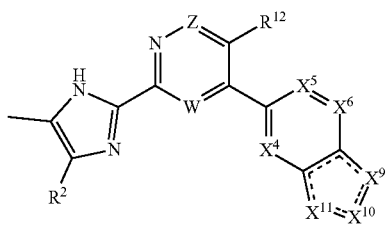

(Ib)

or a pharmaceutically acceptable salt thereof.

In some embodiments, the compound of Formula (I) is a compound of Formula (II):

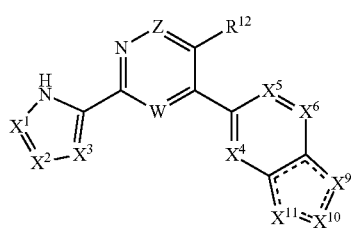

(II)

or a pharmaceutically acceptable salt thereof.

In some embodiments, the compound of Formula (I) is a compound of Formula (IIb):

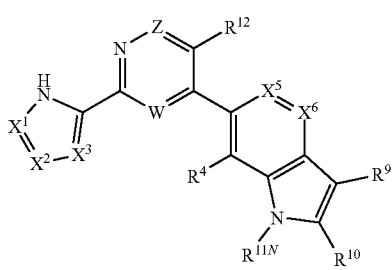

(IIb)

or a pharmaceutically acceptable salt thereof.

In some embodiments, the compound of Formula (I) is a compound of Formula (IIc):

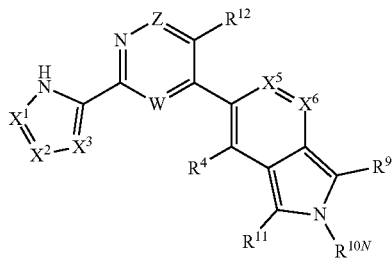

(IIc)

or a pharmaceutically acceptable salt thereof.

In some embodiments, the compound of Formula (I) is a compound of Formula (IId):

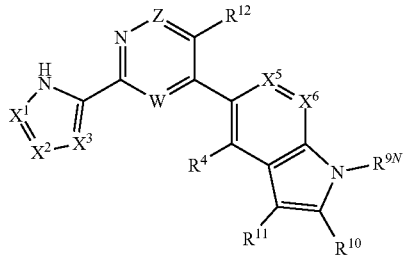

(IId)

or a pharmaceutically acceptable salt thereof.

In some embodiments, the compound of Formula (I) is a compound of Formula (IIe):

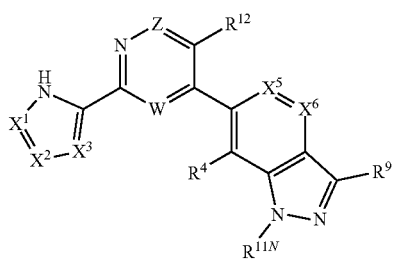

(IIe)

or a pharmaceutically acceptable salt thereof.

In some embodiments, the compound of Formula (I) is a compound of Formula (IIf):

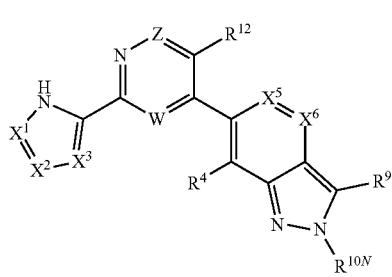
(IIf)

or a pharmaceutically acceptable salt thereof.

In some embodiments, the compound of Formula (I) is a compound of Formula (IIg):

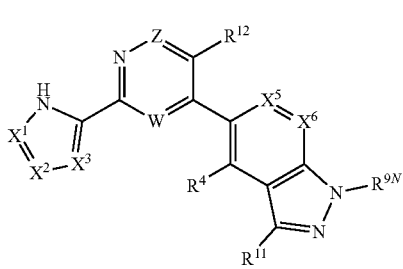
(IIg)

or a pharmaceutically acceptable salt thereof.

In some embodiments, the compound of Formula (I) is a compound of Formula (IIh):

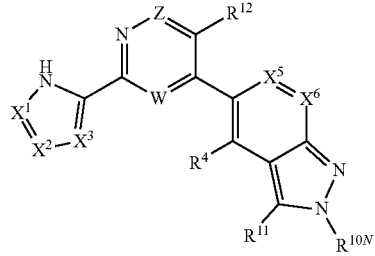
(IIh)

or a pharmaceutically acceptable salt thereof.

In some embodiments, the compound of Formula (I) is a compound of Formula (IIi):

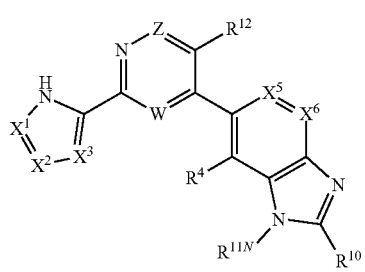
(IIi)

or a pharmaceutically acceptable salt thereof.

In some embodiments, the compound of Formula (I) is a compound of Formula (IIj):

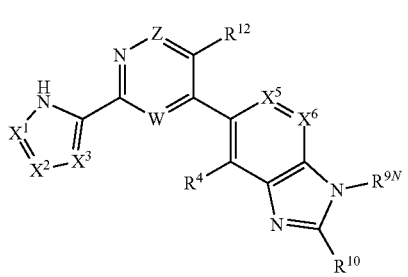
(IIj)

or a pharmaceutically acceptable salt thereof.

In some embodiments, the compound of Formula (I) is a compound of Formula (IIk):

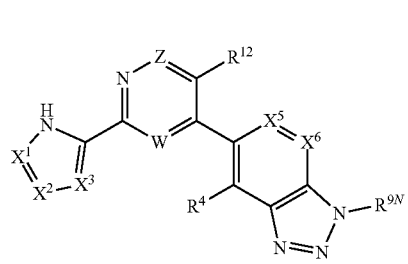
(IIk)

In some embodiments, the compound of Formula (I) is a compound of Formula (IIm):

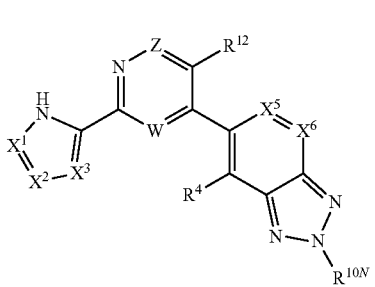
(IIm)

or a pharmaceutically acceptable salt thereof.

In some embodiments, the compound of Formula (I) is a compound of Formula (IIn):

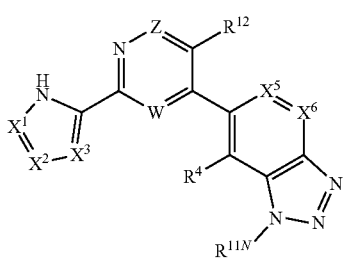
(IIn)

or a pharmaceutically acceptable salt thereof.

In some embodiments, the compound of Formula (I) is a compound of Formula (IIo):

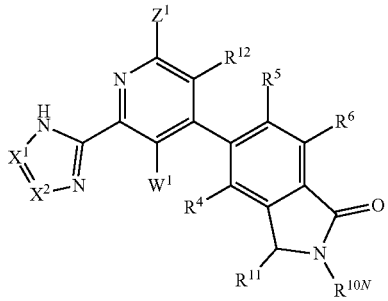

(IIo)

or a pharmaceutically acceptable salt thereof.

In some embodiments of Formula (IIo), $X^1$ is $CR^1$ and $X^2$ is $CR^2$.

In some embodiments of Formula (IIo), $X^1$ is N and $X^2$ is $CR^2$.

In some embodiments of Formula (IIo), $X^1$ is $CR^1$ and $X^2$ is N.

In some embodiments of Formula (IIo):

$X^1$ is N or $CR^1$;

$R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, $NR^{c1}C(O)NR^{c1}R^{d1}$, $S(O)R^{b1}$, $S(O)NR^{c1}R^{d1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $X^2$ is N or $CR^2$;

$R^2$ is H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{c2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}C(O)R^{b2}$, $NR^{c2}C(O)OR^{a2}$, $NR^{c2}C(O)NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a2}$, $R^{b2}$, $R^{c2}$ and $R^{d2}$ are each optionally substituted with 1 or 2 independently selected $R^{2A}$ substituents;

each $R^{2A}$ is selected from H, D, halo, $C_{1-6}$ alkyl, $C_{1-6}$ haloalkyl, $C_{2-6}$ alkenyl, and $C_{2-6}$ alkyny;

$W^1$, $Z^1$, and $R^{12}$ are each independently selected from H, D, $C_{1-3}$ alkyl, $C_{1-3}$ haloalkyl, $C_{2-3}$ alkenyl, and $C_{2-3}$ alkynyl;

$R^4$ and $R^5$ are each independently selected from H, D, halo, CN, OH, $NH_2$, and $C_{1-6}$ alkyl;

$R^6$ is selected from H, D, halo, $C_{1-6}$ alkyl, $SR^{a6}$, $C(O)R^{b6}$, and $S(O)_2R^{b6}$, wherein the $C_{1-6}$ alkyl is optionally substituted with 1, 2, 3, or 4 independently selected $R^{6A}$ substituents;

each $R^{a6}$ and $R^{b6}$ is independently selected from H and $C_{1-6}$ alkyl;

each $R^{6A}$ is selected from H, D, halo, CN, OH, $NH_2$, and $C_{1-6}$ alkyl;

$R^{10N}$ is selected from $C_{1-6}$ alkyl, $C_{3-6}$ cycloalkyl, and $C_{3-6}$ cycloalkyl-$C_{1-6}$ alkyl-, wherein the $C_{1-6}$ alkyl, $C_{3-6}$ cycloalkyl, and $C_{3-6}$ cycloalkyl-$C_{1-6}$ alkyl- of $R^{10N}$ are each optionally substituted with 1 or 2 independently selected $R^{10NA}$ substituents;

each $R^{10NA}$ is selected from H, D, halo, CN, OH, $NH_2$, $C_{1-6}$ alkyl, $C_{1-6}$ alkyl, $C_{1-6}$ haloalkyl, $C_{2-6}$ alkenyl, and $C_{2-6}$ alkynyl; and $R^{11}$ is selected from H, D, halo, CN, OH, $NH_2$, and $C_{1-6}$ alkyl;

or, alternatively, two $R^{11}$ groups together form an oxo group.

In some embodiments, the compound of Formula (I) is a compound of Formula (IIp):

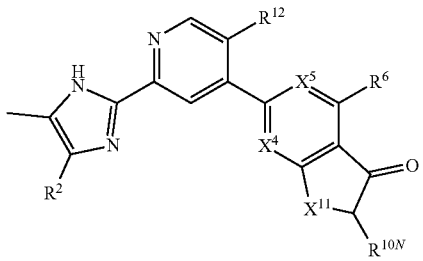

(IIp)

or a pharmaceutically acceptable salt thereof.

In some embodiments of Formula (IIp), $X^4$ is $CR^4$; $X^5$ is $CR^5$; and $X^{11}$ is N, NH, $CR^{11}$, or $C(R^{11})_2$.

In some embodiments of Formula (IIp), $X^4$ is $CR^4$; $X^5$ is N; and $X^{11}$ is N, NH, $CR^{11}$, or $C(R^{11})_2$.

In some embodiments of Formula (IIp), $X^4$ is N; $X^5$ is $CR^5$; and $X^{11}$ is N, NH, $CR^{11}$, or $C(R^{11})_2$.

In some embodiments of Formula (IIp), $X^4$ is N; $X^5$ is N; and $X^{11}$ is N, NH, $CR^{11}$, or $C(R^{11})_2$.

In some embodiments of Formula (IIp), $X^4$ is $CR^4$; $X^5$ is CR; and $X^{11}$ is $C(R^{11})_2$.

In some embodiments of Formula (IIp), $X^4$ is $CR^4$; $X^5$ is N; and $X^{11}$ is $C(R^{11})_2$.

In some embodiments of Formula (IIp), $X^4$ is N; $X^5$ is CR; and $X^{11}$ is $C(R^{11})_2$.

In some embodiments of Formula (IIp), $X^4$ is N; $X^5$ is N; and $X^{11}$ is $C(R^{11})_2$.

In some embodiments of Formula (IIp):

$R^2$ is H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{c2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}C(O)R^{b2}$, $NR^{c2}C(O)OR^{a2}$, $NR^{c2}C(O)NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a2}$, $R^{b2}$, $R^{c2}$ and $R^{d2}$ are each optionally substituted with 1 or 2 independently selected $R^{2A}$ substituents;

each $R^{2A}$ is selected from H, D, halo, $C_{1-6}$ alkyl, $C_{1-6}$ haloalkyl, $C_{2-6}$ alkenyl, and $C_{2-6}$ alkyny;

$R^{12}$ is selected from H, D, $C_{1-3}$ alkyl, $C_{1-3}$ haloalkyl, $C_{2-3}$ alkenyl, and $C_{2-3}$ alkynyl;

$X^4$ is N or $CR^4$;

$X^5$ is N or $CR^5$;

$R^4$ and $R^5$ are each independently selected from H, D, halo, CN, OH, $NH_2$, and $C_{1-6}$ alkyl;

$R^6$ is selected from H, D, halo, $C_{1-6}$ alkyl, $SR^{a6}$, $C(O)R^{b6}$, and $S(O)_2R^{b6}$, wherein the $C_{1-6}$ alkyl is optionally substituted with 1, 2, 3, or 4 independently selected $R^{6A}$ substituents;

each $R^{a6}$ and $R^{b6}$ is independently selected from H and $C_{1-6}$ alkyl;

each $R^{6A}$ is selected from H, D, halo, CN, OH, $NH_2$, and $C_{1-6}$ alkyl;

$R^{10N}$ is selected from $C_{1-6}$ alkyl, $C_{3-6}$ cycloalkyl, and $C_{3-6}$ cycloalkyl-$C_{1-6}$ alkyl-, wherein the $C_{1-6}$ alkyl, $C_{3-6}$ cycloalkyl, and $C_{3-6}$ cycloalkyl-$C_{1-6}$ alkyl- of $R^{10N}$ are each optionally substituted with 1 or 2 independently selected $R^{10NA}$ substituents;

each $R^{10NA}$ is selected from H, D, halo, CN, OH, $NH_2$, $C_{1-6}$ alkyl, $C_{1-6}$ alkyl, $C_{1-6}$ haloalkyl, $C_{2-6}$ alkenyl, and $C_{2-6}$ alkynyl; and $R^{11}$ is selected from H, D, halo, CN, OH, $NH_2$, and $C_{1-6}$ alkyl;

or, alternatively, two $R^{11}$ groups together form an oxo group.

In some embodiments, the compound of Formula (I) is a compound of Formula (IIq):

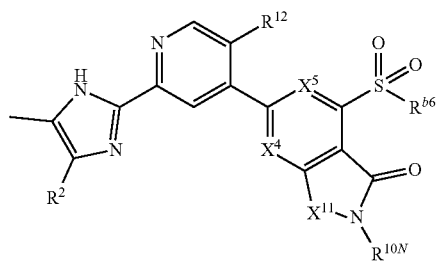

(IIq)

or a pharmaceutically acceptable salt thereof.

In some embodiments of Formula (IIq), $X^4$ is $CR^4$; $X^5$ is $CR^5$; and $X^{11}$ is N, NH, $CR^{11}$, or $C(R^{11})_2$.

In some embodiments of Formula (IIq), $X^4$ is $CR^4$; $X^5$ is N; and $X^{11}$ is N, NH, $CR^{11}$, or $C(R^{11})_2$.

In some embodiments of Formula (IIq), $X^4$ is N; $X^5$ is $CR^5$; and $X^{11}$ is N, NH, $CR^{11}$, or $C(R^{11})_2$.

In some embodiments of Formula (IIq), $X^4$ is N; $X^5$ is N; and $X^{11}$ is N, NH, $CR^{11}$, or $C(R^{11})_2$.

In some embodiments of Formula (IIq), $X^4$ is $CR^4$; $X^5$ is $CR^5$; and $X^{11}$ is $C(R^{11})_2$.

In some embodiments of Formula (IIq), $X^4$ is $CR^4$; $X^5$ is N; and $X^{11}$ is $C(R^{11})_2$.

In some embodiments of Formula (IIq), $X^4$ is N; $X^5$ is $CR^5$; and $X^{11}$ is $C(R^{11})_2$.

In some embodiments of Formula (IIq), $X^4$ is N; $X^5$ is N; and $X^{11}$ is $C(R^{11})_2$.

In some embodiments of Formula (IIq):

$R^2$ is H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{c2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}C(O)R^{b2}$, $NR^{c2}C(O)OR^{a2}$, $NR^{c2}C(O)NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a2}$, $R^{b2}$, $R^{c2}$ and $R^{d2}$ are each optionally substituted with 1 or 2 independently selected $R^{2A}$ substituents;

each $R^{2A}$ is selected from H, D, halo, $C_{1-6}$ alkyl, $C_{1-6}$ haloalkyl, $C_{2-6}$ alkenyl, and $C_{2-6}$ alkyny;

$R^{12}$ is selected from H, D, $C_{1-3}$ alkyl, $C_{1-3}$ haloalkyl, $C_{2-3}$ alkenyl, and $C_{2-3}$ alkynyl;

$X^4$ is N or $CR^4$;

$X^5$ is N or $CR^5$;

$R^4$ and $R^5$ are each independently selected from H, D, halo, CN, OH, $NH_2$, and $C_{1-6}$ alkyl;

$R^{10N}$ is selected from $C_{1-6}$ alkyl, $C_{3-6}$ cycloalkyl, and $C_{3-6}$ cycloalkyl-$C_{1-6}$ alkyl-, wherein the $C_{1-6}$ alkyl, $C_{3-6}$ cycloalkyl, and $C_{3-6}$ cycloalkyl-$C_{1-6}$ alkyl- of $R^{10N}$ are each optionally substituted with 1 or 2 independently selected $R^{10NA}$ substituents;

each $R^{10NA}$ is selected from H, D, halo, CN, OH, $NH_2$, $C_{1-6}$ alkyl, $C_{1-6}$ alkyl, $C_{1-6}$ haloalkyl, $C_{2-6}$ alkenyl, and $C_{2-6}$ alkynyl; and $R^{11}$ is selected from H, D, halo, CN, OH, $NH_2$, and $C_{1-6}$ alkyl;

or, alternatively, two $R^{11}$ groups together form an oxo group.

In some embodiments, the compound of Formula (I) is a compound of Formula (IIu):

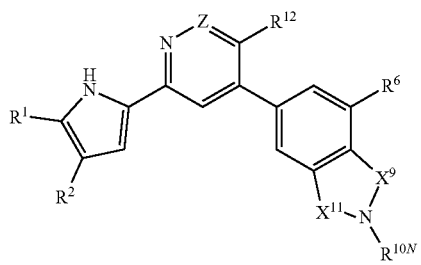

(IIu)

or a pharmaceutically acceptable salt thereof.

In some embodiments of Formula (IIu):

Z is $CZ^1$ or N;

$Z^1$ and $R^{12}$ are each independently selected from H, D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-6}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1N}R^{c1}R^{d1}$, $NR^{c1}C(O)R^{b1}$, $NR^{c1}C(O)OR^{a1}$, and $NR^{c1}C(O)NR^{c1}R^{d1}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^{1A}$ substituents;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{b1}$, $R^{c1}$ and $R^{d1}$ are each optionally substituted with 1, 2, 3, 4, 5, 6, 7, or 8 independently selected $R^{1A}$ substituents;

or, any $R^{c1}$ and $R^{d1}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{1A}$ substituents;

each $R^{1A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{d11}$, $NR^{c11}C(O)R^{b11}$, $NR^{c11}C(O)OR^{a11}$, and $NR^{c11}C(O)NR^{c11}R^{d11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1A}$ are each optionally substituted with 1, 2, 3, 4, 5, 6, 7, or 8 independently selected $R^M$ substituents;

each $R^{a11}$, $R^{b11}$, $R^{c111}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{b11}$, $R^{c11}$ and $R^{d11}$ are each optionally substituted with 1, 2, 3, 4, 5, 6, 7, or 8 independently selected $R^M$ substituents;

or, any $R^{c11}$ and $R^{d11}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^M$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{13}$_alkyl, $C_{3-6}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{c2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, and $NR^{c2}C(O)NR^{c2}R^{d2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, 6, 7, or 8 independently selected $R^{2A}$ substituents;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{b2}$, $R^{c2}$ and $R^{d2}$ are each optionally substituted with 1, 2, 3, 4, 5, 6, 7, or 8 independently selected $R^{2A}$ substituents;

or, any $R^{c2}$ and $R^{d2}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{2A}$ substituents;

each $R^{2A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$alkyl-, (4-10 membered heterocycloalkyl)-C$_{1-6}$ alkyl-, CN, NO$_2$, OR$^{a21}$, SR$^{a21}$, NHOR$^{a21}$, C(O)R$^{b21}$, C(O)NR$^{c21}$R$^{d21}$, C(O)NR$^{c21}$(OR$^{a21}$), C(O)OR$^{a21}$, OC(O)R$^{b21}$, OC(O)NR$^{c21}$R$^{d21}$, NR$^{c21}$R$^{d21}$, NR$^{c21}$NR$^{c21}$R$^{d21}$, NR$^{c21}$C(O)R$^{b21}$, NR$^{c21}$C(O)OR$^{a21}$, and NR$^{c21}$C(O)NR$^{c21}$R$^{d21}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{2A}$ are each optionally substituted with 1, 2, 3, 4, 5, 6, 7, or 8 independently selected R$^M$ substituents;

each R$^{a21}$, R$^{b21}$, R$^{c21}$, and R$^{d21}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a21}$, R$^{b21}$, R$^{c21}$ and R$^{d21}$ are each optionally substituted with 1, 2, 3, 4, 5, 6, 7, or 8 independently selected R$^M$ substituents;

or, any R$^{c21}$ and R$^{d21}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected R$^M$ substituents;

or alternatively, R$^1$ and R$^2$, taken together with the carbon atoms to which they are attached form a monocyclic 4-7 membered cycloalkyl ring, a phenyl ring, a monocyclic 4-7 membered heterocycloalkyl ring, or a monocyclic 5-6 membered heteroaryl ring, each of which is optionally substituted by 1, 2, 3, 4, 5, 6, 7 or 8 independently selected R$^{1A}$ groups;

R$^6$ is selected from H, D, halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a6}$, SR$^{a6}$, NHOR$^{a6}$, C(O)R$^{b6}$, C(O)NR$^{c6}$R$^{d6}$, C(O)NR$^{v6}$(OR$^{a6}$), C(O)OR$^{a6}$, OC(O)R$^{b6}$, OC(O)NR$^{c6}$R$^{d6}$, NR$^{c6}$R$^{d6}$, NR$^{c6}$NR$^{c6}$R$^{d6}$, NR$^{c6}$C(O)R$^{b6}$, NR$^{c6}$C(O)OR$^{a6}$, NR$^{c6}$C(O)NR$^{c6}$R$^{d6}$, C(=NR$^{e6}$)R$^{b6}$, C(=NOH)R$^{b6}$, C(=NCN)R$^{b6}$, C(=NR$^{e6}$)NR$^{c6}$R$^{d6}$, NR$^{c6}$C(=NR$^{e6}$)NR$^{c6}$R$^{d6}$, NR$^{c6}$C(=NOH)NR$^{c6}$R$^{d6}$, NR$^{c6}$C(=NCN)NR$^{c6}$R$^{d6}$, NR$^{c6}$C(=NR$^{e6}$)R$^{b6}$, NR$^{c6}$S(O)NR$^{c6}$R$^{d6}$, NR$^{c6}$S(O)R$^{b6}$, NR$^{c6}$S(O)$_2$R$^{b6}$, NR$^{c6}$S(O)(=NR$^{e6}$)R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, S(O)$_2$NR$^{c6}$R$^{d6}$, S(O)(=NR$^{e6}$)R$^{b6}$, OS(O)(=NR$^{e6}$)R$^{b6}$, OS(O)$_2$R$^{b6}$, and SF$_5$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^6$ are each optionally substituted with 1, 2, 3, 4, 5, 6, 7, or 8 independently selected R$^{6A}$ substituents;

each R$^{a6}$, R$^{b6}$, R$^{c6}$, and R$^{d6}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a6}$, R$^{b6}$, R$^{c6}$ and R$^{d6}$ are each optionally substituted with 1, 2, 3, 4, 5, 6, 7, or 8 independently selected R$^{6A}$ substituents;

or, any R$^{c6}$ and R$^{d6}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected R$^{6A}$ substituents;

each R$^{6A}$ is selected from H, D, halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a61}$, SR$^{a61}$, NHOR$^{a61}$, C(O)R$^{b61}$, C(O)NR$^{c61}$R$^{d61}$, C(O)NR$^{c61}$(OR$^{a61}$), C(O)OR$^{a61}$, OC(O)R$^{b61}$, OC(O)NR$^{c61}$R$^{d61}$, NR$^{c61}$R$^{d61}$, NR$^{c61}$NR$^{c61}$R$^{d61}$, NR$^{c61}$C(O)R$^{b61}$, NR$^{c61}$C(O)OR$^{a61}$, and NR$^{c61}$C(O)NR$^{c61}$R$^{d61}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{6A}$ are each optionally substituted with 1, 2, 3, 4, 5, 6, 7, or 8 independently selected R$^M$ substituents;

each R$^{a61}$, R$^{b61}$, R$^{c61}$, and R$^{d61}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a61}$, R$^{b61}$, R$^{c61}$ and R$^{d61}$ are each optionally substituted with 1, 2, 3, 4, 5, 6, 7, or 8 independently selected R$^M$ substituents;

or, any R$^{c61}$ and R$^{d61}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected R$^M$ substituents;

X$^9$ is NR$^{9N}$ or C(R$^9$)$_2$;

X$^{11}$ is NR$^{11N}$ or C(R$^{11}$)$_2$;

R$^{9N}$ is selected from H, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, C(O)R$^{b9N}$, C(O)NR$^{c9N}$R$^{d9N}$, C(O)OR$^{a9N}$, C(=NR$^{e9N}$)R$^{b9N}$, C(=NR$^{e9N}$)NR$^{c9N}$R$^{d9N}$, C(=NCN)NR$^{c9N}$R$^{d9N}$, C(=NOR$^{a9N}$)NR$^{c9N}$, S(O)$_2$R$^{b9N}$, S(O)(=NR$^{c9N}$)R$^{d9N}$, and S(O)$_2$NR$^{c9N}$R$^{d9N}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-$C_{1-6}$ alkyl- and (4-10 membered heterocycloalkyl)-$C_{1-6}$ alkyl- of $R^{9N}$ are each optionally substituted with 1, 2, 3, 4, 5, 6, 7, or 8 independently selected $R^{9NA}$ substituents;

each $R^{a9N}$, $R^{b9N}$, $R^{c9N}$, and $R^{d9N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9N}$, $R^{b9N}$, $R^{c9N}$, and $R^{d9N}$ are each optionally substituted with 1, 2, 3, 4, 5, 6, 7, or 8 independently selected $R^{9NA}$ substituents;

or, any $R^{c9N}$ and $R^{d9N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9NA}$ substituents;

each $R^{e9N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{9NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a9N2}$, $SR^{a9N2}$, $NHOR^{a9N2}$, $C(O)R^{b9N2}$, $C(O)NR^{c9N2}R^{d9N2}$, $C(O)NR^{c9N2}(OR^{a9N2})$, $C(O)OR^{a9N2}$, $OC(O)R^{b9N2}$, $OC(O)NR^{c9N2}R^{d9N2}$, $NR^{c9N2}R^{d9N2}$, $NR^{c9N2}NR^{c9N2}R^{d9N2}$, $NR^{c9N2}C(O)R^{b9N2}$, $NR^{c9N2}C(O)OR^{a9N2}$, and $NR^{c9N2}C(O)NR^{c9N2}R^{d9N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9NA}$ are each optionally substituted with 1, 2, 3, or 4 independently selected $R^M$ substituents;

each $R^{a9N2}$, $R^{b9N2}$, $R^{c9N2}$, and $R^{d9N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a9N2}$, $R^{b9N2}$, $R^{c9N2}$ and $R^{d9N2}$ are each optionally substituted with 1, 2, 3, or 4 independently selected $R^M$ substituents;

or, any $R^{c9N2}$ and $R^{d9N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^9$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a91}$, $SR^{a91}$, $NHOR^{a91}$, $C(O)R^{b91}$, $C(O)NR^{c91}R^{d91}$, $C(O)NR^{c91}(OR^{a91})$, $C(O)OR^{a91}$, $OC(O)R^{b91}$, $OC(O)NR^{c91}R^{d91}$, $NR^{c91}R^{d91}$, $NR^{c91}NR^{c91}R^{d91}$, $NR^{c91}C(O)R^{b91}$, $NR^{c91}C(O)OR^{a91}$, and $NR^{c91}C(O)NR^{c91}R^{d91}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^9$ are each optionally substituted with 1, 2, 3, 4, 5, 6, 7, or 8 independently selected $R^{9A}$ substituents;

or, alternatively, two $R^9$ groups together form an oxo group;

each $R^{a91}$, $R^{b91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a91}$, $R^{b91}$, $R^{c91}$ and $R^{d91}$ are each optionally substituted with 1, 2, 3, 4, 5, 6, 7, or 8 independently selected $R^{9A}$ substituents;

or, any $R^{c91}$ and $R^{d91}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9A}$ substituents;

each $R^{9A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a92}$, $SR^{a92}$, $NHOR^{a92}$, $C(O)R^{b92}$, $C(O)NR^{c92}R^{d92}$, $C(O)NR^{c92}(OR^{a92})$, $C(O)OR^{a92}$, $OC(O)R^{b92}$, $OC(O)NR^{c92}R^{d92}$, $NR^{c92}R^{d92}$, $NR^{c92}NR^{c92}R^{d92}$, $NR^{c92}C(O)R^{b92}$, $NR^{c92}C(O)OR^{a92}$, and $NR^{c92}C(O)NR^{c92}R^{d92}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9A}$ are each optionally substituted with 1, 2, 3, or 4 independently selected $R^M$ substituents;

each $R^{a92}$, $R^{b92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a92}$, $R^{b92}$, $R^{c92}$ and $R^{d92}$ are each optionally substituted with 1, 2, 3, or 4 independently selected $R^M$ substituents;

or, any $R^{c92}$ and $R^{d92}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b10N}$, $C(O)NR^{c10N}R^{d10N}$, $C(O)OR^{a10N}$, $C(=NR^{e10N})R^{b10N}$, $C(=NR^{e10N})NR^{c10N}R^{d10N}$, $C(=NCN)NR^{c10N}R^{d10N}$, $C(=NOR^{a10N})NR^{c10N}$, $S(O)_2R^{b10N}$, $S(O)(=NR^{c10N})R^{d10N}$, and $S(O)_2NR^{c10N}R^{d10N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$alkyl- and (4-10 membered heterocycloalkyl)-$C_{1-6}$ alkyl- of $R^{10N}$ are each optionally substituted with 1, 2, 3, 4, 5, 6, 7, or 8 independently selected $R^{10NA}$ substituents;

each $R^{a10N}$, $R^{b10N}$, $R^{c10N}$, and $R^{d10N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a10N}$, $R^{b10N}$, $R^{c10N}$, and $R^{d10N}$ are each optionally substituted with 1, 2, 3, 4, 5, 6, 7, or 8 independently selected $R^{10NA}$ substituents;

or, any $R^{c10N}$ and $R^{d10N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{10NA}$ substituents;

each $R^{e10N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{10NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a10N2}$, $SR^{a10N2}$, $NHOR^{a10N2}$, $C(O)R^{b10N2}$, $C(O)NR^{c10N2}R^{d10N2}$, $C(O)NR^{c10N2}(OR^{a10N2})$, $C(O)OR^{a10N2}$, $OC(O)R^{b10N2}$, $OC(O)NR^{c10N2}R^{d10N2}$, $NR^{c10N2}R^{d10N2}$, $NR^{c10N2}NR^{c10N2}R^{d10N2}$, $NR^{c10N2}C(O)R^{b10N2}$, $NR^{c10N2}C(O)OR^{a10N2}$, and $NR^{c10N2}C(O)NR^{c10N2}R^{d10N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{10NA}$ are each optionally substituted with 1, 2, 3, or 4 independently selected $R^M$ substituents;

each $R^{a10N2}$, $R^{b10N2}$, $R^{c10N2}$, and $R^{d10N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a10N2}$, $R^{b10N2}$, $R^{c10N2}$ and $R^{d10N2}$ are each optionally substituted with 1, 2, 3, or 4 independently selected $R^M$ substituents;

or, any $R^{c10N2}$ and $R^{d10N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$R^{11N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b11N}$, $C(O)NR^{c11N}R^{d11N}$, $C(O)OR^{a11N}$, $C(=NR^{e11N})R^{b11N}$, $C(=NR^{e11N})NR^{c11N}R^{d11N}$, $C(=NCN)NR^{c11N}R^{d11N}$, $C(=NOR^{a11N})NR^{c11N}$, $S(O)_2R^{b11N}$, $S(O)(=NR^{c11N})R^{d11N}$, and $S(O)_2NR^{c11N}R^{d11N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{11N}$ are each optionally substituted with 1, 2, 3, 4, 5, 6, 7, or 8 independently selected $R^{11NA}$ substituents;

each $R^{a11N}$, $R^{b11N}$, $R^{c11N}$, and $R^{d11N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11N}$, $R^{b11N}$, $R^{c11N}$, and $R^{d11N}$ are each optionally substituted with 1, 2, 3, 4, 5, 6, 7, or 8 independently selected $R^{11NA}$ substituents;

or, any $R^{c11N}$ and $R^{d11N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{11NA}$ substituents;

each $R^{e11N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{11NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a11N2}$, $SR^{a11N2}$, $NHOR^{a11N2}$, $C(O)R^{b11N2}$, $C(O)NR^{c11N2}R^{d11N2}$, $C(O)NR^{c11N2}(OR^{a11N2})$, $C(O)OR^{a11N2}$, $OC(O)R^{b11N2}$, $OC(O)NR^{c11N2}R^{d11N2}$, $NR^{c11N2}R^{d11N2}$, $NR^{c11N2}NR^{c11N2}R^{d11N2}$, $NR^{c11N2}C(O)R^{b11N2}$, $NR^{c11N2}C(O)OR^{a11N2}$, and $NR^{c11N2}C$ (O)NR$^{c11N2}$R$^{d11N2}$, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{11NA}$ are each optionally substituted with 1, 2, 3, or 4 independently selected R$^M$ substituents;

each R$^{a11N2}$, R$^{b11N2}$, R$^{c11N2}$, and R$^{d11N2}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{a11N2}$, R$^{b11N2}$, R$^{c11N2}$ and R$^{d11N2}$ are each optionally substituted with 1, 2, 3, or 4 independently selected R$^M$ substituents;

or, any R$^{c11N2}$ and R$^{d11N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected R$^M$ substituents;

each R$^{11}$ is independently selected from H, D, halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a111}$, SR$^{a111}$, NHOR$^{a111}$, C(O)R$^{b111}$, C(O)NR$^{c111}$R$^{d111}$, C(O)NR$^{c111}$(OR$^{a111}$), C(O)OR$^{a111}$, OC(O)R$^{b111}$, OC(O)NR$^{c111}$R$^{d111}$, NR$^{c111}$R$^{d111}$, NR$^{c111}$NR$^{c111}$R$^{d111}$, NR$^{c111}$C(O)R$^{b111}$, NR$^{c111}$C(O)OR$^{a111}$, and NR$^{c111}$C(O)NR$^{c111}$R$^{d111}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{11}$ are each optionally substituted with 1, 2, 3, 4, 5, 6, 7, or 8 independently selected R$^{11A}$ substituents;

or, alternatively, two R$^{11}$ groups together form an oxo group;

each R$^{a111}$, R$^{b111}$, R$^{c111}$, and R$^{d111}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a111}$, R$^{b111}$, R$^{c111}$, and R$^{d111}$ are each optionally substituted with 1, 2, 3, 4, 5, 6, 7, or 8 independently selected R$^{11A}$ substituents;

or, any R$^{c111}$ and R$^{d111}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected R$^{11A}$ substituents; and each R$^{11A}$ is selected from H, D, halo, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, (4-7 membered heterocycloalkyl)-C$_{1-6}$ alkyl-, CN, NO$_2$, OR$^{a112}$, SR$^{a112}$, NHOR$^{a112}$, C(O)R$^{b112}$, C(O)NR$^{c112}$R$^{d112}$, C(O)NR$^{c112}$(OR$^{a112}$), C(O)OR$^{a112}$, OC(O)R$^{b112}$, OC(O)NR$^{c112}$R$^{d112}$, NR$^{c112}$R$^{d112}$, NR$^{c112}$NR$^{c112}$R$^{d112}$, NR$^{c112}$C(O)R$^{b112}$, NR$^{c112}$C(O)OR$^{a112}$, and NR$^{c112}$C(O)NR$^{c112}$R$^{d112}$, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{11A}$ are each optionally substituted with 1, 2, 3, or 4 independently selected R$^M$ substituents; and each R$^{a112}$, R$^{b112}$, R$^{c112}$, and R$^{d112}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{a112}$R$^{b112}$, R$^{c112}$ and R$^{d112}$ are each optionally substituted with 1, 2, 3, or 4 independently selected R$^M$ substituents;

or, any R$^{c112}$ and R$^{a112}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected R$^M$ substituents.

In some embodiments of Formula (IIu):

Z is CZ$^1$ or N;

Z$^1$ and R$^{12}$ are each independently selected from H, D, OH, NO$_2$, CN, halo, C$_{1-3}$ alkyl, C$_{2-3}$ alkenyl, C$_{2-3}$ alkynyl, C$_{1-3}$ haloalkyl, cyano-C$_{1-3}$ alkyl, HO—C$_{1-3}$ alkyl, C$_{1-3}$ alkoxy-C$_{1-3}$ alkyl, C$_{3-6}$ cycloalkyl, C$_{1-3}$ alkoxy, C$_{1-3}$ haloalkoxy, amino, C$_{1-3}$ alkylamino, di(C$_{1-3}$ alkyl)amino, thio, C$_{1-3}$ alkylthio, C$_{1-3}$ alkylsulfinyl, C$_{1-3}$ alkylsulfonyl, carbamyl, C$_{1-3}$ alkylcarbamyl, di(C$_{1-3}$ alkyl)carbamyl, carboxy, C$_{1-3}$ alkylcarbonyl, C$_{1-4}$ alkoxycarbonyl, C$_{1-3}$ alkylcarbonylamino, C$_{1-3}$ alkoxycarbonylamino, C$_{1-3}$ alkylcarbonyloxy, aminocarbonyloxy, C$_{1-3}$ alkylaminocarbonyloxy, di(C$_{1-3}$ alkyl)aminocarbonyloxy, C$_{1-3}$ alkylsulfonylamino, aminosulfonyl, C$_{1-3}$ alkylaminosulfonyl, di(C$_{1-3}$ alkyl)aminosulfonyl, aminosulfonylamino, C$_{1-3}$ alkylaminosulfonylamino, di(C$_{1-3}$ alkyl)aminosulfonylamino, aminocarbonylamino, C$_{1-3}$ alkylaminocarbonylamino, and di(C$_{1-3}$ alkyl)aminocarbonylamino;

R$^1$ is selected from H, D, halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a1}$, SR$^{a1}$, NHOR$^{a1}$, C(O)R$^{b1}$, C(O)NR$^{c1}$R$^{d1}$, C(O)NR$^{c1}$(OR$^{a1}$), C(O)OR$^{a1}$, OC(O)R$^{b1}$, OC(O)NR$^{c1}$R$^{d1}$, NR$^{c1}$R$^{d1}$, NR$^{c1}$NR$^{c1}$R$^{d1}$, NR$^{c1}$C(O)R$^{b1}$, NR$^{c1}$C(O)OR$^{a1}$, and NR$^{c1}$C(O)NR$^{c1}$R$^{d1}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^{1A}$ substituents;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{b1}$, $R^{c1}$ and $R^{d1}$ are each optionally substituted with 1, 2, 3, 4, 5, 6, 7, or 8 independently selected $R^{1A}$ substituents;

or, any $R^{c1}$ and $R^{d1}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{1A}$ substituents;

each $R^{1A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, and $NR^{c11}C(O)NR^{c11}R^{d11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1A}$ are each optionally substituted with 1, 2, 3, 4, 5, 6, 7, or 8 independently selected $R^M$ substituents;

each $R^{a11}$, $R^{b11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{b11}$, $R^{c11}$ and $R^{d11}$ are each optionally substituted with 1, 2, 3, 4, 5, 6, 7, or 8 independently selected $R^M$ substituents;

or, any $R^{c11}$ and $R^{d11}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^M$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$alkyl, $C_{3-6}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{c2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, and $NR^{c2}C(O)NR^{c2}R^{d2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, 6, 7, or 8 independently selected $R^{2A}$ substituents;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{b2}$, $R^{c2}$ and $R^{d2}$ are each optionally substituted with 1, 2, 3, 4, 5, 6, 7, or 8 independently selected $R^{2A}$ substituents;

or, any $R^{c2}$ and $R^{d2}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{2A}$ substituents;

each $R^{2A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}NR^{c21}R^{d21}$, $NR^{c21}C(O)R^{b21}$, $NR^{c21}C(O)OR^{a21}$, and $NR^{c21}C(O)NR^{c21}R^{d21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, 4, 5, 6, 7, or 8 independently selected $R^M$ substituents;

each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{b21}$, $R^{c21}$ and $R^{d21}$ are each optionally substituted with 1, 2, 3, 4, 5, 6, 7, or 8 independently selected $R^M$ substituents;

or, any $R^{c21}$ and $R^{d21}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

or alternatively, $R^1$ and $R^2$, taken together with the carbon atoms to which they are attached form a monocyclic 4-7 membered cycloalkyl ring, a phenyl ring, a monocyclic 4-7 membered heterocycloalkyl ring, or a monocyclic 5-6 membered heteroaryl ring, each of which is optionally substituted by 1, 2, 3, 4, 5, 6, 7 or 8 independently selected $R^{1A}$ groups;

$R^6$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOH)R^{b6}$, $C(=NCN)R^{b6}$, $C(=NR^{e6})NR^{c6}R^{d6}$, $NR^{c6}C(=NR^{e6})NR^{c6}R^{d6}$, $NR^{c6}C(=NOH)NR^{c6}R^{d6}$, $NR^{c6}C(=NCN)NR^{c6}R^{d6}$, $NR^{c6}C(=NR^{e6})R^{b6}$, $NR^{c6}S(O)NR^{c6}R^{d6}$, $NR^{c6}S(O)R^{b6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $S(O)(=NR^{e6})R^{b6}$, $N=S(O)R^{a6}R^{b6}$, $OS(O)(=NR^{e6})R^{b6}$, $OS(O)_2R^{b6}$, and $SF_5$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, 4, 5, 6, 7, or 8 independently selected $R^{6A}$ substituents;

each $R^{a6}$, $R^{b6}$, $R^{c6}$, $R^{d6}$ and $R^{e6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$, $R^{d6}$ and $R^{e6}$ are each optionally substituted with 1, 2, 3, 4, 5, 6, 7, or 8 independently selected $R^{6A}$ substituents;

or, any $R^{c6}$ and $R^{d6}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{6A}$ substituents;

each $R^{6A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a61}$, $SR^{a61}$, $NHOR^{a61}$, $C(O)R^{b61}$, $C(O)NR^{c61}R^{d61}$, $C(O)NR^{c61}(OR^{a61})$, $C(O)OR^{a61}$, $OC(O)R^{b61}$, $OC(O)NR^{c61}R^{d61}$, $NR^{c61}R^{d61}$, $NR^{c61}NR^{c61}R^{d61}$, $NR^{c61}C(O)R^{b61}$, $NR^{c61}C(O)OR^{a61}$, and $NR^{c61}C(O)NR^{c61}R^{d61}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{6A}$ are each optionally substituted with 1, 2, 3, 4, 5, 6, 7, or 8 independently selected $R^M$ substituents;

each $R^{a61}$, $R^{b61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a61}$, $R^{b61}$, $R^{c61}$ and $R^{d61}$ are each optionally substituted with 1, 2, 3, 4, 5, 6, 7, or 8 independently selected $R^M$ substituents;

or, any $R^{c61}$ and $R^{d61}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

$X^9$ is $NR^{9N}$ or $C(R^9)_2$;

$X^{11}$ is $NR^{11N}$ or $C(R^{11})_2$;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b9N}$, $C(O)NR^{c9N}R^{d9N}$, $C(O)OR^{a9N}$, $C(=NR^{e9N})R^{b9N}$, $C(=NR^{e9N})NR^{c9N}R^{d9N}$, $C(=NCN)NR^{c9N}R^{d9N}$, $C(=NOR^{a9N})NR^{c9N}$, $S(O)_2R^{b9N}$, $S(O)(=NR^{e9N})R^{a9N}$, and $S(O)_2NR^{c9N}R^{d9N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{9N}$ are each optionally substituted with 1, 2, 3, 4, 5, 6, 7, or 8 independently selected $R^{9NA}$ substituents;

each $R^{a9N}$, $R^{b9N}$, $R^{c9N}$, and $R^{d9N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9N}$, $R^{b9N}$, $R^{c9N}$, and $R^{d9N}$ are each optionally substituted with 1, 2, 3, 4, 5, 6, 7, or 8 independently selected $R^{9NA}$ substituents;

or, any $R^{c9N}$ and $R^{d9N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9NA}$ substituents;

each $R^{e9N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{9NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, NO$_2$, OR$^{a9N2}$, SR$^{a9N2}$, NHOR$^{a9N2}$, C(O)R$^{b9N2}$, C(O)NR$^{c9N2}$R$^{d9N2}$, C(O)NR$^{c9N2}$(OR$^{a9N2}$), C(O)OR$^{a9N2}$, OC(O)R$^{b9N2}$, OC(O)NR$^{c9N2}$R$^{d9N2}$, NR$^{c9N2}$R$^{d9N2}$, NR$^{c9N2}$NR$^{c9N2}$R$^{d9N2}$, NR$^{c9N2}$C(O)R$^{b9N2}$, NR$^{c9N2}$C(O)OR$^{a9N2}$, and NR$^{c9N2}$C(O)NR$^{c9N2}$R$^{d9N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9NA}$ are each optionally substituted with 1, 2, 3, or 4 independently selected $R^M$ substituents;

each $R^{a9N2}$, $R^{b9N2}$, $R^{c9N2}$, and $R^{d9N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a9N2}$, $R^{b9N2}$, $R^{c9N2}$ and $R^{d9N2}$ are each optionally substituted with 1, 2, 3, or 4 independently selected $R^M$ substituents;

or, any $R^{c9N2}$ and $R^{d9N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^9$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a91}$, SR$^{a91}$, NHOR$^{a91}$, C(O)R$^{b91}$, C(O)NR$^{c91}$R$^{d91}$, C(O)NR$^{c91}$(OR$^{a91}$), C(O)OR$^{a91}$, OC(O)R$^{b91}$, OC(O)NR$^{c91}$R$^{d91}$, NR$^{c91}$R$^{d91}$, NR$^{c91}$NR$^{c91}$R$^{d91}$, NR$^{c91}$C(O)R$^{b91}$, NR$^{c91}$C(O)OR$^{a91}$, and NR$^{c91}$C(O)NR$^{c91}$R$^{d91}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^9$ are each optionally substituted with 1, 2, 3, 4, 5, 6, 7, or 8 independently selected $R^{9A}$ substituents;

or, alternatively, two $R^9$ groups together form an oxo group;

each $R^{a91}$, $R^{b91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a91}$, $R^{b91}$, $R^{c91}$ and $R^{d91}$ are each optionally substituted with 1, 2, 3, 4, 5, 6, 7, or 8 independently selected $R^{9A}$ substituents;

or, any $R^{c91}$ and $R^{d91}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9A}$ substituents;

each $R^{9A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, NO$_2$, OR$^{a92}$, SR$^{a92}$, NHOR$^{a92}$, C(O)R$^{b92}$, C(O)NR$^{c92}$R$^{d92}$, C(O)NR$^{c92}$(OR$^{a92}$), C(O)OR$^{a92}$, OC(O)R$^{b92}$, OC(O)NR$^{c92}$R$^{d92}$, NR$^{c92}$R$^{d92}$, NR$^{c92}$NR$^{c92}$R$^{d92}$, NR$^{c92}$C(O)R$^{b92}$, NR$^{c92}$C(O)OR$^{a92}$, and NR$^{c92}$C(O)NR$^{c92}$R$^{d92}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9A}$ are each optionally substituted with 1, 2, 3, or 4 independently selected $R^M$ substituents;

each $R^{a92}$, $R^{b92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a92}$, $R^{b92}$, $R^{c92}$ and $R^{d92}$ are each optionally substituted with 1, 2, 3, or 4 independently selected $R^M$ substituents;

or, any $R^{c92}$ and $R^{d92}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b10N}$, $C(O)NR^{c10N}R^{d10N}$, $C(O)OR^{a10N}$, $C(=NR^{e10N})R^{b10N}$, $C(=NR^{e10N})NR^{c10N}R^{d10N}$, $C(=NCN)NR^{c10N}R^{d10N}$, $C(=NOR^{a10N})NR^{c10N}$, $S(O)_2R^{b10N}$, $S(O)(=NR^{c10N})R^{d10N}$, and $S(O)_2NR^{c10N}R^{d10N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, 4, 5, 6, 7, or 8 independently selected $R^{10NA}$ substituents;

each $R^{a10N}$, $R^{b10N}$, $R^{c10N}$, and $R^{d10N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a10N}$, $R^{b10N}$, $R^{c10N}$, and $R^{d10N}$ are each optionally substituted with 1, 2, 3, 4, 5, 6, 7, or 8 independently selected $R^{10NA}$ substituents;

or, any $R^{c10N}$ and $R^{d10N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{10NA}$ substituents;

each $R^{e10N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{10NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a10N2}$, $SR^{a10N2}$, $NHOR^{a10N2}$, $C(O)R^{b10N2}$, $C(O)NR^{c10N2}R^{d10N2}$, $C(O)NR^{c10N2}(OR^{a10N2})$, $C(O)OR^{a10N2}$, $OC(O)R^{b10N2}$, $OC(O)NR^{c10N2}R^{d10N2}$, $NR^{c10N2}R^{d10N2}$, $NR^{c10N2}NR^{c10N2}R^{d10N2}$, $NR^{c10N2}C(O)R^{b10N2}$, $NR^{c10N2}C(O)OR^{a10N2}$, and $NR^{c10N2}C(O)NR^{c10N2}R^{d10N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{10NA}$ are each optionally substituted with 1, 2, 3, or 4 independently selected $R^M$ substituents;

each $R^{a10N2}$, $R^{b10N2}$, $R^{c10N2}$, and $R^{d10N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a10N2}$, $R^{b10N2}$, $R^{c10N2}$ and $R^{d10N2}$ are each optionally substituted with 1, 2, 3, or 4 independently selected $R^M$ substituents;

or, any $R^{c10N2}$ and $R^{d10N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$R^{11N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b11N}$, $C(O)NR^{c11N}R^{d11N}$, $C(O)OR^{a11N}$, $C(=NR^{e11N})R^{b11N}$, $C(=NR^{e11N})NR^{c11N}R^{d11N}$, $C(=NCN)NR^{c11N}R^{d11N}$, $C(=NOR^{a11N})NR^{c11N}$, $S(O)_2R^{b11N}$, $S(O)(=NR^{c11N})R^{d11N}$, and $S(O)_2NR^{c11N}R^{d11N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{11N}$ are each optionally substituted with 1, 2, 3, 4, 5, 6, 7, or 8 independently selected $R^{11NA}$ substituents;

each $R^{a11N}$, $R^{b11N}$, $R^{c11N}$, and $R^{d11N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11N}$, $R^{b11N}$, $R^{c11N}$, and $R^{d11N}$ are each optionally substituted with 1, 2, 3, 4, 5, 6, 7, or 8 independently selected $R^{11NA}$ substituents;

or, any $R^{c11N}$ and $R^{d11N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{11NA}$ substituents;

each $R^{e11N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{11NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a11N2}$, $SR^{a11N2}$, $NHOR^{a11N2}$, $C(O)R^{b11N2}$, $C(O)NR^{c11N2}R^{d11N2}$, $C(O)NR^{c11N2}(OR^{a11N2})$, $C(O)OR^{a11N2}$, $OC(O)R^{b11N2}$, $OC(O)NR^{c11N2}R^{d11N2}$, $NR^{c11N2}R^{d11N2}$, $NR^{c11N2}NR^{c11N2}R^{d11N2}$, $NR^{c11N2}C(O)R^{b11N2}$, $NR^{c11N2}C(O)OR^{a11N2}$, and $NR^{c11N2}C(O)NR^{c11N2}R^{d11N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{11NA}$ are each optionally substituted with 1, 2, 3, or 4 independently selected $R^M$ substituents;

each $R^{a11N2}$, $R^{b11N2}$, $R^{c11N2}$, and $R^{d11N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a11N2}$, $R^{b11N2}$, $R^{c11N2}$ and $R^{d11N2}$ are each optionally substituted with 1, 2, 3, or 4 independently selected $R^M$ substituents;

or, any $R^{c11N2}$ and $R^{d11N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{11}$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a111}$, $SR^{a111}$, $NHOR^{a111}$, $C(O)R^{b111}$, $C(O)NR^{c111}R^{d111}$, $C(O)NR^{c111}(OR^{a111})$, $C(O)OR^{a111}$, $OC(O)R^{b111}$, $OC(O)NR^{c111}R^{d111}$, $NR^{c111}R^{d111}$, $NR^{c111}NR^{c111}R^{d111}$, $NR^{c111}C(O)R^{b111}$, $NR^{c111}C(O)OR^{a111}$, and $NR^{c111}C(O)NR^{c111}R^{d1111}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{11}$ are each optionally substituted with 1, 2, 3, 4, 5, 6, 7, or 8 independently selected $R^{11A}$ substituents;

or, alternatively, two $R^{11}$ groups together form an oxo group;

each $R^{a111}$, $R^{b111}$, $R^{c111}$, and $R^{d111}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a111}$, $R^{b111}$, $R^{c111}$, and $R^{d111}$ are each optionally substituted with 1, 2, 3, 4, 5, 6, 7, or 8 independently selected $R^{11A}$ substituents;

or, any $R^{c111}$ and $R^{d111}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{11A}$ substituents; and each $R^{11A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a112}$, $SR^{a112}$, $NHOR^{a112}$, $C(O)R^{b112}$, $C(O)NR^{c112}R^{d112}$, $C(O)NR^{c112}(OR^{a112})$, $C(O)OR^{a112}$, $OC(O)R^{b112}$, $OC(O)NR^{c112}R^{d112}$, $NR^{c112}R^{d112}$, $NR^{c112}NR^{c112}R^{d112}$, $NR^{c112}C(O)R^{b112}$, $NR^{c112}C(O)OR^{a112}$, and $NR^{c112}C(O)NR^{c112}R^{d112}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{11A}$ are each optionally substituted with 1, 2, 3, or 4 independently selected $R^M$ substituents; and each $R^{a112}$, $R^{b112}$, $R^{c112}$, and $R^{d112}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a112}$, $R^{b112}$, $R^{c112}$ and $R^{d112}$ are each optionally substituted with 1, 2, 3, or 4 independently selected $R^M$ substituents;

or, any $R^{c112}$ and $R^{d112}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents.

In some embodiments of Formula (IIu):

$R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, and $NR^{c1}C(O)NR^{c1}R^{d1}$;

$R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{c2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}C(O)R^{b2}$, $NR^{c2}C(O)OR^{a2}$, and $NR^{c2}C(O)NR^{c2}R^{d2}$;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a2}$, $R^{b2}$, $R^{c2}$ and $R^{d2}$ are each optionally substituted with 1 or 2 independently selected $R^{2A}$ substituents;

Z is N or $CZ^1$;

$Z^1$ is selected from H, D, $C_{1-3}$ alkyl, $C_{1-3}$ haloalkyl, $C_{2-3}$ alkenyl, and $C_{2-3}$ alkynyl;

$R^6$ is selected from H, D, halo, $C_{1-6}$ alkyl, $C_{1-6}$ haloalkyl, $C_{2-6}$ alkenyl, $C_{2-6}$ alkynyl, $S(O)R^{b6}$, $S(O)NR^{c6}R^{d6}$, $S(O)_2R^{b6}$, and $S(O)_2NR^{c6}R^{d6}$;

each $R^{b6}$, $R^{c6}$, and $R^{d6}$ is independently selected from H, $C_{1-6}$ alkyl, $C_{1-6}$ haloalkyl, $C_{2-6}$ alkenyl, and $C_{2-6}$ alkynyl;

$X^9$ is N or $C(R^9)_2$;

$X^{11}$ is N or $C(R^{11})_2$;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^9$ are each optionally substituted with 1, 2, 3, or 4 independently selected $R^{9A}$ substituents;

or, alternatively, two $R^9$ groups together form an oxo group;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, or 4 independently selected $R^{10NA}$ substituents; and each $R^{11}$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^{11}$ are each optionally substituted with 1, 2, 3, or 4 independently selected $R^{11A}$ substituents.

In some embodiments of Formula (IIu):

$R^1$ is selected from H and $C_{1-6}$ alkyl;

$R^2$ is selected from H, $C_{1-6}$ alkyl, $C(O)R^{b2}$, $C(O)NR^{c2}R^{d2}$, $NR^{c2}C(O)R^{b2}$, $NR^{c2}C(O)OR^{a2}$, and $NR^{c2}C(O)NR^{c2}R^{d2}$;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, and 4-6 membered heterocycloalkyl, wherein the $C_{1-6}$ alkyl, $C_{2-6}$ alkenyl, $C_{2-6}$ alkynyl, and 4-6 membered heterocycloalkyl of $R^{a2}$, $R^{b2}$, $R^{c2}$ and $R^{d2}$ are each optionally substituted with 1 or 2 independently selected $R^{2A}$ substituents;

Z is $CZ^1$;

$Z^1$ is selected from H, D, $C_{1-3}$ alkyl, $C_{1-3}$ haloalkyl, $C_{2-3}$ alkenyl, and $C_{2-3}$ alkynyl;

$R^6$ is selected from H, halo, $C_{1-6}$ alkyl, $S(O)R^{b6}$, and $S(O)_2R^{b6}$;

$X^9$ is $C(R^9)_2$;

$X^{11}$ is $C(R^{11})_2$;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^9$ are each optionally substituted with 1, 2, 3, or 4 independently selected $R^{9A}$ substituents; or, alternatively, two $R^9$ groups together form an oxo group;

$R^{10N}$ is selected from $C_{1-6}$ alkyl, $C_{3-6}$ cycloalkyl, and $C_{3-6}$ cycloalkyl-$C_{1-6}$ alkyl-, wherein the $C_{1-6}$ alkyl, $C_{3-6}$ cycloalkyl, and $C_{3-6}$ cycloalkyl-$C_{1-6}$ alkyl- of $R^{10N}$ are each optionally substituted with 1 or 2 independently selected $R^{10NA}$ substituents; and each $R^{11}$ is independently selected from H, D, $C_{1-6}$ alkyl, $C_{1-6}$ haloalkyl, $C_{2-6}$ alkenyl, $C_{2-6}$ alkynyl.

In some embodiments of Formula (IIu):

$R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, and $NR^{c1}C(O)NR^{c1}R^{d1}$;

$R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{c2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}C(O)R^{b2}$, $NR^{c2}C(O)OR^{a2}$, and $NR^{c2}C(O)NR^{c2}R^{d2}$;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{a2}$, $R^{b2}$, $R^{c2}$ and $R^{d2}$ are each optionally substituted with 1 or 2 independently selected $R^{2A}$ substituents;

or, any $R^{c2}$ and $R^{d2}$, attached to the same N atom, together with the N atom to which they are attached, form a 4-7 membered heterocycloalkyl group, wherein the 4-7 membered heterocycloalkyl group is optionally substituted with 1 or 2 independently selected $R^{2A}$ substituents;

each $R^{2A}$ is selected from halo, $C_{1-6}$ alkyl, $C_{1-6}$ haloalkyl, CN, and OH, Z is N or CH;

$R^6$ is selected from H, D, halo, $C_{1-6}$ alkyl, $C_{1-6}$ haloalkyl, $C_{2-6}$ alkenyl, $C_{2-6}$ alkynyl, $S(O)R^{b6}$, $S(O)NR^{c6}R^{d6}$, $S(O)_2R^{b6}$, $S(O)_2NR^{c6}R^{d6}$, $S(O)(=NR^{e6})R^{b6}$, and $N=S(O)R^{a6}R^{b6}$, wherein the $C_{1-6}$ haloalkyl is optionally substituted with 1, 2 or 3 $R^{6A}$ independently selected from D, halo, CN, OH, $NH_2$, and $C_{1-6}$ alkyl;

each $R^{a6}$, $R^{b6}$, $R^{c6}$, $R^{d6}$, and $R^{e6}$ is independently selected from H and $C_{1-6}$ alkyl;

$X^9$ is N or $C(R^9)_2$;

$X^{11}$ is N or $C(R^{11})_2$;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^9$ are each optionally substituted with 1, 2, 3, or 4 independently selected $R^{9A}$ substituents;

or, alternatively, two $R^9$ groups together form an oxo group;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, or 4 independently selected $R^{10NA}$ substituents selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl; and each $R^{11}$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^{11}$ are each optionally substituted with 1, 2, 3, or 4 independently selected $R^{11A}$ substituents.

In some embodiments of Formula (IIu):

$R^1$ is selected from H and $C_{1-6}$ alkyl;

$R^2$ is selected from H, $C_{1-6}$ alkyl, $C(O)R^{b2}$, $C(O)NR^{c2}R^{d2}$, $NR^{c2}C(O)R^{b2}$, $NR^{c2}C(O)OR^{a2}$, and $NR^{c2}C(O)NR^{c2}R^{d2}$;

each $R^{a2}$, $R^{b2}$, $R^{c2}$, and $R^{d2}$ is independently selected from H, $C_{1-6}$ alkyl, $C_{1-6}$ haloalkyl, $C_{3-7}$ cycloalkyl, and 4-7 membered heterocycloalkyl, wherein the $C_{1-6}$ alkyl, $C_{3-7}$ cycloalkyl, and 4-7 membered heterocycloalkyl of $R^{a2}$, $R^{b2}$, $R^{c2}$ and $R^{d2}$ are each optionally substituted with 1 or 2 independently selected $R^{2A}$ substituents selected from halo, $C_{1-6}$ alkyl, $C_{1-6}$ haloalkyl, CN, and OH;

or, any $R^{c2}$ and $R^{d2}$, attached to the same N atom, together with the N atom to which they are attached, form a 4-7 membered heterocycloalkyl group, wherein the 4-7 membered heterocycloalkyl group is optionally substituted with 1 or 2 independently selected $R^{2A}$ substituents selected from halo, $C_{1-6}$ alkyl, $C_{1-6}$ haloalkyl, CN, and OH;

Z is N or CH;

$R^6$ is selected from H, halo, $C_{1-6}$ alkyl, $S(O)R^{b6}$, $S(O)_2 R^{b6}$, $S(O)(=NR^{e6})R^{b6}$, and $N=S(O)R^{a6}R^{b6}$, wherein the $C_{1-6}$ alkyl is optionally substituted with 1 or 2 OH; each $R^{a6}$, $R^{b6}$, and $R^{e6}$ is independently selected from H, and $C_{1-6}$ alkyl.

$X^9$ is $C(R^9)_2$;

$X^{11}$ is $C(R^{11})_2$;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^9$ are each optionally substituted with 1, 2, 3, or 4 independently selected $R^{9A}$ substituents; or, alternatively, two $R^9$ groups together form an oxo group;

$R^{10N}$ is selected from $C_{1-6}$ alkyl, $C_{3-6}$ cycloalkyl, and $C_{3-6}$ cycloalkyl-$C_{1-6}$ alkyl-, wherein the $C_{1-6}$ alkyl, $C_{3-6}$ cycloalkyl, and $C_{3-6}$ cycloalkyl-$C_{1-6}$ alkyl- of $R^{10N}$ are each optionally substituted with 1 or 2 independently selected $R^{10NA}$ substituents selected from $C_{1-6}$ alkyl, $C_{3-7}$ cycloalkyl, and 4-7 membered heterocycloalkyl; and each $R^{11}$ is independently selected from H, D, $C_{1-6}$ alkyl, $C_{1-6}$ haloalkyl, $C_{2-6}$ alkenyl, $C_{2-6}$ alkynyl. In some embodiments, the disclosure provides a compound of Formula (IIw)

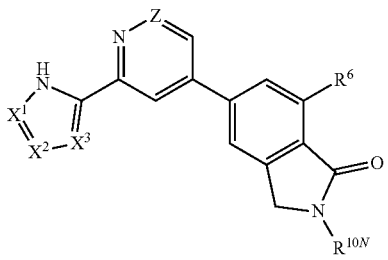

(IIw)

or a pharmaceutically acceptable salt thereof; wherein:
$X^1$ is $CR^1$ or N;
$X^2$ is $CR^2$ or N;
$X^3$ is $CR^3$ or N;
wherein $X^1$, $X^2$, and $X^3$ are not each simultaneously N;

$R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, and $NR^{c1}C(O)NR^{c1}R^{d1}$;

$R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{c2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}C(O)R^{b2}$, $NR^{c2}C(O)OR^{a2}$, and $NR^{c2}C(O)NR^{c2}R^{d2}$;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{a2}$, $R^{b2}$, $R^{c2}$ and $R^{d2}$ are each optionally substituted with 1 or 2 independently selected $R^{2A}$ substituents;

or, any $R^{c2}$ and $R^{d2}$, attached to the same N atom, together with the N atom to which they are attached, form a 4-7 membered heterocycloalkyl group, wherein the 4-7 membered heterocycloalkyl group is optionally substituted with 1 or 2 independently selected $R^{2A}$ substituents;

each $R^{2A}$ is selected from halo, $C_{1-6}$ alkyl, $C_{1-6}$ haloalkyl, CN, and OH, $R^3$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, and $NR^{c1}C(O)NR^{c1}R^{d1}$;

Z is N or CH;

$R^6$ is selected from H, D, halo, $C_{1-6}$ alkyl, $C_{1-6}$ haloalkyl, $C_{2-6}$ alkenyl, $C_{2-6}$ alkynyl, $S(O)R^{b6}$, $S(O)NR^{c6}R^{d6}$, $S(O)_2 R^{b6}$, $S(O)_2NR^{c6}R^{d6}$, $S(O)(=NR^{e6})R^{b6}$, and $N=S(O)R^{a6}R^{b6}$, wherein the $C_{1-6}$ haloalkyl is optionally substituted with 1, 2 or 3 $R^{6A}$ independently selected from D, halo, CN, OH, $NH_2$, and $C_{1-6}$ alkyl;

each $R^{a6}$, $R^{b6}$, $R^{c6}$, $R^{d6}$, and $R^{e6}$ is independently selected from H and $C_{1-6}$ alkyl; and $R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, or 4 independently selected $R^{10NA}$ substituents selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl.

In some embodiments of Formula (IIw):
$R^1$ is selected from H and $C_{1-6}$ alkyl;
$R^2$ is selected from H, $C_{1-6}$ alkyl, $C(O)R^{b2}$, $C(O)NR^{c2}R^{d2}$, $NR^{c2}C(O)R^{b2}$, $NR^{c2}C(O)OR^{a2}$, and $NR^{c2}C(O)NR^{c2}R^{d2}$;

each $R^{a2}$, $R^{b2}$, $R^{c2}$, and $R^{d2}$ is independently selected from H, $C_{1-6}$ alkyl, $C_{1-6}$ haloalkyl, $C_{3-7}$ cycloalkyl, and 4-7 membered heterocycloalkyl, wherein the $C_{1-6}$ alkyl, $C_{3-7}$ cycloalkyl, and 4-7 membered heterocycloalkyl of $R^{a2}$, $R^{b2}$, $R^{c2}$ and $R^{d2}$ are each optionally substituted with 1 or 2 independently selected $R^{2A}$ substituents selected from halo, $C_{1-6}$ alkyl, $C_{1-6}$ haloalkyl, CN, and OH;

or, any $R^{c2}$ and $R^{d2}$, attached to the same N atom, together with the N atom to which they are attached, form a 4-7 membered heterocycloalkyl group, wherein the 4-7 membered heterocycloalkyl group is optionally substituted with 1 or 2 independently selected $R^{2A}$ substituents selected from halo, $C_{1-6}$ alkyl, $C_{1-6}$ haloalkyl, CN, and OH;

R³ is selected from H and C₁₋₆ alkyl;

Z is N or CH;

R⁶ is selected from H, halo, C₁₋₆ alkyl, S(O)R^{b6}, S(O)₂R^{b6}, S(O)(=NR^{e6})R^{b6}, and N=S(O)R^{a6}R^{b6}, wherein the C₁₋₆ alkyl is optionally substituted with 1 or 2 OH;

each R^{a6}, R^{b6}, and R^{e6} is independently selected from H, and C₁₋₆ alkyl; and R^{10N} is selected from C₁₋₆ alkyl, C₃₋₆ cycloalkyl, and C₃₋₆ cycloalkyl-C₁₋₆ alkyl-, wherein the C₁₋₆ alkyl, C₃₋₆ cycloalkyl, and C₃₋₆ cycloalkyl-C₁₋₆ alkyl- of R^{10N} are each optionally substituted with 1 or 2 independently selected R^{10NA} substituents independently selected from C₁₋₆ alkyl, C₃₋₇ cycloalkyl, and 4-7 membered heterocycloalkyl.

In some embodiments, the compound of Formula (I) is a compound of Formula (III):

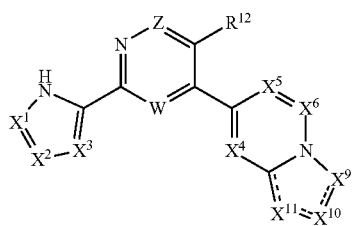

(III)

or a pharmaceutically acceptable salt thereof.

In some embodiments, the compound of Formula (I) is a compound of Formula (IIIb):

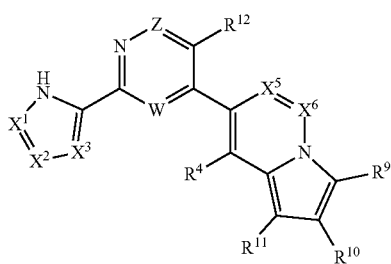

(IIIb)

or a pharmaceutically acceptable salt thereof.

In some embodiments, the compound of Formula (I) is a compound of Formula (IIIc):

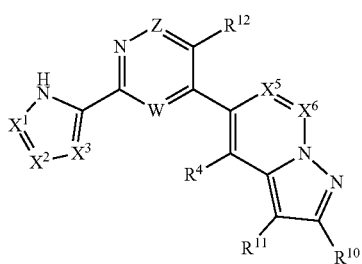

(IIIc)

or a pharmaceutically acceptable salt thereof.

In some embodiments, the compound of Formula (I) is a compound of Formula (IIId):

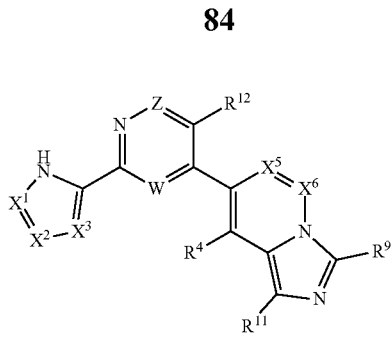

(IIId)

or a pharmaceutically acceptable salt thereof.

In some embodiments, the compound of Formula (I) is a compound of Formula (IIIe):

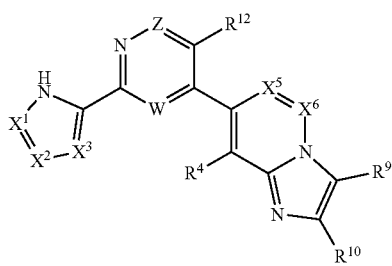

(IIIe)

or a pharmaceutically acceptable salt thereof.

In some embodiments, the compound of Formula (I) is a compound of Formula (IIIf):

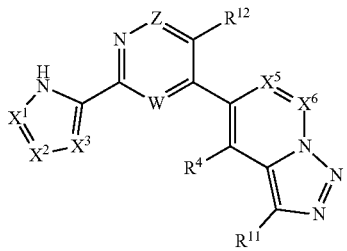

(IIIf)

or a pharmaceutically acceptable salt thereof.

In some embodiments, the compound of Formula (I) is a compound of Formula (IIIg):

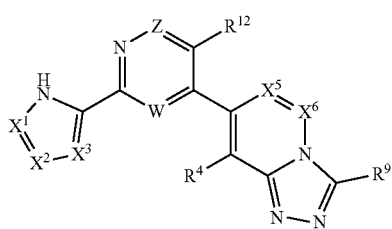

(IIIg)

or a pharmaceutically acceptable salt thereof.

In some embodiments, the compound of Formula (I) is a compound of Formula (IIIh):

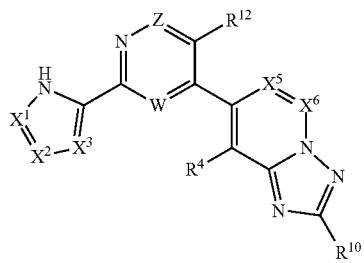

(IIIh)

or a pharmaceutically acceptable salt thereof.

In some embodiments, the compound of Formula (I) is a compound of Formula (IV):

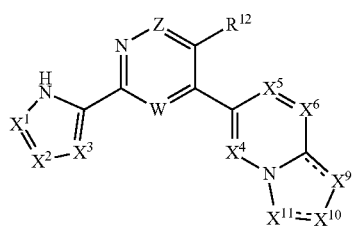

(IV)

or a pharmaceutically acceptable salt thereof.

In some embodiments, the compound of Formula (I) is a compound of Formula (IVb):

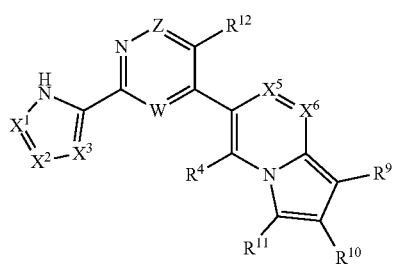

(IVb)

or a pharmaceutically acceptable salt thereof.

In some embodiments, the compound of Formula (I) is a compound of Formula (IVc):

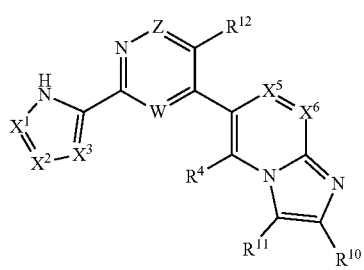

(IVc)

or a pharmaceutically acceptable salt thereof.

In some embodiments, the compound of Formula (I) is a compound of Formula (IVd):

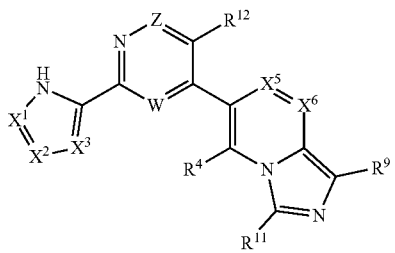

(IVd)

or a pharmaceutically acceptable salt thereof.

In some embodiments, the compound of Formula (I) is a compound of Formula (IVe):

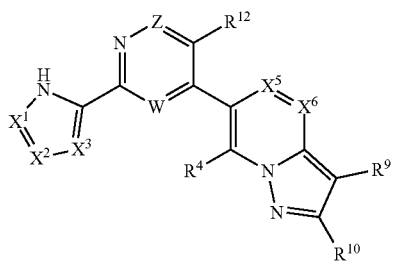

(IVe)

or a pharmaceutically acceptable salt thereof.

In some embodiments the compound of Formula (is a compound of Formula (IVf):

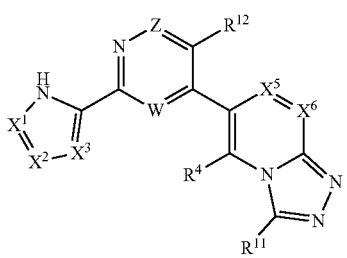

(IVf)

or a pharmaceutically acceptable salt thereof.

In some embodiments, the compound of Formula (I) is a compound of Formula (IVg):

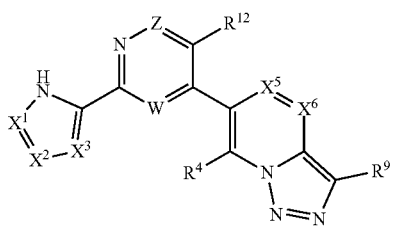

(IVg)

or a pharmaceutically acceptable salt thereof.

In some embodiments, the compound of Formula (I) is a compound of Formula (IVh):

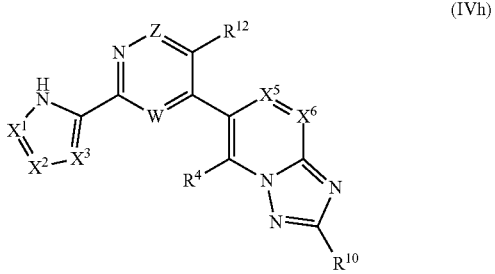

(IVh)

or a pharmaceutically acceptable salt thereof.

In some embodiments, the compound of Formula (I) is a compound of Formula 3-6 of Scheme III, a compound of Formula 5-2 of Scheme V, a compound of Formula 13-8 of Scheme XIII, a compound of Formula 14-5 of Scheme XIV, or a compound of Formula 15-5 of Scheme XV, or a pharmaceutically acceptable salt thereof.

In some embodiments, the compound is the (S)-enantiomer of one of the preceding compounds, or a pharmaceutically acceptable salt thereof. In some embodiments, the compound is the (R)-enantiomer of one of the preceding compounds, or a pharmaceutically acceptable salt thereof.

It is further appreciated that certain features of the present disclosure, which are, for clarity, described in the context of separate embodiments, can also be provided in combination in a single embodiment. Conversely, various features of the present disclosure which are, for brevity, described in the context of a single embodiment, can also be provided separately or in any suitable subcombination. The present disclosure is intended to include all combinations of embodiments for each variable described hereinabove including salts thereof.

At various places in the present specification, divalent linking substituents are described.

It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the term "$C_{n-m}$" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms.

Aryl groups include, e.g., phenyl, naphthyl, anthracenyl, phenanthrenyl, indanyl, indenyl, and the like. In some embodiments, aryl groups have from 6 to 10 carbon atoms. In some embodiments, the aryl group is phenyl or naphthyl. In some embodiments, the aryl is phenyl.

As used herein, "halo" refers to F, Cl, Br, or I. In some embodiments, a halo is F, Cl, or Br. In some embodiments, a halo is F or Cl. In some embodiments, a halo is F. In some embodiments, a halo is Cl.

As used herein, "$C_{n-m}$ haloalkoxy" refers to a group of formula —O-haloalkyl having n to m carbon atoms. Example haloalkoxy groups include OCF$_3$ and OCHF$_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include CF$_3$, C$_2$F$_5$, CHF$_2$, CH$_2$F, CCl$_3$, CHCl$_2$, C$_2$Cl$_5$ and the like.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonylamino" refers to a group of formula —NHC(O)O($C_{n-m}$ alkyl), wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms. As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "carbamyl" to a group of formula —C(O)NH$_2$.

As used herein, the term "carbonyl", employed alone or in combination with other terms, refers to a —C(O)— group.

As used herein, the term "cyano-$C_{1-3}$ alkyl" refers to a group of formula —($C_{1-3}$ alkylene)-CN.

As used herein, the term "HO—$C_{1-6}$ alkyl" refers to a group of formula —($C_{1-6}$ alkylene)-OH.

As used herein, the term "HO—$C_{1-3}$ alkyl" refers to a group of formula —($C_{1-3}$ alkylene)-OH.

As used herein, the term "$C_{1-6}$ alkoxy-$C_{1-6}$ alkyl" refers to a group of formula —($C_{1-6}$ alkylene)-O($C_{1-6}$ alkyl).

As used herein, the term "$C_{1-3}$ alkoxy-$C_{1-3}$ alkyl" refers to a group of formula —($C_{1-3}$ alkylene)-O($C_{1-3}$ alkyl).

As used herein, the term "carboxy" refers to a group of formula —C(O)OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "aminocarbonyloxy" refers to a group of formula —OC(O)NH$_2$.

As used herein, the term "$C_{1-3}$ alkylcarbonyloxy" refers to a group of formula —OC(O)($C_{1-3}$ alkyl).

As used herein, the term "$C_{1-3}$ alkylaminocarbonyloxy" refers to a group of formula —OC(O)NH($C_{1-3}$ alkyl).

As used herein, the term "di($C_{1-3}$ alkyl)aminocarbonyloxy" refers to a group of formula —OC(O)N($C_{1-3}$ alkyl)$_2$, wherein the two alkyl groups each has, independently, 1 to 3 carbon atoms.

As used herein, "cycloalkyl" refers to non-aromatic cyclic hydrocarbons including cyclized alkyl and alkenyl groups. Cycloalkyl groups can include mono- or polycyclic (e.g., having 2 fused rings) groups, spirocycles, and bridged rings (e.g., a bridged bicycloalkyl group).

Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons (i.e., $C_{3-10}$). In some embodiments, the cycloalkyl is a $C_{3-10}$ monocyclic or bicyclic cycloalkyl. In some embodiments, the cycloalkyl is a $C_{3-10}$ monocyclic cycloalkyl which is optionally substituted by CH$_2$F, CHF$_2$, CF$_3$, and CF$_2$CF$_3$. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo [2.1.1]hexyl, bicyclo[2.2.1]heptanyl, bicyclo[3.1.1] heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2 fused rings) aromatic heterocycle having at least one heteroatom ring member selected from N, O, S and B, wherein any ring forming N is optionally an N-oxide group. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, S and B. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-10 membered monocyclic or bicyclic heteroaryl having 1, 2, 3, or 4 heteroatom ring members independently selected from N, O, S and B. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-6 monocyclic heteroaryl having 1 or 2 heteroatom ring members independently selected from N, O, S and B. In some embodiments, the heteroaryl is a 5-6 monocyclic heteroaryl ring having 1 or 2 heteroatom ring members independently selected from N, O or S. In some embodiments, the heteroaryl group contains 3 to 10, 4 to 10, 3 to 7, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, isoxazole, thiophene, thiazole, isothiazole, imidazole, furan, thiophene, triazole, tetrazole, thiadiazole, quinoline, isoquinoline, indole, benzothiophene, benzofuran, benzisoxazole, imidazo[1,2-b]thiazole, purine, triazine, thieno[3,2-b]pyridine, imidazo[1,2-a]pyridine, 1,5-naphthyridine, 1H-pyrazolo[4,3-b]pyridine, 1,2,3-triazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl, 1,2-dihydro-1,2-azaborine, and the like.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S and B, and wherein the ring-forming carbon atoms and heteroatoms of the heterocycloalkyl group can be optionally substituted by one or more oxo or sulfido (e.g., C(O), S(O), C(S), or S(O)$_2$, etc.). Heterocycloalkyl groups include monocyclic and polycyclic (e.g., having 2 fused rings) systems. Included in heterocycloalkyl are monocyclic and polycyclic 3-10-, 4-10-, 3-7-, 4-7-, and 5-6-membered heterocycloalkyl groups. Heterocycloalkyl groups can also include spirocycles and bridged rings (e.g., a 5-10 membered bridged biheterocycloalkyl ring having one or more of the ring-forming carbon atoms replaced by a heteroatom independently selected from N, O, S and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 3 to 10 ring-forming atoms, 4 to 10 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members.

Example heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, 1,2,3,4-tetrahydroisoquinoline, azabicyclo [3.1.0]hexanyl, diazabicyclo[3.1.0]hexanyl, oxabicyclo [2.1.1]hexanyl, azabicyclo[2.2.1]heptanyl, diazabicyclo [2.2.1]heptanyl, azabicyclo[3.1.1]heptanyl, diazabicyclo [3.1.1]heptanyl, azabicyclo[3.2.1]octanyl, diazabicyclo [3.2.1]octanyl, oxabicyclo[2.2.2]octanyl, azabicyclo[2.2.2] octanyl, azaadamantanyl, diazaadamantanyl, oxa-adamantanyl, azaspiro[3.3]heptanyl, diazaspiro[3.3] heptanyl, oxa-azaspiro[3.3]heptanyl (e.g. 2-oxa-6-azaspiro [3.3]heptan-6-yl), oxaspiro[3.3]heptanyl (e.g. 2-oxaspiro [3.3]heptan-6-yl), azaspiro[3.4]octanyl, diazaspiro[3.4] octanyl, oxa-azaspiro[3.4]octanyl, azaspiro[2.5]octanyl, diazaspiro[2.5]octanyl, azaspiro[4.4]nonanyl, diazaspiro [4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl and the like.

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl or sulfonyl group.

As used herein, the term "independently selected from" means that each occurrence of a variable or substituent are independently selected at each occurrence from the applicable list.

As used herein, a dashed bond (—) represents a single or double bond depending on the nature of the atoms in each ring and as required to complete the valencies of the atoms being linked by the bond.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula (I), (II), etc.) provided herein include stereoisomers of the compounds.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein.

Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in Remington's Pharmaceutical Sciences, 17th ed., Mack Publishing Company, Easton, Pa., 1985, p. 1418 and *Journal of Pharmaceutical Science*, 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes.

Compounds of Formula (I) can be prepared as shown in Scheme 1. Appropriately substituted starting materials 1-1 wherein $Y^B$ is a halogen (e.g., Cl, Br or I) can be converted to an appropriately substituted metal 1-2 (e.g., $M^B$ is $B(OR)_2$, $BF_3K$, $Sn(R)_3$, or Zn) under standard conditions (e.g., in the presence of a diboron reagent such as bis(pinacolato) diboron, a palladium catalyst, such as dichloro[bis(triphenylphosphoranyl)]palladium or [1,1'-bis(diphenylphosphino)ferrocene]dichloropalladium(II), complex with dichloromethane, and a base, such as potassium acetate). Intermediate 1-3 wherein $Y^A$ is a halogen (e.g., Cl, Br or I) or pseudohalogen (e.g., OMs or OTf) and P is a suitable protecting group (e.g., trimethylsilylethoxymethyl) can be coupled with metal 1-2 under standard Suzuki conditions (e.g., in the presence of a palladium catalyst, such as tetrakis(triphenylphosphine)palladium(0), [1,1'-bis(diphenylphosphino)ferrocene]dichloropalladium(II), complex with dichloromethane or bis(di-tert-butyl(4-dimethylaminophenyl)phosphine)dichloropalladium(II) and a base (e.g., a carbonate base such as potassium carbonate, or cesium fluoride)) or standard Stille conditions (e.g., in the presence of a palladium(0) catalyst, such as tetrakis(triphenylphosphine)palladium(O)) or standard Negishi conditions (e.g., in the presence of a palladium catalyst, such as tetrakis(triphenylphosphine)palladium(0) or [1,1'-bis(diphenylphosphino)ferrocene]dichloropalladium (II)) to give compounds of Formula (I).

Alternatively, compounds of Formula (I) can be prepared as shown in Scheme 2. Optionally protected intermediates such as 2-1, wherein $Y^A$ is an appropriate halogen (e.g., Cl, Br, or I) or pseudohalogen (e.g., OMs or OTf), can be converted to an appropriately substituted metal $M^A$ (e.g., $M^A$ is $B(OR)_2$, $BF_3K$, $SnR_3$, or Zn) under standard conditions (e.g., in the presence of a diboron reagent such as bis(pinacolato)diboron, a palladium catalyst, such as dichloro[bis(triphenylphosphoranyl)]palladium or [1,1'-bis(diphenylphosphino)ferrocene]dichloropalladium(II), complex with dichloromethane, and a base, such as potassium acetate). Intermediate 2-2 can undergo Suzuki, Stille or Negishi couplings with appropriate halo-derivatives 2-3, wherein $Y^B$ is a suitable halogen (e.g., Cl, Br, or I) or pseudohalogen (e.g., OMs or OTf), to provide compounds of Formula (I). The compounds of Formula (I) can be prepared by either route depending on the compatibility of functional groups present in the intermediates.

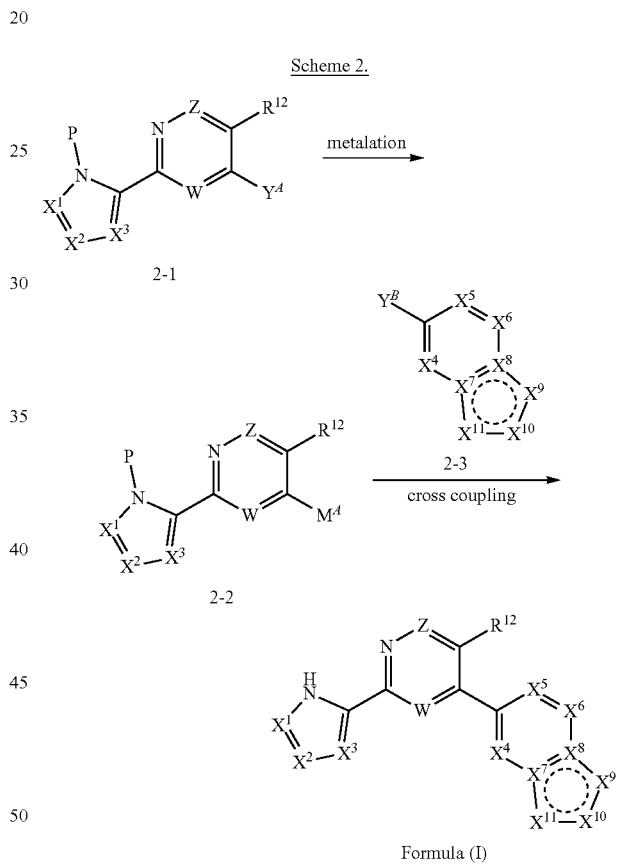

Scheme 2.

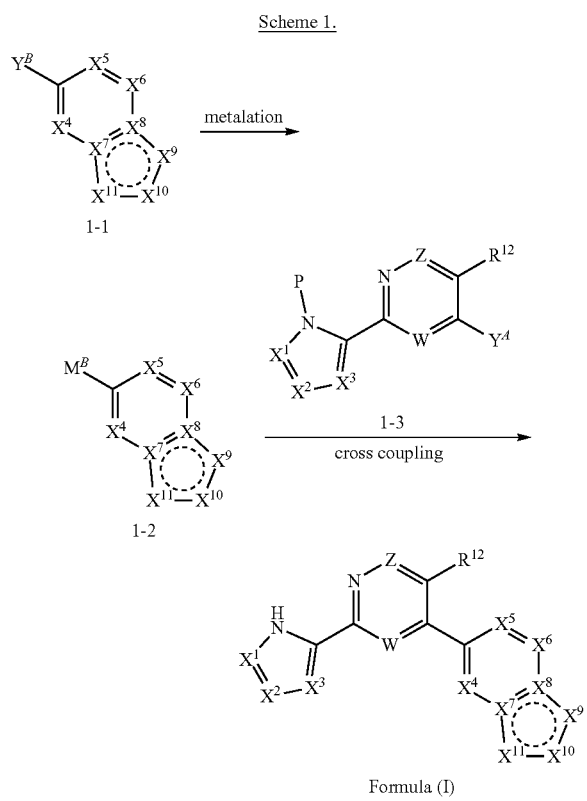

Scheme 1.

Compounds of Formula (I) wherein $X^1$ is $CR^1$, $X^2$ is $CR^2$, and $X^3$ is N (e.g., 3-6) can be prepared as shown in Scheme 3. Nitrile containing starting material 3-4, wherein $Y^A$ is a suitable halogen (e.g., Cl, Br or I) or pseudohalogen (e.g., OMs or OTf), can be reacted with a suitable metal 3-2, wherein $M^B$ is a boronic acid, boronic ester, or an appropriately substituted metal such as $Sn(Bu)_4$ or Zn, under standard Suzuki conditions or standard Stille conditions (e.g., in the presence of a palladium(0) catalyst, such as tetrakis(triphenylphosphine)palladium(0) or 4-(di-tert-butylphosphino)-N,N-dimethylaniline-dichloropalladium (2:1) and a base (e.g., a bicarbonate or carbonate base, or CsF) or standard Negishi conditions (e.g., in the presence of a palladium(0) catalyst, such as tetrakis(triphenylphosphine)

palladium(0)), to give intermediate 3-5. The nitrile of intermediate 3-5 can be converted to a substituted imidazole as shown in 3-6 via several routes, some of which are outlined in Scheme 4. The order of steps can be reversed, such that imidazole formation to furnish 3-7 (by methods such as shown in Scheme 4) can precede the coupling to 3-2. In this case, the NH of the heterocycle (3-7) can be optionally protected (e.g., using SEM-Cl and base) to give a N-protected derivative (3-8), which can be coupled with 3-2 as described for the transformation from 3-4 to 3-5 above, to provide 3-9, which upon N-deprotection (e.g., reaction with a strong acid, such as TFA) will furnish compounds 3-6. The compounds of Formula (I) can be prepared by either route depending on the compatibility of functional groups present in the intermediates. Where the nitrile is not present in starting material 3-4, it can be installed from an appropriately substituted starting material 3-1, wherein $Y^C$ and $Y^A$ are independently halogen (e.g., $Y^C$ is Cl or Br) or pseudohalogen (OMs or OTf), via Negishi coupling with $Zn(CN)_2$ (e.g., in the presence of a Pd(O) catalyst, such as tetrakis(triphenylphosphine)palladium(0)). Alternatively, a selective Suzuki, Stille or Negishi cross coupling of appropriately substituted starting material 3-1 with appropriately substituted metal 3-2 can provide intermediate 3-3, which can be converted to nitrile-containing intermediate 3-5 via Negishi coupling with $Zn(CN)_2$ (e.g., in the presence of a Pd(O) catalyst, such as tetrakis(triphenylphosphine)palladium(0)).

Scheme 3.

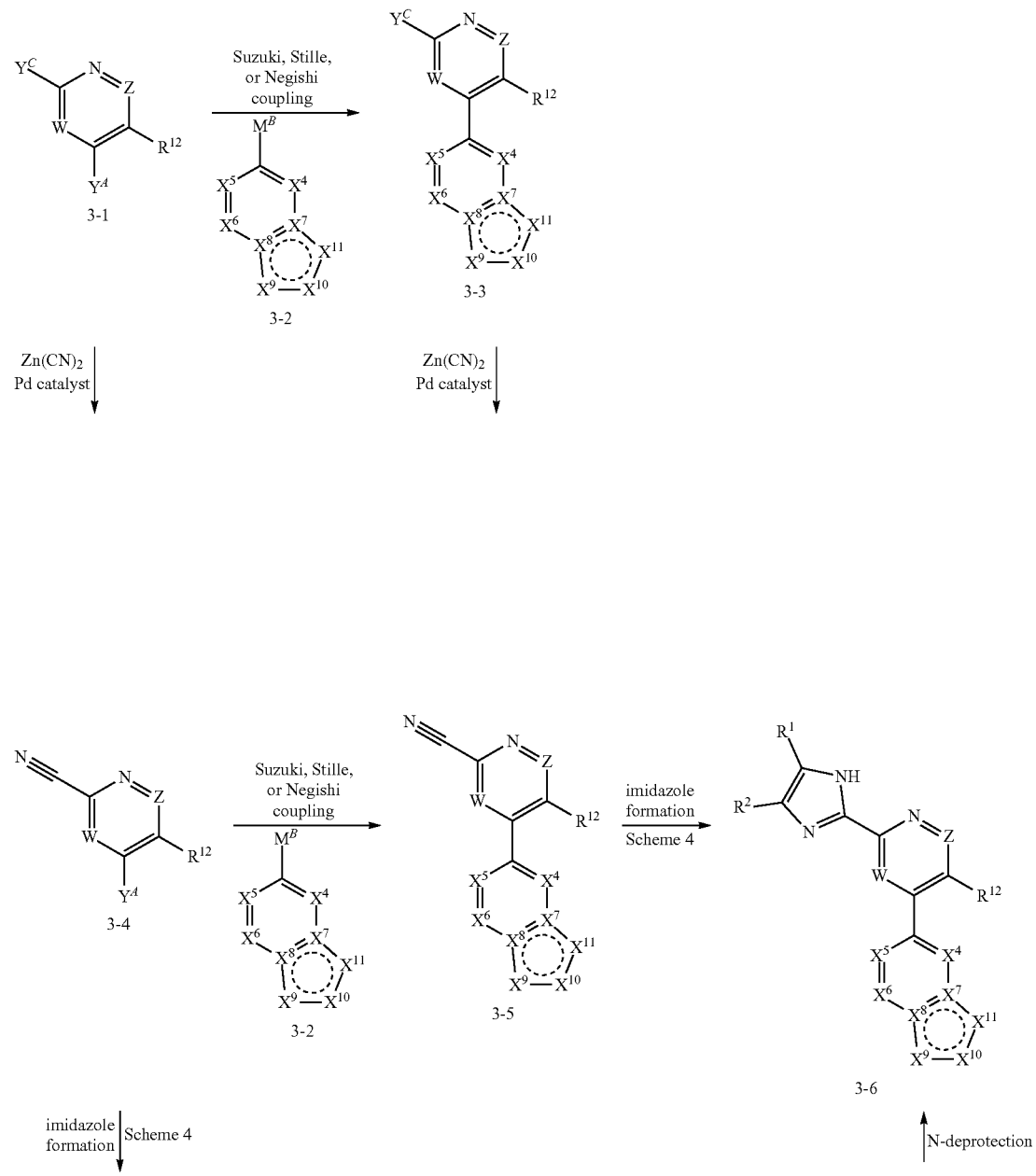

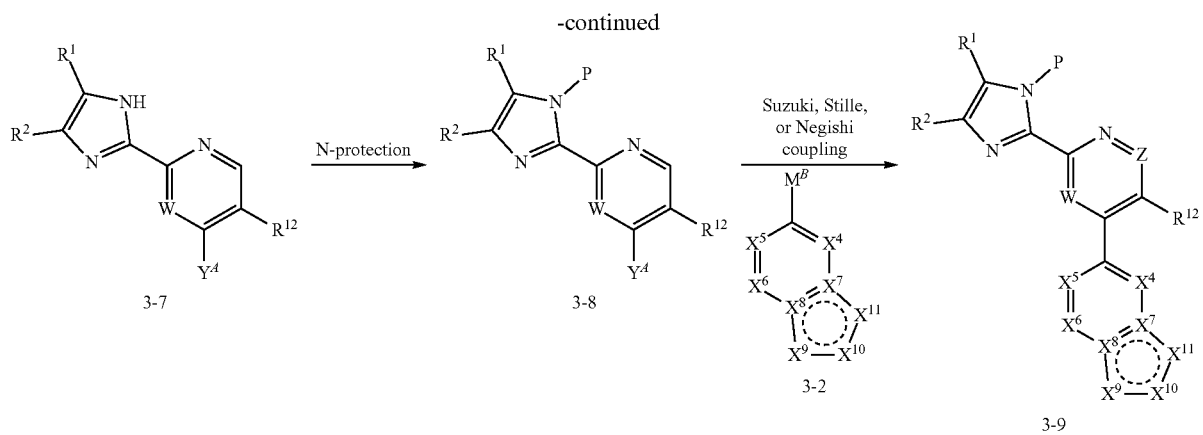

Methods for formation of the imidazole are outlined in Scheme 4, in which both nitriles and carboxylic acids serve as useful starting materials. The imidazole formations may be carried out with $R^A$=Cy (a bicyclic moiety shown in the intermediates 1-1, 1-2 and Formula (I) of Scheme 1), or alternatively with $R^A$ =$X^A$ (halo). Nitrile containing intermediate 4-1 can be converted to an imidate (e.g., by reacting with catalytic sodium methoxide in an alcohol or by reacting with HCl in an alcohol) and the intermediate imidate can be reacted with an amino ketal or amino acetal (4-2, wherein R is an alkyl group such as methyl or ethyl) in the presence of acid (e.g., AcOH or HCl) and heat to form imidazole 4-3. Alternatively, the intermediate imidate can be reacted with $NH_4Cl$ to afford an amidine, which can be alkylated with an α-halo ketone (4-4) in the presence of base (e.g., $KHCO_3$, or $K_2CO_3$) in a solvent such as an alcohol, or preferably, DMF, to furnish imidazole 4-3. The imidate intermediate formed by reacting nitrile 4-1 with catalytic sodium methoxide can be treated with a diamine (4-5) (e.g., a phenylenediamine derivative) and cyclized under acidic conditions and heat to afford imidazole 4-3. Alternatively, carboxylic acid 4-6 can be coupled to a diamine (4-5) in the presence of a coupling reagent (e.g., HATU) and base (e.g., Hunig's Base or triethylamine). The intermediate amide can be cyclized to imidazole 4-3 by heating in acid (e.g., AcOH). Carboxylic acid 4-6 can also be reacted with α-halo ketones (4-4) in the presence of base (e.g., $K_2CO_3$) to afford an ester intermediate that can be heated in the presence of $NH_4OAc$ to afford imidazole 4-3.

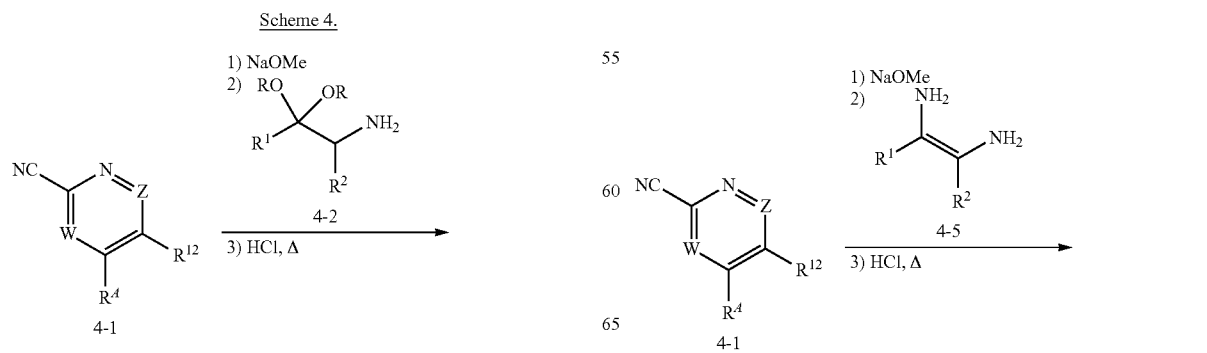

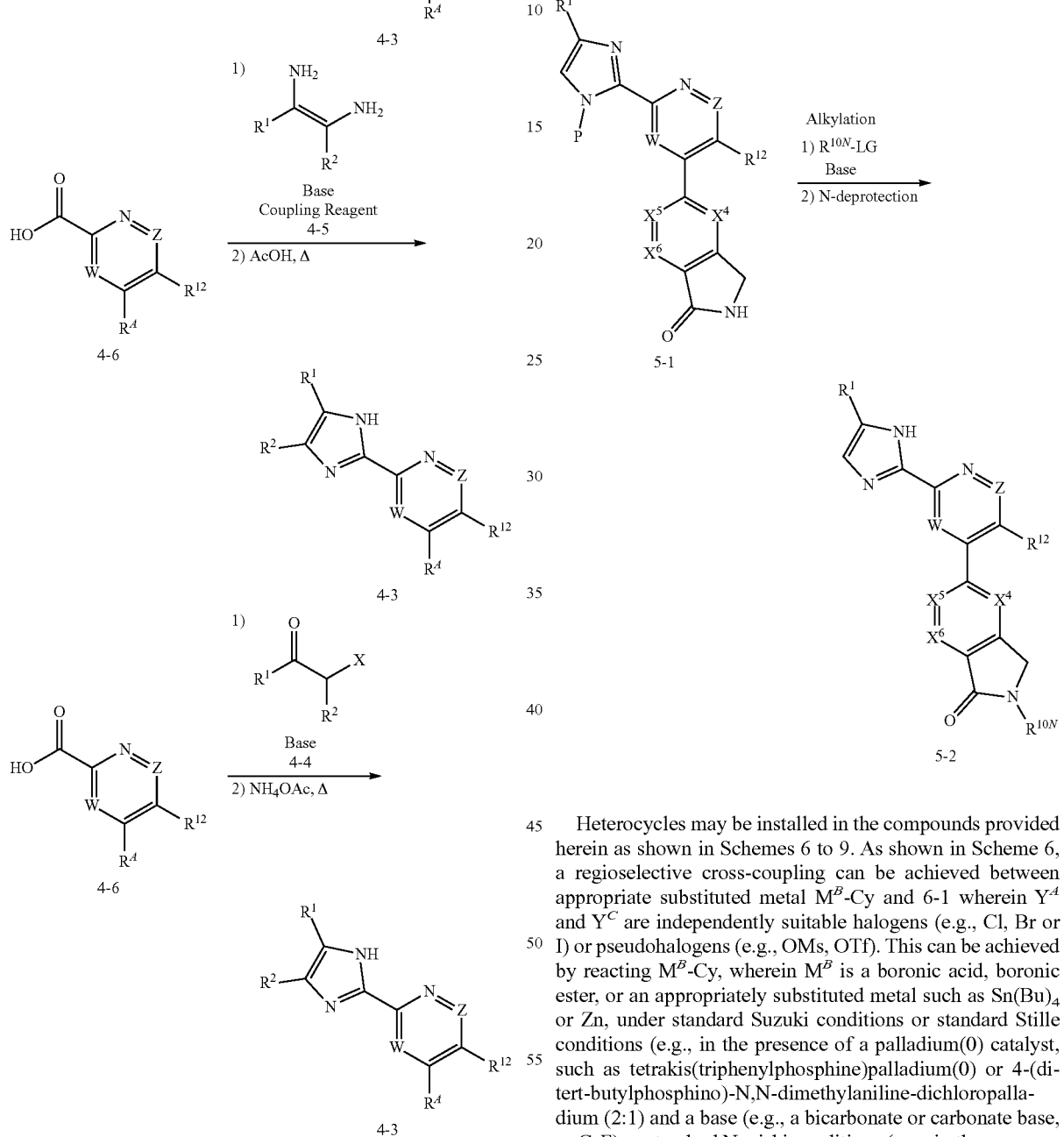

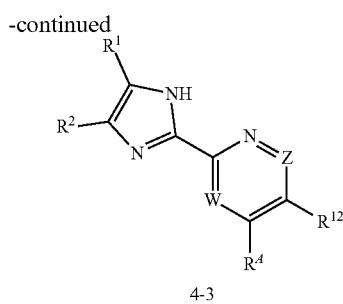

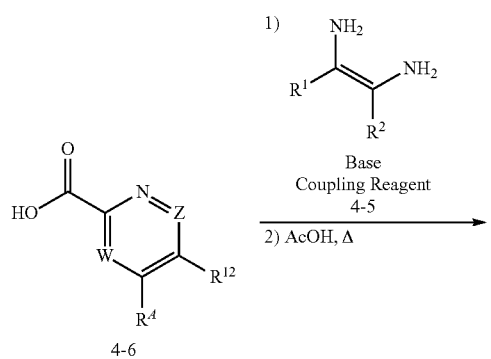

afford, after N-deprotection, the alkylated product 5-2. Where desired, if the alkylated product contains a manipulatable functional group, further transformations (e.g., hydrolysis, amide formation, reduction, alkylation, acylation, sulfonylation) are possible.

In Scheme 4, when $R^A$ is Cy that contains a nucleophilic functional group (e.g., isoindolinone), further transformations may be carried out as shown in Scheme 5. For example, alkylation of suitably protected intermediate 5-1 with $R^{10}$-LG, wherein LG is a leaving group (e.g., LG=Br, I, OSO$_2$Me, etc.), can be carried out in the presence of base (e.g., Na$_2$CO$_3$, K$_2$CO$_3$, Cs$_2$CO$_3$, NaH, KO$^t$Bu, etc.) to afford, after N-deprotection, the alkylated product 5-2. Where desired, if the alkylated product contains a manipulatable functional group, further transformations (e.g., hydrolysis, amide formation, reduction, alkylation, acylation, sulfonylation) are possible.

Heterocycles may be installed in the compounds provided herein as shown in Schemes 6 to 9. As shown in Scheme 6, a regioselective cross-coupling can be achieved between appropriate substituted metal $M^B$-Cy and 6-1 wherein $Y^A$ and $Y^C$ are independently suitable halogens (e.g., Cl, Br or I) or pseudohalogens (e.g., OMs, OTf). This can be achieved by reacting $M^B$-Cy, wherein $M^B$ is a boronic acid, boronic ester, or an appropriately substituted metal such as Sn(Bu)$_4$ or Zn, under standard Suzuki conditions or standard Stille conditions (e.g., in the presence of a palladium(0) catalyst, such as tetrakis(triphenylphosphine)palladium(0) or 4-(di-tert-butylphosphino)-N,N-dimethylaniline-dichloropalladium (2:1) and a base (e.g., a bicarbonate or carbonate base, or CsF) or standard Negishi conditions (e.g., in the presence of a palladium(0) catalyst, such as tetrakis(triphenylphosphine)palladium(0)), with intermediate 6-1 to give derivative 6-2. The desired heterocycle (e.g., illustrated by optionally protected imidazole isomer 6-3 wherein $M^D$ is a boronic acid, boronic ester, or an appropriately substituted metal such as Sn(Bu)$_4$ or Zn) can be coupled with 6-2 under Suzuki, Stille or Negishi conditions as described above to afford (on subsequent N-deprotection) product 6-4.

Scheme 6.

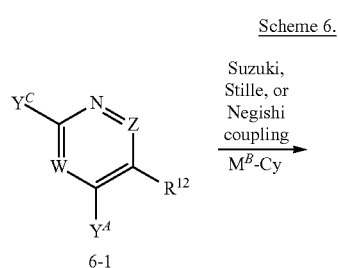

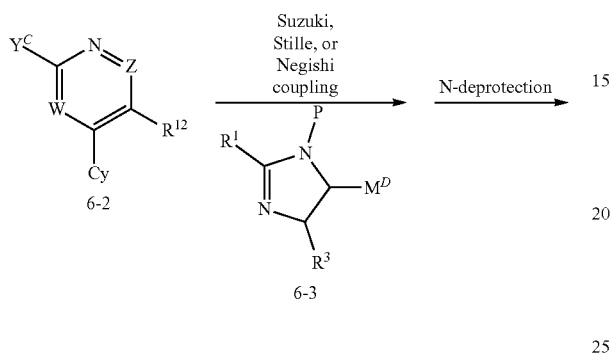

Compounds of Formula (I) wherein $X^1$ is C—NHR$^{c1}$, $X^2$ is N, and $X^3$ is C—R$^3$ (e.g., 7-4 and 7-5) can be prepared, as shown in Scheme 7, by reacting an α-halo ketone (7-1) with 2-aminopyrimidine in the presence of base to form intermediate 7-2. After coupling with M$^B$-Cy under standard Suzuki, Stille or Negishi conditions to afford 7-3, the aminoimidazole moiety can be liberated by reaction of intermediate 7-3 with hydrazine hydrate at elevated temperature (e.g., about 100° C.) to afford 7-4. The amine of 7-4 can optionally be alkylated by reaction of the amine with an aldehyde (e.g., RCHO) in the presence of a reducing agent (e.g., sodium cyanoborohydride or sodium triacetoxyborohydride) to give 7-5.

Scheme 7.

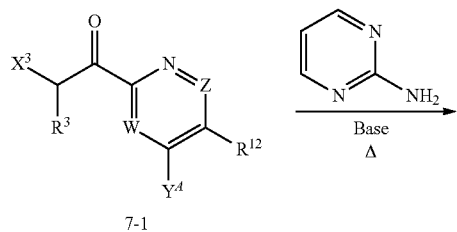

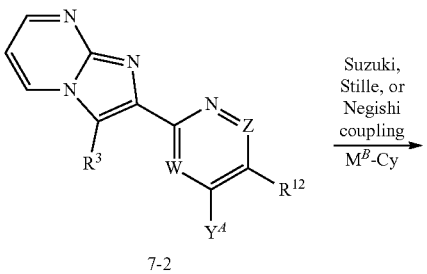

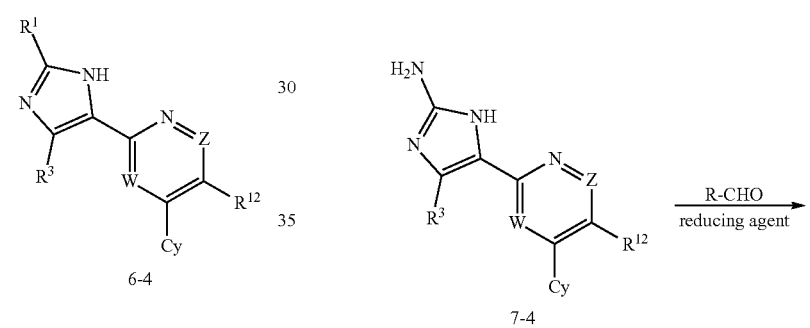

Compounds of Formula (I) wherein $X^1$ is C—NHR$^{c1}$, and $X^2$ and $X^3$ are N (e.g., 8-6) can be prepared, as shown in Scheme 8, by reacting an ester (8-2, wherein R is an alkyl group (e.g., methyl or ethyl), prepared by Suzuki, Stille or Negishi coupling of 8-1 with M$^B$-Cy) with hydrazine hydrate at elevated temperature to form an acyl hydrazide 8-3. Intermediate 8-3 can be reacted with an alkylated thiourea (8-5) in the presence of heat and base (e.g., 2,6-lutidine) to afford aminotriazole product 8-6. When unavailable commercially, the requisite intermediate 8-5 can be prepared by alkylating available thiourea 8-4 with methyl iodide.

Scheme 8.

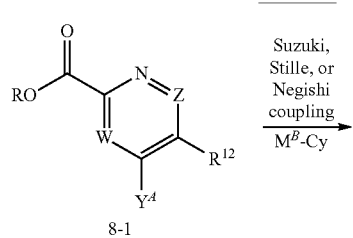

8-1

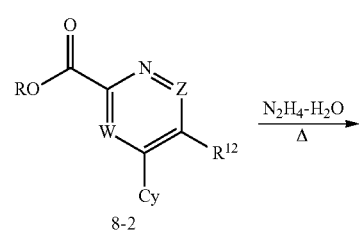

8-2

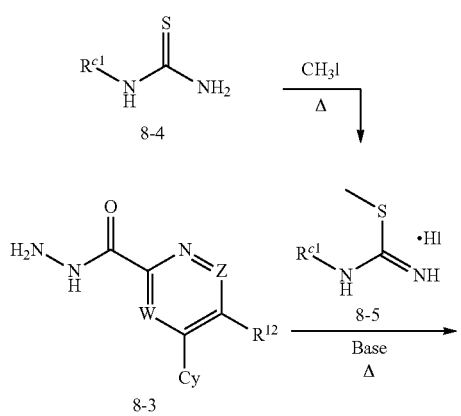

8-3

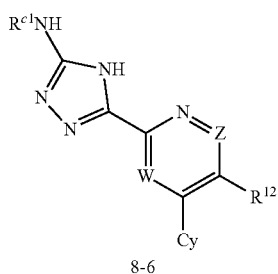

8-6

Compounds of Formula (I) wherein $X^1$ is C—$R^1$, and $X^2$ and $X^3$ are N (9-4) can be synthesized as shown in Scheme 9. Suzuki, Stille or Negishi coupling of appropriately substituted nitrile-containing intermediate 9-1 (e.g., $Y^A$ =Cl, Br, I or OTf) with $M^B$-Cy provides intermediate 9-2. Treatment of the nitrile intermediate 9-2 first with catalytic sodium methoxide, followed by an acyl hydrazide (9-3) at elevated temperature, furnishes triazole-containing product 9-4.

Scheme 9.

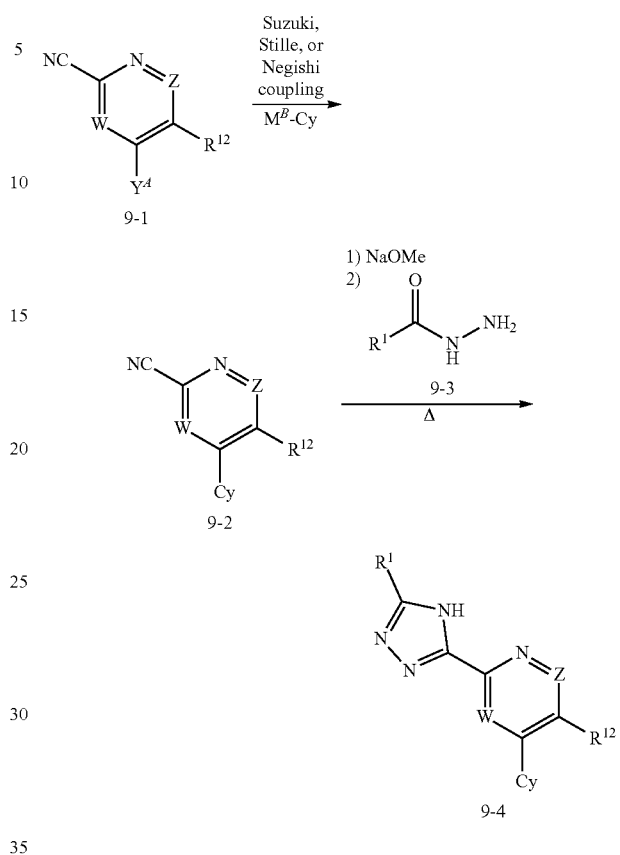

Compounds provided herein that contain an imidazole can be further functionalized as shown, for example, in Schemes 10 and 11. As shown in Scheme 10, an imidazole such as 10-1, containing an unfunctionalized carbon, can be nitrated (e.g., using $HNO_3$ in $H_2SO_4$) to provide nitro derivative 10-2, which can be reduced (e.g., using iron in AcOH or in aq. HCl and alcoholic solvent) to amino derivative 10-3. If the group Cy is not anticipated to be stable to the conditions, the synthesis may alternatively be carried out with a halogen at that position, and the desired cyclic group (Cy) introduced by Suzuki, Stille, or Negishi conditions on the product of nitration or reduction (10-2, or 10-3, respectively), as appropriate. The compounds of Formula (I) can be prepared by either route depending on the compatibility of functional groups present in the intermediates.

Scheme 10.

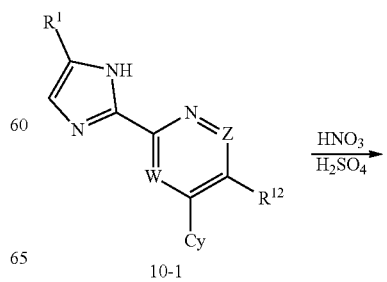

10-1

107
-continued

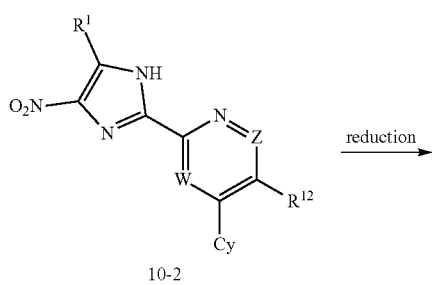

10-2 reduction →

108
-continued

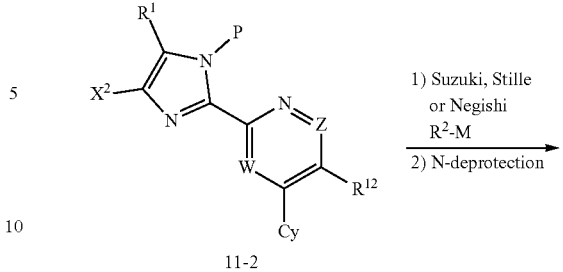

11-2

1) Suzuki, Stille or Negishi
   $R^2$-M
2) N-deprotection →

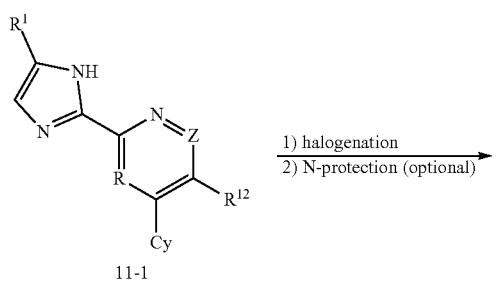

10-3

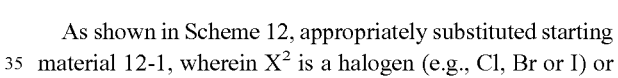

11-3

As shown in Scheme 11, an imidazole such as 11-1, containing an unfunctionalized carbon, can be treated with a halogenating reagent (e.g., N-iodosuccinimide or N-bromosuccinimide) to form halo-containing intermediate 11-2 (e.g., to provide a compound wherein $X^2$ is Cl, Br or I). Subjection of an optionally protected intermediate 11-2 to a Pd-catalyzed cross-coupling reaction (e.g., Suzuki, Stille, Negishi and the like) can furnish (after N-deprotection) compounds 11-3.

Scheme 11.

As shown in Scheme 12, appropriately substituted starting material 12-1, wherein $X^2$ is a halogen (e.g., Cl, Br or I) or pseudohalogen (e.g., OMs or OTf) can be converted to carbonyl-containing products. Reaction of starting material 12-1 with carbon monoxide in the presence of an alcohol (e.g., R=$CH_3$ or $CH_2CH_3$) and a Pd catalyst (e.g., [1,1'-bis (diphenylphosphino)ferrocene]dichloropalladium(II), complex with dichloromethane (1:1)) affords an ester (12-2). Hydrolysis of the ester in 12-2 under standard conditions (e.g., aq. NaOH in THF and an alcohol) can be carried out to afford a carboxylic acid which can be coupled with an amine, $R^{2c}R^{2d}$ NH, under standard conditions (e.g., HATU in the presence of Hunig's base or triethylamine) to form amide 12-3. Amide 12-3 can also be prepared by heating ester 12-2 with amine $R^{2c}R^{2d}$ NH in the presence of a suitable lewis acid (e.g., $AlCl_3$). Direct conversion of halo-containing intermediate 12-1 to amide 12-3 can also be effected by reacting 12-1 with carbon monoxide and a Pd catalyst in the presence of an amine $R^{2c}R^{2d}$ NH. If the CO insertion reaction on 12-1 is carried out in the absence of alcohol and in the presence of a reducing agent (e.g., triethylsilane), aldehyde 12-4 can be prepared. The aldehyde can be converted to an amine-containing compound (12-5) by reductive amination with $R^{2c}R^{2d}$ NH in the presence of a reducing agent (e.g., sodium cyanoborohydride, sodium triacetoxyborohydride). Numerous other functional group transformations can be carried out on intermediates 12-2 and 12-4, such as, but not limited to, Grignard addition, reduction, and deoxyfluorination (e.g., with Deoxo-Fluor®).

Scheme 12.

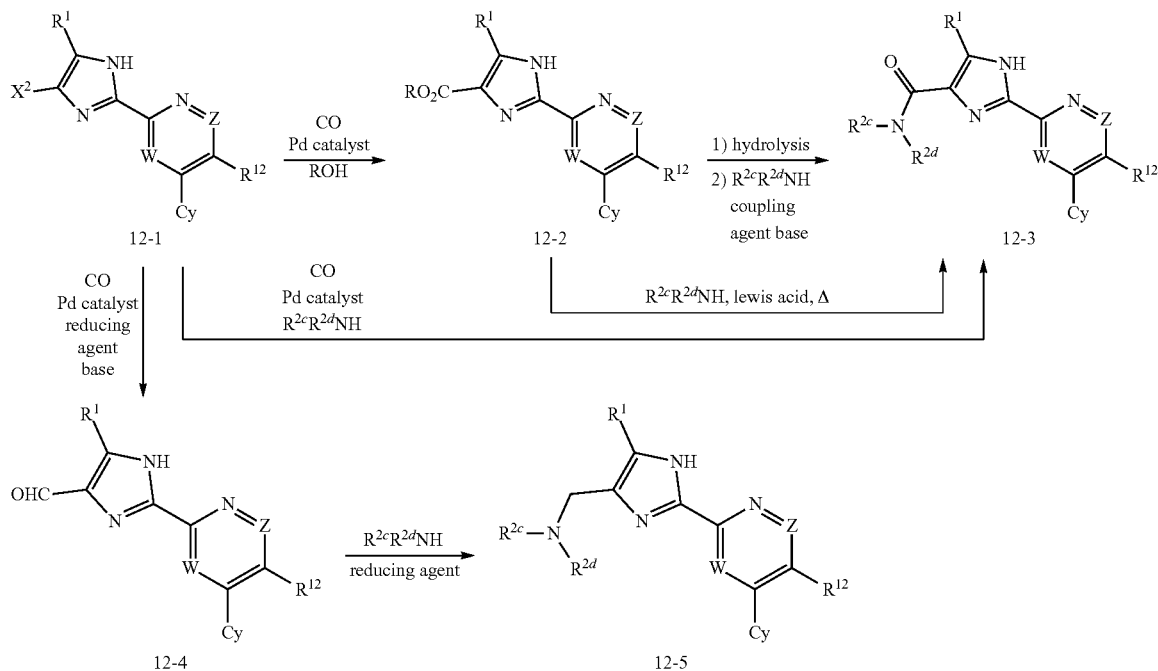

The Cy group in compounds of Formula (I) can be prepared as shown in Scheme 13. Appropriately substituted ester 13-1 (e.g., R is —$CH_3$, —$CH_2CH_3$ and the like) wherein $Y^B$ is a halo (e.g., Cl, Br, or I) or pseudohalo group (e.g., OTf or OMs), $Y^6$ is a suitable halogen (e.g. Cl, Br or I), and substituent $X^{11}$ is a suitable alkyl group, can be halogenated by treatment with a halogenating reagent such as an N-halosuccinimide (e.g., N-chlorosuccinimide, N-bromosuccinimide or N-iodosuccinimide) to afford intermediate 13-3 wherein $L^{11}$ is a halogen (e.g., Cl, Br or I). Alternatively, a suitably substituted starting material 13-2 bearing an alcohol substituent on alkyl group $X^{11}$ can be halogenated by treatment with a suitable halogenating reagent (e.g., $SOCl_2$ or triphenylphosphine dibromide) to afford 13-3 wherein $L^{11}$ is a halogen (e.g., Cl, Br or I). Alternatively, 13-2 can be treated with a sulfonyl chloride (e.g., p-toluenesulfonyl chloride or methanesulfonyl chloride) in the presence of a base (e.g., triethylamine or Hunig's base) to afford 13-3 wherein $L^{11}$ is a sulfonyl-based leaving group (e.g., OMs or OTs). Intermediate 13-3 can be converted to intermediate 13-4 via reaction with an amine ($R^{10N}$ $NH_2$) in the presence of base (e.g., triethylamine or N,N-diisopropylethylamine), or in the presence of acid (e.g., boric acid) and base (e.g., a carbonate base such as $K_2CO_3$, $Cs_2CO_3$ or $Na_2CO_3$). Intermediate 13-4 wherein $Y^6$ is a suitable halogen (e.g., Cl, Br or I) can be converted to thioether 13-5 by heating in the presence of a suitable sulfur nucleophile $R^{b6}$ SM wherein M is a suitable metal such as sodium (e.g., sodium methanethiolate). Oxidation of intermediate 13-5 with a suitable oxidizing agent (e.g., m-CPBA) provides sulfone intermediate 13-6. The $Y^B$ halo (e.g., Cl, Br, or I) or pseudohalo group (e.g., OTf or OMs) of intermediate 13-6 can be converted to an appropriately substituted metal (e.g., $M^B$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or [1,1'-bis(diphenylphosphino)ferrocene]dichloropalladium(II), complex with dichloromethane, and a base, such as potassium acetate) to afford compound 13-7. Intermediates 13-4, 13-5, 13-6 and 13-7 can be used as shown in the preceding and following Schemes to prepare compounds 13-8.

Scheme 13.

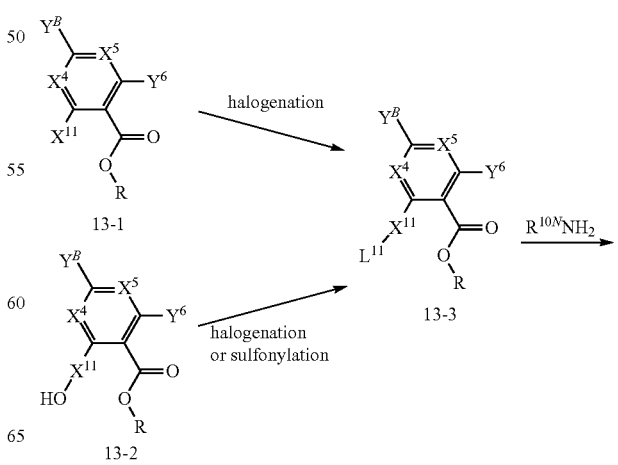

Scheme 14.

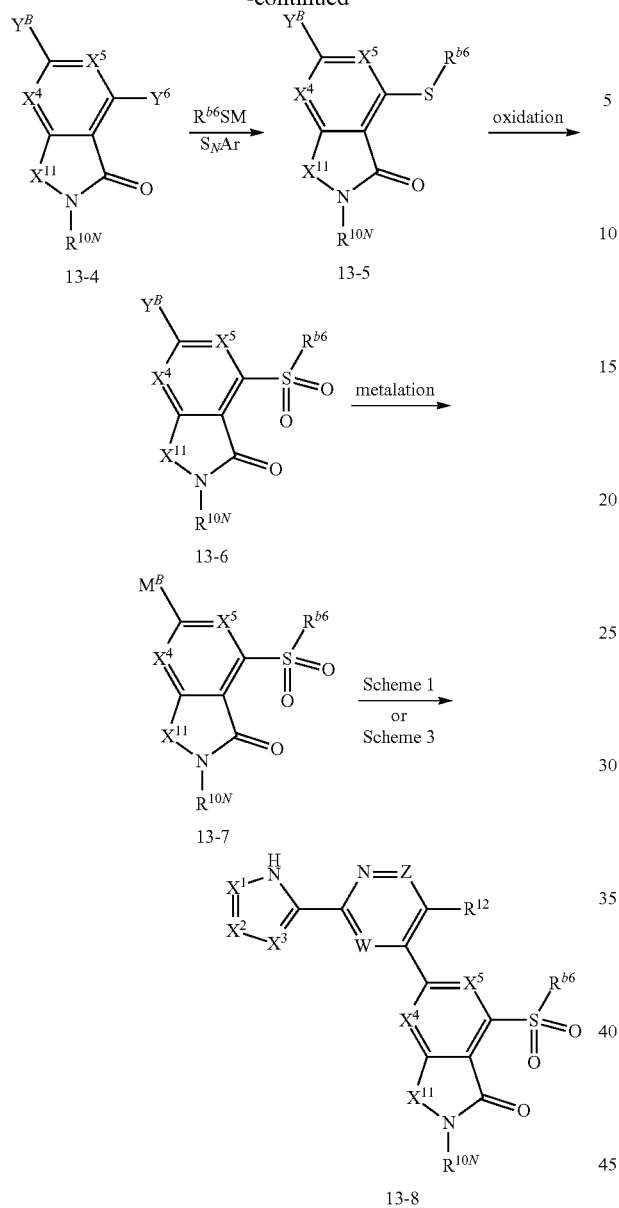
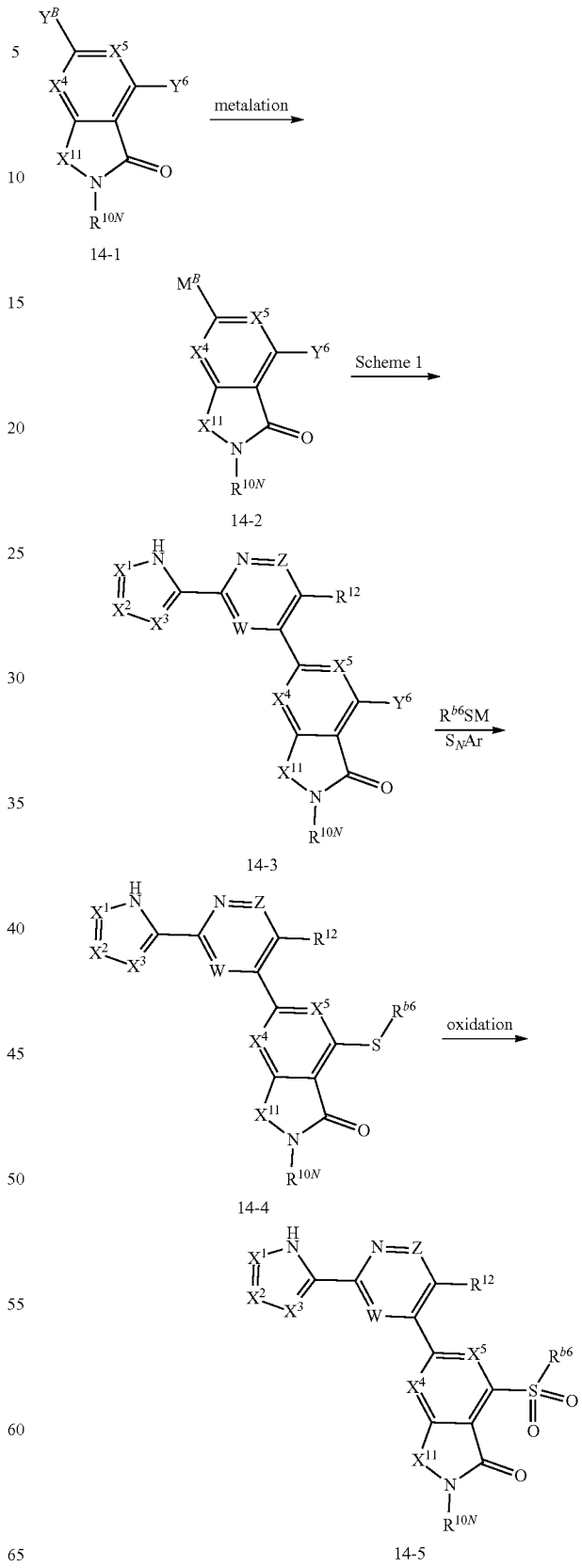

Compounds of Formula (I) can be prepared as shown in Scheme 14. A suitably substituted intermediate 14-1 wherein $Y^B$ and $Y^6$ are independently halogen (e.g., Cl, Br, or I) or pseudohalogen (e.g., OTf or OMs) can be converted to an appropriately substituted metal 14-2 (e.g., $M^B$ is $B(OH)_2$, Bpin, $BF_3K$, $Sn(Bu)_3$, or Zn) under standard conditions (e.g., in the presence of a diboron reagent such as bis (pinacolato)diboron, a palladium catalyst, such as dichloro [bis(triphenylphosphoranyl)]palladium or [1,1'-bis(diphenylphosphino)ferrocene]dichloropalladium(II), complex with dichloromethane, and a base, such as potassium acetate). Intermediate 14-2 can be transformed to 14-3 via the methods shown in preceding Schemes (e.g., Scheme 1). Compound 14-3 wherein $Y^6$ is a suitable halogen (e.g., Cl, Br or I) can be converted to thioether 14-4 by heating in the presence of a suitable sulfur nucleophile $R^{b6}$ SM wherein M is a suitable metal such as sodium (e.g., sodium methanethiolate). Oxidation of compound 14-4 with a suitable oxidizing agent (e.g., m-CPBA) can provide compounds 14-5.

Compounds of Formula (I) can be prepared as shown in Scheme 15. Intermediate 15-1 wherein $Y^B$ is a halogen (e.g., Cl, Br, or I) or pseudohalogen (e.g., OTf or OMs) can be converted to an appropriately substituted metal 15-2 (e.g., $M^B$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or [1,1'-bis(diphenylphosphino)ferrocene]dichloropalladium(II), complex with dichloromethane, and a base, such as potassium acetate). In some cases, treatment of intermediate 15-2 with an alkylating agent $R^{10N}$-L, wherein L is a suitable leaving group (e.g., a halogen (e.g., Cl, Br, or I) or pseudohalo group (e.g., OTs or OMs)), in the presence of a base (e.g., sodium hydride or carbonate base (e.g., cesium carbonate)) can provide intermediate 15-3. Alternatively, the steps can be performed in reverse order (i.e., 15-1 may be alkylated with $R^{10N}$-L under conditions described above, to provide compound 15-4, which can subsequently converted to metal 15-3 under conditions described above) to afford intermediate 15-3, which can be converted to compounds of Formula (I) as outlined in preceding Schemes (e.g., Scheme 1)

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Scheme 15.

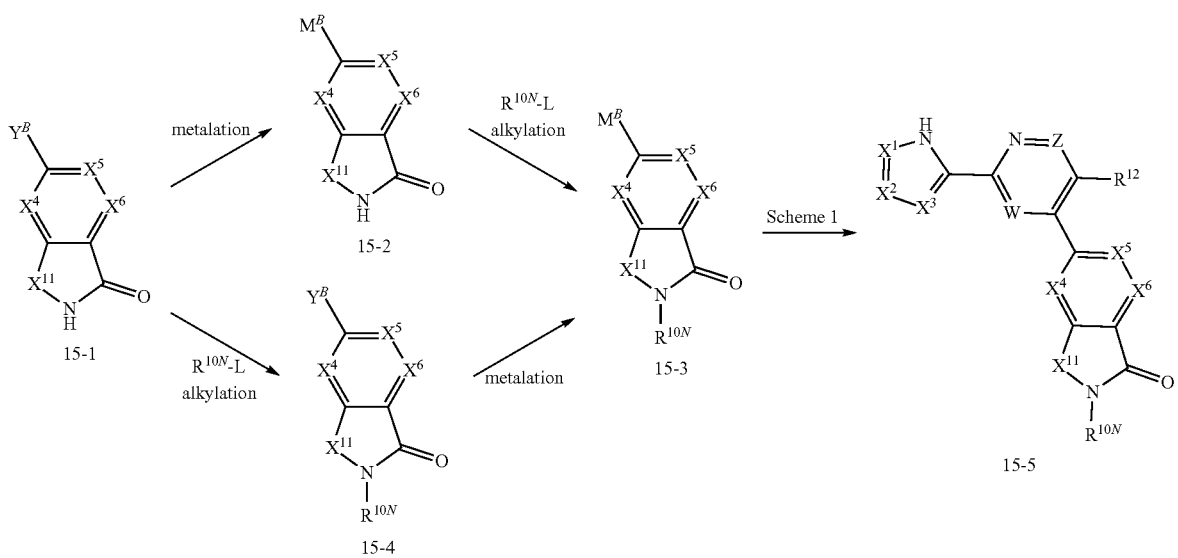

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" or "room temperature" or "rt" as used herein, are understood in the art, and refer generally to a temperature, e.g., a reaction temperature, that is about the temperature of the room in which the reaction is carried out, for example, a temperature from about 20° C. to about 30° C.

Methods of Use

The compounds, salts or stereoisomers thereof described herein inhibit activity of PI3Kγ kinase. Accordingly, the compounds, salts or stereoisomers described herein can be used in methods of inhibiting PI3Kγ kinase by contacting the kinase with any one or more of the compounds, salts, or compositions described herein. In some embodiments, the compounds or salts can be used in methods of inhibiting activity of PI3Kγ in an individual/patient in need of the inhibition by administering an effective amount of a compound or salt of described herein. In some embodiments, modulating is inhibiting. In some embodiments, the contacting is in vivo. In some embodiments, the contacting is ex vivo. Advantageously, the compounds as described herein demonstrate better efficacy and favorable safety and toxicity profiles in animal studies.

In some embodiments, the PI3Kγ includes a mutation. A mutation can be a replacement of one amino acid for another, or a deletion of one or more amino acids. In such embodiments, the mutation can be present in the kinase domain of the PI3Kγ.

In some embodiments, the compound or salt further inhibits PI3Kδ.

The compounds or salts described herein can be selective. By "selective" is meant that the compound binds to or inhibits PI3Kγ with greater affinity or potency, respectively, compared to at least one other kinase. In some embodiments, the compounds of the disclosure are selective inhibitors of PI3Kγ over PI3Kδ, PI3Kα, and PI3Kβ. In some embodiments, the compounds of the disclosure are selective inhibitors of PI3Kγ over PI3Kα and PI3Kβ. In some embodiments, selectivity can be at least about 2-fold, 3-fold, 5-fold, 10-fold, at or 20-fold over PI3Kδ as measured by the assays described herein. In some embodiments, selectivity can be tested at the 2 µM ATP concentration of each enzyme. In some embodiments, the selectivity of compounds of the disclosure can be determined by cellular assays associated with particular PI3K kinase activity.

Another aspect of the present disclosure pertains to methods of treating a kinase PI3Kγ-associated disease or disorder in an individual (e.g., patient) by administering to the individual in need of such treatment a therapeutically effective amount or dose of one or more compounds of the present disclosure or a pharmaceutical composition thereof. A PI3Kγ-associated disease or disorder can include any disease, disorder or condition that is directly or indirectly linked to expression or activity of the PI3Kγ, including overexpression and/or abnormal activity levels.

In some embodiments, the disease or disorder is an autoimmune disease or disorder, cancer, cardiovascular disease, or neurodegenerative disease.

In some embodiments, the disease or disorder is lung cancer (e.g., non-small cell lung cancer), melanoma, pancreatic cancer, breast cancer, head and neck squamous cell carcinoma, prostate cancer, liver cancer, color cancer, endometrial cancer, bladder cancer, skin cancer, cancer of the uterus, renal cancer, gastric cancer, or sarcoma. In some embodiments, the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

In some embodiments, the disease or disorder is mesothelioma or adenocarcinoma. In some embodiments, the disease or disorder is mesothelioma. In some embodiments, the disease or disorder is adenocarcinoma.

In some embodiments, the disease or disorder is acute myeloid leukemia (e.g., acute monocytic leukemia), small lymphocytic lymphoma, chronic lymphocytic leukemia (CLL), chronic myelogenous leukemia (CML), multiple myeloma, T-cell acute lymphoblastic leukemia (T-ALL), cutaneous T-cell lymphoma, large granular lymphocytic leukemia, mature (peripheral) t-cell neoplasm (PTCL), anaplastic large cell lymphoma (ALCL), or lymphoblastic lymphoma. In some embodiments, the mature (peripheral) t-cell neoplasm (PTCL) is T-cell prolymphocytic leukemia, T-cell granular lymphocytic leukemia, aggressive NK-cell leukemia, mycosis fungoides/Sezary syndrome, naplastic large cell lymphoma (T-cell type), enteropathy type T-cell lymphoma, adult T-cell leukemia/lymphoma, or angioimmunoblastic T-cell lymphoma In some embodiments, the anaplastic large cell lymphoma (ALCL) is systemic ALCL or primary cutaneous ALCL.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, xenoderoma pigmentosum, keratoctanthoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

MDSC (myeloid-derived suppressor cells) are a heterogenous group of immune cells from the myeloid lineage (a family of cells that originate from bone marrow stem cells). MDSCs strongly expand in pathological situations such as chronic infections and cancer, as a result of an altered haematopoiesis. MDSCs are discriminated from other myeloid cell types in which they possess strong immunosuppressive activities rather than immunostimulatory properties. Similar to other myeloid cells, MDSCs interact with other immune cell types including T cells, dendritic cells, macrophages and natural killer cells to regulate their functions. In some embodiments, the compounds, etc. described herein can be used in methods related to cancer tissue (e.g., tumors) with high infiltration of MDSCs, including Solid tumors with high basal level of macrophage and/or MDSC infiltration.

In some embodiments, the non-Hodgkin's lymphoma (NHL) is relapsed NHL, refractory NHL, recurrent follicular NHL, indolent NHL (iNHL), or aggressive NHL (aNHL).

In some embodiments, the diffuse large B cell lymphoma is activated B-cell like (ABC) diffuse large B cell lymphoma, or germinal center B cell (GCB) diffuse large B cell lymphoma. In some embodiments, the Burkitt's lymphoma is endemic Burkitt's lymphoma, sporadic Burkitt's lymphoma, or Burkitt's-like lymphoma.

In some embodiments, the disease or disorder is rheumatoid arthritis, multiple sclerosis, systemic lupus erythematous, asthma, allergy (e.g, allergic rhinitis), pancreatitis, psoriasis, anaphylaxis, glomerulonephritis, inflammatory bowel disease (e.g., Crohn's disease and ulcerative colitis), thrombosis, meningitis, encephalitis, diabetic retinopathy, benign prostatic hypertrophy, myasthenia gravis, Sjögren's syndrome, osteoarthritis, restenosis, or atherosclerosis.

In some embodiments, the disease or disorder is heart hypertropy, cardiac myocyte dysfunction, acute coronary syndrome, chronic obstructive pulmonary disease (COPD), chronic bronchitis, elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft-versus-host disease, allogeneic or xenogeneic transplantation, glomerulosclerosis, progressive renal fibrosis, idiopathic thrombocytopenic purpura (ITP), idiopathic pulmonary fibrosis, autoimmune hemolytic anemia, vasculitis, lupus nephritis, pemphigus, or membranous nephropathy.

In some embodiments, disease or disorder is heart hypertropy, cardiac myocyte dysfunction, chronic obstructive pulmonary disease (COPD), elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft rejection, glomerulosclerosis, progressive renal fibrosis, idiopathic thrombocytopenic purpura (ITP), autoimmune hemolytic anemia, vasculitis, systemic lupus erythematosus, lupus nephritis, pemphigus, or membranous nephropathy.

In some embodiments, the disease or disorder is Alzheimer's disease, central nervous system trauma, or stroke.

In some embodiments, the idiopathic thrombocytopenic purpura (ITP) is relapsed ITP or refractory ITP.

In some embodiments, the vasculitis is Behçet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis nodosa, Churg-Strauss syndrome, mixed cryoglobulinemia vasculitis (essential or hepatitis C virus (HCV)-induced), Henoch-Schönlein purpura (HSP), hypersensitivity vasculitis, microscopic polyangiitis, Wegener's granulomatosis, or anti-neutrophil cytoplasm antibody associated (ANCA) systemic vasculitis (AASV).

The present disclosure further provides a compound described herein, or a pharmaceutically acceptable salt thereof, for use in any of the methods described herein.

The present disclosure further provides use of a compound described herein, or a pharmaceutically acceptable salt thereof, for the preparation of a medicament for use in any of the methods described herein.

As used herein, the term "contacting" refers to the bringing together of indicated moieties in an in vitro system or an in vivo system. For example, "contacting" a PI3K with a compound of the disclosure includes the administration of a compound of the present disclosure to an individual or patient, such as a human, having a PI3K, as well as, for example, introducing a compound of the disclosure into a sample containing a cellular or purified preparation containing the PI3K.

It is believed that compounds of provided herein (e.g., compounds of Formula (I), or pharmaceutically acceptable salts thereof) or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" can refer to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the disclosure are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

I. Immune-Checkpoint Therapies

In some embodiments, the PI3Kγ inhibitors provided herein can be used in combination with one or more immune checkpoint inhibitors for the treatment of cancer as described herein. In one embodiment, the combination with one or more immune checkpoint inhibitors as described herein can be used for the treatment of melanoma. Compounds of the present disclosure can be used in combination with one or more immune checkpoint inhibitors. Exemplary immune checkpoint inhibitors include inhibitors against immune checkpoint molecules such as CD20, CD28, CD40, CD122, CD96, CD73, CD47, GITR, CSF1R, JAK, PI3K delta, PI3K gamma, TAM, arginase, HPK1, CD137 (also known as 4-1BB), ICOS, B7-H3, B7-H4, BTLA, CTLA-4, LAG3, TIM3, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds of the disclosure provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the PI3Kγ inhibitors provided herein can be used in combination with one or more agonists of immune checkpoint molecules, e.g., OX40, CD27, OX40, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MED14736, MPDL3280A (also known as RG7446), or MSB0010718C. In some embodiments, the anti-PD-L1 monoclonal antibody is MPDL3280A or MED14736.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675, 206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the PI3Kγ inhibitors provided herein can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors or one or more therapies for the treatment of diseases, such as cancer. Examples of diseases and indications treatable with combination therapies include those as described herein. Examples of cancers include solid tumors and liquid tumors, such as blood cancers.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF, and FAK kinase inhibitors such as, for example, those described in WO 2006/056399. Other agents such as therapeutic antibodies can be used in combination with the compounds of the present disclosure for treatment of PI3K-associated diseases, disorders or conditions. The one or more additional pharmaceutical agents can be administered to a patient simultaneously or sequentially.

For example, the compounds as disclosed herein can be combined with one or more inhibitors of the following kinases for the treatment of cancer and other diseases or disorders described herein: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf Non-limiting examples of inhibitors that can be combined with the compounds of the present disclosure for treatment of cancer and other diseases and disorders described herein include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat, NLG919, or BMS-986205), an LSD1 inhibitor (e.g., INCB59872 and INCB60003), a TDO inhibitor, a PI3K-delta inhibitor (e.g., INCB50797 and INCB50465), a Pim inhibitor, a CSF1R inhibitor, a TAM receptor tyrosine kinases (Tyro-3, Axl, and Mer), a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643) and an adenosine receptor antagonist or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositomumab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumortargeted therapy, adjuvant therapy, immunotherapy, or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olaparib, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, streptozocin, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a PI3K inhibitor of the present disclosure with an additional agent.

In some embodiments, the compounds of the disclosure can be used in combination with an inhibitor of JAK or PI3Kδ.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp 100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fc alpha or Fc gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, *Giardia*, Malaria, *Leishmania, Staphylococcus aureus, Pseudomonas Aeruginosa*.

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*. Pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated.

Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Substitution of one or more of the atoms of the compounds of the present disclosure can also be useful in generating differentiated ADME (Adsorption, Distribution, Metabolism and Excretion). Accordingly, the present disclosure includes PI3K assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). In some embodiments, alkyl groups of the disclosed Formulas (e.g., Formula (I), (II), etc.), can be per-deuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —$CD_3$ being substituted for —$CH_3$). In some embodiments, the compound includes two or more deuterium atoms. In some embodiments, the compound includes 1, 1-2, 1-3, 1-4, 1-5, 1-6, 1-7, 1-8, or 1-9 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of any alkyl, alkenyl, alkynyl, aryl, phenyl, cycloalkyl, heterocycloalkyl, or heteroaryl substituents, or —$C_{1-6}$ alkyl-, alkylene, alkenylene, and alkynylene linking groups, as described herein, are each optionally replaced by a deuterium atom.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011).

Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro PI3K labeling and competition assays, compounds that incorporate $^3H$, $^{14}C$, $^{82}Br$, $^{125}I$, $^{131}I$ or $^{35}S$ can be useful. For radio-imaging applications $^{1}C$, $^{8}F$, $^{125}I$, $^{123}I$, $^{124}I$, $^{131}I$, $^{75}Br$, $^{76}Br$ or $^{77}Br$ can be useful.

It is understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of PI3K-associated diseases or disorders, such as cancer, which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be PI3Kγ inhibitors according to at least one assay described herein.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J. Combi. Chem.,* 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.,* 5, 670 (2003); and "Preparative LC-MS Purification: Improved Compound Specific Method Optimization", K. Blom, B. Glass, R. Sparks, A. Combs, *J. Combi. Chem.,* 6, 874-883 (2004)).

The compounds separated were typically subjected to analytical liquid chromatography mass spectrometry (LCMS) for purity analysis under the following conditions: Instrument=Agilent 1100 series, LC/MSD; Column: Waters Sunfire™ $C_{18}$ 5 μm, 2.1×50 mm, Buffers: mobile phase A: 0.025% TFA in water and mobile phase B: acetonitrile; gradient 2% to 80% B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ C$_{18}$ 5 µm, 30×100 mm or Waters XBridge™ C$_{18}$ 5 µm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g., "Preparative LCMS Purification: Improved Compound Specific Method Optimization", K. Blom, B. Glass, R. Sparks, A. Combs, *J. Comb. Chem.*, 6, 874-883 (2004)).

pH=6.5 purifications: Waters XBridge™ C$_{18}$ 5 µm, 30×100 mm column, eluting with mobile phase A: 100 mM ammonium acetate (NH$_4$OAc) in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

pH=10 purifications: Waters XBridge™ C$_{18}$ 5 µm, 30×100 mm column, eluting with mobile phase A: 0.1% NH$_4$OH in water and mobile phase B: acetonitrile; the flow rate was 60 mL/minute, the separating gradient was optimized for each compound using the Compound Specific Method Optimization protocol as described in the literature (see e.g., "Preparative LCMS Purification: Improved Compound Specific Method Optimization", K. Blom, B. Glass, R. Sparks, A. Combs, *J. Comb. Chem.*, 6, 874-883 (2004)).

Stereochemical Rationale

The Sharpless asymmetric dihydroxylation of olefins has been studied extensively, and its basis as a model for enantioselectivity is well established (Sharpless, K. B.; Amberg, W.; Bennani, Y. L.; Crispino, G. A.; Hartung, J.; Jeong, K.-S.; Kwong, H.-L.; Morikawa, K.; Wang, Z.-M.; Xu, D.; Zhang, X.-L. *J. Org. Chem.*, 1992, 57, 2768-2771; and Kolb, H. C.; VanNieuwenhze, M. S.; Sharpless, K. B. *Chem. Rev.*, 1994, 94, 2483-2547). Briefly, the application of AD-mix-α (containing (DHQ)$_2$-PHAL) in the dihydroxylation of prop-1-en-2-ylbenzene affords (S)-2-phenylpropane-1,2-diol. Application of AD-mix-β (containing (DHQD)$_2$-PHAL) in the dihydroxylation of prop-1-en-2-ylbenzene affords (R)-2-phenylpropane-1,2-diol (Sharpless and Kolb, supra). Moreno-Dorado et al. extended the method to the trifluoromethyl case (e.g., (3,3,3-trifluoroprop-1-en-2-yl)benzene affords (S)-3,3,3-trifluoro-2-phenylpropane-1,2-diol when treated with AD-mix-α and affords (R)-3,3,3-trifluoro-2-phenylpropane-1,2-diol when treated with AD-mix-β), and the stereochemical outcome was verified by subsequent conversion to well known compounds whose specific rotations were found to be in agreement with the literature values (Moreno-Dorado, F. J.; Guerra, F. M.; Ortega, M. J.; Zubia, E.; Massanet, G. M. *Tetrahedron: Asymmetry*, 2003, 14, 503-510). While not wishing to be bound by any one theory, in the dihydroxylations performed on vinyl arenes in the examples, we expect to obtain the (S)-configuration with AD-mix-α and the (R)-configuration with AD-mix-β.

Example 1. (S)-7-Chloro-2-(1-cyclopropylethyl)-5-(2-(4,5-dimethyl-1H-imidazol-2-yl)pyridin-4-yl)isoindolin-1-one

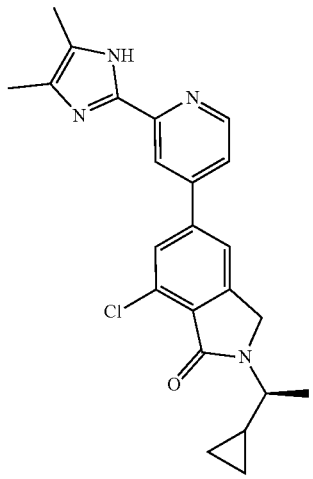 [SMILES: Cc1nc(-c2cc(-c3cc(Cl)c4c(c3)CN([C@@H](C)C3CC3)C4=O)ccn2)[nH]c1C]

Step 1.
4-Bromo-2-(4,5-dimethyl-1H-imidazol-2-yl)pyridine

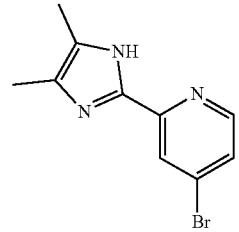

4-Bromopyridine-2-carbonitrile (1.0 g, 5.5 mmol, Synthonix) in MeOH (10 mL) was treated with sodium methoxide (25 wt % in methanol (MeOH), 0.095 mL, 0.47 mmol) and the reaction mixture was stirred for 1 hour. Ammonium chloride (0.37 g, 6.9 mmol) was added, and the reaction mixture was stirred for 4 days. Solvent was then removed in vacuo. Water (4.0 mL) and ethyl acetate (EtOAc) (6.0 mL) were added, the mixture was saturated with solid NaCl, and the mixture was stirred overnight. The solid product was isolated by filtration and dried at 40° C. under vacuum overnight. The product was used below without further purification.

To 4-bromopyridine-2-carboximidamide (0.50 g, 2.5 mmol) in DMF (5.0 mL) was added K$_2$CO$_3$ (0.52 g, 3.7 mmol) and 3-bromo-2-butanone (0.24 mL, 3.2 mmol). The reaction mixture was stirred for 4 days. The reaction mixture was partitioned between EtOAc and H$_2$O, and the layers were separated. The aqueous layer was extracted with two further portions of EtOAc. The combined organic extracts were washed sequentially with water and saturated NaCl solution. The organic solution was dried over Na$_2$SO$_4$, filtered, and concentrated. The crude product was slurried in methyl tert-butyl ether (MTBE, 2.0 mL) and the solid product was isolated by filtration and dried under vacuum at 40° C. for 3 hours to afford the title compound (370 mg, 59%). LCMS for $C_{10}H_{11}BrN_3$ (M+H)$^+$: calculated monoisotopic m/z=252.0; found 252.0.

Step 2. Methyl 4-bromo-2-(bromomethyl)-6-chlorobenzoate

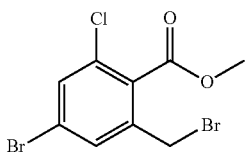

To methyl 4-bromo-2-chloro-6-methylbenzoate (1.5 g, 5.7 mmol, Astatech) in CCl$_4$ (28 mL) was added N-bromosuccinimide (1.1 g, 6.3 mmol) and benzoyl peroxide (0.028 g, 0.11 mmol) and the reaction was heated to reflux for 1.5 hours, then stirred at room temperature overnight. A further portion of benzoyl peroxide (0.050 g, 0.20 mmol) was added, and heating at reflux was continued for 3 hours. The reaction mixture was washed with a solution of Na$_2$S$_2$O$_3$ and the aqueous layer was extracted twice with EtOAc. The combined organic extracts were dried over Na$_2$SO$_4$, filtered, and concentrated. Flash chromatography, eluting with a gradient from 0-50% EtOAc in hexanes, afforded the title compound (0.15 g, 67%).

Step 3. (S)-5-Bromo-7-chloro-2-(1-cyclopropylethyl)isoindolin-1-one

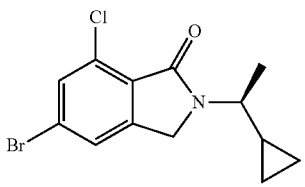 [SMILES: C[C@@H](C1CC1)N1Cc2cc(Br)cc(Cl)c2C1=O]

To a flask containing methyl 4-bromo-2-(bromomethyl)-6-chlorobenzoate (1.9 g, 5.6 mmol) in acetonitrile (19 mL) was added (S)-1-cyclopropylethan-1-amine (0.48 g, 5.6 mmol, Aldrich), followed by boric acid (0.35 g, 5.6 mmol). Potassium carbonate (1.5 g, 11 mmol) was added portionwise over 2 min, and the reaction was stirred overnight. The reaction mixture was filtered and solids were washed with acetonitrile. The filtrate was concentrated in vacuo. Flash chromatography, eluting with a gradient from 0-30% EtOAc in hexanes, afforded the title compound (1.1 g, 62%). LCMS for $C_{13}H_{14}BrClNO$ (M+H)$^+$: calculated monoisotopic m/z=314.0; found 314.0.

Step 4. (S)-7-Chloro-2-(1-cyclopropylethyl)-5-(4,5,5-tetramethyl-1,3,2-dioxaborolan-2-yl) isoindolin-1-one

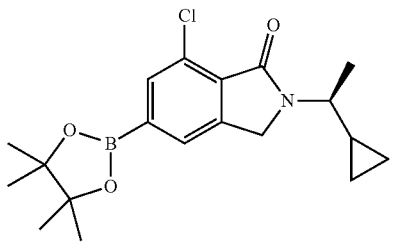 [SMILES: C[C@@H](C1CC1)N1Cc2cc(B3OC(C)(C)C(C)(C)O3)cc(Cl)c2C1=O]

A degassed mixture of (S)-5-bromo-7-chloro-2-(1-cyclopropylethyl)isoindolin-1-one (0.25 g, 0.80 mmol), bis(pinacolato)diboron (0.30 g, 1.2 mmol), potassium acetate (0.47 g, 4.78 mmol) and dichloro[1,1'-bis(diphenylphosphino)ferrocene]palladium (II) dichloromethane adduct (0.039 g, 0.048 mmol) in dioxane (4.0 mL) was heated to 80° C. overnight. Upon cooling to room temperature, water was added and the mixture was extracted with EtOAc (3×). The combined organic extracts were dried over Na$_2$SO$_4$, filtered and concentrated. Flash chromatography, eluting with a gradient from 0-100% EtOAc in hexanes, afforded the title compound (0.25 g, 87%). LCMS for $C_{19}H_{26}BClNO_3$ (M+H)$^+$: calculated monoisotopic m/z=362.1; found 362.1.

Step 5. (S)-7-Chloro-2-(1-cyclopropylethyl)-5-(2-(4,5-dimethyl-1H-imidazol-2-yl)pyridin-4-yl) isoindolin-1-one A mixture of (S)-7-chloro-2-(1-cyclopropylethyl)-5-(4,4,5,5-tetramethyl-1,3,2-dioxaborolan-2-yl)isoindolin-1-one (0.13 g, 0.36 mmol), 4-bromo-2-(4,5-dimethyl-1H-imidazol-2-yl)pyridine (0.091 g, 0.36 mmol) and dichloro[1,1'-bis(diphenylphosphino)ferrocene]palladium(II) dichloromethane adduct (0.059 g, 0.072 mmol) in THF (2.4 mL) and aq. K$_2$CO$_3$ solution (1.0 M, 1.1 ml, 1.1 mmol) was sparged with N$_2$ for 10 min, and was heated in the microwave reactor for 60 min at 120° C., then in an oil bath at 80° C. over 3 nights. Upon cooling to room temperature, the reaction mixture was diluted with MeCN and MeOH, filtered and purified via preparative HPLC-MS (pH=10) to afford the title compound (36 mg, 25%). LCMS for $C_{23}H_{24}ClN_4O$ (M+H)$^+$: calculated monoisotopic m/z=407.2; found 407.1. $^1$H NMR (400 MHz, DMSO-d$_6$) δ 12.43 (s, 1H), 8.65 (d, J=5.2 Hz, 1H), 8.23 (d, J=1.8 Hz, 1H), 8.06 (d, J=1.5 Hz, 1H), 7.92 (d, J=1.5 Hz, 1H), 7.69 (dd, J=5.2, 1.9 Hz, 1H), 4.63 (s, 2H), 3.70-3.48 (m, 1H), 2.19 (s, 3H), 2.12 (s, 3H), 1.31 (d, J=6.9 Hz, 3H), 1.21-1.09 (m, 1H), 0.66-0.54 (m, 1H), 0.50-0.35 (m, 2H), 0.32-0.20 (m, 1H).

Example 2. (S)-2-(1-Cyclopropylethyl)-5-(2-(4,5-dimethyl-1H-imidazol-2-yl)pyridin-4-yl)-7-(methylsulfonyl)isoindolin-1-one Trifluoroacetate Salt

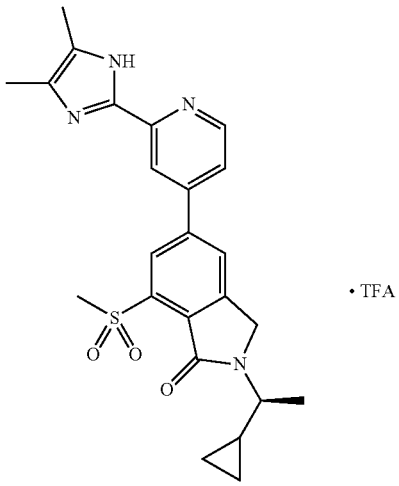 [SMILES: Cc1nc(-c2cc(-c3cc4c(c(S(C)(=O)=O)c3)C(=O)N([C@@H](C)C3CC3)C4)ccn2)[nH]c1C ; "· TFA"]

Step 1. (S)-5-Bromo-2-(1-cyclopropylethyl)-7-(methylthio)isoindolin-1-one

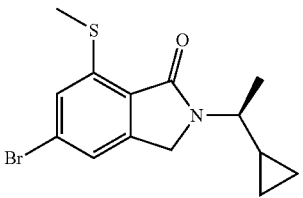 [SMILES: CSc1cc(Br)cc2c1C(=O)N([C@@H](C)C1CC1)C2]

Sodium methanethiolate (0.30 g, 4.3 mmol) was added to (S)-5-bromo-7-chloro-2-(1-cyclopropylethyl)isoindolin-1-one (0.45 g, 1.4 mmol) in acetonitrile (6.0 mL) and the mixture was heated to 120° C. overnight. Upon cooling to room temperature, the reaction mixture was filtered through Celite®, and the Celite® was washed with EtOAc. The organic solution was washed with water (2×), and brine, dried over MgSO₄, filtered and concentrated to afford the title compound as a yellow solid (250 mg, 53%). LCMS for $C_{14}H_{17}BrNOS$ (M+H)⁺: calculated monisotopic m/z=326.0; found 326.1.

Step 2. (S)-5-Bromo-2-(1-cyclopropylethyl)-7-(ethylsulfonyl)isoindolin-1-one

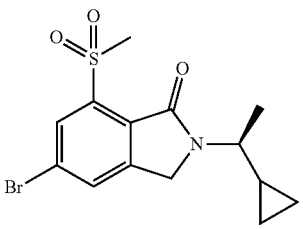 [SMILES: C[C@@H](C1CC1)N1Cc2cc(Br)cc(S(C)(=O)=O)c2C1=O]

To (S)-5-bromo-2-(1-cyclopropylethyl)-7-(methylthio)isoindolin-1-one (0.10 g, 0.31 mmol) in DCM (2.0 mL) at 0° C. was added m-CPBA (130 mg, 0.77 mmol). After stirring for 2 hours, the reaction mixture was diluted with DCM and washed with saturated NaHCO₃ solution and brine. The organic layer was dried over MgSO₄, filtered and concentrated. Purification via flash chromatography, eluting with a gradient from 0-80% EtOAc in hexanes, provided the title compound as a yellow solid (0.080 g, 72%). LCMS for $C_{14}H_{17}BrNO_3S$ (M+H)⁺: calculated monoisotopic m/z=358.0; found 358.1.

Step 3. (S)-2-(1-Cyclopropylethyl)-7-(methylsulfonyl)-5-(4,4,5,5-tetramethyl-1,3,2-dioxaborolan-2-yl)isoindolin-1-one

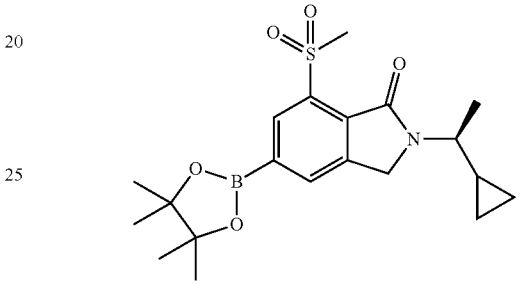

A mixture of (S)-5-bromo-2-(1-cyclopropylethyl)-7-(methylsulfonyl)isoindolin-1-one (0.10 g, 0.28 mmol), bis(pinacolato)diboron (0.11 g, 0.42 mmol), potassium acetate (0.082 g, 0.84 mmol) and dichloro[1,1'-bis(diphenylphosphino)ferrocene]palladium (II) dichloromethane adduct (0.060 g, 0.017 mmol) in dioxane (3 mL) was degassed by sparging with N₂ for 10 min. The reaction was then heated at 80° C. for 2 hours. Upon cooling to room temperature, the reaction mixture was diluted with water and extracted with EtOAc. The combined organic extracts were dried over Na₂SO₄, filtered and concentrated. Flash chromatography, eluting with a gradient from 0-100% EtOAc in hexanes, afforded the title compound (0.080 g, 80%).

Step 4. (S)-2-(1-Cyclopropylethyl)-5-(2-(4,5-dimethyl-1H-imidazol-2-yl)pyridin-4-yl)-7-(methylsulfonyl)isoindolin-1-one, Trifluoroacetate Salt A mixture of (S)-2-(1-cyclopropylethyl)-7-(methylsulfonyl)-5-(4,4,5,5-tetramethyl-1,3,2-dioxaborolan-2-yl)isoindolin-1-one (0.020 g, 0.049 mmol), 4-bromo-2-(4,5-dimethyl-1H-imidazol-2-yl)pyridine (12 mg, 0.049 mmol), and dichloro[1,1'-bis(diphenylphosphino)ferrocene]palladium (II) dichloromethane adduct (8.1 mg, 9.9 μmol) in THF (0.33 mL) and aq. K₂CO₃ solution (1.0 M, 0.15 mL, 0.15 mmol) was degassed by sparging with N₂, and was heated to 120° C. in a microwave reactor for 1 hour. Upon cooling to room temperature, the reaction mixture was diluted with MeCN and MeOH, filtered and purified via preparative HPLC-MS (pH=10) to afford the title compound (3.0 mg, 11%). LCMS for $C_{24}H_{27}N_4O_3S$ (M+H)⁺: calculated m/z=451.2; found 451.1. ¹H NMR (400 MHz, DMSO) δ 14.79 (br s, 1H), 8.95 (d, J=5.2 Hz, 1H), 8.56 (s, 1H), 8.48 (d, J=1.6 Hz, 1H), 8.44 (d, J=1.6 Hz, 1H), 8.05 (dd, J=5.0, 1.3 Hz, 1H), 4.78 (s, 2H), 3.69 (s, 3H), 3.68-3.62 (m, 1H), 2.33 (s, 6H), 1.36 (d, J=6.8 Hz, 3H), 1.30-1.09 (m, 1H), 0.70-0.54 (m, 1H), 0.54-0.37 (m, 2H), 0.37-0.12 (m, 1H).

Example 3. (S)-2-(4-(2-(1-Cyclopropylethyl)-1-oxoisoindolin-5-yl)pyridin-2-yl)-N-isopropyl-5-methyl-1H-imidazole-4-carboxamide Trifluoroacetate Salt

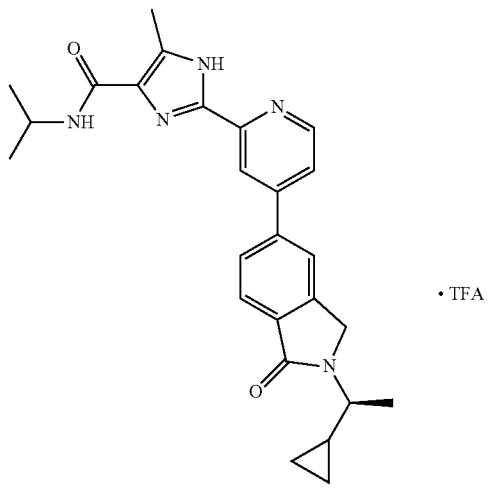 [SMILES: Cc1[nH]c(-c2cc(-c3ccc4c(c3)CN([C@@H](C)C3CC3)C4=O)ccn2)nc1C(=O)NC(C)C ; "· TFA"]

· TFA

Step 1. (S)-5-Bromo-2-(1-cyclopropylethyl)isoindolin-1-one

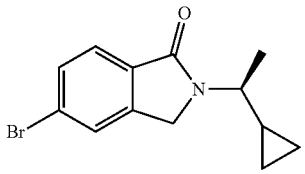 [SMILES: C[C@@H](C1CC1)N1Cc2cc(Br)ccc2C1=O]

A mixture of methyl 4-bromo-2-(bromomethyl)benzoate (1.00 g, 3.25 mmol, Ark Pharm, AK-26333), (S)-1-cyclopropylethan-1-amine (0.304 g, 3.57 mmol, Aldrich 727245), and $K_2CO_3$ (0.898 g, 6.49 mmol) in acetonitrile (8.1 mL) in a microwave vial was sealed and heated at 120° C. in a microwave oven for 30 min. The reaction mixture was filtered and solvent was removed in vacuo. The product was purified via flash chromatography, eluting with a gradient of 0-25% EtOAc in hexanes, to afford product as a white solid (0.42 g, 46%). LCMS for $C_{13}H_{15}BrNO$ (M+H)$^+$: calculated monoisotopic m/z=280.0; found 280.0.

Step 2. (S)-2-(1-Cyclopropylethyl)-5-(4,4,5,5-tetramethyl-1,3,2-dioxaborolan-2-yl) isoindolin-1-one

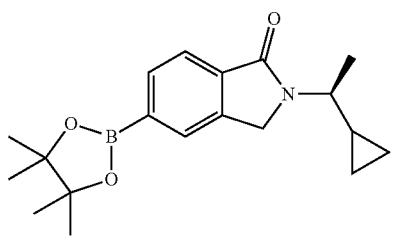 [SMILES: C[C@@H](C1CC1)N1Cc2cc(B3OC(C)(C)C(C)(C)O3)ccc2C1=O]

(S)-5-Bromo-2-(1-cyclopropylethyl)isoindolin-1-one (0.421 g, 1.50 mmol) was combined with bis(pinacolato)diboron (0.572 g, 2.25 mmol), potassium acetate (0.885 g, 9.02 mmol) and dichloro[1,1'-bis(diphenylphosphino)ferrocene]palladium (II) dichloromethane adduct (0.074 g, 0.090 mmol) in dioxane (7.5 mL), and the mixture was degassed. The reaction was heated to 80° C. for 3 hours. Upon cooling to room temperature, the mixture was diluted with EtOAc, filtered over Celite®, and concentrated. The product was purified via flash chromatography, eluting with a gradient from 0-20% EtOAc in hexanes, to afford product as a light yellow solid (theoretical yield assumed). LCMS for $C_{19}H_{27}BNO_3$ (M+H)$^+$: calculated m/z=328.2; found 328.2.

Step 3.
4-Bromo-2-(4-methyl-1H-imidazol-2-yl)pyridine

To 4-bromopyridine-2-carbonitrile (0.50 g, 2.7 mmol, Synthonix) in methanol (3.0 mL) was added sodium methoxide in methanol (25 wt %, 69 μL, 0.30 mmol), and the reaction mixture was heated to 40° C. for 1 hour. The mixture was cooled to room temperature, and 1,1-diethoxypropan-2-amine (0.40 g, 2.7 mmol) and then acetic acid (0.30 mL, 5.2 mmol) were added dropwise. The reaction mixture was heated at 100° C. for 30 min. After the reaction mixture was cooled to room temperature, methanol (1.5 mL) and 6.0 M HCl in water (7.5 mmol) were added, and the mixture was heated at 70° C. for 5 hours. Heating was discontinued, and the reaction mixture was stirred overnight. The reaction mixture was concentrated. Aqueous $K_2CO_3$ solution (saturated) was added slowly to the crude residue until the solution reached pH 10, and the slurry was stirred for 1 hour. The resulting tan precipitate was isolated by filtration and washed with aq. $K_2CO_3$ solution (sat.) and then cold water. The resulting solid was air dried to afford a tan solid (0.57 g, 88%). LCMS for $C_9H_9BrN_3$ (M+H)$^+$: calculated monoisotopic m/z=238.0; found 238.0. $^1$H NMR (400 MHz, DMSO-$d_6$) δ 12.65 (br s, 1H), 8.45 (d, J=5.3 Hz, 1H), 8.11 (d, J=1.6 Hz, 1H), 7.58 (dd, J=5.3, 1.9 Hz, 1H), 6.88 (s, 1H), 2.21 (s, 3H).

Step 4. 4-Bromo-2-(4-methyl-1-((2-(trimethylsilyl)ethoxy)methyl)-1H-imidazol-2-yl)pyridine (Mixture of Regioisomers Prepared—Single Regioisomer Isolated)

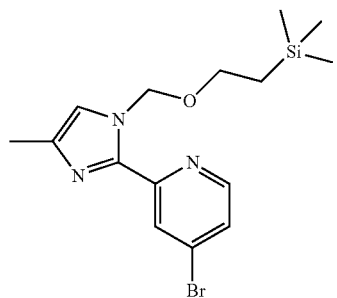

To a solution of 4-bromo-2-(5-methyl-1H-imidazol-2-yl)pyridine (120 mg, 0.50 mmol) in THF (6.0 mL) at 0° C. was added potassium tert-butoxide (1.0 M, 0.71 mL, 0.71 mmol). The reaction mixture was stirred for 30 min, and 2-(trimethylsilyl)ethoxymethyl chloride (0.125 mL, 0.71 mmol) was added. After stirring for 30 min at 0° C., aq. NH$_4$Cl (sat.) solution was added. After stirring for an additional 30 min, the aqueous mixture was extracted with EtOAc (3×). The combined organic extracts were washed with water, followed by brine. The organic solution was dried over MgSO$_4$, filtered and concentrated. Flash chromatography, eluting with a gradient from 0-10% EtOAc in hexanes, afforded the title compound (85 mg, 46%). The major isomer (first to elute) was collected. LCMS for C$_{15}$H$_{23}$BrN$_3$OSi (M+H)$^+$: calculated monoisotopic m/z=368.1; found 368.0.

Step 5. (S)-2-(1-Cyclopropylethyl)-5-(2-(4-methyl-1-((2-(trimethylsilyl)ethoxy)methyl)-1H-imidazol-2-yl)pyridin-4-yl)isoindolin-1-one

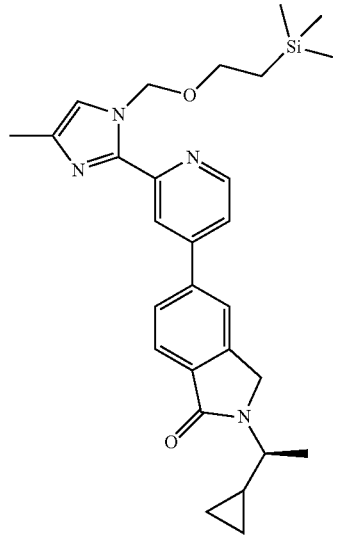

To a solution of 4-bromo-2-(5-methyl-1-((2-(trimethylsilyl)ethoxy)methyl)-1H-imidazol-2-yl)pyridine (0.020 g, 0.054 mmol) and (S)-2-(1-cyclopropylethyl)-5-(4,4,5,5-tetramethyl-1,3,2-dioxaborolan-2-yl)isoindolin-1-one (0.020 g, 0.060 mmol) in THF (1.0 mL) was added sodium carbonate (12 mg, 0.11 mmol) in water (0.5 mL). The reaction mixture was degassed by sparging with N$_2$ for 10 min, at which time PdCl$_2$(dppf)-CH$_2$Cl$_2$ adduct (8.9 mg, 11 μmol) was added. The mixture was again sparged with N$_2$ for 1 min, and the reaction mixture was then heated at 100° C. for 1 hour. Upon cooling to room temperature, the reaction mixture was diluted with water and EtOAc. The layers were separated, and the organic layer was washed with brine, dried over MgSO$_4$, filtered and concentrated. Flash chromatography, eluting with a gradient from 0-80% EtOAc in hexanes, afforded the title compound (0.020 g, 75%). LCMS for C$_{28}$H$_{37}$N$_4$O$_2$Si (M+H)$^+$: calculated monoisotopic m/z=489.3; found 489.2.

Step 6. (S)-2-(1-Cyclopropylethyl)-5-(2-(5-iodo-4-methyl-1-((2-(trimethylsilyl)ethoxy)methyl)-1H-imidazol-2-yl)pyridin-4-yl)isoindolin-1-one

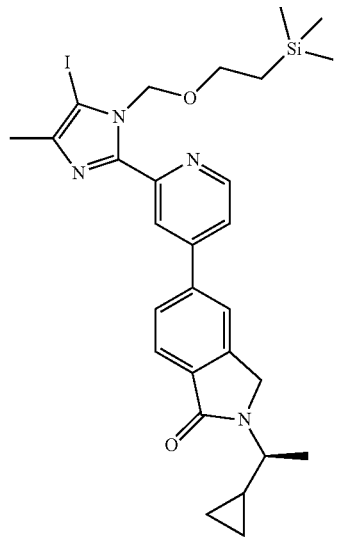

To a mixture of (S)-2-(1-cyclopropylethyl)-5-(2-(5-methyl-1-((2-(trimethylsilyl)ethoxy)methyl)-1H-imidazol-2-yl)pyridin-4-yl)isoindolin-1-one (0.080 g, 0.16 mmol) in DMF (6.0 mL) was added NIS (43 mg, 0.19 mmol). The mixture was stirred for 20 min at room temperature, and then at 50° C. for 2 hours. Upon cooling to room temperature, the reaction mixture was diluted with water and extracted with EtOAc (3×). The combined organic extracts were washed with brine, dried over MgSO$_4$, filtered and concentrated to afford the title compound (0.10 g, 99%). LCMS for C$_{28}$H$_{37}$IN$_4$O$_2$Si (M+H)$^+$: calculated m/z=615.2; found 615.1.

Step 7. Methyl (S)-2-(4-(2-(1-cyclopropylethyl)-1-oxoisoindolin-5-yl)pyridin-2-yl)-4-methyl-1-((2-(trimethylsilyl)ethoxy)methyl)-1H-imidazole-5-carboxylate

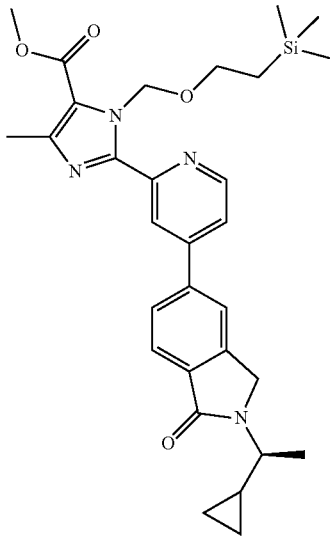

A solution of (S)-2-(1-cyclopropylethyl)-5-(2-(4-iodo-5-methyl-1-((2-(trimethylsilyl)ethoxy)methyl)-1H-imidazol-2-yl)pyridin-4-yl)isoindolin-1-one (0.10 g, 0.16 mmol) in methanol (3.0 mL) was treated with triethylamine (0.091 mL, 0.65 mmol) and dichloro[1,1'-bis(diphenylphosphino)ferrocene]palladium(II) dichloromethane adduct (27 mg, 0.033 mmol). Carbon monoxide was bubbled through the solution for 10 min. The reaction mixture was heated at 60° C. under 1 atm of CO overnight. Solvent was removed in vacuo. Flash chromatography, eluting with a gradient from 0-80% EtOAc in hexanes, afforded the title compound (0.060 g, 67%). LCMS for $C_{30}H_{39}N_4O_4Si$ (M+H)$^+$: calculated m/z=547.3; found 547.1.

Step 8. (S)-2-(4-(2-(1-Cyclopropylethyl)-1-oxoisoindolin-5-yl)pyridin-2-yl)-4-methyl-1-((2-(trimethylsilyl)ethoxy)methyl)-1H-imidazole-5-carboxylic Acid

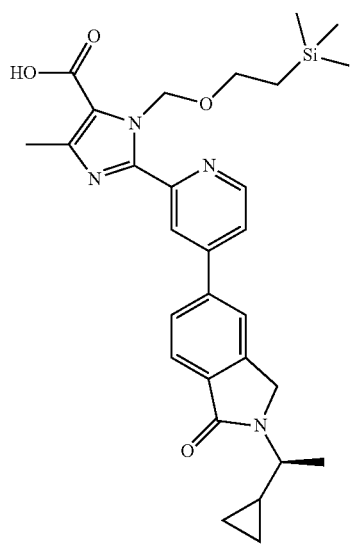

To a solution of methyl (S)-2-(4-(2-(1-cyclopropylethyl)-1-oxoisoindolin-5-yl)pyridin-2-yl)-5-methyl-1-((2-(trimethylsilyl)ethoxy)methyl)-1H-imidazole-4-carboxylate (45 mg, 0.082 mmol) in methanol (2.0 mL) was added lithium hydroxide (5.9 mg, 0.25 mmol) in water (2.0 mL). The reaction mixture was stirred for 2 hours. Solvent was removed in vacuo. 1.0 N HCl solution was added to adjust to pH=2, and the aqueous mixture was extracted with EtOAc (2×). The combined organic extracts were dried over $MgSO_4$, filtered and concentrated, to afford the title compound which was used without further purification (0.040 g, 92%). LCMS for C29H$_{37}$N$_4$O$_4$Si (M+H)$^+$: calculated m/z=533.3; found 533.2.

Step 9. (S)-2-(4-(2-(1-Cyclopropylethyl)-1-oxoisoindolin-5-yl)pyridin-2-yl)-N-isopropyl-5-methyl-1H-imidazole-4-carboxamide Trifluoroacetate Salt To a solution of (S)-2-(4-(2-(1-cyclopropylethyl)-1-oxoisoindolin-5-yl)pyridin-2-yl)-N-isopropyl-5-methyl-1-((2-(trimethylsilyl)ethoxy)methyl)-1H-imidazole-4-carboxamide (8.0 mg, 0.015 mmol) in DMF (1.0 mL) was added N,N-diisopropylethylamine (7 μL, 0.04 mmol) and HATU (6.9 mg, 0.018 mmol). After stirring for 5 min, propan-2-amine (1.1 mg, 0.018 mmol) was added. The reaction mixture was stirred for 1 hour. Water was added and the mixture was extracted with EtOAc. The organic layer was dried over $MgSO_4$, filtered and concentrated. The residue was dissolved in DCM (0.5 mL) and trifluoroacetic acid (TFA) (0.035 mL, 0.45 mmol) was added. After stirring for 1 hour, volatiles were removed in vacuo, the residue was reconstituted in acetonitrile and methanol, and the product was purified via preparative HPLC-MS (pH=2) to afford the title compound (4 mg, 40%). LCMS for $C_{26}H_{30}N_5O_2$ (M+H)$^+$: calculated m/z=444.2; found 444.2. $^1$H NMR (400 MHz, DMSO-d$_6$) δ 8.73 (d, J=5.2 Hz, 1H), 8.43 (d, J=1.7 Hz, 1H), 8.12 (d, J=1.4 Hz, 1H), 7.97 (dd, J=7.9, 1.3 Hz, 1H), 7.85 (d, J=7.9 Hz, 1H), 7.79 (dd, J=5.3, 1.8 Hz, 1H), 4.67 (s, 2H), 4.18-3.99 (m, 1H), 3.71-3.55 (m, 1H), 2.53 (s, 3H), 1.33 (d, J=6.9 Hz, 3H), 1.19 (d, J=6.6 Hz, 6H), 1.23-1.10 (m, 1H), 0.66-0.50 (m, 1H), 0.48-0.33 (m, 2H), 0.30-0.16 (m, 1H).

Examples 4-6

Compounds in Table 1 were prepared by the procedure of Example 3, substituting the appropriate amine for propan-2-amine in Step 9.

TABLE 1

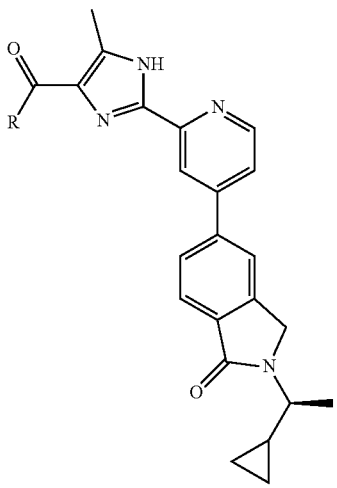

| Example No. | Compound Name | R<br>¹H NMR | LCMS |
|---|---|---|---|
| 4 | (S)-2-(4-(2-(1-Cyclopropylethyl)-1-oxoisoindolin-5-yl)pyridin-2-yl)-5-methyl-N-(tetrahydro-2H-pyran-4-yl)-1H-imidazole-4-carboxamide trifluoroacetate salt | tetrahydropyranyl-NH- | Calculated for $C_{28}H_{32}N_5O_3$ $(M + H)^+$: m/z = 486.2, found: 486.2 |

¹H NMR (400 MHz, DMSO-d$_6$) δ 8.73 (d, J = 5.2 Hz, 1H), 8.44 (d, J = 1.8 Hz, 1H), 8.11 (d, J = 1.4 Hz, 1H), 7.97 (dd, J = 7.9, 1.6 Hz, 1H), 7.85 (d, J = 7.9 Hz, 1H), 7.79 (dd, J = 5.2, 1.9 Hz, 1H), 7.76 (br, 1H), 4.67 (s, 2H), 4.02-3.93 (m, 1H), 3.92-3.83 (m, 2H), 3.68-3.57 (m, 1H), 3.39 (td, J = 11.7, 2.3 Hz, 2H), 2.53 (s, 3H), 1.80-1.72 (m, 2H), 1.66 (qd, J = 12.0, 4.3 Hz, 2H), 1.33 (d, J = 6.8 Hz, 3H), 1.24-1.12 (m, 1H), 0.66-0.52 (m, 1H), 0.50-0.36 (m, 2H), 0.31-0.20 (m, 1H).

| 5 | (S)-2-(4-(2-(1-Cyclopropylethyl)-1-oxoisoindolin-5-yl)pyridin-2-yl)-N,N,5-trimethyl-1H-imidazole-4-carboxamide trifluoroacetate salt | -N(CH3)- | Calculated for $C_{25}H_{28}N_5O_2$ $(M + H)^+$: m/z = 430.2, found: 430.2 |

¹H NMR (400 MHz, DMSO-d$_6$) δ 8.74 (d, J = 5.2 Hz, 1H), 8.34 (d, J = 1.9 Hz, 1H), 8.10 (d, J = 1.4 Hz, 1H), 7.96 (dd, J = 7.9, 1.6 Hz, 1H), 7.84 (d, J = 7.9 Hz, 1H), 7.79 (dd, J = 5.2, 1.9 Hz, 1H), 4.66 (s, 2H), 3.68-3.58 (m, 1H), 3.33 (s, 3H), 2.98 (s, 3H), 2.40 (s, 3H), 1.33 (d, J = 6.8 Hz, 3H), 1.22-1.10 (m, 1H), 0.67-0.53 (m, 1H), 0.49-0.35 (m, 2H), 0.31-0.20 (m, 1H).

| 6 | (S)-2-(4-(2-(1-Cyclopropylethyl)-1-oxoisoindolin-5-yl)pyridin-2-yl)-N,5-dimethyl-1H-imidazole-4-carboxamide trifluoroacetate salt | -NH(CH3)- | Calculated for $C_{24}H_{26}N_5O_2$ $(M + H)^+$: m/z = 416.2, found: 416.2 |

¹H NMR (400 MHz, DMSO-d$_6$) δ 8.73 (d, J = 5.2 Hz, 1H), 8.43 (d, J = 1.7 Hz, 1H), 8.10 (d, J = 1.3 Hz, 1H), 7.96 (dd, J = 7.9, 1.6 Hz, 1H), 7.94-7.88 (m, 1H), 7.85 (d, J = 7.9 Hz, 1H), 7.78 (dd, J = 5.2, 1.9 Hz, 1H), 4.66 (s, 2H), 3.68-3.59 (m, 1H), 2.78 (d, J = 4.7 Hz, 3H), 2.53 (s, 3H), 1.33 (d, J = 6.8 Hz, 3H), 1.23-1.10 (m, 1H), 0.65-0.56 (m, 1H), 0.49-0.33 (m, 2H), 0.33-0.19 (m, 1H).

Examples 7 and 7a-7u

The compounds in Table 2 were prepared by the procedure of Example 3, Steps 5-9, using (S)-2-(1-cyclopropylethyl)-7-(methylsulfonyl)-5-(4,4,5,5-tetramethyl-1,3,2-dioxaborolan-2-yl)isoindolin-1-one instead of (S)-2-(1-cyclopropylethyl)-5-(4,4,5,5-tetramethyl-1,3,2-dioxaborolan-2-yl)isoindolin-1-one in Step 5, and using the appropriate amine instead of isopropylamine in Step 9.

TABLE 2

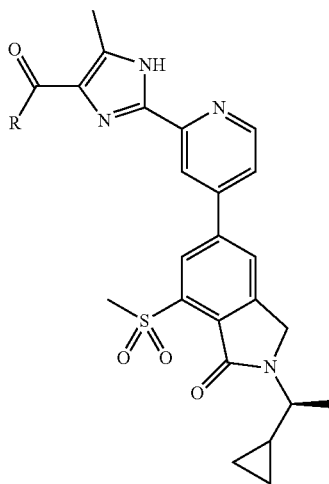

| Example No. | Compound Name | R | LCMS |
|---|---|---|---|
| | | ¹H NMR | |

| 7 | (S)-2-(4-(2-(1-Cyclopropylethyl)-7-(methylsulfonyl)-1-oxoisoindolin-5-yl)pyridin-2-yl)-N,4-dimethyl-1H-imidazole-5-carboxamide, trifluoroacetate salt | methylamino | Calculated for $C_{25}H_{28}N_5O_4S$ $(M + H)^+$: m/z = 494.2, found: 494.1 |

¹H NMR (500 MHz, DMSO-d₆) δ 8.79 (d, J = 5.1 Hz, 1H), 8.45 (s, 1H), 8.40-8.37 (m, 1H), 8.33 (d, J = 1.5 Hz, 1H), 7.89 (q, J = 4.5 Hz, 1H), 7.80 (dd, J = 5.2, 1.9 Hz, 1H), 4.77 (s, 2H), 3.68 (s, 3H), 3.68-3.61 (m, 1H), 2.77 (d, J = 4.7 Hz, 3H), 2.53 (s, 3H), 1.35 (d, J = 6.8 Hz, 3H), 1.28-1.16 (m, 1H), 0.71-0.57 (m, 1H), 0.51-0.38 (m, 2H), 0.36-0.24 (m, 1H).

| 7a | (S)-2-(4-(2-(1-Cyclopropylethyl)-7-(methylsulfonyl)-1-oxoisoindolin-5-yl)pyridin-2-yl)-N-isopropyl-4-methyl-1H-imidazole-5-carboxamide, trifluoroacetate salt | isopropylamino | Calculated for $C_{27}H_{32}N_5O_4S$ $(M + H)^+$: m/z = 522.2, found: 522.2 |
| 7b | (S)-2-(4-(2-(1-Cyclopropylethyl)-7-(methylsulfonyl)-1-oxoisoindolin-5-yl)pyridin-2-yl)-4-methyl-N-(tetrahydro-2H-pyran-4-yl)-1H-imidazole-5-carboxamide, trifluoroacetate salt | tetrahydropyran-4-ylamino | Calculated for $C_{29}H_{34}N_5O_5S$ $(M + H)^+$: m/z = 564.2, found: 564.2 |
| 7c | (S)-N-(Bicyclo[1.1.1]pentan-1-yl)-2-(4-(2-(1-cyclopropylethyl)-7-(methylsulfonyl)-1-oxoisoindolin-5-yl)pyridin-2-yl)-4-methyl-1H-imidazole-5-carboxamide, trifluoroacetate salt | bicyclo[1.1.1]pentan-1-ylamino | Calculated for $C_{29}H_{32}N_5O_4S$ $(M + H)^+$: m/z = 546.2, found: 546.2 |
| 7d | (S)-2-(1-Cyclopropylethyl)-5-(2-(5-(3,3-difluoroazetidine-1-carbonyl)-4-methyl-1H-imidazol-2-yl)pyridin-4-yl)-7-(methylsulfonyl)isoindolin-1-one, trifluoroacetate salt | 3,3-difluoroazetidin-1-yl | Calculated for $C_{27}H_{28}F_2N_5O_4S$ $(M + H)^+$: m/z = 556.2, found: 556.2 |
| 7e | (S)-2-(1-Cyclopropylethyl)-5-(2-(5-(3-hydroxyazetidine-1-carbonyl)-4-methyl-1H-imidazol-2-yl)pyridin-4-yl)-7-(methylsulfonyl)isoindolin-1-one, trifluoroacetate salt | 3-hydroxyazetidin-1-yl | Calculated for $C_{27}H_{30}N_5O_5S$ $(M + H)^+$: m/z = 536.2, found: 536.2 |

TABLE 2-continued

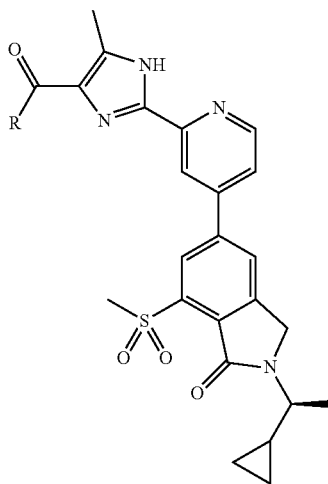

| Example No. | Compound Name | R $^1$H NMR | LCMS |
|---|---|---|---|
| 7f | (S)-2-(4-(2-(1-Cyclopropylethyl)-7-(methylsulfonyl)-1-oxoisoindolin-5-yl)pyridin-2-yl)-N-(3-hydroxycyclobutyl)-4-methyl-1H-imidazole-5-carboxamide, trifluoroacetate salt (mixture of two diastereomers) | HO-cyclobutyl-NH- | Calculated for $C_{28}H_{32}N_5O_5S$ $(M + H)^+$: m/z = 550.2, found: 550.2 |
| 7g | 2-(4-(2-((S)-1-Cyclopropylethyl)-7-(methylsulfonyl)-1-oxoisoindolin-5-yl)pyridin-2-yl)-4-methyl-N-(1,1,1-trifluoropropan-2-yl)-1H-imidazole-5-carboxamide, trifluoroacetate salt (mixture of two diastereomers) | CF$_3$-CH(CH$_3$)-NH- | Calculated for $C_{27}H_{29}F_3N_5O_4S$ $(M + H)^+$: m/z = 576.2, found: 576.2 |
| 7h | (S)-N-(4-Cyanobicyclo[2.1.1]hexan-1-yl)-2-(4-(2-(1-cyclopropylethyl)-7-(methylsulfonyl)-1-oxoisoindolin-5-yl)pyridin-2-yl)-4-methyl-1H-imidazole-5-carboxamide, trifluoroacetate salt | NC-bicyclohexyl-NH- | Calculated for $C_{31}H_{33}N_6O_4S$ $(M + H)^+$: m/z = 585.2, found: 585.2 |
| 7i | (S)-2-(4-(2-(1-Cyclopropylethyl)-7-(methylsulfonyl)-1-oxoisoindolin-5-yl)pyridin-2-yl)-4-methyl-N-(2-oxaspiro[3.3]heptan-6-yl)-1H-imidazole-5-carboxamide, trifluoroacetate salt | oxaspiro[3.3]heptanyl-NH- | Calculated for $C_{30}H_{34}N_5O_5S$ $(M + H)^+$: m/z = 576.2, found: 576.3 |
| 7j | (S)-5-(2-(5-(Azetidine-1-carbonyl)-4-methyl-1H-imidazol-2-yl)pyridin-4-yl)-2-(1-cyclopropylethyl)-7-(methylsulfonyl)isoindolin-1-one, trifluoroacetate salt | azetidin-1-yl | Calculated for $C_{27}H_{30}N_5O_4S$ $(M + H)^+$: m/z = 520.2, found: 520.2 |
| 7k | (S)-N-Cyclobutyl-2-(4-(2-(1-cyclopropylethyl)-7-(methylsulfonyl)-1-oxoisoindolin-5-yl)pyridin-2-yl)-4-methyl-1H-imidazole-5-carboxamide, trifluoroacetate salt | cyclobutyl-NH- | Calculated for $C_{28}H_{32}N_5O_4S$ $(M + H)^+$: m/z = 534.2, found: 534.2 |

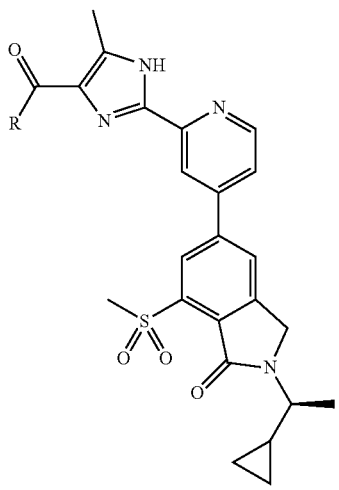

| Example No. | Compound Name | R | LCMS |
|---|---|---|---|
| | | ¹H NMR | |
| 7l | N-(sec-Butyl)-2-(4-(2-((S)-1-cyclopropylethyl)-7-(methylsulfonyl)-1-oxoisoindolin-5-yl)pyridin-2-yl)-4-methyl-1H-imidazole-5-carboxamide, trifluoroacetate salt (mixture of two diastereomers) | | Calculated for $C_{28}H_{34}N_5O_4S$ $(M + H)^+$: m/z 536.2, found: 536.2 |
| 7m | (S)-2-(4-(2-(1-Cyclopropylethyl)-7-(methylsulfonyl)-1-oxoisoindolin-5-yl)pyridin-2-yl)-4-methyl-N-(1-methylazetidin-3-yl)-1H-imidazole-5-carboxamide, trifluoroacetate salt | | Calculated for $C_{28}H_{33}N_6O_4S$ $(M + H)^+$: m/z = 549.2, found: 549.2 |
| 7n | 2-(4-(2-((S)-1-Cyclopropylethyl)-7-(methylsulfonyl)-1-oxoisoindolin-5-yl)pyridin-2-yl)-4-methyl-N-(tetrahydrofuran-3-yl)-1H-imidazole-5-carboxamide, trifluoroacetate salt (mixture of two diastereomers) | | Calculated for $C_{28}H_{32}N_5O_5S$ $(M + H)^+$: m/z = 550.2, found: 550.2 |
| 7o | (S)-2-(4-(2-(1-Cyclopropylethyl)-7-(methylsulfonyl)-1-oxoisoindolin-5-yl)pyridin-2-yl)-N,4-dimethyl-N-(tetrahydro-2H-pyran-4-yl)-1H-imidazole-5-carboxamide, trifluoroacetate salt | | Calculated for $C_{30}H_{36}N_5O_5S$ $(M + H)^+$: m/z = 578.2, found: 578.2 |
| 7p | (S)-2-(1-Cyclopropylethyl)-5-(2-(4-methyl-5-(2-oxa-6-azaspiro[3.3]heptane-6-carbonyl)-1H-imidazol-2-yl)pyridin-4-yl)-7-(methylsulfonyl)isoindolin-1-one, trifluoroacetate salt | | Calculated for $C_{29}H_{32}N_5O_5S$ $(M + H)^+$: m/z = 562.2, found: 562.2 |
| 7q | (S)-2-(4-(2-(1-Cyclopropylethyl)-7-(methylsulfonyl)-1-oxoisoindolin-5-yl)pyridin-2-yl)-4-methyl-1H-imidazole-5-carboxamide, trifluoroacetate salt | | Calculated for $C_{24}H_{26}N_5O_4S$ $(M + H)^+$: m/z = 480.2, found: 480.2 |
| 7r | (S)-2-(4-(2-(1-Cyclopropylethyl)-7-(methylsulfonyl)-1-oxoisoindolin-5-yl)pyridin-2-yl)-N-ethyl-4-methyl-1H-imidazole-5-carboxamide, trifluoroacetate salt | | Calculated for $C_{26}H_{30}N_5O_4S$ $(M + H)^+$: m/z = 508.2, found: 508.2 |

TABLE 2-continued

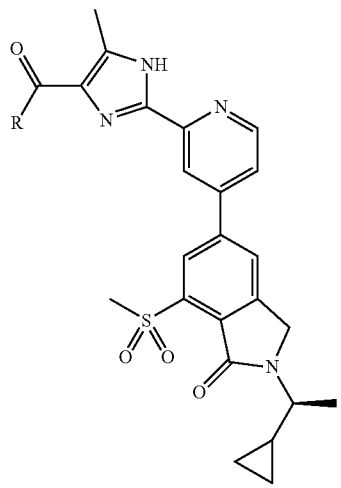

| Example No. | Compound Name | R $^1$H NMR | LCMS |
|---|---|---|---|
| 7s | (S)-2-(4-(2-(1-Cyclopropylethyl)-7-(methylsulfonyl)-1-oxoisoindolin-5-yl)pyridin-2-yl)-N-ethyl-N,4-dimethyl-1H-imidazole-5-carboxamide, trifluoroacetate salt | [ethyl-N-methyl] | Calculated for $C_{27}H_{32}N_5O_4S$ $(M + H)^+$: m/z = 522.2, found: 522.2 |
| 7t | (S)-2-(4-(2-(1-Cyclopropylethyl)-7-(methylsulfonyl)-1-oxoisoindolin-5-yl)pyridin-2-yl)-N-isopropyl-N,4-dimethyl-1H-imidazole-5-carboxamide, trifluoroacetate salt | [isopropyl-N-methyl] | Calculated for $C_{28}H_{34}N_5O_4S$ $(M + H)^+$: m/z = 536.2, found: 536.2 |
| 7u | (S)-N-Cyclobutyl-2-(4-(2-(1-cyclopropylethyl)-7-(methylsulfonyl)-1-oxoisoindolin-5-yl)pyridin-2-yl)-N,4-dimethyl-1H-imidazole-5-carboxamide, trifluoroacetate salt | [cyclobutyl-N-methyl] | Calculated for $C_{29}H_{34}N_5O_4S$ $(M + H)^+$: m/z = 548.2, found: 548.2 |

Example 8. (S)-2-(1-Cyclopropylethyl)-5-(6-(4,5-dimethyl-1H-imidazol-2-yl)pyridazin-4-yl)-7-(methylsulfonyl)isoindolin-1-one Trifluoroacetate Salt

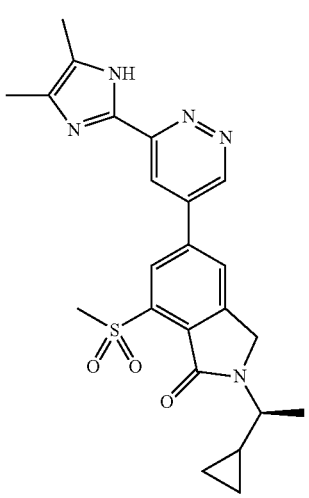

Step 1. (S)-5-(6-Chloropyridazin-4-yl)-2-(1-cyclopropylethyl)-7-(methylsulfonyl)isoindolin-1-one

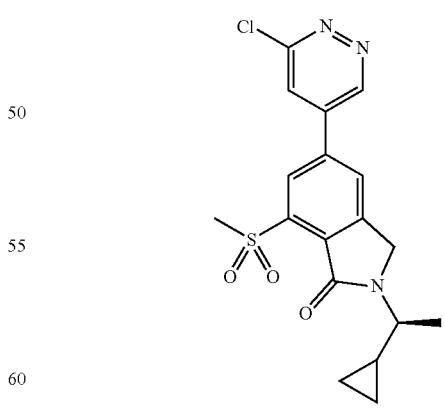

A mixture of (S)-2-(1-cyclopropylethyl)-7-(methylsulfonyl)-5-(4,4,5,5-tetramethyl-1,3,2-dioxaborolan-2-yl)isoindolin-1-one (0.57 g, 1.4 mmol, from Example 2, Step 3), 3,5-dichloropyridazine (0.21 g, 1.4 mmol, Aldrich MNO000179), palladium(II) acetate (0.031 g, 0.14 mmol), 1,2,3,4,5-pentaphenyl-1'-(di-tert-butylphosphino)ferrocene (0.099 g, 0.14 mmol), and cesium carbonate (1.4 g, 4.2 mmol) in water (1.4 mL) and 1,4-dioxane (5.6 mL) was degassed by sparging with N₂, and was heated at 70° C. for 18 hours. Upon cooling to room temperature, the reaction mixture was diluted with water, and was extracted with EtOAc (3×). The combined organic extracts were dried over Na₂SO₄, filtered and concentrated. Flash chromatography, eluting with a gradient from 0-100% EtOAc in hexanes, afforded the title compound (0.13 g, 24%). ¹H NMR (400 MHz, CD₃OD) δ 9.63 (d, J=2.0 Hz, 1H), 8.51 (d, J=1.6 Hz, 1H), 8.42 (d, J=1.7 Hz, 1H), 8.30 (d, J=2.0 Hz, 1H), 4.86 (d, J=18.7 Hz, 1H), 4.79 (d, J=18.9 Hz, 1H), 3.81-3.68 (m, 1H), 3.62 (s, 3H), 1.44 (d, J=6.8 Hz, 3H), 1.27-1.16 (m, 1H), 0.78-0.67 (m, 1H), 0.60-0.50 (m, 1H), 0.50-0.42 (m, 1H), 0.42-0.34 (m, 1H). LCMS for $C_{18}H_{19}ClN_3O_3S$ (M+H)⁺: calculated monoisotopic m/z=392.1; found 392.0.

Step 2. (S)-5-(2-(1-Cyclopropylethyl)-7-(methylsulfonyl)-1-oxoisoindolin-5-yl)pyridazine-3-carbonitrile

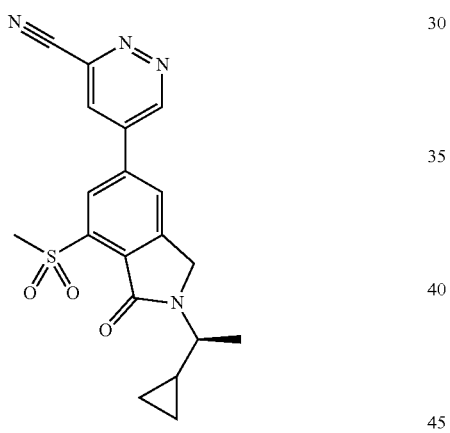

A degassed mixture of (S)-5-(6-chloropyridazin-4-yl)-2-(1-cyclopropylethyl)-7-(methylsulfonyl)isoindolin-1-one (0.065 g, 0.17 mmol), zinc cyanide (0.058 g, 0.50 mmol), zinc powder (2.2 mg, 0.033 mmol), palladium(II) trifluoroacetate (5.5 mg, 0.017 mmol) and 2-(di-tert-butylphosphino)biphenyl (9.9 mg, 0.033 mmol) in N,N-dimethylacetamide (1.7 mL) was heated at 95° C. overnight. Upon cooling to room temperature, the reaction mixture was diluted with water and extracted with EtOAc (3×). The reaction mixture was filtered through Celite®. The combined organic extracts were dried over Na₂SO₄, filtered and concentrated. Flash chromatography, eluting with a gradient from 0-10% MeOH/DCM, afforded the title compound (38 mg, 60%). LCMS for $C_{19}H_{19}N_4O_3S$ (M+H)⁺: calculated monoisotopic m/z=383.1; found 383.1.

Step 3. (S)-5-(2-(1-Cyclopropylethyl)-7-(methylsulfonyl)-1-oxoisoindolin-5-yl)pyridazine-3-carboximidamide

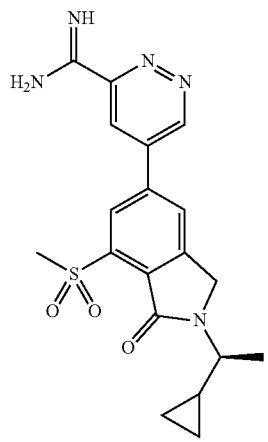 [SMILES: C[C@@H](C1CC1)N1Cc2cc(-c3cnnc(C(=N)N)c3)cc(S(C)(=O)=O)c2C1=O]

To a degassed solution of (S)-5-(2-(1-cyclopropylethyl)-7-(methylsulfonyl)-1-oxoisoindolin-5-yl)pyridazine-3-carbonitrile (0.038 g, 0.099 mmol) in MeOH (1.0 mL) and THF (1.0 mL) was added sodium methoxide (1.7 mg, 8.0 μmol, 25 wt % in MeOH). The reaction mixture was heated to reflux for 2 hours. Ammonium chloride (8.0 mg, 0.15 mmol) was added, and the reaction was stirred overnight. Solvent was removed in vacuo, and the product was used without further purification (theoretical yield assumed). LCMS for $C_{19}H_{22}N_5O_3S$ (M+H)⁺: calculated monoisotopic m/z=400.1; found 400.1.

Step 4. (S)-2-(1-Cyclopropylethyl)-5-(6-(4,5-dimethyl-1H-imidazol-2-yl)pyridazin-4-yl)-7-(methylsulfonyl)isoindolin-1-one Trifluoroacetate Salt To (S)-5-(2-(1-cyclopropylethyl)-7-(methylsulfonyl)-1-oxoisoindolin-5-yl)pyridazine-3-carboximidamide (0.040 g, 0.10 mmol) in DMF (1.0 mL) was added 3-bromobutan-2-one (0.016 ml, 0.15 mmol, Alfa Aesar A10186) and K₂CO₃ (0.021 g, 0.15 mmol). The reaction was stirred overnight, then was diluted with water and MeOH, filtered and purified via preparative HPLC-MS (pH=2). ¹H NMR (400 MHz, CD₃OD) δ 9.82 (s, 1H), 8.71 (s, 1H), 8.63 (s, 1H), 8.52 (s, 1H), 4.95-4.77 (m, 2H), 3.81-3.69 (m, 1H), 3.64 (s, 3H), 2.44 (s, 6H), 1.45 (d, J=6.8 Hz, 3H), 1.29-1.10 (m, 1H), 0.80-0.69 (m, 1H), 0.61-0.51 (m, 1H), 0.51-0.43 (m, 1H), 0.43-0.32 (m, 1H). LCMS for $C_{23}H_{26}N_5O_3S$ (M+H)⁺: calculated monoisotopic m/z=452.2; found 452.1.

Example 9. (S)-5-(6-(1H-Pyrazol-5-yl)pyridazin-4-yl)-2-(1-cyclopropylethyl)-7-(methylsulfonyl)isoindolin-1-one Trifluoroacetate Salt

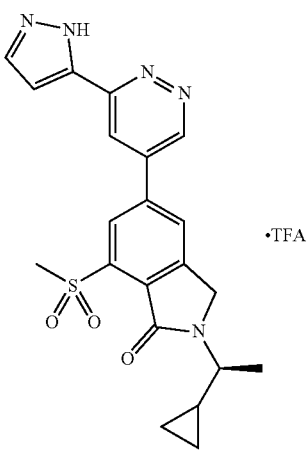 [SMILES: C[C@@H](C1CC1)N1Cc2cc(-c3cnnc(-c4ccn[nH]4)c3)cc(S(C)(=O)=O)c2C1=O]

A degassed mixture of (S)-5-(6-chloropyridazin-4-yl)-2-(1-cyclopropylethyl)-7-(methylsulfonyl)isoindolin-1-one (10 mg, 0.026 mmol, from Example 8, Step 1), 3-(4,4,5,5-tetramethyl-1,3,2-dioxaborolan-2-yl)-1H-pyrazole (5.9 mg, 0.031 mmol, Combi-Blocks # PN-8344), Cs$_2$CO$_3$ (17 mg, 0.051 mmol), and dichloro[1,1'-bis(diphenylphosphino)ferrocene]palladium (II) dichloromethane adduct (2.1 mg, 2.6 µmol) in dioxane (0.50 mL) and water (0.13 mL) was heated to 100° C. for 2 h. Upon cooling to room temperature, the reaction mixture was diluted with acetonitrile and methanol and was filtered. The product was purified via preparative HPLC-MS (pH=2) to afford the title compound (3.0 mg, 21%). $^1$H NMR (400 MHz, DMSO-d$_6$) δ 9.63 (d, J=2.3 Hz, 1H), 8.58 (d, J=1.6 Hz, 1H), 8.49 (d, J=2.3 Hz, 1H), 8.41 (d, J=1.6 Hz, 1H), 7.93 (d, J=2.5 Hz, 1H), 7.14 (d, J=2.3 Hz, 1H), 4.78 (s, 2H), 3.70-3.62 (m, 1H), 3.67 (s, 3H), 1.35 (d, J=6.8 Hz, 3H), 1.29-1.09 (m, 1H), 0.70-0.56 (m, 1H), 0.56-0.37 (m, 2H), 0.37-0.16 (m, 1H). LCMS for C$_{21}$H$_{22}$N$_5$O$_3$S (M+H)$^+$: calculated m/z=424.1; found 424.1.

Example 10

The compound in Table 3 was prepared by the procedure of Example 9, using 5-methyl-3-(4,4,5,5-tetramethyl-1,3,2-dioxaborolan-2-yl)-1H-pyrazole (6.4 mg, 0.031 mmol, Astatech # P18160) instead of 3-(4,4,5,5-tetramethyl-1,3,2-dioxaborolan-2-yl)-1H-pyrazole.

TABLE 3

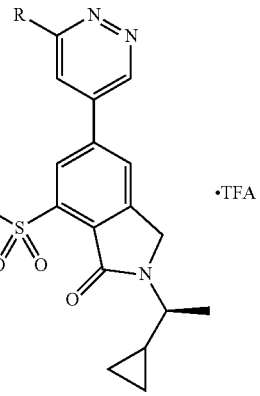

| Example No. | Compound Name | R | LCMS $^1$H NMR |
|---|---|---|---|
| 10 | (S)-2-(1-Cyclopropylethyl)-5-(6-(3-methyl-1H-pyrazol-5-yl)pyridazin-4-yl)-7-(methylsulfonyl)isoindolin-1-one, trifluoroacetate salt | 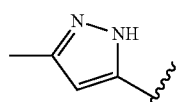 | Calculated for C$_{22}$H$_{24}$N$_5$O$_3$S (M + H)$^+$: m/z = 438.2, found: 438.2 |

$^1$H NMR (400 MHz, DMSO-d$_6$) δ 9.61 (d, J = 2.3 Hz, 1H), 8.57 (d, J = 1.6 Hz, 1H), 8.44 (d, J = 2.3 Hz, 1H), 8.40 (d, J = 1.6 Hz, 1H), 6.87 (s, 1H), 4.77 (s, 2H), 3.71-3.61 (m, 1H), 3.66 (s, 3H), 2.35 (s, 3H), 1.35 (d, J = 6.8 Hz, 3H), 1.27-1.09 (m, 1H), 0.68-0.54 (m, 1H), 0.54-0.36 (m, 2H), 0.36-0.14 (m, 1H).

Example 11. (S)-2-(1-Cyclopropylethyl)-5-(6-(3-methyl-1H-pyrazol-5-yl)pyridazin-4-yl)isoindolin-1-one Trifluoroacetate Salt

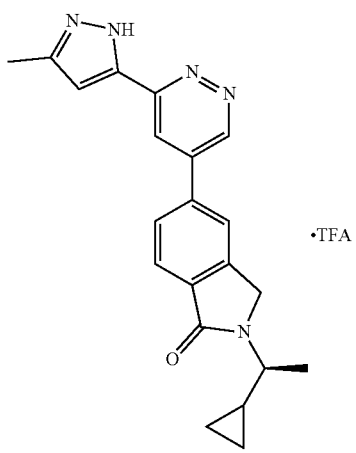 [SMILES: Cc1cc(-c2cc(-c3ccc4c(c3)CN([C@@H](C)C3CC3)C4=O)cnn2)[nH]n1]

Step 1. 5-Chloro-3-(3-methyl-1-(tetrahydro-2H-pyran-2-yl)-1H-pyrazol-5-yl)pyridazine

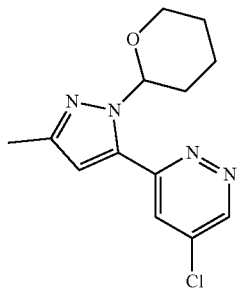 [SMILES: Cc1cc(-c2cc(Cl)cnn2)n(C2CCCCO2)n1]

A degassed mixture of 3-methyl-1-(tetrahydro-2H-pyran-2-yl)-5-(4,4,5,5-tetramethyl-1,3,2-dioxaborolan-2-yl)-1H-pyrazole (0.080 g, 0.27 mmol, Combi Block # PN-4298), 3,5-dichloropyridazine (41 mg, 0.27 mmol, Aldrich # MNO000179), dichloro[1,1'-bis(diphenylphosphino)ferrocene]palladium (II) dichloromethane adduct (11 mg, 0.014 mmol) and $Cs_2CO_3$ (220 mg, 0.680 mmol) in dioxane (1.0 mL) and water (0.25 mL) was heated to 70° C. for 3 h. Upon cooling to room temperature, the reaction mixture was diluted with EtOAc (6.0 mL), filtered through Celite® and concentrated. The product was initially purified via flash column chromatography, eluting with a gradient of 0-70% EtOAc/hexanes. The product was further purified via preparative HPLC-MS (pH=10) to afford the title compound (12 mg, 16%). The major isomer was the desired product. $^1$H NMR (400 MHz, $CDCl_3$) δ 9.16 (d, J=2.4 Hz, 1H), 7.77 (d, J=2.3 Hz, 1H), 6.53 (s, 1H), 6.20 (dd, J=10.3, 2.1 Hz, 1H), 4.11-3.98 (m, 1H), 3.63 (td, J=11.6, 2.6 Hz, 1H), 2.38 (s, 3H), 2.18-2.05 (m, 2H), 1.83-1.49 (m, 4H). LCMS for $C_{13}H_{16}ClN_4O$ $(M+H)^+$: calculated monoisotopic m/z=279.1; found 279.1.

Step 2. (S)-2-(1-Cyclopropylethyl)-5-(6-(3-methyl-1H-pyrazol-5-yl)pyridazin-4-yl)isoindolin-1-one Trifluoroacetate Salt A degassed mixture of (S)-2-(1-cyclopropylethyl)-5-(4,4,5,5-tetramethyl-1,3,2-dioxaborolan-2-yl)isoindolin-1-one (14 mg, 0.043 mmol, from Example 3, Step 2), 5-chloro-3-(3-methyl-1-(tetrahydro-2H-pyran-2-yl)-1H-pyrazol-5-yl) pyridazine (12 mg, 0.043 mmol, from Step 1), dichloro[1,1'-bis(diphenylphosphino)ferrocene]palladium (II) dichloromethane adduct (7.0 mg, 8.6 μmol) and $Cs_2CO_3$ (42 mg, 0.13 mmol) in dioxane (0.50 mL) and water (0.13 mL) was heated to 95° C. for 5.5 hours. Upon cooling to room temperature, the reaction mixture was diluted with MeOH and MeCN and was filtered. Solvent was removed in vacuo and the residue was stirred with 1.0 N HCl (1.0 mL) in MeCN and MeOH (1.0 mL each) overnight. The product was purified via preparative HPLC-MS (pH=2) to afford the title compound (3.6 mg, 18%). $^1$H NMR (400 MHz, DMSO-$d_6$) δ 9.59 (d, J=2.3 Hz, 1H), 8.41 (d, J=2.3 Hz, 1H), 8.22 (s, 1H), 8.07 (dd, J=8.0, 1.6 Hz, 1H), 7.85 (d, J=7.9 Hz, 1H), 6.86 (s, 1H), 4.66 (s, 1H), 3.70-3.54 (m, 1H), 2.35 (s, 3H), 1.33 (d, J=6.8 Hz, 3H), 1.23-1.09 (m, 1H), 0.70-0.53 (m, 1H), 0.51-0.33 (m, 2H), 0.33-0.16 (m, 1H). LCMS for $C_{21}H_{22}N_5O$ $(M+H)^+$: calculated m/z=360.2; found 360.1.

Example 12. (S)-2-(1-Cyclopropylethyl)-5-(2-(5-methyl-4H-1,2,4-triazol-3-yl)pyridin-4-yl)-7-(methylsulfonyl)isoindolin-1-one

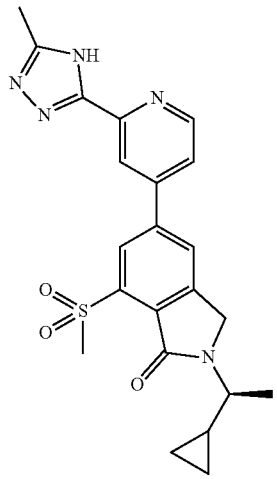 [SMILES: Cc1nnc(-c2cc(-c3cc4c(c(S(C)(=O)=O)c3)C(=O)N([C@@H](C)C3CC3)C4)ccn2)[nH]1]

Step 1. (S)-4-(2-(1-Cyclopropylethyl)-7-(methylsulfonyl)-1-oxoisoindolin-5-yl)picolinonitrile

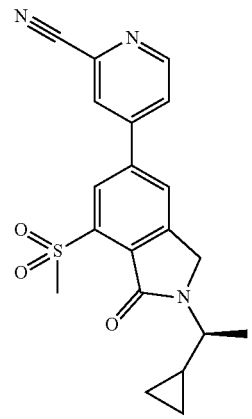 [SMILES: C[C@@H](C1CC1)N1Cc2cc(-c3ccnc(C#N)c3)cc(S(C)(=O)=O)c2C1=O]

A degassed mixture of 4-bromopicolinonitrile (0.050 g, 0.27 mmol, Synthonix # B0041), (S)-2-(1-cyclopropylethyl)-7-(methylsulfonyl)-5-(4,4,5,5-tetramethyl-1,3,2-dioxaborolan-2-yl)isoindolin-1-one (110 mg, 0.27 mmol, from Example 2, Step 3), cesium fluoride (120 mg, 0.80 mmol) and 4-(di-tert-butylphosphino)-N,N-dimethylaniline-dichloropalladium (2:1) (19 mg, 0.027 mmol) in dioxane (1.0 mL) and water (0.25 mL) was heated to 100° C. for 2 h. Upon cooling to room temperature, the reaction mixture was diluted with water and extracted with EtOAc (2×). The combined organic extracts were dried over $Na_2SO_4$, filtered and concentrated. The product was purified via flash column chromatography, eluting with a gradient of 0-80% EtOAc in hexanes to afford the title compound (55 mg, 54%). LCMS for $C_{20}H_{20}N_3O_3S$ $(M+H)^+$: calculated m/z=382.1; found 382.1.

Step 2. (S)-2-(1-Cyclopropylethyl)-5-(2-(5-methyl-4H-1,2,4-triazol-3-yl)pyridin-4-yl)-7-(methylsulfonyl)isoindolin-1-one Sodium methoxide (25 wt % in MeOH, 33 μL, 0.14 mmol) was added to a suspension of (S)-4-(2-(1-cyclopropylethyl)-7-(methylsulfonyl)-1-oxoisoindolin-5-yl)picolinonitrile (55 mg, 0.14 mmol, from Step 1) in MeOH (1.0 mL), and the reaction mixture was stirred for one hour. An aliquot of ⅓ of the reaction mixture was removed and acetohydrazide (7.2 mg, 0.097 mmol) was added. The reaction mixture was heated to reflux overnight. Upon cooling to room temperature, the reaction mixture was diluted with MeOH, filtered and purified via preparative HPLC-MS (pH=10) to afford the title compound (1.2 mg, 2%). $^1$H NMR (400 MHz, DMSO-$d_6$) δ 8.83 (d, J=5.1 Hz, 1H), 8.49 (d, J=1.6 Hz, 1H), 8.39 (d, J=1.7 Hz, 1H), 8.34 (d, J=1.6 Hz, 1H), 7.89 (d, J=5.1 Hz, 1H), 4.77 (s, 2H), 3.69-3.63 (m, 1H), 3.67 (s, 3H), 3.30 (s, 3H), 1.35 (d, J=6.8 Hz, 3H), 1.25-1.14 (m, 1H), 0.66-0.57 (m, 1H), 0.53-0.35 (m, 2H), 0.34-0.25 (m, 1H). LCMS for $C_{22}H_{24}N_5O_3S$ (M+H)$^+$: calculated m/z=438.2; found 438.2.

Example 13

The compound in Table 4 was prepared by the procedure of Example 12, using (S)-2-(1-cyclopropylethyl)-5-(4,4,5,5-tetramethyl-1,3,2-dioxaborolan-2-yl)isoindolin-1-one (from Example 3, Step 2) instead of (S)-2-(1-cyclopropylethyl)-7-(methylsulfonyl)-5-(4,4,5,5-tetramethyl-1,3,2-dioxaborolan-2-yl)isoindolin-1-one in Step 1.

TABLE 4

| Example No. | Compound Name | R | LCMS<br>$^1$H NMR |
|---|---|---|---|
| 13 | (S)-2-(1-Cyclopropylethyl)-5-(2-(5-methyl-4H-1,2,4-triazol-3-yl)pyridin-4-yl)isoindolin-1-one | 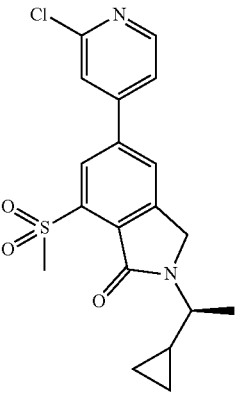 | Calculated for $C_{21}H_{22}N_5O$ (M + H)$^+$:<br>m/z = 360.2, found: 360.2 |

$^1$H NMR (400 MHz, DMSO-$d_6$) δ 8.77 (d, J = 5.2 Hz, 1H), 8.35 (d, J = 1.8 Hz, 1H), 8.11 (s, 1H), 7.96 (dd, J = 8.1, 1.6 Hz, 1H), 7.85-7.80 (m, 2H), 4.65 (s, 2H), 3.69-3.57 (m, 1H), 2.40 (s, 3H), 1.32 (d, J = 6.8 Hz, 3H), 1.21-1.11 (m, 1H), 0.65-0.52 (m, 1H), 0.48-0.36 (m, 2H), 0.33-0.19 (m, 1H).

Example 14. (S)-2-(1-Cyclopropylethyl)-5-(2-(3-methyl-1H-pyrazol-5-yl)pyridin-4-yl)-7-(methylsulfonyl)isoindolin-1-one, Trifluoroacetate Salt

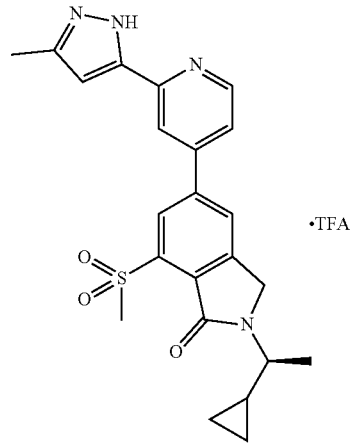 [SMILES: Cc1cc(-c2cc(-c3cc4c(c(S(C)(=O)=O)c3)C(=O)N([C@@H](C)C3CC3)C4)ccn2)[nH]n1]

Step 1. ((S)-5-(2-Chloropyridin-4-yl)-2-(1-cyclopropylethyl)-7-(methylsulfonyl)isoindolin-1-one Dichloro[1,1'-bis(diphenylphosphino)ferrocene]palladium (II) dichloromethane adduct (38 mg, 0.046 mmol) was added to a degassed mixture of(S)-2-(1-cyclopropylethyl)-7-(methylsulfonyl)-5-(4,4,5,5-tetramethyl-1,3,2-dioxaborolan-2-yl)isoindolin-1-one (190 mg, 0.46 mmol, from Example 2, Step 3), 2-chloro-4-iodopyridine (110 mg, 0.459 mmol, Matrix #009790) and $K_2CO_3$ (190 mg, 1.378 mmol) in THF (3.0 mL) and water (1.0 mL). The reaction was then heated to 66° C. for 3 h. Upon cooling to room temperature, the reaction mixture was diluted with water and extracted with EtOAc (3×). The combined organic extracts were dried over $Na_2SO_4$, filtered and concentrated. The product was purified via flash column chromatography, eluting with a gradient from 0-100% EtOAc in hexanes to afford the title compound (0.060 g, 33%). LCMS for $C_{19}H_{20}ClN_2O_3S$ (M+H)$^+$: calculated monoisotopic m/z=391.1; found 391.0.

Step 2. (S)-2-(1-Cyclopropylethyl)-5-(2-(3-methyl-1H-pyrazol-5-yl)pyridin-4-yl)-7-(methylsulfonyl)isoindolin-1-one, Trifluoroacetate Salt Dichloro[1,1'-bis(diphenylphosphino)ferrocene]palladium (II) dichloromethane adduct (3.1 mg, 3.84 μmol) was added to a degassed mixture of (S)-5-(2-chloropyridin-4-yl)-2-(1-cyclopropylethyl)-7-(methylsulfonyl)isoindolin-1-one (15 mg, 0.038 mmol, from Step 1), 3-methyl-1-(tetrahydro-2H-pyran-2-yl)-5-(4,4,5,5-tetramethyl-1,3,2-dioxaborolan-2-yl)-1H-pyrazole (13 mg, 0.046 mmol, Combi Block PN-4298) and $Cs_2CO_3$ (25 mg, 0.077 mmol) in dioxane (2.0 mL) and water (1.0 mL). The reaction mixture was then heated to 100° C. for 3 h. Upon cooling to room temperature, the reaction mixture was partitioned between EtOAc and water. The organic layer was dried over $MgSO_4$, filtered and concentrated. LCMS for $C_{28}H_{33}N_4O_4S$ (M+H)$^+$: calculated m/z=521.2; found 521.1. The crude product was stirred with TFA (0.090 mL, 1.2 mmol) in DCM (1.0 mL) for 12 hours. Volatiles were removed in vacuo and the product was dissolved in MeCN and purified via HPLC-MS (pH=2) to afford the title compound (8.0 mg, 38%). $^1$H NMR (400 MHz, DMSO-$d_6$) δ 8.74 (d, J=5.3 Hz, 1H), 8.46 (d, J=1.6 Hz, 1H), 8.34 (d, J=1.6 Hz, 1H), 8.31 (d, J=1.7 Hz, 1H), 7.75 (dd, J=5.5, 1.9 Hz, 1H), 6.74 (s, 1H), 4.77 (s, 2H), 3.70-3.61 (m, 1H), 3.67 (s, 3H), 2.32 (s, 3H), 1.34 (d, J=6.8 Hz, 3H), 1.26-1.13 (m, 1H), 0.67-0.55 (m, 1H), 0.54-0.34 (m, 2H), 0.34-0.25 (m, 1H). LCMS for $C_{23}H_{25}N_4O_3S$ (M+H)$^+$: calculated m/z=437.2; found 437.1.

Example 15

The compound in Table 5 was prepared by the procedure of Example 14, using 1-(tetrahydro-2H-pyran-2-yl)-5-(4,4,5,5-tetramethyl-1,3,2-dioxaborolan-2-yl)-1H-pyrazole (Combi Blocks # PN-8344) instead of 3-methyl-1-(tetrahydro-2H-pyran-2-yl)-5-(4,4,5,5-tetramethyl-1,3,2-dioxaborolan-2-yl)-1H-pyrazole in Step 2, and performing the deprotection by stirring with HCl (1.0 N in water, 0.21 mL, 0.21 mmol) in MeCN (1.0 mL) for 20 min instead of with TFA in DCM.

TABLE 5

| Example No. | Compound Name | R | LCMS $^1$H NMR |
|---|---|---|---|
| 15 | (S)-5-(2-(1H-Pyrazol-5-yl)pyridin-4-yl)-2-(1-cyclopropylethyl)-7-(methylsulfonyl)isoindolin-1-one, trifluoroacetate salt | N—NH pyrazole | Calculated for $C_{22}H_{23}N_4O_3S$ (M + H)$^+$: m/z = 423.1, found: 423.1 |

$^1$H NMR (400 MHz, DMSO-$d_6$) δ 8.76 (d, J = 5.3 Hz, 1H), 8.47 (s, 1H), 8.37-8.31 (m, 2H), 7.82 (s, 1H), 7.75 (d, J = 4.6 Hz, 1H), 6.97 (s, 1H), 4.77 (s, 2H), 3.71-3.61 (m, 1H), 3.67 (s, 3H), 1.35 (d, J = 6.8 Hz, 3H), 1.28-1.13 (m, 1H), 0.67-0.57 (m, 1H), 0.52-0.38 (m, 2H), 0.34-0.25 (m, 1H).

Example 16. (S)-2-(1-Cyclopropylethyl)-5-(2-(5-methyl-1H-imidazol-2-yl)pyridin-4-yl)-7-(methylsulfonyl)isoindolin-1-one, Trifluoroacetate Salt

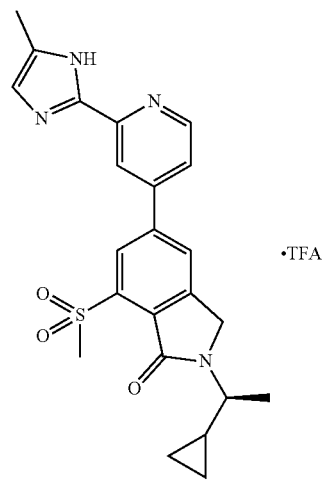 [SMILES: Cc1cnc(-c2cc(-c3cc4c(c(S(C)(=O)=O)c3)C(=O)N([C@@H](C)C3CC3)C4)ccn2)[nH]1]

To a suspension of (S)-4-(2-(1-cyclopropylethyl)-7-(methylsulfonyl)-1-oxoisoindolin-5-yl)picolinonitrile (18 mg, 0.047 mmol, from Example 12, Step 1) in MeOH (0.30 mL) was added NaOMe (25 wt % in MeOH, 11 μL, 0.047 mmol), and the reaction mixture was stirred for 1 h. To the mixture was then added 1,1-diethoxypropan-2-amine (8.0 μL, 0.047 mmol, Astatech #84948) and acetic acid (7.0 μl, 0.12 mmol). The mixture was sealed and heated at 100° C. for 2.5 hours. The mixture was cooled to rt, and c.HCl (0.012 mL, 0.19 mmol) was added and the mixture was heated to 85° C. for 2 h. Upon cooling to rt, the reaction mixture was diluted with MeOH, and the product was purified via preparative HPLC-MS (pH=2) to afford the title compound (0.010 g, 38%). $^1$H NMR (400 MHz, DMSO-$d_6$) δ 8.95 (d, J=5.2 Hz, 1H), 8.62 (d, J=1.8 Hz, 1H), 8.48 (d, J=1.7 Hz, 1H), 8.44 (d, J=1.6 Hz, 1H), 8.06 (dd, J=5.2, 1.8 Hz, 1H), 7.57 (s, 1H), 4.78 (s, 2H), 3.69 (s, 3H), 3.67-3.62 (m, 1H), 2.39 (s, 3H), 1.36 (d, J=6.8 Hz, 3H), 1.28-1.14 (m, 1H), 0.68-0.55 (m, 1H), 0.51-0.39 (m, 2H), 0.35-0.24 (m, 1H). LCMS for $C_{23}H_{25}N_4O_3S$ (M+H)$^+$: calculated m/z=437.2; found 437.1.

Example 17

The compound in Table 6 was prepared by the procedure of Example 16, using 2,2-diethoxyethan-1-amine (6.3 mg, 0.047 mmol, Aldrich # A37200) instead of 1,1-diethoxypropan-2-amine.

TABLE 6

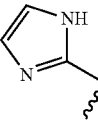

| Example No. | Compound Name | R | LCMS<br>¹H NMR |
|---|---|---|---|
| 17 | (S)-5-(2-(1H-Imidazol-2-yl)pyridin-4-yl)-2-(1-cyclopropylethyl)-7-(methylsulfonyl)isoindolin-1-one, trifluoroacetate salt | 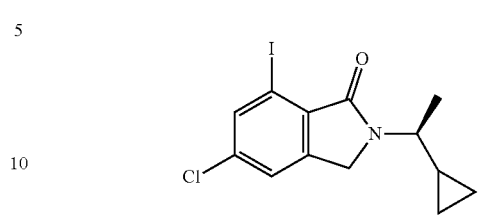 | Calculated for $C_{22}H_{23}N_4O_3S$ $(M + H)^+$: m/z = 423.1, found: 423.1 |

¹H NMR (400 MHz, DMSO-d₆) δ 8.95 (d, J = 5.1 Hz, 1H), 8.66 (s, 1H), 8.49 (d, J = 1.6 Hz, 1H), 8.45 (d, J = 1.6 Hz, 1H), 8.06 (dd, J = 5.3, 1.7 Hz, 1H), 7.80 (s, 2H), 4.78 (s, 2H), 3.69 (s, 3H), 3.68-3.61 (m, 1H), 1.36 (d, J = 6.8 Hz, 3H), 1.29-1.15 (m, 1H), 0.69-0.56 (m, 1H), 0.50-0.40 (m, 2H), 0.35-0.25 (m, 1H).

Example 18. 2-((S)-1-Cyclopropylethyl)-7-(1,2-dihydroxyethyl)-5-(2-(4,5-dimethyl-1H-imidazol-2-yl)pyridin-4-yl)isoindolin-1-one (Mixture of Two Diastereomers)

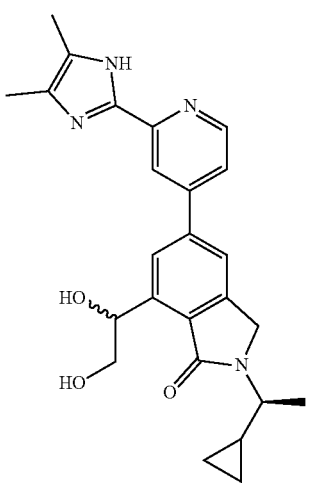 [SMILES: Cc1nc(-c2cc(-c3cc4c(c(C(O)CO)c3)C(=O)N([C@@H](C)C3CC3)C4)ccn2)[nH]c1C]

Step 1. (S)-5-Chloro-2-(1-cyclopropylethyl)-7-iodoisoindolin-1-one

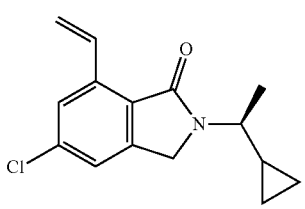 [SMILES: C=Cc1cc(Cl)cc2c1C(=O)N([C@@H](C)C1CC1)C2]

The title compound was prepared as described in Example 1, Steps 2 and 3, using methyl 4-chloro-2-iodo-6-methylbenzoate (6.9 g, 22 mmol, prepared as described in WO 2011006794) instead of methyl 4-bromo-2-chloro-6-methylbenzoate in Step 2 (3.7 g, 52% over 2 steps). LCMS for $C_{13}H_{14}ClINO$ $(M+H)^+$: calculated monoisotopic m/z=362.0; found 361.9.

Step 2. (S)-5-Chloro-2-(1-cyclopropylethyl)-7-vinylisoindolin-1-one

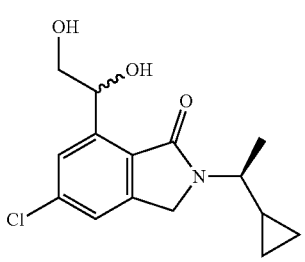 [SMILES: C[C@@H](C1CC1)N1Cc2cc(Cl)cc(C(O)CO)c2C1=O]

A degassed mixture of (S)-5-chloro-2-(1-cyclopropylethyl)-7-iodoisoindolin-1-one (0.50 g, 1.4 mmol, from Step 2), 4,4,5,5-tetramethyl-2-vinyl-1,3,2-dioxaborolane (260 mg, 1.7 mmol, Combi Blocks # PN-8602), and dichloro[1,1'-bis(diphenylphosphino)ferrocene]palladium (II) dichloromethane adduct (56 mg, 0.069 mmol) in dioxane (8.5 mL) and aq. K₂CO₃ solution (1.0 M, 4.2 mL, 4.2 mmol) was heated to 80° C. for 2 h. Upon cooling to room temperature, the reaction mixture was diluted with water and extracted with EtOAc (2×). The combined organic extracts were washed with brine, dried over Na₂SO₄, filtered and concentrated. The product was purified via flash column chromatography, eluting with a gradient of 0-20% EtOAc in hexanes to afford the title compound (0.31 g, 86%). LCMS for $C_{15}H_{17}ClNO$ $(M+H)^+$: calculated monoisotopic m/z=262.1; found 262.1.

Step 3. 5-Chloro-2-((S)-1-cyclopropylethyl)-7-(1,2-dihydroxyethyl)isoindolin-1-one (Mixture of Two Diastereomers)

To a solution of (S)-5-chloro-2-(1-cyclopropylethyl)-7-vinylisoindolin-1-one (0.31 g, 1.2 mmol, a mixture of two diastereomers from Step 2) in acetone (15 mL) and water (5.0 mL) was added NMO (0.18 g, 1.5 mmol) and OsO$_4$ (4% w/v in water, 0.45 mL, 0.071 mmol). The mixture was stirred for 1 h, followed by the addition of sodium sulfite (0.30 g, 2.4 mmol). After stirring for 10 min, the reaction mixture was filtered. The filtrate was diluted with EtOAc and brine. The layers were shaken and separated and the aqueous layer was extracted with EtOAc (2×). The combined organic extracts were dried over Na$_2$SO$_4$, filtered and concentrated. The product was purified via flash column chromatography, eluting with a gradient of 0-100% EtOAc in hexanes to afford the title compound (0.31 g, 88%). LCMS for C$_{15}$H$_{19}$ClNO$_3$ (M+H)$^+$: calculated monoisotopic m/z=296.1; found 296.1.

Step 4. 2-((S)-1-Cyclopropylethyl)-7-(1,2-dihydroxyethyl)-5-(4,4,5,5-tetramethyl-1,3,2-dioxaborolan-2-yl)isoindolin-1-one (Mixture of Two Diastereomers)

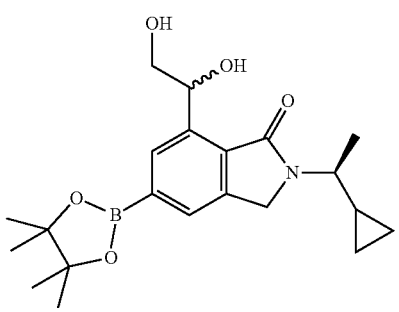 [SMILES: C[C@@H](C1CC1)N1Cc2cc(B3OC(C)(C)C(C)(C)O3)cc(C(O)CO)c2C1=O]

A degassed mixture of 5-chloro-2-((S)-1-cyclopropylethyl)-7-(1,2-dihydroxyethyl)isoindolin-1-one (0.31 g, 1.0 mmol, a mixture of two diastereomers from Step 3), bis(pinacolato)diboron (0.80 g, 3.1 mmol), potassium acetate (0.62 g, 6.3 mmol), Pd$_2$(dba)$_3$ (0.048 g, 0.052 mmol) and 2-dicyclohexylphosphino-2',4',6'-tri-iso-propyl-1,1'-biphenyl (0.10 g, 0.21 mmol) in dioxane (8.0 mL) was heated in a sealed vial to 120° C. for 45 min. Upon cooling to room temperature, the reaction mixture was diluted with EtOAc, filtered through Celite® and concentrated. The product was purified via flash column chromatography, eluting with a gradient of 0-100% EtOAc in hexanes to afford the title compound (0.23 g, 57%). LCMS for C$_{21}$H$_{31}$BNO$_5$ (M+H)$^+$: calculated m/z=388.2; found 388.2.

Step 5. 4-Bromo-2-(4,5-dimethyl-1-((2-(trimethylsilyl)ethoxy)methyl)-1H-imidazol-2-yl)pyridine

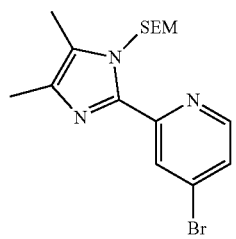 [SMILES: Cc1nc(-c2cc(Br)ccn2)n(COCC[Si](C)(C)C)c1C]

To a solution of 4-bromo-2-(4,5-dimethyl-1H-imidazol-2-yl)pyridine (0.60 g, 2.4 mmol, prepared as in Example 1, Step 1) in THF (26 mL) at 0° C. was added potassium tert-butoxide (1.0 M in THF, 3.3 mL, 3.3 mmol). After stirring for 30 min, 2-(trimethylsilyl)ethoxymethyl chloride, stabilized, tech. (0.59 mL, 3.3 mmol) was added, and the reaction was stirred for 30 min at 0° C. The reaction was quenched by the addition of NH$_4$Cl solution and was stirred for 30 min. The mixture was extracted with EtOAc, and the organic extract was washed with water, followed by brine. The organic solution was dried over Na$_2$SO$_4$, filtered and concentrated. Purification via flash column chromatography, eluting with a gradient from 0-20% EtOAc in hexanes, provided the title compound (0.63 g, 69%). LCMS for C$_{16}$H$_{25}$BrN$_3$OSi (M+H)$^+$: calculated monoisotopic m/z=382.1; found 382.0.

Step 6. 2-((S)-1-Cyclopropylethyl)-7-(1,2-dihydroxyethyl)-5-(2-(4,5-dimethyl-1-((2-(trimethylsilyl)ethoxy)methyl)-1H-imidazol-2-yl)pyridin-4-yl)isoindolin-1-one (Mixture of Two Diastereomers)

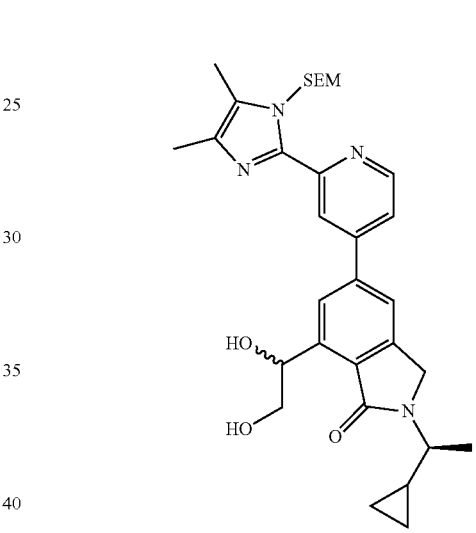

A degassed mixture of 2-((S)-1-cyclopropylethyl)-7-(1,2-dihydroxyethyl)-5-(4,4,5,5-tetramethyl-1,3,2-dioxaborolan-2-yl)isoindolin-1-one (31 mg, 0.080 mmol, a mixture of two diastereomers from Step 4), 4-bromo-2-(4,5-dimethyl-1-((2-(trimethylsilyl)ethoxy)methyl)-1H-imidazol-2-yl)pyridine (37 mg, 0.096 mmol, from Step 5) and dichloro[1,1'-bis(diphenylphosphino)ferrocene]palladium (II) dichloromethane adduct (13 mg, 0.016 mmol) in THF (1.0 mL) and aq. Na$_2$CO$_3$ (1.0 M, 0.24 mL, 0.24 mmol) was heated in a sealed vial at 95° C. for 1 h. Upon cooling to room temperature, the reaction mixture was diluted with water and extracted with EtOAc (3×). The combined organic extracts were dried over Na$_2$SO$_4$, filtered and concentrated. The product was purified via flash column chromatography, eluting with a gradient of 0-100% EtOAc in hexanes, followed by 5% MeOH in EtOAc to afford the title compound (29 mg, 64%). LCMS for C$_{31}$H$_{43}$N$_4$O$_4$Si (M+H)$^+$: calculated m/z=563.3; found 563.3.

Step 7. 2-((S)-1-Cyclopropylethyl)-7-(1,2-dihydroxyethyl)-5-(2-(4,5-dimethyl-1H-imidazol-2-yl)pyridin-4-yl)isoindolin-1-one (Mixture of Two Diastereomers)

A solution of 2-((S)-1-cyclopropylethyl)-7-(1,2-dihydroxyethyl)-5-(2-(4,5-dimethyl-1-((2-(trimethylsilyl)

ethoxy)methyl)-1H-imidazol-2-yl)pyridin-4-yl)isoindolin-1-one (29 mg, 0.052 mmol, from Step 6) in DCM (1.0 mL) and TFA (0.1 mL) was stirred overnight. Volatiles were removed in vacuo and the residue was dissolved MeOH (1.0 mL). Concentrated aq. NH$_4$OH (25 L) was added, and the mixture was stirred for 20 min and then evaporated. The residue was dissolved in a mixture of MeOH and MeCN and was purified via preparative HPLC-MS (pH=10) to afford the title compound (0.010 g, 45%). $^1$H NMR (400 MHz, DMSO-d$_6$, diastereomers) δ 12.41 (s, 1H), 8.65 (d, J=5.2 Hz, 1H), 8.28-8.20 (m, 1H), 7.96 (s, 1H), 7.94 (s, 1H), 7.63 (dd, J=5.2, 1.8 Hz, 1H), 5.77 (d, J=6.8 Hz, 1H), 5.54-5.45 (m, 1H), 4.73-4.67 (m, 1H), 4.65 (s, 2H), 3.66-3.57 (m, 2H), 3.56-3.49 (m, 1H), 2.19 (s, 3H), 2.12 (s, 3H), 1.32 (d, J=6.8 Hz, 1.5H), 1.31 (d, J=6.8 Hz, 1.5H), 1.22-1.10 (m, 1H), 0.64-0.55 (m, 1H), 0.50-0.35 (m, 2H), 0.31-0.21 (m, 1H). LCMS for C$_{25}$H$_{29}$N$_4$O$_3$ (M+H)$^+$: calculated m/z=433.2; found 433.3.

Example 19. 2-((S)-1-Cyclopropylethyl)-7-(1,2-dihydroxyethyl)-5-(6-(4,5-dimethyl-1H-imidazol-2-yl)pyridazin-4-yl)isoindolin-1-one, Trifluoroacetate Salt (Mixture of Two Diastereomers)

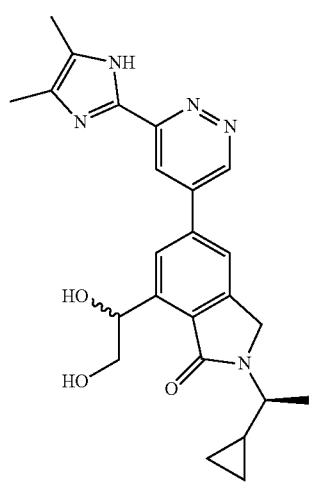 [SMILES: Cc1nc(-c2cc(-c3cc4c(c(C(O)CO)c3)C(=O)N([C@@H](C)C3CC3)C4)ccn2)n(COCC[Si](C)(C)C)c1C]

The procedure of Example 8, Steps 1 through 4 were followed, using 2-((S)-1-cyclopropylethyl)-7-(1,2-dihydroxyethyl)-5-(4,4,5,5-tetramethyl-1,3,2-dioxaborolan-2-yl)isoindolin-1-one (a mixture of two diastereomers from Example 18, Step 4) instead of (S)-2-(1-cyclopropylethyl)-7-(methylsulfonyl)-5-(4,4,5,5-tetramethyl-1,3,2-dioxaborolan-2-yl)isoindolin-1-one in Step 1. $^1$H NMR (400 MHz, DMSO-d$_6$, diastereomers) δ 9.78 (s, 1H), 8.64 (s, 1H), 8.11 (s, 2H), 5.63-5.57 (m, 1H), 4.68 (s, 2H), 3.67-3.49 (m, 3H), 2.33 (s, 6H), 1.34 (d, J=6.8 Hz, 1.5H), 1.33 (d, J=6.9 Hz, 1.5H), 1.26-1.14 (m, 1H), 0.65-0.55 (m, 1H), 0.48-0.36 (m, 2H), 0.31-0.22 (m, 1H). LCMS for C$_{24}$H$_{28}$N$_5$O$_3$ (M+H)$^+$: calculated m/z=434.2; found 434.2.

Example 20. 2-((S)-1-Cyclopropylethyl)-5-(2-(4,5-dimethyl-1H-imidazol-2-yl)pyridin-4-yl)-7-(S-methylsulfonimidoyl)isoindolin-1-one, Trifluoroacetate Salt (Mixture of Two Diastereomers)

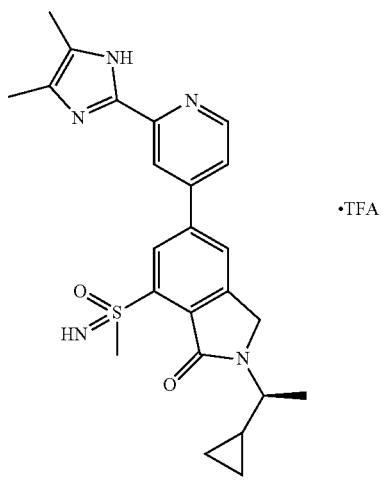 [SMILES: Cc1nc(-c2cc(-c3cc4c(c(S(C)(=N)=O)c3)C(=O)N([C@@H](C)C3CC3)C4)ccn2)[nH]c1C]

Step 1. (S)-2-(1-Cyclopropylethyl)-7-(methylthio)-5-(4,4,5,5-tetramethyl-1,3,2-dioxaborolan-2-yl)isoindolin-1-one

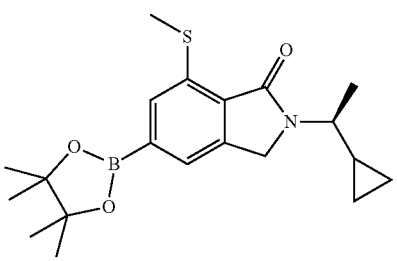 [SMILES: CSc1cc(B2OC(C)(C)C(C)(C)O2)cc2c1C(=O)N([C@@H](C)C1CC1)C2]

The procedure of Example 2, Step 3 was followed, using (S)-5-bromo-2-(1-cyclopropylethyl)-7-(methylthio)isoindolin-1-one (0.10 g, 0.31 mmol, from Example 2, Step 1) instead of (S)-5-bromo-2-(1-cyclopropylethyl)-7-(methylsulfonyl)isoindolin-1-one as starting material, to afford the title compound which was used without further purification (theoretical yield assumed). LCMS for C$_{20}$H$_{29}$BNO$_3$S (M+H)$^+$: calculated m/z=374.2; found 374.2.

Step 2. (S)-2-(1-Cyclopropylethyl)-5-(2-(4,5-dimethyl-1-((2-(trimethylsilyl)ethoxy)methyl)-1H-imidazol-2-yl)pyridin-4-yl)-7-(methylthio)isoindolin-1-one

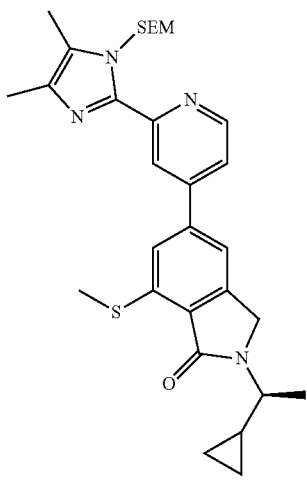 [SMILES: CSc1cc(-c2ccnc(-c3nc(C)c(C)n3COCC[Si](C)(C)C)c2)cc2c1C(=O)N([C@@H](C)C1CC1)C2]

The procedure of Example 18, Step 6 was followed, using (S)-2-(1-cyclopropylethyl)-7-(methylthio)-5-(4,4,5,5-tetramethyl-1,3,2-dioxaborolan-2-yl)isoindolin-1-one (110 mg, 0.31 mmol) instead of 2-((S)-1-cyclopropylethyl)-7-(1,2-dihydroxyethyl)-5-(4,4,5,5-tetramethyl-1,3,2-dioxaborolan-2-yl)isoindolin-1-one as starting material, to afford the title compound (0.080 g, 48%). LCMS for $C_{30}H_{41}N_4O_2SSi$ $(M+H)^+$: calculated m/z=549.3; found 549.2.

Step 3. (S)-2-(1-Cyclopropylethyl)-5-(2-(4,5-dimethyl-1H-imidazol-2-yl)pyridin-4-yl)-7-(methylthio)isoindolin-1-one

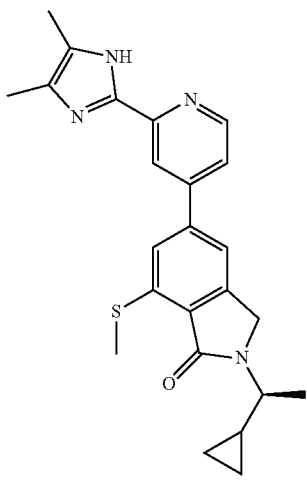 [SMILES: CSc1cc(-c2ccnc(-c3nc(C)c(C)[nH]3)c2)cc2c1C(=O)N([C@@H](C)C1CC1)C2]

A solution of (S)-2-(1-cyclopropylethyl)-5-(2-(4,5-dimethyl-1-((2-(trimethylsilyl)ethoxy)methyl)-1H-imidazol-2-yl)pyridin-4-yl)-7-(methylthio)isoindolin-1-one (0.040 g, 0.073 mmol) in TFA (3.3 mL) and DCM (1.2 mL) was stirred for 3 h. Volatiles were removed in vacuo. The residue was partitioned between EtOAc and saturated aq. NaHCO₃, and the layers were separated. The aqueous layer was extracted with two further portions of EtOAc. The combined organic extracts were dried over $Na_2SO_4$, filtered and concentrated and used without further purification (theoretical yield assumed). LCMS for $C_{24}H_{27}N_4OS$ $(M+H)^+$: calculated m/z=419.2; found 419.2.

Step 4. 2-((S)-1-Cyclopropylethyl)-5-(2-(4,5-dimethyl-1H-imidazol-2-yl)pyridin-4-yl)-7-(S-methylsulfonimidoyl)isoindolin-1-one, Trifluoroacetate Salt (Mixture of Two Diastereomers)

To (S)-2-(1-cyclopropylethyl)-5-(2-(4,5-dimethyl-1H-imidazol-2-yl)pyridin-4-yl)-7-(methylthio)isoindolin-1-one (0.030 g, 0.072 mmol) in MeOH (0.14 mL) was added aq. NH₄OH (28%, 10 µl, 0.14 mmol), followed by (diacetoxyiodo)benzene (0.046 g, 0.14 mmol). The reaction was stirred for 45 minutes, then was diluted with MeOH and purified via preparative HPLC-MS (pH=2) to afford the title compound (6.0 mg, 15%). ¹H NMR (400 MHz, DMSO-d₆, diastereomers) δ 8.96 (d, J=5.2 Hz, 1H), 8.55 (s, 1H), 8.43 (d, J=1.6 Hz, 1H), 8.37 (s, 1H), 8.07 (dd, J=5.1, 1.7 Hz, 1H), 4.78 (s, 2H), 3.70-3.62 (m, 1H), 3.56 (s, 3H), 2.33 (s, 6H), 1.36 (d, J=6.8 Hz, 1.5H), 1.36 (d, J=6.8 Hz, 1.5H), 1.28-1.14 (m, 1H), 0.68-0.55 (m, 1H), 0.55-0.38 (m, 2H), 0.37-0.19 (m, 1H). LCMS for $C_{24}H_{28}N_5O_2S$ $(M+H)^+$: calculated m/z=450.2; found 450.2.

Examples 21 and 22. 2-((S)-1-Cyclopropylethyl)-5-(2-(4,5-dimethyl-1H-imidazol-2-yl)pyridin-4-yl)-7-(S-methylsulfonimidoyl)isoindolin-1-one (Single Diastereomers Isolated)

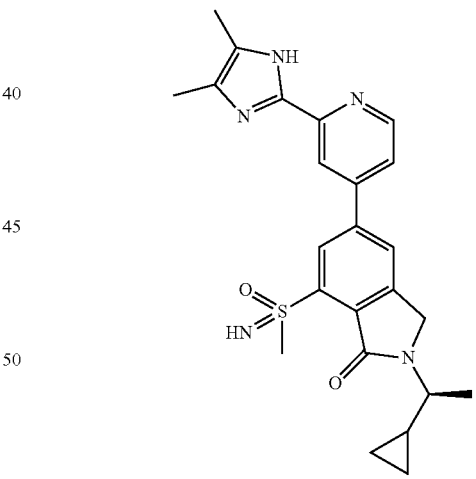

To (S)-2-(1-cyclopropylethyl)-5-(2-(4,5-dimethyl-1H-imidazol-2-yl)pyridin-4-yl)-7-(methylthio)isoindolin-1-one (0.22 g, 0.52 mmol, prepared as in Example 20, Step 3) in MeOH (1.7 mL) and DCM (0.90 mL) was added aq. NH₄OH (28%, 0.071 mL, 1.0 mmol), followed by (diacetoxyiodo)benzene (0.34 g, 1.0 mmol). After stirring for 2 hours, volatiles were removed in vacuo and the mixture was dissolved in DCM and purified via flash column chromatography, eluting with a gradient from 0-10% MeOH in DCM to obtain a mixture of diastereomers (37 mg, 16%). The diastereomers were separated via chiral HPLC (Phenomenex Lux Cellulose-1, 21.2×250 mm, 5 μm, loading: 2.5 mg in 250 μL EtOH and eluting with 45% EtOH in hexanes at 20 mL/min over 15 min).

Peak 1 (Example 21) (retention time 6.8 min): LCMS for $C_{24}H_{28}N_5O_2S$ (M+H)$^+$: calculated m/z=450.2; found 450.2.

Peak 2 (Example 22) (retention time 10.2 min): LCMS for $C_{24}H_{28}N_5O_2S$ (M+H)$^+$: calculated m/z=450.2; found 450.2.

Example 23. 2-((S)-1-Cyclopropylethyl)-5-(2-(4,5-dimethyl-1H-imidazol-2-yl)pyridin-4-yl)-7-(N,S-dimethylsulfonimidoyl)isoindolin-1-one (Mixture of Two Diastereomers)

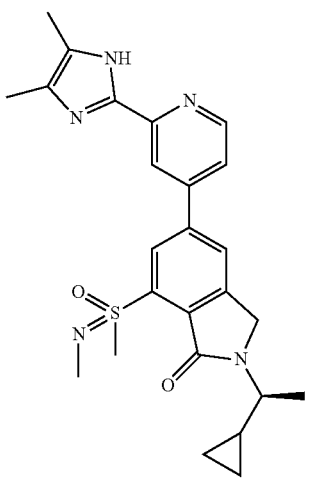 [SMILES: CN=S(C)(=O)c1cc(-c2ccnc(-c3nc(C)c(C)[nH]3)c2)cc2c1C(=O)N([C@@H](C)C1CC1)C2]

2-((S)-1-Cyclopropylethyl)-5-(2-(4,5-dimethyl-1H-imidazol-2-yl)pyridin-4-yl)-7-(S-methylsulfonimidoyl)isoindolin-1-one (0.076 g, 0.17 mmol, mixture of two diastereomers prepared as in Example 20) and paraformaldehyde (0.011 g, 0.37 mmol) were dissolved in formic acid (0.5 mL, 13 mmol) and the mixture was heated to reflux for 36 hours. The reaction was diluted with MeOH and purified via preparative HPLC-MS (pH=6.5) to afford the title compound (0.010 g, 13%). $^1$H NMR (500 MHz, DMSO-d$_6$, diastereomers) δ 8.69 (d, J=5.2 Hz, 1H), 8.38 (d, J=1.6 Hz, 1H), 8.31 (d, J=1.5 Hz, 1H), 8.26 (d, J=1.7 Hz, 1H), 7.68 (dd, J=5.2, 1.9 Hz, 1H), 4.73 (s, 2H), 3.69-3.64 (m, 1H), 3.63 (s, 1.5H), 3.62 (s, 1.5H), 2.16 (s, 6H), 1.88 (s, 3H), 1.33 (d, J=6.1 Hz, 1.5H), 1.32 (d, J=6.3 Hz, 1.5H) 1.23-1.11 (m, 1H), 0.68-0.56 (m, 1H), 0.50-0.38 (m, 2H), 0.33-0.24 (m, 1H). LCMS for $C_{25}H_{30}N_5O_2S$ (M+H)$^+$: calculated m/z=464.2; found 464.1.

Examples 24 and 25. 2-((S)-1-Cyclopropylethyl)-5-(2-(4,5-dimethyl-1H-imidazol-2-yl)pyridin-4-yl)-7-(N,S-dimethylsulfonimidoyl)isoindolin-1-one (Single Diastereomers Isolated)

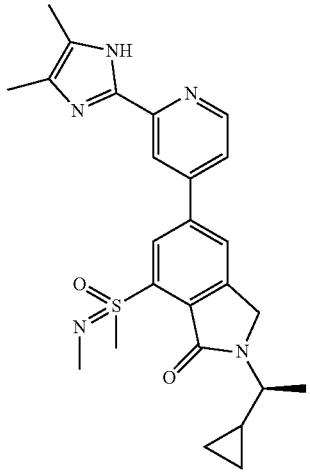 [SMILES: CN=S(C)(=O)c1cc(-c2ccnc(-c3nc(C)c(C)[nH]3)c2)cc2c1C(=O)N([C@@H](C)C1CC1)C2]

The diastereomers of Example 23 were separated via chiral HPLC (Phenomenex Lux Cellulose-1, 21.2×250 mm, 5 μm, loading 3.3 mg in 500 μL EtOH and eluting with 15% EtOH in hexanes at 20 mL/min over 25 min).

Peak 1 (Example 24) (retention time 16.8 min): LCMS for $C_{25}H_{30}N_5O_2S$ (M+H)$^+$: calculated m/z=464.2; found 464.2.

Peak 2 (Example 25) (retention time 19.7 min): LCMS for $C_{25}H_{30}N_5O_2S$ (M+H)$^+$: calculated m/z=464.2; found 464.1.

Example 26. (S)-2-(1-Cyclopropylethyl)-7-((dimethyl(oxo)-λ$^6$-sulfanylidene)amino)-5-(2-(5-methyl-1H-imidazol-2-yl)pyridin-4-yl)isoindolin-1-one (Single Enantiomer Prepared)

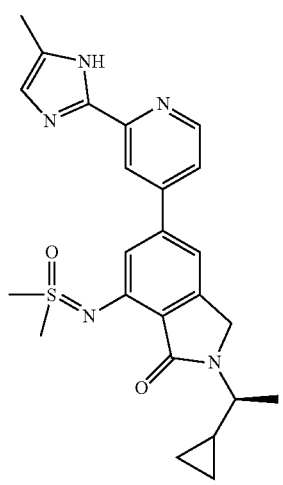 [SMILES: Cc1cnc(-c2cc(-c3cc4c(c(N=S(C)(C)=O)c3)C(=O)N([C@@H](C)C3CC3)C4)ccn2)[nH]1]

Step 1. (S)-5-Chloro-2-(1-cyclopropylethyl)-7-((dimethyl(oxo)-$\lambda^6$-sulfanylidene)amino)isoindolin-1-one

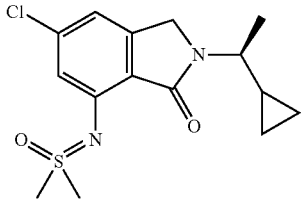 [SMILES: C[C@@H](C1CC1)N1Cc2cc(Cl)cc(N=S(C)(C)=O)c2C1=O]

A degassed mixture of (S)-5-chloro-2-(1-cyclopropylethyl)-7-iodoisoindolin-1-one (0.10 g, 0.28 mmol, from Example 18, Step 1), dimethylsulfoximine (0.026 g, 0.28 mmol, Astatech # F31251), Pd$_2$(dba)$_3$ (0.013 g, 0.014 mmol), 4,5-bis(diphenylphosphino)-9,9-dimethylxanthene (0.016 g, 0.028 mmol) and Cs$_2$CO$_3$ (0.14 g, 0.42 mmol) in dioxane (0.46 mL) was heated to reflux for 3 hours. The reaction mixture was cooled to room temperature and was partitioned between water and EtOAc. The aqueous layer was extracted with two further portions of EtOAc. The combined organic extracts were dried over Na$_2$SO$_4$, filtered and concentrated. The product was used without further purification (theoretical yield assumed). LCMS for C$_{15}$H$_{20}$ClN$_2$O$_2$S (M+H)$^+$: calculated monoisotopic m/z=327.1; found 327.1.

Step 2. (S)-2-(1-cyclopropylethyl)-7-((dimethyl(oxo)-$\lambda^6$-sulfanylidene)amino)-5-(4,4,5,5-tetramethyl-1,3,2-dioxaborolan-2-yl)isoindolin-1-one

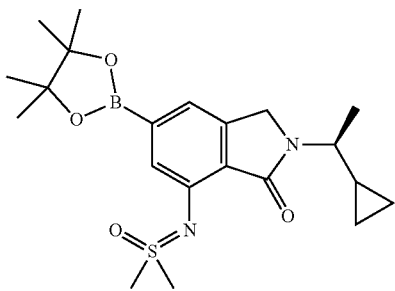 [SMILES: C[C@@H](C1CC1)N1Cc2cc(B3OC(C)(C)C(C)(C)O3)cc(N=S(C)(C)=O)c2C1=O]

A degassed mixture of (S)-5-chloro-2-(1-cyclopropylethyl)-7-((dimethyl(oxo)-λ6-sulfanylidene)amino)isoindolin-1-one (0.090 g, 0.28 mmol), bis(pinacolato)diboron (210 mg, 0.83 mmol), KOAc (160 mg, 1.6 mmol), Pd$_2$(dba)$_3$ (13 mg, 0.014 mmol) and 2-dicyclohexylphosphino-2',4',6'-tri-iso-propyl-1,1'-biphenyl (26 mg, 0.055 mmol) in dioxane (2.7 mL) was heated in a sealed vial at 120° C. for 1.5 hours. The reaction mixture was filtered and solvent was removed in vacuo. The product was purified via flash column chromatography, eluting with a gradient from 0-10% MeOH in DCM to afford the title compound (96 mg, 83%). LCMS for C$_{21}$H$_{32}$BN$_2$O$_4$S (M+H)$^+$: calculated m/z=419.2; found 419.2.

Step 3. (S)-2-(1-Cyclopropylethyl)-7-((dimethyl(oxo)-λ6-sulfanylidene)amino)-5-(2-(5-methyl-1H-imidazol-2-yl)pyridin-4-yl)isoindolin-1-one (Single Enantiomer Prepared)

A degassed mixture of (S)-2-(1-cyclopropylethyl)-7-((dimethyl(oxo)-λ6-sulfanylidene)amino)-5-(4,4,5,5-tetramethyl-1,3,2-dioxaborolan-2-yl)isoindolin-1-one (0.030 g, 0.072 mmol), 4-bromo-2-(4-methyl-1-((2-(trimethylsilyl)ethoxy)methyl)-1H-imidazol-2-yl)pyridine (0.026 g, 0.072 mmol, from Example 3, Step 4) and dichloro[1,1'-bis(diphenylphosphino)ferrocene]palladium (II) dichloromethane adduct (0.080 g, 0.098 mmol), in dioxane (2.0 mL) and aq. Na$_2$CO$_3$ (1.0 M, 0.42 mL, 0.42 mmol) was heated in the microwave at 140° C. for 30 min. Upon cooling to room temperature, the reaction mixture was diluted with water, brine, EtOAc and was filtered. The layers were separated and the aqueous layer was extracted with EtOAc (2×). The combined organic extracts were dried over Na$_2$SO$_4$, filtered and concentrated. The product was purified via flash column chromatography, eluting with a gradient from 0-100% EtOAc in hexanes, followed by 0-10% MeOH in DCM, to afford the SEM protected intermediate. The protected intermediate was deprotected by stirring with TFA in DCM (1:1, 4.0 mL) for 1 hour. Volatiles were removed in vacuo and the residue was reconstituted in MeOH and purified via preparative HPLC-MS (pH=6.5) to afford the title compound as the free base. LCMS for C$_{24}$H$_{28}$N$_5$O$_2$S (M+H)$^+$: calculated m/z=450.2; found 450.1.

Example A. THP-1 RPS6 ELISA Assay

To measure the Phosphorylated Ribosomal Protein S6 (RPS6) in cell lysates, THP-1 cells (Human Acute Monocytic Leukemia) are purchased from ATCC (Manassas, Va.) and maintained in RPMI with 10% FBS (Gibco/Life Technologies, Carlsbad, Calif.). For the assay, THP-1 cells are serum starved overnight in RPMI, then plated in RPMI (2×10$^5$ cells/well in 90 µL) into 96-well flat-bottom tissue culture treated plates (Corning, Corning, N.Y.), in the presence or absence of a concentration range of test compounds. Covered plates are incubated for 2 hours at 37° C., 5% CO$_2$ then treated with or without 10 nM MCP-1 (MYBioSource, San Diego, Calif.) for 15 minutes at 37° C., 5% CO$_2$. Plates are centrifuged at 1600 RPM and supernatants are removed. Cells are lysed in Lysis Buffer (Cell Signaling, Danvers, Mass.) with Protease Inhibitor (Calbiochem/EMD, Germany), PMSF (Sigma, St Louis Mo.), HALTS (Thermo Fisher, Rockford, Ill.) for 30 min on wet ice. Cell lysates are frozen at −80° C. before testing. The lysates are tested in the Human/Mouse/Rat Phospho-RPS6 ELISA (R&D Systems, Inc. Minn, Minn.). The plate is measured using a microplate reader (SpectraMax M5—Molecular Devices, LLC Sunnyvale, Calif.) set to 450 nm with a wavelength correction of 540. IC$_{50}$ determination is performed by fitting the curve of inhibitor percent inhibition versus the log of the inhibitor concentration using the GraphPad Prism 5.0 software.

Example B. PI3K-γ Scintillation Proximity Assay

Materials: [γ-$^{33}$P]ATP (10 mCi/mL) and Wheat Germ Agglutinin (WGA) YSi SPA Scintillation Beads was purchased from Perkin Elmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, Utah). PI3Kγ (p110γ) Recombinant Human Protein was purchased from Life technology (Grand Island, N.Y.). ATP, MgCl$_2$, DTT, EDTA, MOPS and CHAPS were purchased from Sigma Aldrich (St. Louis, Mo.).

The kinase reaction was conducted in polystyrene 384-well Greiner Bio-one white plate from Thermo Fisher Scientific in a final volume of 25 µL. Inhibitors were first diluted serially in DMSO and added to the plate wells before the addition of other reaction components. The final concentration of DMSO in the assay was 2%. The PI3Kγ assay was carried out at room temperature in 20 mM MOPS, pH 6.7, 10 mM $MgCl_2$, 5 mM DTT and CHAPS 0.03%. Reactions were initiated by the addition of ATP, the final reaction mixture consisted of 20 μM PIP2, 2 μM ATP, 0.5 μCi [γ-$^{33}$P] ATP, 13 nM PI3Kγ. Reactions were incubated for 120 min and terminated by the addition of 40 μL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (Perkin-Elmer). $IC_{50}$ determination was performed by fitting the curve of percent of the solvent control activity versus the log of the inhibitor concentration using the GraphPad Prism 6.0 software.

Example C. PI3Kδ Scintillation Proximity Assay

Materials: [γ-$^{33}$P]ATP (10 mCi/mL) and Wheat Germ Agglutinin (WGA) YSi SPA Scintillation Beads was purchased from Perkin Elmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, Utah). PI3Kδ (p110δ/p85α) Recombinant Human Protein was purchased from Eurofins (St Charles, Mo.). ATP, $MgCl_2$, DTT, EDTA, MOPS and CHAPS were purchased from Sigma Aldrich (St. Louis, Mo.).

The kinase reaction was conducted in polystyrene 384-well Greiner Bio-one white plate from Thermo Fisher Scientific in a final volume of 25 μL. Inhibitors were first diluted serially in DMSO and added to the plate wells before the addition of other reaction components. The final concentration of DMSO in the assay was 2%. The PI3Kδ assay was carried out at room temperature in 20 mM MOPS, pH 6.7, 10 mM $MgCl_2$, 5 mM DTT and CHAPS 0.03%. Reactions were initiated by the addition of ATP, the final reaction mixture consisted of 20 μM PIP2, 2 μM ATP, 0.5 μCi [γ-$^{33}$P] ATP, 3.4 nM PI3Kδ. Reactions were incubated for 120 min and terminated by the addition of 40 μL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (PerkinElmer). $IC_{50}$ determination was performed by fitting the curve of percent of the solvent control activity versus the log of the inhibitor concentration using the GraphPad Prism 6.0 software.

The compounds of the Examples were tested in the assays described in Examples A, B and C and found to have the $IC_{50}$ are shown in Table A.

TABLE A

| Ex. No. | PI3Kγ $IC_{50}$ (nM) | PI3Kδ $IC_{50}$ (nM) | PI3Kγ_THP1_RPS6_ELISA $IC_{50}$ (nM) |
| --- | --- | --- | --- |
| 1 | + | ++ | ### |
| 2 | + | ++ | ### |
| 3 | + | +++ | #### |

TABLE A-continued

| Ex. No. | PI3Kγ $IC_{50}$ (nM) | PI3Kδ $IC_{50}$ (nM) | PI3Kγ_THP1_RPS6_ELISA $IC_{50}$ (nM) |
| --- | --- | --- | --- |
| 4 | + | +++ | #### |
| 5 | + | ++++ | #### |
| 6 | + | ++++ | #### |
| 7 | + | +++ | ## |
| 7a | + | ++ | # |
| 7b | + | ++ | ### |
| 7c | + | ++ | #### |
| 7d | + | ++ | ## |
| 7e | + | ++ | #### |
| 7f | + | ++ | #### |
| 7g | + | ++ | #### |
| 7h | + | + | ## |
| 7i | + | + | ## |
| 7j | + | ++ | ## |
| 7k | + | ++ | ## |
| 7l | + | ++ | ## |
| 7m | + | +++ | ### |
| 7n | + | ++ | ## |
| 7o | + | ++ | ## |
| 7p | + | +++ | ## |
| 7q | + | +++ | #### |
| 7r | + | +++ | ## |
| 7s | + | +++ | ### |
| 7t | + | +++ | ## |
| 7u | + | +++ | ## |
| 8 | + | ++++ | NA |
| 9 | ++ | ++++ | #### |
| 10 | ++ | ++++ | #### |
| 11 | +++ | ++++ | NA |
| 12 | + | ++++ | #### |
| 13 | + | ++++ | NA |
| 14 | + | ++++ | #### |
| 15 | + | ++++ | #### |
| 16 | + | +++ | # |
| 17 | + | ++++ | ### |
| 18 | + | ++++ | ## |
| 19 | + | ++++ | NA |
| 20 | + | ++++ | ## |
| 21 | + | ++++ | ### |
| 22 | + | +++ | ### |
| 23 | + | +++ | ## |
| 24 | + | +++ | ## |
| 25 | + | +++ | ### |
| 26 | + | ++++ | #### |

+ refers to $IC_{50}$ of ≤100 nM; ++ refers to $IC_{50}$ of ≤500 nM; +++ refers to an $IC_{50}$ of <2000 nM; ++++ refers to an $IC_{50}$ of ≥2000 nM.
# refers to $IC_{50}$ of ≤100 nM; ## refers to $IC_{50}$ of ≤500 nM; ### refers to $IC_{50}$ of <1000 nM; #### refers to an $IC_{50}$ of ≥1000 nM.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula (IIu):

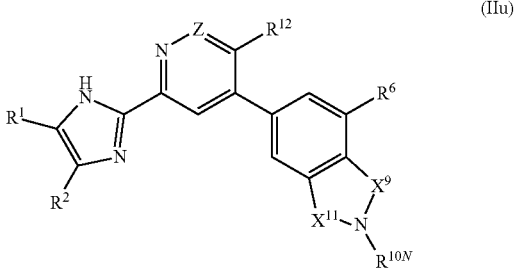

or a pharmaceutically acceptable salt thereof; wherein:

Z is $CZ^{10}$ r N;

$Z^1$ and $R^{12}$ are each independently selected from H, D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-6}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, —$OR^{a1}$, —$SR^{a1}$, —$NHOR^{a1}$, —$C(O)R^{b1}$—$C(O)NR^{c1}R^{d1}$, —$C(O)NR^{c1}(OR^{a1})$, —$C(O)OR^{a1}$—$OC(O)R^{b1}$, —$OC(O)NR^{c1}R^{d1}$, —$NR^{c1}R^{d1}$, —$NR^{c1}NR^{c1}R^{d1}$, —$NR^{c1}C(O)R^{b1}$, —$NR^{c1}C(O)OR^{a1}$, and —$NR^{c1}C(O)NR^{c1}R^{d1}$ wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^{14}$ substituents;

each $R^{a1}R^{b1}$, $R^{c1}$ and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}R^{b1}$, $R^{c1}$ and $R^{d1}$ are each optionally substituted with 1, 2, 3, 4, 5, 6, 7, or 8 independently selected $R^{14}$ substituents;

or, any $R^{c1}$ and $R^{d1}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{14}$ substituents;

each $R^{14}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, —$OR^{a11}$, —$SR^{a11}$, —$NHOR^{a11}$, —$C(O)R^{b11}$, —$C(O)NR^{a11}R^{d11}$, —$C(O)NR^{c11}(OR^{a11})$, —$C(O)OR^{a11}$, —$OC(O)R^{b11}$, —$OC(O)NR^{c11}R^{d11}$, —$NR^{c11}R^{d11}$, —$NR^{c11}NR^{c11}R^{d11}$, —$NR^{c11}C(O)R^{b11}$, —$NR^{c11}C(O)OR^{a11}$, and —$NR^{c11}C(O)NR^{c11}R^{d11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{14}$ are each optionally substituted with 1, 2, 3, 4, 5, 6, 7, or 8 independently selected $R^M$ substituents;

each $R^{a11}$, $R^{b11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{b11}$, $R^{c11}$ and $R^{d11}$ are each optionally substituted with 1, 2, 3, 4, 5, 6, 7, or 8 independently selected $R^M$ substituents;

or, any $R^{c11}$ and $R^{d11}$ attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^M$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-6}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, —$OR^{a2}$, —$SR^{a2}$, —$NHOR^{a2}$, —$C(O)R^{b2}$, —$C(O)NR^{c2}R^{d2}$, —$C(O)NR^{c2}(OR^{a2})$, —$C(O)OR^{a2}$, —$OC(O)R^{b2}$, $OC(O)NR^{c2}R^{d2}$, —$NR^{c2}R^{d2}$, —$NR^{c2}NR^{c2}R^{d2}$, —$NR^{c2}C(O)R^{b2}$, —$NR^{c2}C(O)OR^{a2}$, and —$NR^{c2}C(O)NR^{c2}R^{d2}$, wherein the $C_{1-6}$ alkyl $C_{2-6}$ alkenyl $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, 6, 7, or 8 independently selected $R^{2A}$ substituents;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{b2}$, $R^{c2}$ and $R^{d2}$ are each optionally substituted with 1, 2, 3, 4, 5, 6, 7, or 8 independently selected $R^{2A}$ substituents;

or, any $R^{c2}$ and $R^{d2}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{2A}$ substituents;

each $R^{2A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-11}$) cycloalkyl, 5-10 membered heteroaryl, 4-10 membered heterocycloalkyl, $C_{6-11}$) aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, —$OR^{a21}$, —$SR^{a21}$, —$NHOR^{a21}$, —C(O)$R^{b21}$, —C(O)$NR^{c21}R^{d21}$, —C(O)$NR^{c21}(OR^{a21})$, —C(O)$OR^{a21}$, —OC(O)$R^{b21}$, —OC(O)$NR^{c21}R^{d21}$, —$NR^{c21}R^{d21}$, —$NR^{c21}NR^{c21}R^{d21}$, —$NR^{c21}$C(O)$R^{b21}$, —$NR^{c21}$C(O)$OR^{a21}$, and —$NR^{c21}$C(O)$NR^{c2l}R^{d21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-11}$) cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, 4, 5, 6, 7, or 8 independently selected $R^M$ substituents;

each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$, and $R^{d21}$ are each optionally substituted with 1, 2, 3, 4, 5, 6, 7, or 8 independently selected $R^M$ substituents;

or, any $R^{c21}$ and $R^{d21}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

or alternatively, $R^1$ and $R^2$, taken together with the carbon atoms to which they are attached form a monocyclic 4-7 membered cycloalkyl ring, a phenyl ring, a monocyclic 4-7 membered heterocycloalkyl ring, or a monocyclic 5-6 membered heteroaryl ring, each of which is optionally substituted by 1, 2, 3, 4, 5, 6, 7 or 8 independently selected $R^{14}$ groups;

$R^6$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, —$OR^{a6}$, —$SR^{a6}$, —$NHOR^{a6}$, —C(O)$R^{b6}$, —C(O)$NR^{c6}R^{d6}$, —C(O)$NR^{c6}(OR^{a6})$, —C(O)$OR^{a6}$, —OC(O)$R^{b6}$, —OC(O)$NR^{c6}R^{d6}$, —$NR^{c6}R^{d6}$, —$NR^{c6}NR^{c6}R^{d6}$, —$NR^{c6}$C(O)$R^{b6}$, —$NR^{c6}$C(O)$OR^{a6}$, —$NR^{c6}$C(O)$NR^{c6}R^{d6}$, —C(=$NR^{e6}$)$R^{b6}$, —C(=NOH)$R^{b6}$, —C(=NCN)$R^{b6}$, —C(=$NR^{e6}$)$NR^{c6}R^{a6}$, —$NR^{c6}$C(=$NR^{e6}$)$NR^{c6}R^{a6}$, —$NR^{c6}$C(=NOH)$NR^{c6}R^{d6}$, —$NR^{c6}$C(=NCN)$NR^{c6}R^{d6}$, —$NR^{c6}$C(=$NR^{e6}$)$R^{b6}$, —$NR^{c6}$S(O)$NR^{c6}R^{d6}$, —$NR^{c6}$S(O)$R^{b6}$, —$NR^{c6}$S(O)$_2R^{b6}$, —$NR^{c6}$S(O)(=$NR^{e6}$)$R^{b6}$, —$NR^{c6}$S(O)$_2NR^{c6}R^{a6}$, —S(O)$R^{b6}$, —S(O)$NR^{c6}R^{d6}$, —S(O)$_2R^{b6}$, —S(O)$_2NR^{c6}R^{d6}$, —S(O)(=$NR^{e6}$)$R^{b6}$, —N=S(O)$R^{a6}R^{b6}$, —OS(O)(=$NR^{e6}$)$R^{b6}$, —OS(O)$_2R^{b6}$, and —$SF_5$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, 4, 5, 6, 7, or 8 independently selected $R^{6A}$ substituents;

each $R^{a6}$, $R^{b6}$, $R^{c6}$, $R^{d6}$ and $R^{e6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$, $R^{d6}$ and $R^{e6}$ are each optionally substituted with 1, 2, 3, 4, 5, 6, 7, or 8 independently selected $R^{6A}$ substituents;

or, any $R^{c6}$ and $R^{d6}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{6A}$ substituents;

each $R^{6A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, —$OR^{a61}$, —$SR^{a61}$, —$NHOR^{a61}$, —C(O)$R^{b61}$, —C(O)$NR^{c61}R^{a61}$, —C(O)$NR^{c61}(OR^{a61})$—C(O)$OR^{a61}$, —OC(O)$R^{b61}$, —OC(O)$NR^{c61}R^{d61}$, —$NR^{c61}R^{d61}$, —$NR^{c61}NR^{c61}R^{d61}$, —$NR^{c61}$C(O)$R^{b61}$, —$NR^{C61}$C(O)$OR^{a61}$ and —$NR^{c61}$C(O)$NR^{C61}R^{d61}$ wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{64}$ are each optionally substituted with 1, 2, 3, 4, 5, 6, 7, or 8 independently selected $R^M$ substituents;

each $R^{a61}$, $R^{b61}$, $R^{c61}$ and $R^{d61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5a-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a61}$, $R^{b61}$, $R^{c61}$ and $R^{d61}$ are each optionally substituted with 1, 2, 3, 4, 5, 6, 7, or 8 independently selected $R^M$ substituents;

or, any $R^{c61}$ and $R^{d61}$ attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

$X^9$ is —$NR^{9N}$ or —$C(R^9)_2$;

$X^{11}$ is —$NR^{11N}$ or —$C(R^{11})_2$;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, —C(O)$R^{b9N}$—C(O)$NR^{e9N}R^{d9N}$, —C(O)$OR^{a9N}$—C(=$NR^{e9N}$)$R^{b9N}$, —C(=$NR^{e9N}$)$NR^{c9N}R^{d9N}$, —C(=NCN)$NR^{c9N}R^{d9N}$, —C(=$NOR^{a9N}$)$NR^{c9N}$, —S(O)$_2R^{b9N}$, —S(O)(=$NR^{e9N}$)$R^{d9N}$, and —S(O)$_2NR^{c9N}R^{d9N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{9N}$ are each optionally substituted with 1, 2, 3, 4, 5, 6, 7, or 8 independently selected $R^{9NA}$ substituents;

each $R^{a9N}$, $R^{b9N}$, $R^{c9N}$, and $R^{d9N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9N}$, $R^{b9N}$, $R^{c9N}$, and $R^{d9N}$ are each optionally substituted with 1, 2, 3, 4, 5, 6, 7, or 8 independently selected $R^{9NA}$ substituents;

or, any $R^{c9N}$ and $R^{d9N}$ attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9NA}$ substituents;

each $R^{e9N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{9NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, —$OR^{a9N2}$, —$SR^{a9N2}$, —$NHOR^{a9N2}$, —C(O)$R^{b9N2}$, —C(O)$NR^{c9N2}R^{d9N2}$, —C(O)$NR^{c9N2}(OR^{a9N2})$, —C(O)$OR^{a9N2}$, —OC(O)$R^{b9N2}$, —OC(O)$NR^{c9N2}R^{d9N2}$, —$NR^{c9N2}R^{d9N2}$, —$NR^{c9N2}NR^{c9N2}R^{d9N2}$, —$NR^{c9N2}C(O)R^{b9N2}$, —$NR^{c9N2}C(O)OR^{a9N2}$, and —$NR^{c9N2}C(O)NR^{c9N2}R^{d9N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9NA}$ are each optionally substituted with 1, 2, 3, or 4 independently selected $R^M$ substituents;

each $R^{a9N2}$, $R^{b9N2}$, $R^{c9N2}$, and $R^{d9N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a9N2}$, $R^{b9N2}$, $R^{c9N2}$ and $R^{d9N2}$ are each optionally substituted with 1, 2, 3, or 4 independently selected $R^M$ substituents;

or, any $R^{c9N2}$ and $R^{d9N2}$ attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^9$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, —$OR^{a91}$, —$SR^{a91}$, —$NHOR^{a91}$, —C(O)$R^{b91}$, —C(O)$NR^{c91}$, $R^{d91}$, —C(O)$NR^{c91}(OR^{a91})$, —C(O)$OR^{a91}$, —OC(O)$R^{b91}$, —OC(O)$NR^{c91}R^{d91}$, —$NR^{c91}R^{d91}$, —$NR^{c91}NR^{c91}R^{d91}$, —$NR^{c91}C(O)R^{b91}$, —$NR^{c91}C(O)OR^{a91}$, and —$NR^{c91}C(O)NR^{c91}R^{d91}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^9$ are each optionally substituted with 1, 2, 3, 4, 5, 6, 7, or 8 independently selected $R^{9A}$ substituents;

or, alternatively, two $R^9$ groups together form an oxo group;

each $R^{a91}$, $R^{b91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a91}$, $R^{b91}$, $R^{c91}$, and $R^{d91}$ are each optionally substituted with 1, 2, 3, 4, 5, 6, 7, or 8 independently selected $R^{9A}$ substituents;

or, any $R^{c91}$ and $R^{d91}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9A}$ substituents;

each $R^{9A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $-OR^{a92}$, $-SR^{a92}$, $-NHOR^{a92}$, $-C(O)R^{b92}$, $-C(O)NR^{c92}R^{d92}$, $-C(O)NR^{c92}(OR^{a92})$, $-C(O)OR^{a92}$, $-OC(O)R^{b92}$, $-OC(O)NR^{c92}R^{d92}$, $-NR^{c92}R^{d92}$, $-NR^{c92}NR^{c92}R^{d92}$, $-NR^{c92}C(O)R^{b92}$, $-NR^{c92}C(O)OR^{a92}$, and $-NR^{c92}C(O)NR^{c92}R^{d92}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9A}$ are each optionally substituted with 1, 2, 3, or 4 independently selected $R^M$ substituents;

each $R^{a92}$, $R^{b92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a92}$, $R^{b92}$, $R^{c92}$ and $R^{d92}$ are each optionally substituted with 1, 2, 3, or 4 independently selected $R^M$ substituents;

or, any $R^{c92}$ and $R^{d92}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $-C(O)R^{b10N}$, $-C(O)NR^{c10N}R^{d10N}$, $-C(O)O$ $R^{a10N}$, $-C(=NR^{e10N})R^{b10N}$, $-C(=NR^{e10N})NR^{c10N}R^{d10N}$, $-C(=NCN)NR^{c10N}R^{d10N}$, $-C(=NOR^{a10N})NR^{c10N}$, $-S(O)_2R^{b10N}$, $-S(O)(=NR^{c10N})R^{d10N}$, and $-S(O)_2NR^{e10N}R^{d10N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, 4, 5, 6, 7, or 8 independently selected $R^{10NA}$ substituents;

each $R^{a10N}$, $R^{b10N}$, $R^{c10N}$, and $R^{d10N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a10N}$, $R^{b10N}$, $R^{c10N}$, and $R^{d10N}$ are each optionally substituted with 1, 2, 3, 4, 5, 6, 7, or 8 independently selected $R^{10NA}$ substituents;

or, any $R^{c10N}$ and $R^{d10N}$ attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{10NA}$ substituents;

each $R^{e10N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{10NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $-OR^{a10N2}$, $-SR^{a10N2}$, $-OR^{a10N2}$, $-C(O)R^{b10N2}$, $-C(O)NR^{c10N2}R^{d10N2}$, $-O(O)NR^{c10N2}(OR^{a10N2})$, $-C(O)OR^{a10N2}$, $-OC(O)R^{b10N2}$, $-OC(O)NR^{c10N2}R^{d10N2}$, $-NR^{c10N2}R^{d10N2}$, $-NR^{c10N2}NR^{c10N2}R^{d10N2}$, $-NR^{c10N2}C(O)R^{b10N2}$, $-NR^{c10N2}C(O)OR^{a10N2}$, and $-NR^{c10N2}C(O)NR^{c10N2}R^{d10N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{10NA}$ are each optionally substituted with 1, 2, 3, or 4 independently selected $R^M$ substituents;

each $R^{a10N2}$, $R^{b10N2}$, $R^{c10N2}$, and $R^{d10N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl,

185

$C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a10N2}$, $R^{b10N2}$, $R^{c10N2}$ and $R^{d10N2}$ are each optionally substituted with 1, 2, 3, or 4 independently selected $R^M$ substituents;

or, any $R^{c10N2}$ and $R^{d10N2}$ attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$R^{11N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, —C(O)$R^{b11N}$, —C(O)NR$^{c11N}$R$^{d11N}$, —C(O)OR$^{a11N}$, —C(=NR$^{e11N}$)R$^{b11N}$, —C(=NR$^{e11N}$)NR$^{c11N}$R$^{d11N}$, —C(=NCN)NR$^{c11N}$R$^{d11N}$, —C(=NOR$^{a11N}$)NR$^{c11N}$, —S(O)$_2$R$^{b11N}$, —S(O)(=NR$^{e11N}$)R$^{d11N}$, and —S(O)$_2$NR$^{c11N}$R$^{d11N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{11N}$ are each optionally substituted with 1, 2, 3, 4, 5, 6, 7, or 8 independently selected $R^{11NA}$ substituents;

each $R^{a11N}$, $R^{b11N}$, $R^{c11N}$, and $R^{d11N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11N}$, $R^{b11N}$, $R^{c11N}$, and $R^{d11N}$ are each optionally substituted with 1, 2, 3, 4, 5, 6, 7, or 8 independently selected $R^{11NA}$ substituents;

or, any $R^{c11N}$ and $R^{d11N}$ attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{11NA}$ substituents;

each $R^{e11N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{11NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, NO$_2$, —OR$^{a11N2}$, —SR$^{a11N2}$, —NHOR$^{a11N2}$, —C(O)R$^{b11N2}$, —C(O)NR$^{c11N2}$R$^{d11N2}$, —C(O)NR$^{c11N2}$(OR$^{a11N2}$), —C(O)OR$^{a11N2}$, —OC(O)R$^{b11N2}$, —OC(O)

186

NR$^{c11N2}$R$^{d11N2}$, —NR$^{c11N2}$R$^{d11N2}$, —NR$^{c11N2}$NR$^{c11N2}$R$^{d11N2}$, —NR$^{c11N2}$C(O)R$^{b11N2}$, —NR$^{c11N2}$C(O)OR$^{a11N2}$, and —NR$^{c11N2}$C(O) NR$^{c11N2}$R$^{d11N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{11NA}$ are each optionally substituted with 1, 2, 3, or 4 independently selected $R^M$ substituents;

each $R^{a11N2}$, $R^{b11N2}$, $R^{c11N2}$, and $R^{d11N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a11N2}$, $R^{b11N2}$, $R^{c11N2}$ and $R^{d11N2}$ are each optionally substituted with 1, 2, 3, or 4 independently selected $R^M$ substituents;

or, any $R^{c11N2}$ and $R^{d11N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{11}$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, —OR$^{a111}$, —SR$^{a111}$, —NHOR$^{a111}$, —C(O)R$^{b111}$, —C(O)NR$^{c111}$R$^{d111}$, —C(O)NR$^{c111}$(OR$^{a111}$), —C(O)OR$^{a111}$—OC(O) R$^{b111}$, OC(O)NR$^{c111}$R$^{d111}$, —NR$^{c111}$R$^{d111}$, —NR$^{c111}$NR$^{c111}$R$^{d111}$, —NR$^{c111}$C(O)R$^{b111}$, —NR$^{c111}$C(O)OR$^{a111}$, and —NR$^{c111}$C(O) NR$^{c111}$R$^{d111}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{11}$ are each optionally substituted with 1, 2, 3, 4, 5, 6, 7, or 8 independently selected $R^{11A}$ substituents;

or, alternatively, two $R^{11}$ groups together form an oxo group;

each $R^{a111}$, $R^{b111}$, $R^{c111}$, and $R^{d111}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a111}$, $R^{b111}$, $R^{c111}$, and $R^{d111}$ are each optionally substituted with 1, 2, 3, 4, 5, 6, 7, or 8 independently selected $R^{11A}$ substituents;

or, any $R^{c111}$ and $R^{d111}$ attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{11A}$ substituents; and each $R^{11A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, —$OR^{a112}$, —$SR^{a112}$, —$NHOR^{a112}$, —$C(O)R^{b112}$, —$C(O)NR^{c112}R^{d112}$, —$C(O)NR^{c112}(OR^{a112})$, —$C(O)OR^{a112}$, —$OC(O)R^{b112}$, —$OC(O)NR^{c112}R^{d112}$, —$NR^{c112}R^{d112}$, —$NR^{c112}NR^{c112}R^{d112}$, —$NR^{c112}C(O)R^{b112}$, —$NR^{c112}C(O)OR^{a112}$, and —$NR^{c112}C(O)NR^{c112}R^{d112}$, wherein the $C_{1-6}$ alkyl $C_{2-6}$ alkenyl, $C_{2-6}$ alkynyl phenyl $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{11A}$ are each optionally substituted with 1, 2, 3, or 4 independently selected $R^M$ substituents; and each $R^{a112}$, $R^{b112}$, $R^{c112}$, and $R^{d112}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a112}$, $R^{b112}$, $R^{c112}$ and $R^{d112}$ are each optionally substituted with 1, 2, 3, or 4 independently selected $R^M$ substituents;

or, any $R^{c112}$ and $R^{d112}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents.

2. The compound of claim 1, or a pharmaceutically acceptable salt thereof, wherein $R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, —$OR^{a1}$, —$SR^{a1}$, —$NHOR^{a1}$, —$C(O)R^{b1}$, —$C(O)NR^{c1}R^{d1}$, —$C(O)NR^{c1}(OR^{a1})$, —$C(O)OR^{a1}$, —$OC(O)R^{b1}$, —$OC(O)NR^{c1}R^{d1}$, —$NR^{c1}C(O)R^{b1}$, —$NR^{c1}C(O)OR^{a1}$, and —$NR^{c1}C(O)NR^{c1}R^{d1}$.

3. The compound of claim 1, or a pharmaceutically acceptable salt thereof, wherein $R^1$ is selected from H and $C_{1-6}$ alkyl.

4. The compound of claim 1, or a pharmaceutically acceptable salt thereof, wherein $R^1$ is methyl.

5. The compound of claim 1, or a pharmaceutically acceptable salt thereof, wherein $R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, —$OR^{a2}$, —$SR^{a2}$, —$NHOR^{a2}$, —$C(O)R^{b2}$, —$C(O)NR^{c2}R^{d2}$, —$C(O)NR^{c2}(OR^{a2})$, —$C(O)OR^{a2}$, —$OC(O)R^{b2}$, —$OC(O)NR^{c2}R^{d2}$, —$NR^{c2}C(O)R^{b2}$, —$NR^{c2}C(O)OR^{a2}$, and —$NR^{c2}C(O)NR^{c2}R^{d2}$.

6. The compound of claim 1, or a pharmaceutically acceptable salt thereof, wherein $R^2$ is selected from H, $C_{1-6}$ alkyl, —$C(O)R^{b2}$, —$C(O)NR^{c2}R^{d2}$, —$NR^{c2}C(O)R^{b2}$, $NR^{c2}C(O)OR^{a2}$, and —$NR^{c2}C(O)NR^{c2}R^{d2}$.

7. The compound of claim 1, or a pharmaceutically acceptable salt thereof, wherein $R^2$ is selected H, $C_{1-6}$ alkyl, —$C(O)R^{b2}$ and —$C(O)NR^{c2}R^{d2}$.

8. The compound of claim 1, or a pharmaceutically acceptable salt thereof, wherein each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a2}$, $R^{b2}$, $R^{c2}$ and $R^{d2}$ are each optionally substituted with 1 or 2 independently selected $R^{2A}$ substituents.

9. The compound of claim 1, or a pharmaceutically acceptable salt thereof, wherein each $R^{b2}$, $R^{c2}$ and $R^{d2}$ is independently selected from H, $C_{1-6}$ alkyl, $C_{3-7}$ cycloalkyl and 4-7 membered heterocycloalkyl, wherein the $C_{1-6}$ alkyl, $C_{3-7}$ cycloalkyl and 4-7 membered heterocycloalkyl of $R^{b2}$, $R^{c2}$ and $R^{d2}$ are each optionally substituted with 1 or 2 independently selected $R^{2A}$ substituents.

10. The compound of claim 1, or a pharmaceutically acceptable salt thereof, wherein $R^{b2}$ is selected from azetidin-1-yl, 3,3-difluoroazetidin-1-yl, 3-hydroxyazetidin-1-yl and 2-oxa-6-azaspiro[3.3]heptan-6-yl.

11. The compound of claim 1, or a pharmaceutically acceptable salt thereof, each Roe and $R^{d2}$ is independently selected from H, methyl, ethyl, isopropyl, tetrahydro-2H-pyran-4-yl, bicyclo[1.1.1]pentanyl, cyclobut-1-yl, 3-hydroxycyclobut-1-yl, 1,1,1-trifluoro propan-2-yl, 4-cyanobicyclo[2.1.1]hexan-1-yl, 2-oxaspiro[3.3]heptan-6-yl, sec-butyl, 1-methyl azetidin-3-yl, and tetrahydrofuran-3-yl;

or $R^{c2}$ and $R^{d2}$, attached to the same N atom, together with the N atom to which they are attached, form an azetidin-1-yl, 3,3-difluoroazetidin-1-yl, 3-hydroxyazetidin-1-yl or 2-oxa-6-azaspiro[3.3]heptan-6-yl group.

12. The compound of claim 1, or a pharmaceutically acceptable salt thereof, wherein $R^2$ is selected from H, methyl, methylaminocarbonyl, dimethylaminocarbonyl, tetrahydropyranylaminocarbonyl, isopropylaminocarbonyl, bicyclo[1.1.1]pentan-1-ylcarbamoyl, 3,3-difluoroazetidine-1-carbonyl, 3-hydroxyazetidine-1-carbonyl, (3-hydroxycyclobutyl)carbamoyl, (1,1,1-trifluoropropan-2-yl)carbamoyl, (4-cyanobicyclo[2.1.1]hexan-1-yl)carbamoyl, (2-oxaspiro[3.3]heptan-6-yl)carbamoyl, azetidine-1-carbonyl, cyclobutylcarbamoyl, sec-butylcarbamoyl, (1-methylazetidin-3-yl)carbamoyl, (tetrahydrofuran-3-yl)carbamoyl, methyl (tetrahydro-2H-pyran-4-yl)carbamoyl, 2-oxa-6-azaspiro[3.3]heptane-6-carbonyl, aminocarbonyl, ethylaminocarbonyl, ethylmethylaminocarbonyl, isopropylmethylaminocarbonyl, and cyclobutylmethylaminocarbonyl.

13. The compound of claim 1, or a pharmaceutically acceptable salt thereof, wherein Z is —CZ$^1$.

14. The compound of claim 1, or a pharmaceutically acceptable salt thereof, wherein Z$^1$ is selected from H, D, C$_{1-3}$ alkyl, C$_{1-3}$ haloalkyl, C$_{2-3}$ alkenyl, and C$_{2-3}$ alkynyl.

15. The compound of claim 1, or a pharmaceutically acceptable salt thereof, wherein Z$^1$ is H.

16. The compound of claim 1, or a pharmaceutically acceptable salt thereof, wherein Z is N.

17. The compound of claim 1, or a pharmaceutically acceptable salt thereof, wherein R$^{12}$ is H.

18. The compound of claim 1, or a pharmaceutically acceptable salt thereof, wherein R$^6$ is selected from H, D, halo, C$_{1-6}$ alkyl, C$_{1-6}$ haloalkyl, —SR$^{a6}$, —C(O)NR$^{c6}$R$^{d6}$, —C(O)R$^{b6}$, —S(O)$_2$R$^{b6}$, —S(O)(=NR$^{e6}$)R$^{b6}$, and —N=S(O)R$^{a6}$R$^{b6}$.

19. The compound of claim 1, or a pharmaceutically acceptable salt thereof, wherein each R$^{a6}$, R$^{b6}$, R$^{c6}$, R$^{d6}$ and R$^{e6}$ are independently selected from H and C$_{1-6}$ alkyl.

20. The compound of claim 1, or a pharmaceutically acceptable salt thereof, wherein R$^6$ is selected from H, halo, C$_{1-6}$ alkyl, —S(O)$_2$R$^{b6}$—S(O)(=NR$^{e6}$)R$^{b6}$, and —N=S(O)R$^{a6}$R$^{b6}$, wherein the C$_{1-6}$ alkyl is optionally substituted with 1, 2, 3, or 4 independently selected R$^{6A}$ substituents;
each R$^{a6}$, R$^{b6}$ and R$^{e6}$ are independently selected from H and C$_{1-6}$ alkyl; and
each R$^{6A}$ is OH.

21. The compound of claim 1, or a pharmaceutically acceptable salt thereof, wherein R$^6$ is selected from H, chloro, —S(O)$_2$CH$_3$, 1,2-dihydroxyethyl, —S(O)(=NH)CH$_3$, —S(O)(=NCH$_3$)CH$_3$, and —N=S(O)(CH$_3$)$_2$.

22. The compound of claim 1, or a pharmaceutically acceptable salt thereof, wherein X$^9$ is —C(R$^9$)$_2$.

23. The compound of claim 1, or a pharmaceutically acceptable salt thereof, wherein two R$^9$ groups together form an oxo group.

24. The compound of claim 1, or a pharmaceutically acceptable salt thereof, wherein R$^{10N}$ is selected from C$_{1-6}$ alkyl, C$_{3-6}$ cycloalkyl, and C$_{3-6}$ cycloalkyl-C$_{1-6}$ alkyl-, wherein the C$_{1-6}$ alkyl, C$_{3-6}$ cycloalkyl, and C$_{3-6}$ cycloalkyl-C$_{1-6}$ alkyl- of R$^{10N}$ are each optionally substituted with 1 or 2 independently selected R$^{10NA}$ substituents.

25. The compound of claim 1, or a pharmaceutically acceptable salt thereof, wherein R$^{10N}$ is C$_{3-6}$ cycloalkyl-C$_{1-6}$ alkyl-.

26. The compound of claim 1, or a pharmaceutically acceptable salt thereof, wherein R$^{10N}$ is cyclopropylethyl.

27. The compound of claim 1, or a pharmaceutically acceptable salt thereof, wherein X$^{11}$ is —C(R$^{11}$)$_2$.

28. The compound of claim 1, or a pharmaceutically acceptable salt thereof, wherein each R$_{11}$ is independently selected from H, D, C$_{1-6}$ alkyl, C$_{1-6}$ haloalkyl, C$_{2-6}$ alkenyl, C$_{2-6}$ alkynyl, wherein the C$_{1-6}$ alkyl, C$_{2-6}$ alkenyl, and C$_{2-6}$ alkynyl, of R$^{11}$ are each optionally substituted with 1, 2, 3, or 4 independently selected R$^{11A}$ substituents.

29. The compound of claim 1, or a pharmaceutically acceptable salt thereof, wherein X$^{11}$ is CH$_2$.

30. The compound of claim 1, or a pharmaceutically acceptable salt thereof, wherein:
R$^1$ is selected from H, D, halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, —OR$^{a1}$, —SR$^{a1}$, —NHOR$^{a1}$, —C(O)R$^{b1}$, —C(O)NR$^{c1}$R$^{d1}$, —C(O)NR$^{c1}$(OR$^{a1}$), —C(O)OR$^{a1}$, —OC(O)R$^{b1}$, —OC(O)NR$^{c1}$R$^{d1}$, —NR$^{c1}$C(O)OR$^{a1}$, and —NR$^{c1}$C(O)NR$^{c1}$R$^{d1}$;

R$^2$ is selected from H, D, halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, —OR$^{a2}$, —SR$^{a2}$, —NHOR$^{a2}$, —C(O)R$^{b2}$, —C(O)NR$^{c2}$R$^{d2}$, —C(O)NR$^{c2}$(OR$^{a2}$), —C(O)OR$^{a2}$, —OC(O)R$^{b2}$, —OC(O)NR$^{c2}$R$^{d2}$, —NR$^{c2}$C(O)R$^{b2}$, —NR$^{c2}$C(O)OR$^{a2}$, and —NR$^{c2}$C(O)NR$^{c2}$R$^{d2}$;

each R$^{a2}$, R$^{b2}$, R$^{c2}$, and R$^{d2}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, and 4-7 membered heterocycloalkyl, wherein the C$_{1-6}$ alkyl, C$_{2-6}$ alkenyl, C$_{2-6}$ alkynyl, phenyl, C$_{3-7}$ cycloalkyl, 5-6 membered heteroaryl, and 4-7 membered heterocycloalkyl of R$^{a2}$, R$^{b2}$, R$^{c2}$ and R$^{d2}$ are each optionally substituted with 1 or 2 independently selected R$^{2A}$ substituents;
or, any R$^{c2}$ and R$^{d2}$, attached to the same N atom, together with the N atom to which they are attached, form a 4-7 membered heterocycloalkyl group, wherein the 4-7 membered heterocycloalkyl group is optionally substituted with 1 or 2 independently selected R$^{2A}$ substituents;

each R$^{2A}$ is selected from halo, C$_{1-6}$ alkyl, C$_{1-6}$ haloalkyl, CN, and OH, Z is N or CH;

R$^6$ is selected from H, D, halo, C$_{1-6}$ alkyl, C$_{1-6}$ haloalkyl, C$_{2-6}$ alkenyl, C$_{2-6}$ alkynyl, —S(O)R$^{b6}$, —S(O)NR$^{c6}$R$^{d6}$, —S(O)$_2$R$^{b6}$, —S(O)$_2$NR$^{c6}$R$^{d6}$, —S(O)(=NR$^{c6}$)R$^{b6}$, and —N=S(O)R$^{a6}$R$^{b6}$, wherein the C$_{1-6}$ haloalkyl is optionally substituted with 1, 2 or 3 R$^{6A}$ independently selected from D, halo, CN, OH, NH$_2$, and C$_{1-6}$ alkyl;

each R$^{a6}$, R$^{b6}$, R$^{c6}$, R$^{d6}$, and R$^{e6}$ is independently selected from H and C$_{1-6}$ alkyl;

X$^9$ is —NR$^{9N}$ or —C(R$^9$)$_2$;

X$^{11}$ is —NR$^{11N}$ or —C(R$^{11}$)$_2$;

each R$^9$ is independently selected from H, D, C$_{1-6}$ alkyl, C$_{1-6}$ haloalkyl, C$_{2-6}$ alkenyl, C$_{2-6}$ alkynyl, wherein the C$_{1-6}$ alkyl, C$_{2-6}$ alkenyl, and C$_{2-6}$ alkynyl, of R$^9$ are each optionally substituted with 1, 2, 3, or 4 independently selected R$^{9A}$ substituents;

or, alternatively, two R$^9$ groups together form an oxo group;

R$^{10N}$ is selected from H, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl- of R$^{10N}$ are each optionally substituted with 1, 2, 3, or 4 independently selected R$^{10NA}$ substituents selected from halo, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, and 4-7 membered heterocycloalkyl; and each $R^{11}$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^{11}$ are each optionally substituted with 1, 2, 3, or 4 independently selected $R^{11A}$ substituents.

31. The compound of claim 1, or a pharmaceutically acceptable salt thereof, wherein:

$R^1$ is selected from H and $C_{1-6}$ alkyl;

$R^2$ is selected from H, $C_{1-6}$ alkyl, —C(O)$R^{b2}$, —C(O)N$R^{c2}R^{d2}$, —N$R^{c2}$C(O)$R^{b2}$, —N$R^{c2}$C(O)O$R^{a2}$, and —N$R^{c2}$C(O)N$R^{c2}R^{d2}$;

each $R^{a2}$, $R^{b2}$, $R^{c2}$, and $R^{d2}$ is independently selected from H, $C_{1-6}$ alkyl, $C_{1-6}$ haloalkyl, $C_{3-7}$ cycloalkyl, and 4-7 membered heterocycloalkyl, wherein the $C_{1-6}$ alkyl, $C_{3-7}$ cycloalkyl, and 4-7 membered heterocycloalkyl of $R^{a2}$, $R^{b2}$, $R^{c2}$ and $R^{d2}$ are each optionally substituted with 1 or 2 independently selected $R^{2A}$ substituents selected from halo, $C_{1-6}$ alkyl, $C_{1-6}$ haloalkyl, CN, and OH;

or, any $R^{c2}$ and $R^{d2}$, attached to the same N atom, together with the N atom to which they are attached, form a 4-7 membered heterocycloalkyl group, wherein the 4-7 membered heterocycloalkyl group is optionally substituted with 1 or 2 independently selected $R^{2A}$ substituents selected from halo, $C_{1-6}$ alkyl, $C_{1-6}$ haloalkyl, CN, and OH;

Z is N or CH;

$R^6$ is selected from H, halo, $C_{1-6}$ alkyl, —S(O)$R^{b6}$, —S(O)$_2R^{b6}$—S(O)(—N$R^{e6}$)$R^{b6}$ and —N—S(O)$R^{a6}R^{b6}$, wherein the $C_{1-6}$ alkyl is optionally substituted with 1 or 2 OH;

each $R^{a6}$, $R^{b6}$, and $R^{e6}$ is independently selected from H, and $C_{1-6}$ alkyl;

$X^9$ is —C($R^9$)$_2$;

$X^{11}$ is —C($R^{11}$)$_2$, each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^9$ are each optionally substituted with 1, 2, 3, or 4 independently selected $R^{9A}$ substituents; or, alternatively, two $R^9$ groups together form an oxo group;

$R^{10N}$ is selected from $C_{1-6}$ alkyl, $C_{3-6}$ cycloalkyl, and $C_{3-6}$ cycloalkyl-$C_{1-6}$ alkyl-, wherein the $C_{1-6}$ alkyl, $C_{3-6}$ cycloalkyl, and $C_{3-6}$ cycloalkyl-$C_{1-6}$ alkyl- of $R^{10N}$ are each optionally substituted with 1 or 2 independently selected $R^{10NA}$ substituents selected from $C_{1-6}$ alkyl, $C_{3-7}$ cycloalkyl, and 4-7 membered heterocycloalkyl; and each $R^{11}$ is independently selected from H, D, $C_{1-6}$ alkyl, $C_{1-6}$ haloalkyl, $C_{2-6}$ alkenyl, $C_{2-6}$ alkynyl.

32. The compound of claim 1, selected from:

(S)-7-Chloro-2-(1-cyclopropylethyl)-5-(2-(4,5-dimethyl-1H-imidazol-2-yl)pyridin-4-yl)isoindolin-1-one;

(S)-2-(1-Cyclopropylethyl)-5-(2-(4,5-dimethyl-1H-imidazol-2-yl)pyridin-4-yl)-7-(methylsulfonyl)isoindolin-1-one;

(S)-2-(4-(2-(1-Cyclopropylethyl)-1-oxoisoindolin-5-yl)pyridin-2-yl)-N-isopropyl-5-methyl-1H-imidazole-4-carboxamide;

(S)-2-(4-(2-(1-Cyclopropylethyl)-1-oxoisoindolin-5-yl)pyridin-2-yl)-5-methyl-N-(tetrahydro-2H-pyran-4-yl)-1H-imidazole-4-carboxamide;

(S)-2-(4-(2-(1-Cyclopropylethyl)-1-oxoisoindolin-5-yl)pyridin-2-yl)-N,N, 5-trimethyl-1H-imidazole-4-carboxamide;

(S)-2-(4-(2-(1-Cyclopropylethyl)-1-oxoisoindolin-5-yl)pyridin-2-yl)-N, 5-dimethyl-1H-imidazole-4-carboxamide;

(S)-2-(4-(2-(1-Cyclopropylethyl)-7-(methylsulfonyl)-1-oxoisoindolin-5-yl)pyridin-2-yl)-N,4-dimethyl-1H-imidazole-5-carboxamide; and (S)-2-(1-Cyclopropylethyl)-5-(6-(4,5-dimethyl-1H-imidazol-2-yl)pyridazin-4-yl)-7-(methylsulfonyl)isoindolin-1-one;

or a pharmaceutically acceptable salt thereof.

33. The compound of claim 1, selected from:

(S)-2-(4-(2-(1-Cyclopropylethyl)-7-(methylsulfonyl)-1-oxoisoindolin-5-yl)pyridin-2-yl)-N-isopropyl-4-methyl-1H-imidazole-5-carboxamide;

(S)-2-(4-(2-(1-Cyclopropylethyl)-7-(methylsulfonyl)-1-oxoisoindolin-5-yl)pyridin-2-yl)-4-methyl-N-(tetrahydro-2H-pyran-4-yl)-1H-imidazole-5-carboxamide;

(S)—N-(Bicyclo[1.1.1]pentan-1-yl)-2-(4-(2-(1-cyclopropylethyl)-7-(methylsulfonyl)-1-oxoisoindolin-5-yl)pyridin-2-yl)-4-methyl-1H-imidazole-5-carboxamide;

(S)-2-(1-Cyclopropylethyl)-5-(2-(5-(3,3-difluoroazetidine-1-carbonyl)-4-methyl-1H-imidazol-2-yl)pyridin-4-yl)-7-(methylsulfonyl)isoindolin-1-one;

(S)-2-(1-Cyclopropylethyl)-5-(2-(5-(3-hydroxyazetidine-1-carbonyl)-4-methyl-1H-imidazol-2-yl)pyridin-4-yl)-7-(methylsulfonyl)isoindolin-1-one;

(S)-2-(4-(2-(1-Cyclopropylethyl)-7-(methylsulfonyl)-1-oxoisoindolin-5-yl)pyridin-2-yl)-N-(3-hydroxycyclobutyl)-4-methyl-1H-imidazole-5-carboxamide;

2-(4-(2-((S)-1-Cyclopropylethyl)-7-(methylsulfonyl)-1-oxoisoindolin-5-yl)pyridin-2-yl)-4-methyl-N-(1,1,1-trifluoropropan-2-yl)-1H-imidazole-5-carboxamide;

(S)—N-(4-Cyanobicyclo[2.1.1]hexan-1-yl)-2-(4-(2-(1-cyclopropylethyl)-7-(methylsulfonyl)-1-oxoisoindolin-5-yl)pyridin-2-yl)-4-methyl-1H-imidazole-5-carboxamide;

(S)-2-(4-(2-(1-Cyclopropylethyl)-7-(methylsulfonyl)-1-oxoisoindolin-5-yl)pyridin-2-yl)-4-methyl-N-(2-oxaspiro[3.3]heptan-6-yl)-1H-imidazole-5-carboxamide;

(S)-5-(2-(5-(Azetidine-1-carbonyl)-4-methyl-1H-imidazol-2-yl)pyridin-4-yl)-2-(1-cyclopropylethyl)-7-(methylsulfonyl)isoindolin-1-one;

(S)—N-Cyclobutyl-2-(4-(2-(1-cyclopropylethyl)-7-(methylsulfonyl)-1-oxoisoindolin-5-yl)pyridin-2-yl)-4-methyl-1H-imidazole-5-carboxamide;

N-(sec-Butyl)-2-(4-(2-((S)-1-cyclopropylethyl)-7-(methylsulfonyl)-1-oxoisoindolin-5-yl)pyridin-2-yl)-4-methyl-1H-imidazole-5-carboxamide;

(S)-2-(4-(2-(1-Cyclopropylethyl)-7-(methylsulfonyl)-1-oxoisoindolin-5-yl)pyridin-2-yl)-4-methyl-N-(1-methylazetidin-3-yl)-1H-imidazole-5-carboxamide;

2-(4-(2-((S)-1-Cyclopropylethyl)-7-(methylsulfonyl)-1-oxoisoindolin-5-yl)pyridin-2-yl)-4-methyl-N-(tetrahydrofuran-3-yl)-1H-imidazole- 5-carboxamide;

(S)-2-(4-(2-(1-Cyclopropylethyl)-7-(methylsulfonyl)-1-oxoisoindolin-5-yl)pyridin-2-yl)-N,4-dimethyl-N-(tetrahydro-2H-pyran-4-yl)-1H-imidazole-5-carboxamide;

(S)-2-(1-Cyclopropylethyl)-5-(2-(4-methyl-5-(2-oxa-6-azaspiro[3.3]heptane-6-carbonyl)-1H-imidazol-2-yl)pyridin-4-yl)-7-(methylsulfonyl)isoindolin-1-one;

(S)-2-(4-(2-(1-Cyclopropylethyl)-7-(methylsulfonyl)-1-oxoisoindolin-5-yl)pyridin-2-yl)-4-methyl-1H-imidazole-5-carboxamide;

(S)-2-(4-(2-(1-Cyclopropylethyl)-7-(methylsulfonyl)-1-oxoisoindolin-5-yl)pyridin-2-yl)-N-ethyl-4-methyl-1H-imidazole-5-carboxamide;

(S)-2-(4-(2-(1-Cyclopropylethyl)-7-(methylsulfonyl)-1-oxoisoindolin-5-yl)pyridin-2-yl)-N-ethyl-N,4-dimethyl-1H-imidazole-5-carboxamide;

(S)-2-(4-(2-(1-Cyclopropylethyl)-7-(methylsulfonyl)-1-oxoisoindolin-5-yl)pyridin-2-yl)-N-isopropyl-N,4-dimethyl-1H-imidazole-5-carboxamide;

(S)—N-Cyclobutyl-2-(4-(2-(1-cyclopropylethyl)-7-(methylsulfonyl)-1-oxoisoindolin-5-yl)pyridin-2-yl)-N,4-dimethyl-1H-imidazole-5-carboxamide;

(S)-2-(1-Cyclopropylethyl)-5-(2-(5-methyl-1H-imidazol-2-yl)pyridin-4-yl)-7-(methylsulfonyl)isoindolin-1-one;

(S)-5-(2-(1H-Imidazol-2-yl)pyridin-4-yl)-2-(1-cyclopropylethyl)-7-(methylsulfonyl)isoindolin-1-one;

2-((S)-1-Cyclopropylethyl)-7-(1,2-dihydroxyethyl)-5-(2-(4,5-dimethyl-1H-imidazol-2-yl)pyridin-4-yl)isoindolin-1-one;

2-((S)-1-Cyclopropylethyl)-7-(1,2-dihydroxyethyl)-5-(6-(4,5-dimethyl-1H-imidazol-2-yl)pyridazin-4-yl)isoindolin-1-one;

2-((S)-1-Cyclopropylethyl)-5-(2-(4,5-dimethyl-1H-imidazol-2-yl)pyridin-4-yl)-7-(S-methylsulfonimidoyl)isoindolin-1-one;

2-((S)-1-Cyclopropylethyl)-5-(2-(4,5-dimethyl-1H-imidazol-2-yl)pyridin-4-yl)-7-(S-methylsulfonimidoyl)isoindolin-1-one;

2-((S)-1-Cyclopropylethyl)-5-(2-(4,5-dimethyl-1H-imidazol-2-yl)pyridin-4-yl)-7-(N,S-dimethylsulfonimidoyl)isoindolin-1-one;

2-((S)-1-Cyclopropylethyl)-5-(2-(4,5-dimethyl-1H-imidazol-2-yl)pyridin-4-yl)-7-(N,S-dimethylsulfonimidoyl)isoindolin-1-one; and (S)-2-(1-Cyclopropylethyl)-7-((dimethyl(oxo)-$\lambda^6$-sulfanylidene)amino)-5-(2-(5-methyl-1H-imidazol-2-yl)pyridin-4-yl)isoindolin-1-one;

or a pharmaceutically acceptable salt thereof.

34. A pharmaceutical composition comprising a compound of claim 1, or a pharmaceutically acceptable salt thereof, and a pharmaceutically acceptable excipient or carrier.

* * * * *